US012194108B2

United States Patent
Shim et al.

(10) Patent No.: US 12,194,108 B2
(45) Date of Patent: Jan. 14, 2025

(54) GENE THERAPEUTICS FOR TREATING BONE DISORDERS

(71) Applicant: University of Massachusetts, Westborough, MA (US)

(72) Inventors: Jae-Hyuck Shim, Worcester, MA (US); Guangping Gao, Worcester, MA (US); Jun Xie, Worcester, MA (US); Jung Min Kim, Worcester, MA (US); Dan Wang, Worcester, MA (US); Yeon-Suk Yang, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1057 days.

(21) Appl. No.: 16/982,640

(22) PCT Filed: Mar. 22, 2019

(86) PCT No.: PCT/US2019/023759
§ 371 (c)(1),
(2) Date: Sep. 21, 2020

(87) PCT Pub. No.: WO2019/183605
PCT Pub. Date: Sep. 26, 2019

(65) Prior Publication Data
US 2021/0023241 A1 Jan. 28, 2021

Related U.S. Application Data

(60) Provisional application No. 62/799,843, filed on Feb. 1, 2019, provisional application No. 62/647,595, filed on Mar. 23, 2018.

(51) Int. Cl.
*A61K 48/00* (2006.01)
*A61P 19/10* (2006.01)
(Continued)

(52) U.S. Cl.
CPC ............ *A61K 48/005* (2013.01); *A61P 19/10* (2018.01); *C07K 14/005* (2013.01);
(Continued)

(58) Field of Classification Search
CPC ........ A61K 48/005; A61P 19/10; A61P 19/08; C07K 14/005; C07K 14/635;
(Continued)

(56) References Cited

U.S. PATENT DOCUMENTS

| 5,399,363 A | 3/1995 | Liversidge et al. |
| 5,478,745 A | 12/1995 | Samulski et al. |

(Continued)

FOREIGN PATENT DOCUMENTS

| CN | 107073051 A | 8/2017 |
| CN | 111407758 A | 7/2020 |

(Continued)

OTHER PUBLICATIONS

Gafni et al. Gene therapy platform for bone regeneration using an exogenously regulated, AAV-2-based gene expression system. Mol Ther. Apr. 2004;9(4):587-95. (Year: 2004).*

(Continued)

*Primary Examiner* — Jeremy C Flinders
*Assistant Examiner* — Thomas R. Amick
(74) *Attorney, Agent, or Firm* — Wolf, Greenfield & Sacks, P.C.

(57) ABSTRACT

In some aspects, the disclosure relates to compositions and methods for modulating (e.g., increasing and/or decreasing) bone mass in a subject. In some aspects, the disclosure provides isolated nucleic acids, and vectors such as rAAV vectors, configured to express transgenes that promote (e.g., increase) or inhibit (e.g., decrease) activity, differentiation, or function of certain types of bone cells, for example osteoblasts, osteoclasts, osteocytes, etc. In some embodi- (Continued)

ments, the isolated nucleic acids and vectors described by the disclosure are useful for treating disorders and conditions associated with increased bone mass (e.g., osteopetrosis) or decreased bone mass (e.g., osteoporosis).

10 Claims, 48 Drawing Sheets

Specification includes a Sequence Listing.

(51) Int. Cl.
| | | |
|---|---|---|
| C07K 14/005 | (2006.01) | |
| C07K 14/635 | (2006.01) | |
| C12N 15/113 | (2010.01) | |
| C12N 15/86 | (2006.01) | |

(52) U.S. Cl.
CPC .......... *C07K 14/635* (2013.01); *C12N 15/113* (2013.01); *C12N 15/1137* (2013.01); *C12N 15/86* (2013.01); *C12N 2310/14* (2013.01); *C12N 2310/141* (2013.01); *C12N 2310/531* (2013.01); *C12N 2320/32* (2013.01); *C12N 2750/14122* (2013.01); *C12N 2750/14143* (2013.01); *C12N 2750/14145* (2013.01); *C12N 2750/14171* (2013.01)

(58) Field of Classification Search
CPC .. C12N 15/113; C12N 15/1137; C12N 15/86; C12N 2310/14; C12N 2310/141; C12N 2310/531; C12N 2320/32; C12N 2750/14122; C12N 2750/14143; C12N 2750/14145; C12N 15/111; C12N 2330/51; C12N 15/63; A01K 2217/075; A01K 2267/035
See application file for complete search history.

(56) References Cited

U.S. PATENT DOCUMENTS

| | | | |
|---|---|---|---|
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,641,515 | A | 6/1997 | Ramtoola |
| 5,656,016 | A | 8/1997 | Ogden |
| 5,697,899 | A | 12/1997 | Hillman et al. |
| 5,738,868 | A | 4/1998 | Shinkarenko |
| 5,741,516 | A | 4/1998 | Webb et al. |
| 5,770,219 | A | 6/1998 | Chiang et al. |
| 5,779,708 | A | 7/1998 | Wu |
| 5,783,208 | A | 7/1998 | Venkateshwaran et al. |
| 5,795,587 | A | 8/1998 | Gao et al. |
| 5,797,898 | A | 8/1998 | Santini, Jr. et al. |
| 6,001,650 | A | 12/1999 | Colosi |
| 6,156,303 | A | 12/2000 | Russell et al. |
| 8,859,752 | B2 | 10/2014 | Kaplan et al. |
| 9,458,215 | B2 | 10/2016 | Lau et al. |
| 11,674,154 | B2 | 6/2023 | Shim et al. |
| 2009/0318338 | A1 | 12/2009 | Glimcher et al. |
| 2010/0008979 | A1 | 1/2010 | Tomatsu et al. |
| 2010/0113577 | A1 | 5/2010 | Shi et al. |
| 2010/0239503 | A1 | 9/2010 | Yarbrough et al. |
| 2011/0311487 | A1 | 12/2011 | Tomatsu et al. |
| 2012/0093801 | A1 | 4/2012 | Awad et al. |
| 2013/0136729 | A1 | 5/2013 | French et al. |
| 2013/0202533 | A1 | 8/2013 | Glimcher et al. |
| 2014/0256917 | A1 | 9/2014 | Lau et al. |
| 2014/0271870 | A1 | 9/2014 | O'Shaughnessey et al. |
| 2015/0176027 | A1 | 6/2015 | Gao et al. |
| 2016/0187357 | A1 | 6/2016 | Brunkow et al. |
| 2016/0298099 | A1 | 10/2016 | Kormann et al. |
| 2017/0211070 | A1 | 7/2017 | Hino et al. |
| 2018/0015124 | A1 | 1/2018 | Prockop et al. |
| 2018/0237772 | A1 | 8/2018 | Yu et al. |
| 2018/0298380 | A1 | 10/2018 | Gao et al. |
| 2018/0363061 | A1 | 12/2018 | Grillari et al. |
| 2019/0167712 | A1 | 6/2019 | Chen et al. |
| 2020/0002682 | A1 | 1/2020 | Feary et al. |
| 2020/0231953 | A1 | 7/2020 | Gao et al. |
| 2021/0292755 | A1 | 9/2021 | Cabon et al. |
| 2022/0177915 | A1 | 6/2022 | Shim et al. |
| 2023/0111147 | A1 | 4/2023 | Subramanian et al. |
| 2023/0295662 | A1 | 9/2023 | Shim et al. |
| 2024/0002844 | A1 | 1/2024 | Shim et al. |

FOREIGN PATENT DOCUMENTS

| | | |
|---|---|---|
| JP | H09-509825 A | 10/1997 |
| JP | 2013-531471 A | 10/2011 |
| JP | 2013-545734 | 12/2013 |
| JP | 2017-533715 A | 11/2017 |
| JP | 2018-505695 A | 3/2018 |
| JP | 2018-506304 A | 3/2018 |
| WO | WO 95/22611 A2 | 8/1995 |
| WO | WO 2007/127428 A2 | 11/2007 |
| WO | WO 2011/088163 A1 | 7/2011 |
| WO | WO 2011/133890 A1 | 10/2011 |
| WO | WO 2012/058393 A2 | 5/2012 |
| WO | WO 2013/151672 A2 | 10/2013 |
| WO | WO 2014/005314 A1 | 1/2014 |
| WO | WO 2016/077689 A1 | 5/2016 |
| WO | WO 2016/112870 A1 | 7/2016 |
| WO | WO 2016/118520 A1 | 7/2016 |
| WO | WO 2016/130589 A2 | 8/2016 |
| WO | WO 2016/183297 A1 | 11/2016 |
| WO | WO 2017/191274 A2 | 11/2017 |
| WO | WO 2018/027329 A1 | 2/2018 |
| WO | WO 2018/035503 A1 | 2/2018 |
| WO | WO 2019/183605 A1 | 9/2019 |
| WO | WO 2020/118011 A1 | 6/2020 |
| WO | WO 2020/118239 A1 | 6/2020 |
| WO | WO 2021/202494 A1 | 10/2021 |
| WO | WO 2022/221581 A1 | 10/2022 |
| WO | WO 2023/283531 A2 | 1/2023 |

OTHER PUBLICATIONS

Kim et al, Sclerostin influences body composition by regulating catabolic and anabolic metabolism in adipocytes, Biological Sciences, 114 (52) E11238-E11247, Dec. 11, 2017 (Year: 2017).*
Nasso et al. Adeno-Associated Virus (AAV) as a Vector for Gene Therapy. BioDrugs. Aug. 2017;31(4):317-334. (Herinafter "Nasso"). (Year: 2017).*
Balmayor ER, van Griensven M. Gene therapy for bone engineering. Front Bioeng Biotechnol. Feb. 2, 2015;3:9 (Year: 2015).*
Li et al. (2013) The promotion of bone regeneration through positive regulation of angiogenic-osteogenic coupling using microRNA-26a. Biomaterials 34, 5048-5058. doi:10.1016/j. biomaterials.2013. 03.052) (Year: 2013).*
Xie et al, Semin Liver Dis. Feb. 2015 ; 35(1): 81-88 (Year: 2015).*
Zhang et al. (2016) Biomaterials 80:134-145. (Year: 2016).*
McCarty, D., Fu, H., Monahan, P. et al. Adeno-associated virus terminal repeat (TR) mutant generates self-complementary vectors to overcome the rate-limiting step to transduction in vivo. Gene Ther 10, 2112-2118 (2003). (hereinafter "McCarty"). (Year: 2003).*
Zhang, G., Guo, B., Wu, H. et al. A delivery system targeting bone formation surfaces to facilitate RNAi-based anabolic therapy. Nat Med 18, 307-314 (2012). (Hereinafter "Zhang G.") (Year: 2012).*
Robinson et al, Virology, vol. 546, 2020, pp. 127-132 (Year: 2020).*
Shi, L., Feng, L., Liu, Y. et al. MicroRNA-218 Promotes Osteogenic Differentiation of Mesenchymal Stem Cells and Accelerates Bone Fracture Healing. Calcif Tissue Int 103, 227-236 (2018) (Year: 2018).*
Peng, Yin et al. "The crosstalk between microRNAs and the Wnt/B-catenin signaling pathway in cancer." Oncotarget vol. 8,8 (2017): 14089-14106. doi:10.18632/oncotarget.12923 (Year: 2017).*

(56) References Cited

OTHER PUBLICATIONS

Invitation to Pay Additional Fees for Application No. PCT/US2019/023759, mailed Jun. 12, 2019.
International Search Report and Written Opinion for Application No. PCT/US2019/023759, mailed Aug. 2, 2019.
International Preliminary Report on Patentability for Application No. PCT/US2019/023759, mailed Oct. 8, 2020.
Krause et al., Distinct modes of inhibition by sclerostin on bone morphogenetic protein and Wnt signaling pathways. J Biol Chem. Dec. 31, 2010;285(53):41614-26. doi: 10.1074/jbc.M110.153890. Epub Oct. 15, 2010.
Ouyang et al., Bone Targeting Prodrugs Based on Peptide Dendrimers, Synthesis and Hydroxyapatite Binding In Vitro. Lett Organic Chem. 2009;6(4):272-277. doi: 10.2174/157017809788489981.
Rickel et al., Molecular genetics of osteosarcoma. Bone. Sep. 2017;102:69-79. doi: 10.1016/j.bone.2016.10.017. Epub Oct. 17, 2016.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Extended European Search Report for Application No. 22199907.1, mailed Mar. 24, 2023.
Katsumi et al., Molecular Design of Bisphosphonate-Modified Proteins for Efficient Bone Targeting In Vivo. PLoS One. Aug. 19, 2015;10(8):e0135966. doi: 10.1371/journal.pone.0135966. eCollection 2015.
Liu et al., Bi-directionally selective bone targeting delivery for anabolic and antiresorptive drugs: a novel combined therapy for osteoporosis? Med Hypotheses. Dec. 2014;83(6):694-6. doi: 10.1016/j.mehy.2014.09.020. Epub Oct. 13, 2014.
Oh et al., WNT-modulating gene silencers as a gene therapy for osteoporosis, bone fracture, and critical-sized bone defects. Mol Ther. Feb. 1, 2023;31(2):435-453. doi: 10.1016/j.ymthe.2022.09.018. Epub Oct. 3, 2022.
Ryu et al., Bone-targeted delivery of nanodiamond-based drug carriers conjugated with alendronate for potential osteoporosis treatment. J Control Release. Jun. 28, 2016;232:152-60. doi: 10.1016/j.jconrel.2016.04.025. Epub Apr. 17, 2016.
Shim, Novel therapeutics to promote bone formation in skeletal diseases. Research Features. Jan. 2018; 54-57. https://researchfeatures.com/wp-content/uploads/2018/01/Prof-Jae-Hyuck-Shim-UMASS-Medical-School-Skeletal-biology_2.pdf.
Tomatsu et al., Current and emerging treatments and surgical interventions for Morquio A syndrome: a review. Res Rep Endocr Disord. Dec. 2012;2012(2):65-77. doi: 10.2147/RRED.S37278.
Wu et al., siRNA delivery system mediated by (Aspartate-Serine-Serine)6 peptide for targeting bone formation site in osteoporotic skeleton. Bone. Oct. 2010; 47(3): S370. DOI:10.1016/j.bone.2010.09.115.
Yang et al., Bone-targeting AAV-mediated silencing of Schnurri-3 prevents bone loss in osteoporosis. Nat Commun. Jul. 4, 2019;10(1):2958. doi: 10.1038/s41467-019-10809-6.
PCT/US2019/023759, Jun. 12, 2019, Invitation to Pay Additional Fees.
PCT/US2019/023759, Aug. 2, 2019, International Search Report and Written Opinion.
PCT/US2019/023759, Oct. 8, 2020, International Preliminary Report on Patentability.
Partial European Search Report for Application No. 19771342.3, mailed Dec. 7, 2021.
Extended European Search Report for Application No. 19771342.3, mailed Mar. 11, 2022.
International Search Report and Written Opinion for Application No. PCT/US2021/046447, mailed Nov. 30, 2021.
International Preliminary Report on Patentability for Application No. PCT/US2021/046447, mailed Mar. 2, 2023.
Invitation to Pay Additional Fees for Application No. PCT/US2021/061653, mailed Feb. 10, 2022.
International Search Report and Written Opinion for Application No. PCT/US2021/061653, mailed Apr. 1, 2022.
International Preliminary Report on Patentability for Application No. PCT/US2021/061653 mailed Jun. 15, 2023.
Invitation to Pay Additional Fees for Application No. PCT/US2023/076695, mailed Feb. 8, 2024.
Invitation to Pay Additional Fees for Application No. PCT/US2022/079238, mailed Jan. 25, 2023.
International Search Report and Written Opinion for Application No. PCT/US2022/079238, mailed Mar. 22, 2023.
International Search Report and Written Opinion for Application No. PCT/US2023/070392, mailed Nov. 7, 2023.
Arav et al., Adeno-associated virus-coated allografts: a novel approach for cranioplasty. J Tissue Eng Regen Med. Nov. 2012;6(10):e43-50. doi: 10.1002/term.1594. Epub Sep. 3, 2012.
Asokan et al., The AAV vector toolkit: poised at the clinical crossroads. Mol Ther. Apr. 2012;20(4):699-708. doi: 10.1038/mt.2011.287. Epub Jan. 24, 2012.
Aykul et al., Transforming Growth Factor-beta Family Ligands Can Function as Antagonists by Competing for Type II Receptor Binding. J Biol Chem. May 13, 2016;291(20):10792-804. doi: 10.1074/jbc.M115.713487. Epub Mar. 9, 2016.
Baujat et al., Prevalence of fibrodysplasia ossificans progressiva (FOP) in France: an estimate based on a record linkage of two national databases. Orphanet J Rare Dis. Jun. 30, 2017;12(1):123. doi: 10.1186/s13023-017-0674-5.
Blankinship et al., Efficient transduction of skeletal muscle using vectors based on adeno-associated virus serotype 6. Mol Ther. Oct. 2004;10(4):671-8. doi: 10.1016/j.ymthe.2004.07.016.
Boshart et al., A very strong enhancer is located upstream of an immediate early gene of human cytomegalovirus. Cell. Jun. 1985;41(2):521-30. doi: 10.1016/s0092-8674(85)80025-8.
Bourlais et al., Ophthalmic drug delivery systems—recent advances. Prog Retin Eye Res. Jan. 1998;17(1):33-58. doi: 10.1016/s1350-9462(97)00002-5.
Büning, et al., Receptor targeting of adeno-associated virus vectors. Gene Ther. Jul. 2003;10(14):1142-51. doi: 10.1038/sj.gt.3301976.
Chamberlain et al., Gene targeting of mutant COL1A2 alleles in mesenchymal stem cells from individuals with osteogenesis imperfecta. Mol Ther. Jan. 2008;16(1):187-93. doi: 10.1038/sj.mt.6300339. Epub Oct. 23, 2007.
Chang et al., miR-122, a mammalian liver-specific microRNA, is processed from her mRNA and may downregulate the high affinity cationic amino acid transporter CAT-1. RNA Biol. Jul. 2004;1(2):106-13. doi: 10.4161/rna.1.2.1066. Epub Jul. 1, 2004.
Chu et al., SV40 DNA transfection of cells in suspension: analysis of efficiency of transcription and translation of T-antigen. Gene. Mar. 1981;13(2):197-202. doi: 10.1016/0378-1119(81)90008-1.
Convente et al., Depletion of Mast Cells and Macrophages Impairs Heterotopic Ossification in an Acvr1(R206H) Mouse Model of Fibrodysplasia Ossificans Progressiva. J Bone Miner Res. Feb. 2018;33(2):269-282. doi: 10.1002/jbmr.3304. Epub Jan. 3, 2018.
De Felipe et al., Tricistronic and tetracistronic retroviral vectors for gene transfer. Hum Gene Ther. Sep. 1, 2000;11(13):1921-31. doi: 10.1089/10430340050129530.
De Felipe et al., Use of the 2A sequence from foot-and-mouth disease virus in the generation of retroviral vectors for gene therapy. Gene Ther. Feb. 1999;6(2):198-208. doi: 10.1038/sj.gt.3300811.
Fisher et al., Transduction with recombinant adeno-associated virus for gene therapy is limited by leading-strand synthesis. J Virol. Jan. 1996;70(1):520-32. doi: 10.1128/JVI.70.1.520-532.1996.
Furler et al., Recombinant AAV vectors containing the foot and mouth disease virus 2A sequence confer efficient bicistronic gene expression in cultured cells and rat substantia nigra neurons. Gene Ther. Jun. 2001;8(11):864-73. doi: 10.1038/sj.gt.3301469.
Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.
Gossen et al., Transcriptional activation by tetracyclines in mammalian cells. Science. Jun. 23, 1995;268(5218):1766-9. doi: 10.1126/science.7792603.

(56) References Cited

OTHER PUBLICATIONS

Graham et al., A new technique for the assay of infectivity of human adenovirus 5 DNA. Virology. Apr. 1973;52(2):456-67. doi: 10.1016/0042-6822(73)90341-3.

Gregorevic et al., Systemic delivery of genes to striated muscles using adeno-associated viral vectors. Nat Med. Aug. 2004;10(8):828-34. doi: 10.1038/nm1085. Epub Jul. 25, 2004.

Halpin et al., Self-processing 2A-polyproteins—a system for co-ordinate expression of multiple proteins in transgenic plants. Plant J. Feb. 1999;17(4):453-9. doi: 10.1046/j.1365-313x.1999.00394.x.

Harvey et al., Inducible control of gene expression: prospects for gene therapy. Curr Opin Chem Biol. Aug. 1998;2(4):512-8. doi: 10.1016/s1367-5931(98)80128-2.

Hatsell et al., ACVR1R206H receptor mutation causes fibrodysplasia ossificans progressiva by imparting responsiveness to activin A. Sci Transl Med. Sep. 2, 2015;7(303):303ra137. doi: 10.1126/scitranslmed.aac4358.

Hildebrand et al., The Fibrodysplasia Ossificans Progressiva (FOP) mutation p.R206H in ACVR1 confers an altered ligand response. Cell Signal. Jan. 2017;29:23-30. doi: 10.1016/j.cellsig.2016.10.001. Epub Oct. 4, 2016.

Hino et al., Neofunction of ACVR1 in fibrodysplasia ossificans progressiva. Proc Natl Acad Sci USA. Dec. 15, 2015;112(50):15438-43. doi: 10.1073/pnas.1510540112. Epub Nov. 30, 2015.

Hsieh et al., Evaluation of Salivary Cytokines for Diagnosis of both Trauma-Induced and Genetic Heterotopic Ossification. Front Endocrinol (Lausanne). Apr. 24, 2017;8:74. doi: 10.3389/fendo.2017.00074. eCollection 2017.

Joe et al., Muscle injury activates resident fibro/adipogenic progenitors that facilitate myogenesis. Nat Cell Biol. Feb. 2010;12(2):153-63. doi: 10.1038/ncb2015. Epub Jan. 17, 2010.

Kaplan et al., Fibrodysplasia ossificans progressiva. Best Pract Res Clin Rheumatol. Mar. 2008;22(1):191-205. doi: 10.1016/j.berh.2007.11.007.

Kim et al., Sclerostin influences body composition by regulating catabolic and anabolic metabolism in adipocytes. Proc Natl Acad Sci U S A. Dec. 26, 2017;114(52):E11238-E11247. doi: 10.1073/pnas.1707876115. Epub Dec. 11, 2017.

Klump et al., Retroviral vector-mediated expression of HoxB4 in hematopoietic cells using a novel coexpression strategy. Gene Ther. May 2001;8(10):811-7. doi: 10.1038/sj.gt.3301447.

Koefoed et al., Biological effects of rAAV-caAlk2 coating on structural allograft healing. Mol Ther. Aug. 2005;12(2):212-8. doi: 10.1016/j.ymthe.2005.02.026.

Lagos-Quintana et al., Identification of tissue-specific microRNAs from mouse. Curr Biol. Apr. 30, 2002;12(9):735-9. doi: 10.1016/s0960-9822(02)00809-6.

Levy et al., Cytosine and adenine base editing of the brain, liver, retina, heart and skeletal muscle of mice via adeno-associated viruses. Nat Biomed Eng. Jan. 2020;4(1):97-110. doi: 10.1038/s41551-019-0501-5. Epub Jan. 14, 2020.

Limberis et al., Transduction efficiencies of novel AAV vectors in mouse airway epithelium in vivo and human ciliated airway epithelium in vitro. Mol Ther. Feb. 2009;17(2):294-301. doi: 10.1038/mt.2008.261. Epub Dec. 9, 2008.

Luk et al., Adeno-associated virus-mediated bone morphogenetic protein-4 gene therapy for in vivo bone formation. Biochem Biophys Res Commun. Aug. 29, 2003;308(3):636-45. doi: 10.1016/s0006-291x(03)01429-3.

Magari et al., Pharmacologic control of a humanized gene therapy system implanted into nude mice. J Clin Invest. Dec. 1, 1997;100(11):2865-72. doi: 10.1172/JCI119835.

Martínez-Solís et al., A novel baculovirus-derived promoter with high activity in the baculovirus expression system. PeerJ. Jun. 28, 2016;4:e2183. doi: 10.7717/peerj.2183. eCollection 2016.

Matsumoto et al., Induced pluripotent stem cells from patients with human fibrodysplasia ossificans progressiva show increased mineralization and cartilage formation. Orphanet J Rare Dis. Dec. 9, 2013;8:190. doi: 10.1186/1750-1172-8-190.

Mattion et al., Foot-and-mouth disease virus 2A protease mediates cleavage in attenuated Sabin 3 poliovirus vectors engineered for delivery of foreign antigens. J Virol. Nov. 1996;70(11):8124-7. doi: 10.1128/JVI.70.11.8124-8127.1996.

McCarthy, Self-complementary AAV vectors; advances and applications. Mol Ther. Oct. 2008;16(10):1648-56. doi: 10.1038/mt.2008.171. Epub Aug. 5, 2008.

Medici et al., Conversion of vascular endothelial cells into multipotent stem-like cells. Nat Med. Dec. 2010;16(12):1400-6. doi: 10.1038/nm.2252. Epub Nov. 21, 2010.

Min et al., Diverse repertoire of human adipocyte subtypes develops from transcriptionally distinct mesenchymal progenitor cells. Proc Natl Acad Sci U S A. Sep. 3, 2019;116(36):17970-17979. doi: 10.1073/pnas.1906512116. Epub Aug. 16, 2019.

No Author Listed, Definition of "Optimal". Merriam-Webster.com Dictionary. https://www.merriam-webster.com/dictionary/optimal. Last accessed May 18, 2022.

No et al., Ecdysone-inducible gene expression in mammalian cells and transgenic mice. Proc Natl Acad Sci U S A. Apr. 16, 1996;93(8):3346-51. doi: 10.1073/pnas.93.8.3346.

Olsen et al., Activin A inhibits BMP-signaling by binding ACVR2A and ACVR2B. Cell Commun Signal. Jun. 6, 2015;13:27. doi: 10.1186/s12964-015-0104-z.

Pacifici et al., Common mutations in ALK2/ACVR1, a multifaceted receptor, have roles in distinct pediatric musculoskeletal and neural orphan disorders. Cytokine Growth Factor Rev. Feb. 2016;27:93-104. doi: 10.1016/j.cytogfr.2015.12.007. Epub Dec. 28, 2015.

Ran et al., In vivo genome editing using Staphylococcus aureus Cas9. Nature. Apr. 9, 2015;520(7546):186-91. doi: 10.1038/nature14299. Epub Apr. 1, 2015.

Remington's Pharmaceutical Sciences. 15th Edition. 1975. pp. 1035-1038 and 1570-1580.

Ryan et al., Foot-and-mouth disease virus 2A oligopeptide mediated cleavage of an artificial polyprotein. EMBO J. Feb. 15, 1994;13(4):928-33. doi: 10.1002/j.1460-2075.1994.tb06337.x.

Shi et al., Insertional mutagenesis of the adeno-associated virus type 2 (AAV2) capsid gene and generation of AAV2 vectors targeted to alternative cell-surface receptors. Hum Gene Ther. Sep. 20, 2001;12(14):1697-711. doi: 10.1089/104303401750476212.

Shore et al., A recurrent mutation in the BMP type I receptor ACVR1 causes inherited and sporadic fibrodysplasia ossificans progressiva. Nat Genet. May 2006;38(5):525-7. doi: 10.1038/ng1783. Epub Apr. 23, 2006.

Shore et al., Insights from a rare genetic disorder of extra-skeletal bone formation, fibrodysplasia ossificans progressiva (FOP). Bone. Sep. 2008;43(3):427-33. doi: 10.1016/j.bone.2008.05.013. Epub May 28, 2008.

Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251-3260.1985.

Wang et al., Ligand-inducible and liver-specific target gene expression in transgenic mice. Nat Biotechnol. Mar. 1997;15(3):239-43. doi: 10.1038/nbt0397-239.

Wang et al., Positive and negative regulation of gene expression in eukaryotic cells with an inducible transcriptional regulator. Gene Ther. May 1997;4(5):432-41. doi: 10.1038/sj.gt.3300402.

Wolken et al., The obligatory role of Activin A in the formation of heterotopic bone in Fibrodysplasia Ossificans Progressiva. Bone. Apr. 2018;109:210-217. doi: 10.1016/j.bone.2017.06.011. Epub Jun. 16, 2017.

Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.

Wu et al., Mutational analysis of the adeno-associated virus type 2 (AAV2) capsid gene and construction of AAV2 vectors with altered tropism. J Virol. Sep. 2000;74(18):8635-47. doi: 10.1128/jvi.74.18.8635-8647.2000.

Wu et al., Self-complementary recombinant adeno-associated viral vectors: packaging capacity and the role of rep proteins in vector purity. Hum Gene Ther. Feb. 2007;18(2):171-82. doi: 10.1089/hum.2006.088.

(56) References Cited

OTHER PUBLICATIONS

Xie et al., Effective and Accurate Gene Silencing by a Recombinant AAV-Compatible MicroRNA Scaffold. Mol Ther. Feb. 5, 2020;28(2):422-430. doi: 10.1016/j.ymthe.2019.11.018. Epub Nov. 27, 2019.

Yamamoto et al., Making ends meet: targeted integration of DNA fragments by genome editing. Chromosoma. Dec. 2018;127(4):405-420. doi: 10.1007/s00412-018-0677-6. Epub Jul. 12, 2018.

Yang et al., Adeno-associated virus-mediated osteoprotegerin gene transfer protects against particulate polyethylene-induced osteolysis in a murine model. Arthritis Rheum. Sep. 2002;46(9):2514-23. doi: 10.1002/art.10527.

Yang et al., Bone-Targeting AAV-Mediated Gene Silencing in Osteoclasts for Osteoporosis Therapy. Mol Ther Methods Clin Dev. Apr. 18, 2020;17:922-935. doi: 10.1016/j.omtm.2020.04.010. eCollection Jun. 12, 2020.

Extended European Search Report for Application No. 21859030.5, mailed Jul. 8, 2024.

International Search Report and Written Opinion for Application No. PCT/US2023/076695, mailed Oct. 12, 2023.

International Preliminary Report on Patentability for Application No. PCT/US2022/079238, mailed May 16, 2024.

Invitation to Pay Additional Fees for Application No. PCT/US2024/025340, mailed Jun. 25, 2024.

International Search Report and Written Opinion for Application No. PCT/US2024/025340, mailed Aug. 21, 2024.

Invitation to Pay Additional Fees for Application No. PCT/US2024/025492, mailed Jun. 25, 2024.

International Search Report and Written Opinion for Application No. PCT/US2024/025492, mailed Aug. 23, 2024.

Elefteriou et al., Genetic mouse models for bone studies—strengths and limitations. Bone. Dec. 2011;49(6):1242-54. doi: 10.1016/j.bone.2011.08.021. Epub Aug. 31, 2011.

Maruelli, Gene Therapy Strategy for Classical Osteogenesis Imperfect Due to Mutations in COL1A2 Gene. Thesis from the University of Pavia. 2015/2016. Retrieved from the internet: <https://scholar.google.com/scholar?hl=en&as_sdt=0%2C22&q=MARUELLI%2C+S.2C+Gene+Therapy+Strategy+for+Classical+Osteogenesis+Imperfect+Due+to+Mutations+in+Col1a2+Gene.+Thesis.+University+of+Pavia.&btnG=>.

No Author Listed, GenBank Accession No. AW743747.1, ur28g10.x1 Soares_mouse NMBP Mus musculus cDNA clone IMAGE:3025698 3' similar to GB:J03464 Procollagen Alpha 2(1) Chain Precursor (Human), GB:X58251 Mouse COL1A2 mRNA for pro-alpha-2(1) collagen (MOUSE), mRNA sequence. Jan. 7, 2011. Retrieved from the internet: <URL:https://www.ncbi.nlm.nih.gov/nuccore/AW743747.1/>.

U.S. Appl. No. 18/707,207, filed May 3, 2024, Shim et al.

EP 21859030.5, Jul. 8, 2024, Extended European Search Report.

PCT/US2023/076695, Oct. 12, 2023, International Search Report and Written Opinion.

PCT/US2022/079238, May 16, 2024, International Preliminary Report on Patentability.

PCT/US2024/025340, Jun. 25, 2024, Invitation to Pay Additional Fees.

PCT/US2024/025340, Aug. 21, 2024, International Search Report and Written Opinion.

PCT/US2024/025492, Jun. 25, 2024, Invitation to Pay Additional Fees.

PCT/US2024/025492, Aug. 23, 2024, International Search Report and Written Opinion.

\* cited by examiner

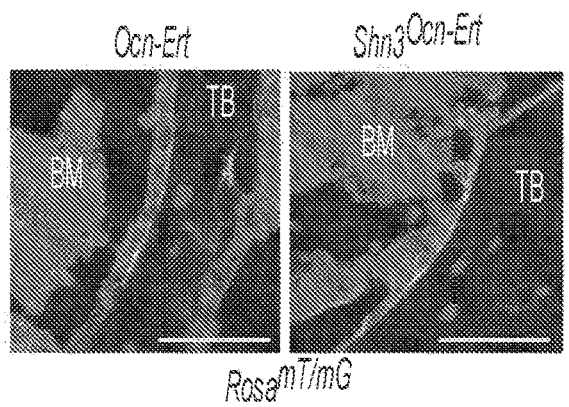
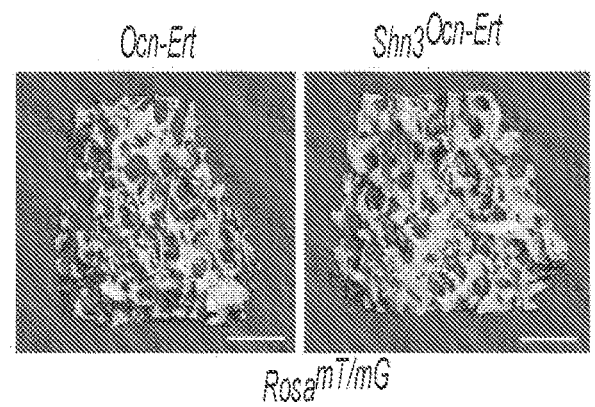
FIG. 23E
FIG. 23F
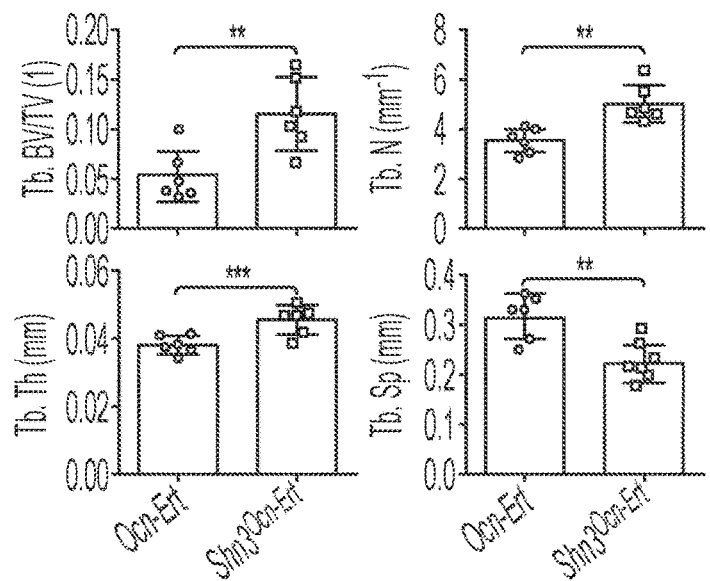
FIG. 23G
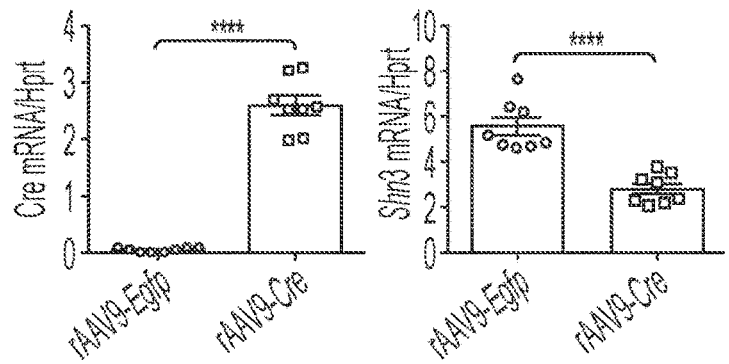
FIG. 23H

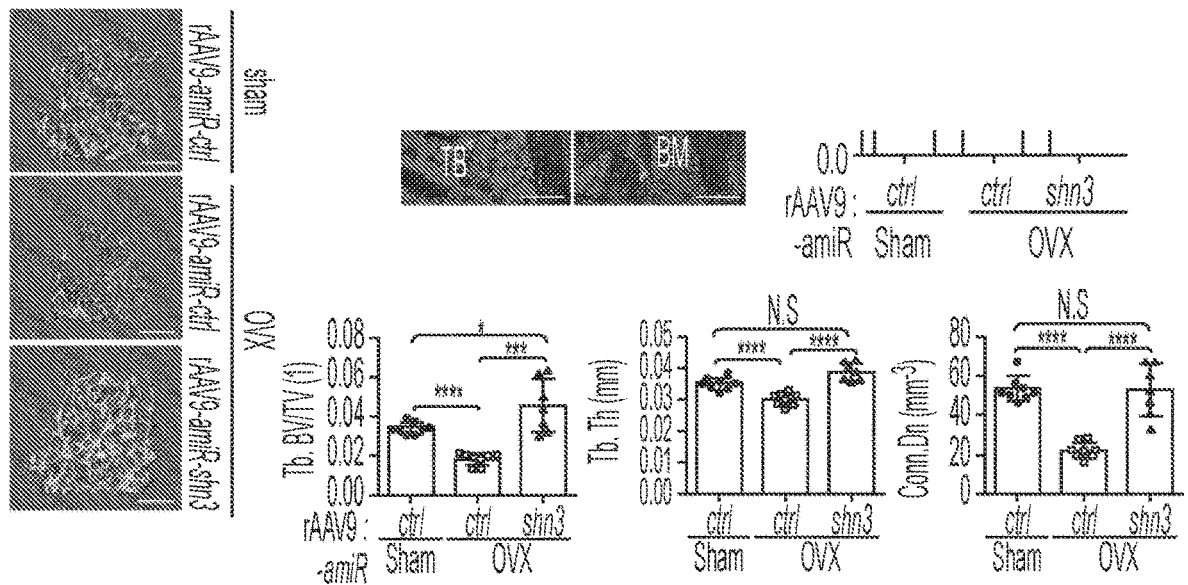
FIG. 25F
FIG. 25G
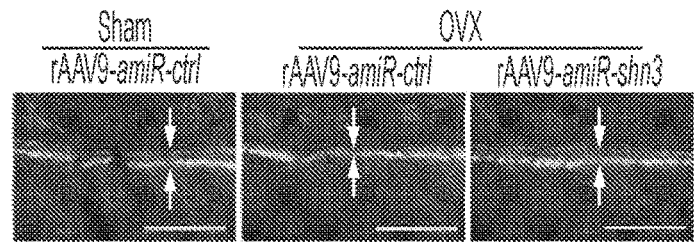
FIG. 25H
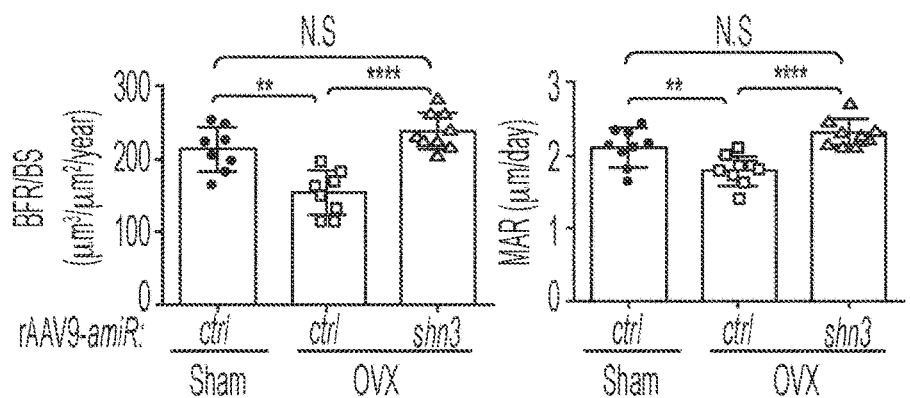
FIG. 25I

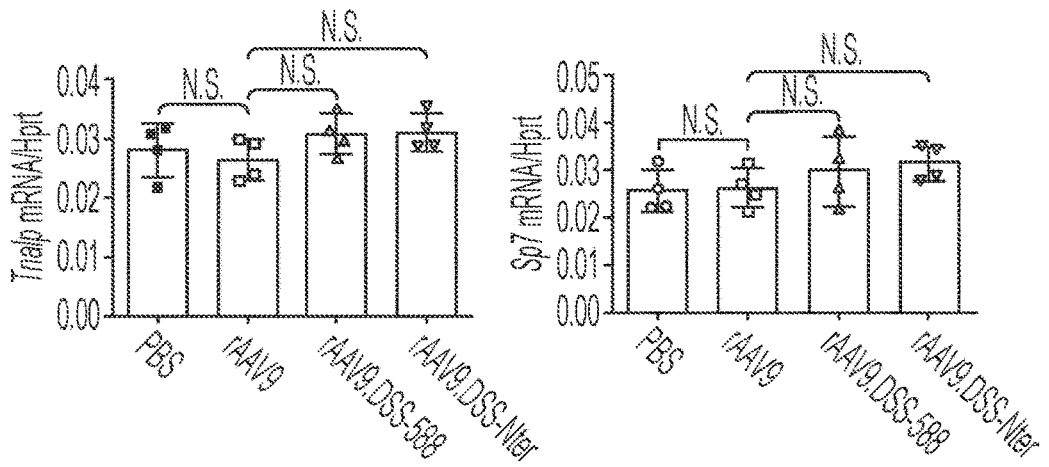
FIG. 35C
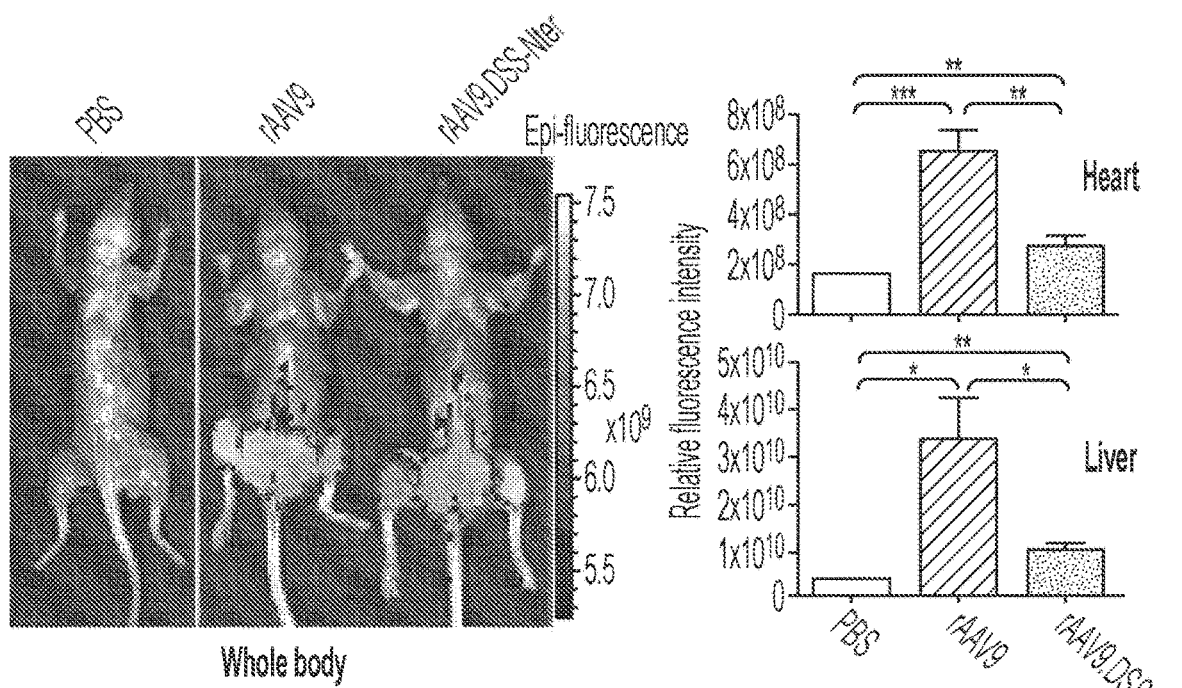
FIG. 36A
FIG. 36B

SEQUENCE LISTING

<160> NUMBER OF SEQ ID NOS: 70

<210> SEQ ID NO 1
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 1 tttgtcttttt atttcaggtc ccagatctag ggctctgcgt ttgctccagg tagtccgctg    60
ctcccttggg cctgggccca ctgacagccc tggtgcctct ggccggctgc acacctcctg   120

| | |
|---|---|
| gcgggcagct gtgtacaaac tacttgagag caggtgttct ggcaatacct gcctgctctg | 180 |
| taatagtttg tacacggagg cctgccctga ctgcccacgg tgccgtggcc aaagaggatc | 240 |
| taagggcacc gctgagggcc tacctaacca tcgtggggaa taaggacagt gtcacccctg | 300 |
| cagggatcc ggtggtggtg caaatca | 327 |

<210> SEQ ID NO 2
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| tttgtcttt atttcaggtc ccagatctag ggctctgcgt ttgctccagg tagtccgctg | 60 |
| ctcccttggg cctgggccca ctgacagccc tggtgcctct ggccggctgc acacctcctg | 120 |
| gcgggcagct gtgactacag gtactcacaa gctctgttct ggcaatacct ggagcttgtc | 180 |
| tgcacctgta gtcacggagg cctgccctga ctgcccacgg tgccgtggcc aaagaggatc | 240 |
| taagggcacc gctgagggcc tacctaacca tcgtggggaa taaggacagt gtcacccctg | 300 |
| cagggatcc ggtggtggtg caaatca | 327 |

<210> SEQ ID NO 3
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| gtctttatt tcaggtccca gatcttaggg ctctgcgttt gctccaggta gtccgctgct | 60 |
| cccttgggcc tgggcccact gacagccctg gtgcctctgg ccggctgcac acctcctggc | 120 |
| gggcagctgt gtttccatgg taagttcaag gctgttctgg caatacctgg ccttgaagat | 180 |
| gccatggaaa cacggaggcc tgccctgact gcccacggtg ccgtggccaa agaggatcta | 240 |
| agggcaccgc tgagggccta cctaaccatc gtggggaata aggacagtgt cacccccctg | 300 |
| cagggatcc ggtggtggtg caaat | 325 |

<210> SEQ ID NO 4
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 4

| | |
|---|---|
| tttgtcttt atttcaggtc ccagatctag ggctctgcgt ttgctccagg tagtccgctg | 60 |
| ctcccttggg cctgggccca ctgacagccc tggtgcctct ggccggctgc acacctcctg | 120 |
| gcgggcagct gtgtttcatc atagtacaca cctctgttct ggcaatacct ggaggtgtga | 180 |
| tccatgatga aacacggagg cctgccctga ctgcccacgg tgccgtggcc aaagaggatc | 240 |
| taagggcacc gctgagggcc tacctaacca tcgtggggaa taaggacagt gtcacccctg | 300 |
| cagggatcc ggtggtggtg caaatca | 327 |

<210> SEQ ID NO 5
<211> LENGTH: 285
<212> TYPE: DNA
<213> ORGANISM: Artificial Sequence

```
<220> FEATURE:
<223> OTHER INFORMATION: Synthetic Polynucleotide

<400> SEQUENCE: 5 tttgtcttttt atttcaggtc ccagatctag ggctctgcgt ttgctccagg tagtccgctg      60
ctcccttggg cctgggccca ctgacagccc tggtgcctct ggccggctgc acacctcctg     120
gcgggcagct gtgttactgt aggatcgaga gggatgttct ggcaatacct gtccctctcc     180
ttactacagt aacacggagg cctgccctga ctgcccacgg tgccgtggcc aaagaggatc     240
taagggcacc gctgagggcc tacctaacca tcgtggggaa taagg                      285

<210> SEQ ID NO 6
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 6
gtctttattt tcaggtccca gatcttaggg ctctgcgttt gctccaggta gtccgctgct      60
cccttgggcc tgggcccact gacagccctg gtgcctctgg ccggctgcac acctcctggc     120
gggcagctgt gattatcgct attgcagctt tctgttctgg caatacctgg aaagctggta     180
cagcgataat cacggaggcc tgccctgact gcccacggtg ccgtggccaa agaggatcta     240
agggcaccgc tgagggccta cctaaccatc gtggggaata aggacagtgt cacccccctg     300 cagggatcc ggtggtggtg caaat                                             325

<210> SEQ ID NO 7
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 7
gtctttattt tcaggtccca gatcttaggg ctctgcgttt gctccaggta gtccgctgct      60
cccttgggcc tgggcccact gacagccctg gtgcctctgg ccggctgcac acctcctggc     120
gggcagctgt gtcagattat cgctattgca gctgttctgg caatacctgg ctgcaattcc     180
aataatctga cacggaggcc tgccctgact gcccacggtg ccgtggccaa agaggatcta     240
agggcaccgc tgagggccta cctaaccatc gtggggaata aggacagtgt cacccccctg     300 cagggatcc ggtggtggtg caaat                                             325

<210> SEQ ID NO 8
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 8 tttgtcttttt atttcaggtc ccagatctag ggctctgcgt ttgctccagg tagtccgctg      60
ctcccttggg cctgggccca ctgacagccc tggtgcctct ggccggctgc acacctcctg     120
gcgggcagct gtgacaagta ggcagatgag gcactgttct ggcaatacct ggtgcctcaa     180
gtacctactt gtcacggagg cctgccctga ctgcccacgg tgccgtggcc aaagaggatc     240
taagggcacc gctgagggcc tacctaacca tcgtggggaa taaggacagt gtcacccctg     300
```

```
cagggatcc ggtggtggtg caaatca                                         327
```

<210> SEQ ID NO 9
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 9

```
tttgtctttt atttcaggtc ccagatctag ggctctgcgt ttgctccagg tagtccgctg    60
ctcccttggg cctgggccca ctgacagccc tggtgcctct ggccggctgc acacctcctg   120
gcgggcagct gtgtgacctc tgtggcatca ttcctgttct ggcaatacct gggaatgatc   180
gcgcagaggt cacacggagg cctgccctga ctgcccacgg tgccgtggcc aaagaggatc   240
taagggcacc gctgagggcc tacctaacca tcgtggggaa taaggacagt gtcacccctg   300
cagggatcc ggtggtggtg caaatca                                        327
```

<210> SEQ ID NO 10
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 10

```
gtcttttatt tcaggtccca gatcttaggg ctctgcgttt gctccaggta gtccgctgct    60
cccttgggcc tgggcccact gacagccctg gtgcctctgg ccggctgcac acctcctggc   120
gggcagctgt gatggtcttg ttgttctcca gctgttctgg caatacctgg ctggagatga   180
gcaagaccat cacggaggcc tgccctgact gcccacggtg ccgtggccaa agaggatcta   240
agggcaccgc tgagggccta cctaaccatc gtggggaata aggacagtgt cacccccctg   300
cagggatcc ggtggtggtg caaat                                          325
```

<210> SEQ ID NO 11
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 11

```
gtcttttatt tcaggtccca gatcttaggg ctctgcgttt gctccaggta gtccgctgct    60
cccttgggcc tgggcccact gacagccctg gtgcctctgg ccggctgcac acctcctggc   120
gggcagctgt gacgtctttg gtctcaaagg ggtgttctgg caatacctgc ccctttgtca   180
tcaaagacgt cacggaggcc tgccctgact gcccacggtg ccgtggccaa agaggatcta   240
agggcaccgc tgagggccta cctaaccatc gtggggaata aggacagtgt cacccccctg   300
cagggatcc ggtggtggtg caaat                                          325
```

<210> SEQ ID NO 12
<211> LENGTH: 411
<212> TYPE: DNA
<213> ORGANISM: Homo sapiens

<400> SEQUENCE: 12

```
ggaattgtac ccgcggccga tccaccggtg ccaccatgat acctgcaaaa gacatggcta    60
aagttatgat tgtcatgttg gcaatttgtt ttcttacaaa atcggatggg aaatctgtta   120
```

```
agaagagatc tgtgagtgaa atacagctta tgcataacct gggaaaacat ctgaactcga    180
tggagagagt agaatggctg cgtaagaagc tgcaggatgt gcacaatttt gttgcccttg    240
gagctcctct agctcccaga gatgctggtt cccagaggcc cgaaaaaag  gaagacaatg    300 tcttggttga gagccatgaa aaaagtcttg gagaggcaga caaagctgat gtgaatgtat    360
taactaaagc taaatcccag tgaagcttat cgataccgtc gactagagct c             411
```

<210> SEQ ID NO 13
<211> LENGTH: 591
<212> TYPE: DNA
<213> ORGANISM: Homo sapiens

<400> SEQUENCE: 13

```
ggaattgtac ccgcggccga tccaccggtg ccaccatgca gcggagactg gttcagcagt     60
ggagcgtcgc ggtgttcctg ctgagctacg cggtgccctc ctgcgggcgc tcggtggagg    120
gtctcagccg ccgcctcaaa agagctgtgt ctgaacatca gctcctccat gacaagggga    180
agtccatcca agatttacgg cgacgattct tccttcacca tctgatcgca gaaatccaca    240
cagctgaaat cagagctacc tcggaggtgt cccctaactc caagccctct cccaacacaa    300
agaaccaccc cgtccgattt gggtctgatg atgagggcag ataccttaact caggaaacta   360 acaaggtgga gacgtacaaa gagcagccgc tcaagacacc tgggaagaaa aagaaaggca    420
agcccgggaa acgcaaggag caggaaaaga aaaaacggcg aactcgctct gcctggttag    480
actctggagt gactgggagt gggctagaag gggaccacct gtctgacacc tccacaacgt    540
cgctggagct cgattcacgg taaagcttat cgataccgtc gactagagct c             591
```

<210> SEQ ID NO 14
<211> LENGTH: 696
<212> TYPE: DNA
<213> ORGANISM: Mus musculus

<400> SEQUENCE: 14

```
ggaattgtac ccgcggccga tccaccggtc gccaccatgg gatggagctg tattatcctg     60
tttctcgtcg ctactgccac cggagctcat tccgcttcca aaagagctct ggtcatcctg    120
gccaaaggag cagaggagat ggagacagtg attcctgtgg atgtcatgcg gcgagccggg    180
atcaaagtca ctgttgcagg cttggctggg aaggaccccg tgcagtgtag ccgtgatgta    240
atgatttgtc cagataccag tctggaagat gcaaaaacgc agggaccata cgatgtggtg    300
gttcttccag gaggaaatct gggtgcacag aatttatctg agtcgcctat ggtgaaggag    360
atcctcaagg agcaggagag caggaagggc ctcatagctg ccatctgtgc aggtcctacg    420
gctctgttgg ctcacgaagt aggttttgga tgcaaggtca acacacaccc actggctaag    480
gacaaaatga tgaatggcag tcactacagc tactcagaga gccgcgtgga aaggacggc     540 ctgatcctca ccagccgcgg gccggggacc agctttgagt ttgcactagc cattgtggag    600
gcactcgtgg ggaaagacat ggccaaccaa gtgaaggcac cgcttgttct caaagactag    660
taaaagctta tcgataccgt cgactagagc tcgctg                              696
```

<210> SEQ ID NO 15
<211> LENGTH: 696
<212> TYPE: DNA
<213> ORGANISM: Homo sapiens

<400> SEQUENCE: 15

```
ggaattgtac ccgcggccga tccaccggtc gccaccatgg gatggagctg tattatcctg    60
tttctcgtcg ctactgccac cggagctcat tccgcttcca aaagagctct ggtcatcctg   120 gctaaggag cagaggaaat ggagacggtc atccctgtag atgtcatgag gcgagctggg   180
attaaggtca ccgttgcagg cctggctgga aaagacccag tacagtgtag ccgtgatgtg   240
gtcatttgtc ctgatgccag ccttgaagat gcaaaaaaag agggaccata tgatgtggtg   300
gttctaccag gaggtaatct gggcgcacag aatttatctg agtctgctgc tgtgaaggag   360
atactgaagg agcaggaaaa ccggaagggc ctgatagccg ccatctgtgc aggtcctact   420
gctctgttgg ctcatgaaat aggttttgga agtaaagtta caacacaccc tcttgctaaa   480
gacaaaatga tgaatggagg tcattacacc tactctgaga tcgtgtgga aaaagacggc   540 ctgattctta caagccgggg gcctgggacc agcttcgagt ttgcgcttgc aattgttgaa   600
gccctgaatg gcaaggaggt ggcggctcaa gtgaaggctc cacttgttct taaagactag   660
taaaagctta tcgataccgt cgactagagc tcgctg                            696
```

```
<210> SEQ ID NO 16
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 16

Asp Ser Ser Asp Ser Ser Asp Ser Ser Asp Ser Ser Asp Ser Ser Asp
1               5                   10                  15

Ser Ser

<210> SEQ ID NO 17
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (2)..(2)
<223> OTHER INFORMATION: is a gamma-carboxylated glutamic acid
<220> FEATURE:
<221> NAME/KEY: MOD_RES
<222> LOCATION: (6)..(6)
<223> OTHER INFORMATION: is a gamma-carboxylated glutamic acid
<220> FEATURE:
<221> NAME/KEY: MOD_RES
<222> LOCATION: (9)..(9)
<223> OTHER INFORMATION: is a gamma-carboxylated glutamic acid
<220> FEATURE:
<221> NAME/KEY: MOD_RES
<222> LOCATION: (11)..(11)
<223> OTHER INFORMATION: is a gamma-carboxylated glutamic acid
<220> FEATURE:
<221> NAME/KEY: MOD_RES
<222> LOCATION: (15)..(15)
<223> OTHER INFORMATION: is a gamma-carboxylated glutamic acid
<220> FEATURE:
<221> NAME/KEY: MOD_RES
<222> LOCATION: (18)..(18)
<223> OTHER INFORMATION: is a gamma-carboxylated glutamic acid

<400> SEQUENCE: 17

Cys Glu Pro Arg Arg Glu Val Ala Glu Leu Glu Pro Arg Arg Glu Val
1               5                   10                  15

Ala Glu Leu
```

```
<210> SEQ ID NO 18
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
```

```
                    370                 375                 380
Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                    405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
                    485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                    565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735

<210> SEQ ID NO 19
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 19

Met Ala Ala Asp Gly Tyr Leu Pro Asp Trp Leu Glu Asp Thr Leu Ser
```

```
1               5                   10                  15
Glu Gly Ile Arg Gln Trp Trp Lys Leu Lys Pro Gly Pro Pro Pro
                20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
     50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Pro Val Lys Thr Ala Pro Gly Lys Lys Arg
                130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
                180                 185                 190
Ala Ala Pro Ser Gly Leu Gly Thr Asn Thr Met Ala Thr Gly Ser Gly
                195                 200                 205
Ala Pro Met Ala Asp Asn Asn Glu Gly Ala Asp Gly Val Gly Asn Ser
                210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
                290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
                370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
```

```
Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 20
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60
```

-continued

```
Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
130                 135                 140

Pro Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
        450                 455                 460

Gln Ala Gly Pro Gln Ser Met Ser Leu Gln Ala Arg Asn Trp Leu Pro
465                 470                 475                 480
```

```
Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 734
<212> TYPE: PRT
<213> ORGANISM: Artificial Sequence
<220> FEATURE:
<223> OTHER INFORMATION: Synthetic Polypeptide

<400> SEQUENCE: 21

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110
```

-continued

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Gly Ala Ala Val Glu Gly
                195                 200                 205

Gly Gln Gly Ala Asp Gly Val Gly Asn Ala Ser Gly Asp Trp His Cys
        210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
        370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
        420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys

```
                530                 535                 540
Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
                580                 585                 590

Arg Leu Thr Ala Leu Gly Ala Val Pro Gly Met Val Trp Gln Asn Arg
                595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
                690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                    725                 730

<210> SEQ ID NO 22
<211> LENGTH: 724
<212> TYPE: PRT
<213> ORGANISM: Artificial Sequence
<220> FEATURE:
<223> OTHER INFORMATION: Synthetic Polypeptide

<400> SEQUENCE: 22

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
```

-continued

```
                165                 170                 175
Gln Leu Gln Ile Pro Ala Gln Pro Ala Ser Leu Gly Ala Asp Thr
                180                 185                 190
Met Ser Ala Gly Gly Gly Pro Leu Gly Asp Asn Gln Gly Ala
                195                 200                 205
Asp Gly Val Gly Asn Ala Ser Gly Asp Trp His Cys Asp Ser Thr Trp
                210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
                260                 265                 270
Phe Asp Phe Asn Arg Phe His Ser His Trp Ser Pro Arg Asp Trp Gln
                275                 280                 285
Arg Leu Ile Asn Asn Tyr Trp Gly Phe Arg Pro Arg Ser Leu Arg Val
                290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
                355                 360                 365
Ala Thr Leu Asn Arg Asp Asn Thr Glu Asn Pro Thr Glu Arg Ser Ser
                370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
                420                 425                 430
Gln Tyr Leu Tyr Arg Phe Val Ser Thr Asn Asn Thr Gly Gly Val Gln
                435                 440                 445
Phe Asn Lys Asn Leu Ala Gly Arg Tyr Ala Asn Thr Tyr Lys Asn Trp
                450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
                500                 505                 510
Asn Asn Leu Gln Gly Ser Asn Thr Tyr Ala Leu Glu Asn Thr Met Ile
                515                 520                 525
Phe Asn Ser Gln Pro Ala Asn Pro Gly Thr Thr Ala Thr Tyr Leu Glu
                530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
                580                 585                 590
```

-continued

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 23
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 23

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
        260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
```

```
                        645                 650                 655
Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 24
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 24

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
```

```
                275                 280                 285
His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
                515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
690                 695                 700
```

```
Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 25
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 25

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335
```

```
Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
                435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 26
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 26

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
```

```
                370                 375                 380
Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 27
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 27
```

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 28
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

-continued

Gly Tyr Lys Tyr Leu Gly Pro Phe Asn Gly Leu Asp Lys Gly Glu Pro
         50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Ser Gly Leu Gly Pro Asn Thr Met Ala Ser Gly Gly Gly
                195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
450                 455                 460

Gln Ala Gly Pro Ser Ser Met Ala Asn Gln Ala Arg Asn Trp Val Pro

```
                465                 470                 475                 480
Gly Pro Cys Tyr Arg Gln Gln Arg Val Ser Thr Thr Asn Gln Asn
                    485                 490                 495

Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
                515                 520                 525

Asp Asp Asp Asp Arg Phe Phe Pro Ser Ser Gly Val Leu Ile Phe Gly
            530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                    565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                    645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 29
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
```

```
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Ala Gly Thr Gln Gln Leu Leu
    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
        515                 520                 525
```

His Lys Asp Asp Glu Glu Arg Phe Phe Pro Ser Ser Gly Val Leu Met
           530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
               565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
               595                 600                 605

Trp Gln Asn Arg Asp Val Tyr Leu Gln Gly Pro Ile Trp Ala Lys Ile
           610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
               645                 650                 655

Pro Ala Asp Pro Pro Thr Thr Phe Ser Gln Ala Lys Leu Ala Ser Phe
               660                 665                 670

Ile Thr Gln Tyr Ser Thr Gly Gln Val Ser Val Glu Ile Glu Trp Glu
675                 680                 685

Leu Gln Lys Glu Asn Ser Lys Arg Trp Asn Pro Glu Ile Gln Tyr Thr
           690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
               725                 730                 735

Asn Leu

<210> SEQ ID NO 30
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

-continued

```
Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
```

```
                    565                 570                 575

Glu Gln Tyr Gly Val Ala Asp Asn Leu Gln Gln Thr Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 31
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 31

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Glu Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Gln Ser Pro Gln Pro Asp Ser Ser Gly Ile Gly
145                 150                 155                 160

Lys Lys Gly Gln Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
        180                 185                 190
```

-continued

```
Ala Ala Pro Ser Gly Val Gly Pro Asn Thr Met Ala Ala Gly Gly Gly
        195                 200                 205
Ala Pro Met Ala Asp Asn Asn Glu Gly Ala Asp Gly Val Gly Ser Ser
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Gly Thr Ser Gly Gly Ala Thr Asn Asp Asn
                260                 265                 270
Thr Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Ser Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Thr Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Arg Thr Gln Thr Thr Gly Gly Thr Ala Asn Thr Gln Thr Leu Gly Phe
    450                 455                 460
Ser Gln Gly Gly Pro Asn Thr Met Ala Asn Gln Ala Lys Asn Trp Leu
465                 470                 475                 480
Pro Gly Pro Cys Tyr Arg Gln Gln Arg Val Ser Thr Thr Thr Gly Gln
                485                 490                 495
Asn Asn Asn Ser Asn Phe Ala Trp Thr Ala Gly Thr Lys Tyr His Leu
            500                 505                 510
Asn Gly Arg Asn Ser Leu Ala Asn Pro Gly Ile Ala Met Ala Thr His
        515                 520                 525
Lys Asp Asp Glu Glu Arg Phe Phe Pro Ser Asn Gly Ile Leu Ile Phe
530                 535                 540
Gly Lys Gln Asn Ala Ala Arg Asp Asn Ala Asp Tyr Ser Asp Val Met
545                 550                 555                 560
Leu Thr Ser Glu Glu Glu Ile Lys Thr Thr Asn Pro Val Ala Thr Glu
                565                 570                 575
Glu Tyr Gly Ile Val Ala Asp Asn Leu Gln Gln Gln Asn Thr Ala Pro
            580                 585                 590
Gln Ile Gly Thr Val Asn Ser Gln Gly Ala Leu Pro Gly Met Val Trp
        595                 600                 605
```

-continued

Gln Asn Arg Asp Val Tyr Leu Gln Gly Pro Ile Trp Ala Lys Ile Pro
610                615                620

His Thr Asp Gly Asn Phe His Pro Ser Pro Leu Met Gly Gly Phe Gly
625                630                635                640

Leu Lys His Pro Pro Pro Gln Ile Leu Ile Lys Asn Thr Pro Val Pro
            645                650                655

Ala Asp Pro Pro Thr Thr Phe Asn Gln Ser Lys Leu Asn Ser Phe Ile
            660                665                670

Thr Gln Tyr Ser Thr Gly Gln Val Ser Val Glu Ile Glu Trp Glu Leu
        675                680                685

Gln Lys Glu Asn Ser Lys Arg Trp Asn Pro Gly Ile Gln Tyr Thr Ser
690                695                700

Asn Tyr Tyr Lys Ser Thr Ser Val Asp Phe Ala Val Asn Thr Glu Gly
705                710                715                720

Val Tyr Ser Glu Pro Arg Pro Ile Gly Thr Arg Tyr Leu Thr Arg Asn
                725                730                735

Leu

<210> SEQ ID NO 32
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 32

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Gln Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile

```
            225                 230                 235                 240
        Thr Thr Ser Thr Arg Thr Trp Ala Leu Pro Thr Tyr Asn Asn His Leu
                        245                 250                 255
        Tyr Lys Gln Ile Ser Ser Gln Ser Gly Ala Ser Asn Asp Asn His Tyr
                        260                 265                 270
        Phe Gly Tyr Ser Thr Pro Trp Gly Tyr Phe Asp Phe Asn Arg Phe His
                        275                 280                 285
        Cys His Phe Ser Pro Arg Asp Trp Gln Arg Leu Ile Asn Asn Asn Trp
                        290                 295                 300
        Gly Phe Arg Pro Lys Arg Leu Asn Phe Lys Leu Phe Asn Ile Gln Val
        305                 310                 315                 320
        Lys Glu Val Thr Gln Asn Asp Gly Thr Thr Thr Ile Ala Asn Asn Leu
                        325                 330                 335
        Thr Ser Thr Val Gln Val Phe Thr Asp Ser Glu Tyr Gln Leu Pro Tyr
                        340                 345                 350
        Val Leu Gly Ser Ala His Gln Gly Cys Leu Pro Pro Phe Pro Ala Asp
                        355                 360                 365
        Val Phe Met Val Pro Gln Tyr Gly Tyr Leu Thr Leu Asn Asn Gly Ser
                        370                 375                 380
        Gln Ala Val Gly Arg Ser Ser Phe Tyr Cys Leu Glu Tyr Phe Pro Ser
        385                 390                 395                 400
        Gln Met Leu Arg Thr Gly Asn Asn Phe Thr Phe Ser Tyr Thr Phe Glu
                        405                 410                 415
        Asp Val Pro Phe His Ser Ser Tyr Ala His Ser Gln Ser Leu Asp Arg
                        420                 425                 430
        Leu Met Asn Pro Leu Ile Asp Gln Tyr Leu Tyr Tyr Leu Ser Lys Thr
                        435                 440                 445
        Asn Ala Pro Ser Gly Thr Thr Thr Met Ser Arg Leu Gln Phe Ser Gln
                        450                 455                 460
        Ala Gly Ala Ser Asp Ile Arg Asp Gln Ser Arg Asn Trp Leu Pro Gly
        465                 470                 475                 480
        Pro Cys Tyr Arg Gln Gln Arg Val Ser Lys Thr Ala Ala Asp Asn Asn
                        485                 490                 495
        Asn Ser Asp Tyr Ser Trp Thr Gly Ala Thr Lys Tyr His Leu Asn Gly
                        500                 505                 510
        Arg Asp Ser Leu Val Asn Pro Gly Pro Ala Met Ala Ser His Lys Asp
                        515                 520                 525
        Asp Glu Glu Lys Tyr Phe Pro Gln Ser Gly Val Leu Ile Phe Gly Lys
                        530                 535                 540
        Gln Asp Ser Gly Lys Thr Asn Val Asp Ile Glu Lys Val Met Ile Thr
        545                 550                 555                 560
        Asp Glu Glu Glu Ile Arg Thr Thr Asn Pro Val Ala Thr Glu Gln Tyr
                        565                 570                 575
        Gly Ser Val Ser Thr Asn Leu Gln Ser Gly Asn Thr Gln Ala Ala Thr
                        580                 585                 590
        Thr Asp Val Asn Thr Gln Gly Val Leu Pro Gly Met Val Trp Gln Asp
                        595                 600                 605
        Arg Asp Val Tyr Leu Gln Gly Pro Ile Trp Ala Lys Ile Pro His Thr
                        610                 615                 620
        Asp Gly His Phe His Pro Ser Pro Leu Met Gly Gly Phe Gly Leu Lys
        625                 630                 635                 640
        His Pro Pro Pro Gln Ile Leu Ile Lys Asn Thr Pro Val Pro Ala Asn
                        645                 650                 655
```

```
Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 33
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 33

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Gln Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
                370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Lys Thr
                435                 440                 445
Asn Ala Pro Ser Gly Thr Thr Thr Met Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ala Ala Asp Asn Asn
                485                 490                 495
Asn Ser Asp Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Tyr Phe Pro Gln Ser Gly Val Leu Ile Phe Gly Lys
                530                 535                 540
Gln Asp Ser Gly Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Ser Gly Asn Thr Gln Ala Ala Thr
                580                 585                 590
Thr Asp Val Asn Thr Gln Gly Val Leu Pro Gly Met Val Trp Gln Asp
                595                 600                 605
Arg Asp Val Tyr Leu Gln Gly Pro Ile Trp Ala Lys Ile Pro His Thr
                610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Leu Ala Ser Phe Ile Thr Gln
                660                 665                 670
Tyr Ser Thr Gly Gln Val Ser Val Glu Ile Glu Trp Glu Leu Gln Lys
                675                 680                 685
Glu Asn Ser Lys Arg Trp Asn Pro Glu Ile Gln Tyr Thr Ser Asn Tyr
                690                 695                 700
```

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 34
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 34

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Ala Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
145                 150                 155                 160

Lys Ser Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Ser Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

-continued

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Thr Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Arg Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ala Ala Asp Asn Asn
                485                 490                 495

Asn Ser Asp Tyr Ser Trp Thr Gly Ala Thr Lys Tyr His Leu Asn Gly
            500                 505                 510

Arg Asp Ser Leu Val Asn Pro Gly Thr Ala Met Ala Ser His Lys Asp
        515                 520                 525

Asp Glu Glu Lys Tyr Phe Pro Gln Ser Gly Val Leu Ile Phe Gly Lys
530                 535                 540

Gln Asp Ser Gly Lys Thr Asn Val Asp Ile Glu Arg Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Ser Gly Asn Thr Gln Ala Ala Thr
            580                 585                 590

Ser Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 35
<211> LENGTH: 21
<212> TYPE: DNA

```
<213> ORGANISM: Artificial Sequence
<220> FEATURE:
<223> OTHER INFORMATION: Synthetic Polynucleotide

<400> SEQUENCE: 35
agaggccatt cagacgagtg t                                              21

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
ctgcggaagc tgagagatgt                                                20

<210> SEQ ID NO 37
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 37
cacaatatca aggatatcga cgtga                                          25

<210> SEQ ID NO 38
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 38
acatcagttc tgttcttcgg gtaca                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 39
tacaaaccat acccagtccc tgttt                                          25

<210> SEQ ID NO 40
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 40
agtgctctaa ccacagtcca tgca                                           24

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
cagggaggca gtgactcttc                                                20
```

```
<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 42
agtgtggaaa gtgtggcgtt                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
atggcgtcct ctctgcttga                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
gaagggtggg tagtcatttg                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
gcagcacagg tcctaaatag                                               20

<210> SEQ ID NO 46
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 46
gggcaataag gtagtgaaca g                                             21

<210> SEQ ID NO 47
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 47
ctgtcccaac ccccaaag                                                 18

<210> SEQ ID NO 48
<211> LENGTH: 20
<212> TYPE: DNA
<213> ORGANISM: Artificial Sequence
<220> FEATURE:
```

```
<223> OTHER INFORMATION: Synthetic Polynucleotide

<400> SEQUENCE: 48
acgtattctt ccgggcagaa                                                   20

<210> SEQ ID NO 49
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 49
ctggtgaaaa ggacctctcg aag                                               23

<210> SEQ ID NO 50
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 50
ccagtttcac taatgacaca aacg                                              24

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 51
agcaaagacc ccaacgagaa                                                   20

<210> SEQ ID NO 52
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 52
ggcggcggtc acgaa                                                        15

<210> SEQ ID NO 53
<211> LENGTH: 22
<212> TYPE: DNA
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: modified by 6FAM
<220> FEATURE:
<221> NAME/KEY: misc_feature
<222> LOCATION: (22)..(22)
<223> OTHER INFORMATION: modified by TAMRA

<400> SEQUENCE: 53
cgcgatcaca tggtcctgct gg                                                22

<210> SEQ ID NO 54
<211> LENGTH: 327
<212> TYPE: DNA
<213> ORGANISM: Artificial Sequence
```

<220> FEATURE:
<223> OTHER INFORMATION: Synthetic Polynucleotide

<400> SEQUENCE: 54

```
tttgtctttt atttcaggtc ccagatctag ggctctgcgt ttgctccagg tagtccgctg    60
ctcccttggg cctgggccca ctgacagccc tggtgcctct ggccggctgc acacctcctg   120
gcgggcagct gtgtacaaac tacttgagag caggtgttct ggcaataacct gcctgctctg  180
taatagtttg tacacggagg cctgccctga ctgcccacgg tgccgtggcc aaagaggatc   240
taagggcacc gctgagggcc tacctaacca tcgtgggaa taaggacagt gtcacccctg    300
caggggatcc ggtggtggtg caaatca                                      327
```

<210> SEQ ID NO 55
<211> LENGTH: 269
<212> TYPE: DNA
<213> ORGANISM: Artificial Sequence
<220> FEATURE:
<223> OTHER INFORMATION: Synthetic Polynucleotide

<400> SEQUENCE: 55

```
agggctctgc gtttgctcca ggtagtccgc tgctcccttg ggcctgggcc cactgacagc    60
cctggtgcct ctggccggct gcacacctcc tggcgggcag ctgtgaatgg tccacatttc   120
agggactgtt ctggcaatac ctggtccctg atttatggac cattcacgga ggcctgccct   180
gactgcccac ggtgccgtgg ccaaagagga tctaagggca ccgctgaggg cctacctaac   240
catcgtgggg aataaggaca gtgtcaccc                                     269
```

<210> SEQ ID NO 56
<211> LENGTH: 265
<212> TYPE: DNA
<213> ORGANISM: Artificial Sequence
<220> FEATURE:
<223> OTHER INFORMATION: Synthetic Polynucleotide

<400> SEQUENCE: 56

```
agggctctgc gtttgctcca ggtagtccgc tgctcccttg ggcctgggcc cactgacagc    60
cctggtgcct ctggccggct gcacacctcc tggcgggcag ctgtgacaaa ttagctgtca   120
gcgctgttct ggcaatacct ggcgctgact gcaaatttgt cacggaggcc tgccctgact   180
gcccacggtg ccgtggccaa agaggatcta agggcaccgc tgagggccta cctaaccatc   240
gtggggaata aggacagtgt caccc                                         265
```

<210> SEQ ID NO 57
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 57

```
Asp Asp Asp Asp Asp Asp Asp Asp
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

```
Asp Asp Asp Asp Asp Asp Asp Asp Asp
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 59

Asp Asp Asp Asp Asp Asp Asp Asp Asp Asp
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 60

Asp Asp Asp Asp Asp Asp Asp Asp Asp Asp Asp
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 61

Asp Asp Asp Asp Asp Asp Asp Asp Asp Asp Asp Asp
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 62

Asp Asp Asp Asp Asp Asp Asp Asp Asp Asp Asp Asp Asp
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 63

Asp Asp Asp Asp Asp Asp Asp Asp Asp Asp Asp Asp Asp Asp
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 64
```

```
Gly Gly Gly Gly Ser
1               5

<210> SEQ ID NO 65
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(25)
<223> OTHER INFORMATION: may be absent

<400> SEQUENCE: 65

Gly Gly Gly Gly Gly Gly Gly Gly Gly Gly Gly Gly Gly Gly Gly
1               5                   10                  15

Gly Gly Gly Gly Gly Gly Gly Gly Gly
            20                  25

<210> SEQ ID NO 66
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(25)
<223> OTHER INFORMATION: may be absent

<400> SEQUENCE: 66

Gly Gly Gly Gly Gly Gly Gly Gly Gly Gly Gly Gly Gly Gly Gly
1               5                   10                  15

Gly Gly Gly Gly Gly Gly Gly Gly Gly Ser
            20                  25

<210> SEQ ID NO 67
<211> LENGTH: 50
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(50)
<223> OTHER INFORMATION: may be absent

<400> SEQUENCE: 67

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
                20                  25                  30

Gly Ser Gly Ser Gly Ser Gly Ser Gly Ser Gly Ser Gly Ser Gly Ser
        35                  40                  45

Gly Ser
    50

<210> SEQ ID NO 68
<211> LENGTH: 100
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(100)
```

<223> OTHER INFORMATION: may be absent

<400> SEQUENCE: 68

Gly Gly Ser Gly Gly Ser Gly Gly Gly Ser Gly Gly Gly Ser Gly
1               5                   10                  15

Gly Gly Ser Gly Gly Ser Gly Gly Gly Ser Gly Gly Gly Ser Gly
            20                  25                  30

Gly Gly Ser Gly Gly Ser Gly Gly Gly Ser Gly Gly Gly Ser Gly
        35                  40                  45

Gly Gly Ser Gly Gly Ser Gly Gly Gly Ser Gly Gly Gly Ser Gly
    50                  55                  60

Gly Gly Ser Gly Gly Ser Gly Gly Gly Ser Gly Gly Gly Ser Gly
65                  70                  75                  80

Gly Gly Ser Gly Gly Ser Gly Gly Gly Ser Gly Gly Gly Ser Gly
                85                  90                  95

Gly Gly Ser Gly
            100

<210> SEQ ID NO 69
<211> LENGTH: 12322
<212> TYPE: DNA
<213> ORGANISM: Homo sapiens

<400> SEQUENCE: 69

```
ctcacaacca gccgactctc ccattatcca gctgcctagt ttggtgcttc aatgtacatg      60
gctattccgt gtgcatatgt gtgtatacaa acacgcatgc atgcctggat ggacatacgt     120
atgcacaggt tattttttaa ggacaattct ttcaataagg tctttacccc ttacttgaaa     180
caggtgttca tgaaaaaaat gcacaaaatc ctgcctggcc ggaataattc atgaagaagg     240
ggctggatcc gtgggtcaga gaacacagga ccagtttgcc atcccaaggc cgaaggattc     300
gaggcacaaa cccagcagcc tcaacctagt tcatggagga gcctcgcggg gtcctggcca     360
agcaagcccg cccctctggt gggaagagcg gcgcctaggt ggagggtggc tgccgtagga     420
gtggacatga atgctggctt tcagagagaa cagcgtttca gttttggtca tcggaagtgg     480
tgccttcagc acagaagaag agcgtgattt ctcctccaag gccgttgatc tccaacccag     540
aactaaaggg gagaagagcc accccccagca tccagcgtgg catctcttgt gccaggacca     600
gggatgactg ggccatggac acagatgtct ccaaccttca accgtttgca tagcacacgg     660
gggactcgtg ggggccacct gccactgcca gctgaaacaa tacaatggca atactgacat     720
ccttcatgac gttttcccga cagacattca ggcagaaagt gctggtgcgt tttctgtctg     780
caaagtagag ggccatgcct caccaataga atagcgtggg ccctgatgac ctgctccgag     840
tccactcaca gccagtgaca cttgcaaaaa actcccaaag ccgtcttggg tttggctccc     900
acagctcttg accaatgtgg ccaaagctgg acacctcctt gggacactgg gattattcat     960
aaatgcagcc cgcccctgact ctccctgaat agcatctgaa gtctttgtga aggtcatgga    1020
tcctgaacaa agtgtcaagg gcaccaagaa ggctgaggga agtccccgga agcggctgac    1080
caaaggagag gccattcaga ccagtgtttc ttccagcgtc ccatacccag gcagcggcac    1140
agctgccacc aagagagcc ccgcccaaga gctcttagcc ccgcagccct tcccgggccc    1200
ctcatcagtt cttagggaag gctctcagga gaaaacgggc cagcagcaga agccccccaa    1260
aaggcccccc atcgaagcat ccgtccacat ctcacagctt ccgcagcacc ctctgacacc    1320
agcattcatg tcgcctggca aacctgagca tctcctggag gggtccacat ggcaactggt    1380
```

```
tgaccccatg agacctggac cctctggctc cttcgtggcc cctgggctcc atcctcagag    1440
ccagctcctt ccttcccacg cttccatcat tccccccgag gaccttcctg gagtccccaa    1500
agtcttcgtg cctcgtcctt cccaggtctc cttgaagccc acagaagagg cacacaagaa    1560
ggagaggaag ccccagaagc caggcaagta catctgccag tactgcagcc ggccctgtgc    1620
caagcccagc gtgctccaga agcacattcg ctcacacaca ggtgagaggc cctacccctg    1680
cggcccctgt ggcttctcct tcaagaccaa gagtaatctc tacaagcaca ggaagtccca    1740
tgcccaccgc atcaaagcag gcctggcctc aggcatgggt ggcgagatgt acccacatgg    1800
gctggagatg gagcggatcc ctggggaaga gtttgaggag cccactgagg gagaaagcac    1860
agattctgaa gaggagacta gtgccaccct ctggtcaccct gcagagctct ccccaagacc    1920
caagcagccc cttctctcca gcgggctata cagctctggg agccacagtt ccagccacga    1980
acgctgttcc ctgtcccagt ccagcacagc ccagtcactc gaagacccccc ctccatttgt    2040
ggaaccctca tctgagcacc ccctgagcca taaacctgaa gacacccaca cgattaagca    2100
gaagctggcc ctccgcttaa gcgagaggaa gaaggtgatc gatgagcagg cgtttctgag    2160
cccaggcagc aaagggagta ctgagtctgg gtatttctct cgctccgaga gtgcagagca    2220
gcaggtcagc ccccccaaaca ccaacgccaa gtcctacgct gagatcatct ttggcaagtg    2280
tgggcgaata ggacagcgga ccgccatgct gacagccacc tccacccagc cctcctgcc    2340
cctgtccacc gaagacaagc ccagcctggt gcctttgtct gtaccccgga cgcaggtgat    2400
cgagcacatc acgaagctca tcaccatcaa cgaggccgtg gtggacacca gcgagatcga    2460
cagcgtgaag ccaaggcgga gctcactgtc caggcgcagc agcatggagt cccccaaaatc    2520
cagcctctac cgggagcccc tgtcatccca cagtgagaaa accaagcctg aacaatcact    2580
gctgagcctc cagcacccgc ccagtaccgc ccccctgtg cctctcctga aagccactc    2640
aatgccttct gccgcctgca ctatcagcac ccccaccac cccttccgag gtagctactc    2700
cttcgatgac catatcaccg actccgaagc cctgagccac agcagtcacg tgtttacctc    2760
ccacccccgg atgctgaagc gccagccggc aatcgaatta cctttgggag gggaatacag    2820
ttctgaggag cctggcccaa gcagcaaaga cacagcctcc aagccctcgg acgaagtgga    2880
acccaaggaa agcgagctta ccaaaaagac caagaagggt ttgaaaacaa aagggggtgat    2940
ctacgaatgt aacatatgtg gtgctcggta caagaaaagg gataactacg aagcccacaa    3000
aaaatactac tgctcagagc ttcagatcgc aaagcccatc tctgcaggca cccacacatc    3060
tccagaagct gaaaagagtc agattgagca tgagccgtgg tcccaaatga tgcattacaa    3120
actgggaacc acccctggaac tcactccact gaggaagagg aggaaagaga gagccttgg    3180
ggacgaggaa gagccacctg cctttgagtc cacaaaaagt cagtttggca gccccgggcc    3240
atctgatgct gctcggaacc ttcccctgga gtccaccaag tcaccagcag aaccaagtaa    3300
atcagtgccc tccttggagg gacccacggg cttccagcca aggactccca agccagggtc    3360
cggttcagaa tcagggaagg agaggagaac aacgtccaaa gaaatttctg tcatccagca    3420
caccagctcc tttgagaaat ctgattctct cgagcagccg agtggcttgg aaggggaaga    3480
caaacctctg gccagttcc catcacccccc acctgcccca cacggacgct ctgctcactc    3540
cctgcagcct aagttggtcc gccagcccaa cattcaggtt cctgagatcc tagtaactga    3600
ggagcctgac cggccggaca cagagccaga gccgcccccct aaggaacctg agaagactga    3660
ggagttccaa tggcccccagc gcagccagac acttgcccag ctcccagctg agaagctgcc    3720
acccaaaaag aagaggttgc gcctggcaga gatggcccaa tcatcagggg agtccagctt    3780
```

```
cgagtcctct gtgcctctgt ctcgcagccc gagccaggaa agcaatgtct ctttgagtgg   3840
gtccagccgc tcagcctcgt ttgagaggga tgaccatggg aaagccgagg cccccagtcc   3900
ctcatctgac atgcgcccca aacccctggg cacccacatg ttgactgtcc ccagccacca   3960
cccacatgcc cgagagatgc ggaggtcagc ctcagagcag agcccaacg tttcccattc    4020 tgcccacatg accgagacac gcagcaaatc ctttgactat ggcagcttgt ccttgacagg   4080
cccttctgct ccagccccag tggctccacc agcgcgggtg gccccgccag agaagaaa    4140 atgcttcttg gtgagacagg cctctctgag caggcctcca gaatctgagt tggaggttgc   4200
ccccaaggga agacaggaga gcgaagaacc acagccctca tccagtaaac cctctgccaa   4260
aagctcattg tcccagattt cctctgcggc cacctcacat ggtggacccc cgggaggcaa   4320
gggcccaggg caggacaggc cccattggg gcccactgtg ccctacacag aagcactgca    4380
agtgttccac caccccgttg cccagacacc cctgcatgag aagccatacc tgcccccacc   4440
agtctccctt ttctccttcc agcatctcgt gcagcatgag ccaggacagt ctccagaatt   4500
cttctccacc caggccatgt ccagcctcct gtcctcacca tactccatgc cccacttcc    4560 tccctcctta tttcaagccc caccgcttcc tctccagcct actgttctgc acccaggcca   4620
actccatctc ccccagctca tgcctcaccc agccaacatc cccttcaggc agcccccttc   4680
cttcctcccc atgccatacc cgacctcctc agcactgtct tctgggtttt tcctgcctct   4740
gcaatcccag tttgcacttc agctccctgg tgatgtggaa agccatctgc cccagatcaa   4800
aaccagcctg gccccactgg caacaggaag tgctggcctc tcccccagca cagagtacag   4860
cagtgacatc cggctacccc ctgtggctcc cccagccagc cctcagcac ctacatcagc     4920 tcctccactg gccctgcctg cctgtccaga ccatggtg tccctggttg tgcctgtccg      4980
tgttcagacc aatatgccgt cctatgggag cgcaatgtac accacccttt cccagatctt   5040
ggtcacccag tcccaaggca gctcagcaac tgtggcactt cccaagtttg aggaaccccc   5100
atcaaagggg acgactgtat gtggtcagaa tgtgcatgag gttgggcccg gcccttctgg   5160
gttaagtgaa gagcaaagca gagctttccc aactccatac ctgagagtgc ctgtgacatt   5220
acctgaaaga aaaggcactt ccctgtcatc agagagtatc ttgagcctgg aggggagttc   5280
atcaacagca gggggaagca aacgtgtcct ttcaccagct ggcagccttg aacttaccat   5340
ggaaacccag cagcaaaaaa gagtgaagga ggaggaggct tccaaggcag atgaaaaact   5400
tgagctggta aaaccatgca gtgtggtcct accagcaccg aggatgggaa gaggccagag   5460
aaatcccact taggcaacca gggccaaggc aggagggagc tagaaatgct gtccagcctg   5520
tcctcagatc catctgacac aaaggaaatt cctcccctcc ctcaccctgc attgtcccat   5580
gggacagccc caggctcaga agctttgaag gaatatcccc agccatctgg caaacctcac   5640
cgaagagggt tgacccccact gagcgtgaag aaagaagatt ccaaggaaca acctgatctc   5700
ccctccttgg cacctccgag ctctctgcct cgtcagaaa cgtcctccag accagccaag    5760
tcacaagaag gtacggactc aaagaaggta ctgcagttcc ccagcctcca cacaaccact   5820
aatgtcagtt ggtgctattt aaactacatt aagccaaatc acatccagca tgcagatagg   5880
aggtcctctg tttacgctgg ttggtgcata agtttgtaca accccaacct tccgggggtt   5940
tccactaaag ctgctttgtc cctcctgagg tctaagcaga aagtgagcaa agagacatac   6000
accatggcca cagctccgca tcctgaggca ggaaggcttg tgccatccag ctcccgcaag   6060
ccccgcatga cagaggttca cctcccttca ctggtttccc cggaaggcca gaaagatcta   6120
```

```
gctagagtgg agaaggaaga agagaggaga ggggagccgg aggaggatgc tcctgcctcc    6180
cagagagggg agccggcgag gatcaaaatc ttcgaaggag ggtacaaatc aaacgaagag    6240
tatgtatatg tgcgaggccg cggccgaggg aaatatgttt gtgaggagtg tggaattcgc    6300
tgcaagaagc ccagcatgct gaagaaacac atccgcaccc acactgacgt ccggccctat    6360
gtgtgcaagc actgtcactt tgcttttaaa accaagggga atctgactaa gcacatgaag    6420
tcgaaggccc acagcaaaaa gtgccaagag acaggggtgc tggaggagct ggaagccgaa    6480
gaaggaacca gtgacgacct gttccaggac tcggaaggac gagagggttc agaggctgtg    6540
gaggagcacc agttttcgga cctggaggac tcggactcag actcagacct ggacgaagac    6600
gaggatgagg atgaggagga gagccaggat gagctgtcca gaccatcctc agaggcgccc    6660
ccgcctggcc caccacatgc actgcgggca gactcctcac ccatcctggg ccctcagccc    6720
ccagatgccc ccgcctctgg cacgaggct acacgaggca gctcggtctc ggaagctgag    6780
cgcctgacag ccagcagctg ctccatgtcc agcagagca tgccgggcct ccctggctg    6840
ggaccggccc ctctgggctc tgtggagaaa gacacaggct cagccttgag ctacaagcct    6900
gtgtccccaa gaagaccgtg gtccccaagc aaagaagcag gcagccgtcc accactagcc    6960
cgcaaacact cgctaaccaa aaacgactca tctccccagc gatgctcccc ggcccgagaa    7020
ccacaggcct cagccccaag cccacctggc ctgcacgtgg acccaggaag gggcatgggc    7080
gctctcccctt gtgggtctcc aagacttcag ctgtctcctc tcaccctctg cccctggga    7140
agagaactgg cccctcgagc acatgtgctc tccaaactcg agggtaccac cgacccaggc    7200
ctccccagat actcgcccac caggagatgg tctccaggtc aggccgagtc accaccacgg    7260
tcagcgccgc cagggaagtg ggccttggct gggccgggca gcccctcagc ggggagcat    7320
ggcccaggct tggggctgga cccacgggtt tcttcccgc ccgcgcctct acctcacaag    7380
ctcctcagca gaagcccaga gacctgcgcc tccccgtgga aggccgagtc ccgaagtccc    7440
tcctgctcac ccgcccctgc tcatcctctc tcctcccgac ccttctccgc cctccatgac    7500
ttccacggcc acatcctggc ccggacagag gagaacatct tcagccacct gcctctgcac    7560
tcccagcact tgaccgtgc cccatgtccc ttgattccca tcggtgggat ccagatggtg    7620
caggcccggc caggagccca cccacccctg ctgccagggc ccaccgcagc ctgggtcagt    7680
ggcttctccg ggggtggcag cgacctgaca ggggcccggg aggcccagga gcgaggccgc    7740
tggagtccca ctgagagctc gtcagcctcc gtgtcgcctg tggctaaggt ctccaaattc    7800
acactctcct cagagctgga gggcggggac taccccaagg agagggagag gaccggcgga    7860
ggcccgggca ggcctcctga ctggacaccc catgggaccg gggcacctgc agagcccaca    7920
cccacgcaca gccctgcac cccacccgac accttgcccc ggccgcccca gggacgccgg    7980
gcagcgcagt cctggagccc ccgcttgggt ccccgcgtgc accgaccaac cccgagcctt    8040
ctgccacccc gccgctggac cgcagcagct ctgtgggctg cctggcagag gcctctgccc    8100
gcttccagc ccggacgagg aacctctccg gggaacccag gaccaggcag gactccccca    8160
agccctcagg aagtggggag cccagggcac atccacatca gcctgaggac agggttcccc    8220
ccaacgctta gcctctctcc aactgcttca gcatctggct tccagtgtcc agcaacagac    8280
gtttccagcc actttcctcg aatcatccca cttcctcagc cccatctgtc cctccgtcca    8340
ggagctctca cggccccatc tgttgtacct tccatgtat gcagttacct gtgccttttt    8400
ctacaccttt tgttgcttaa aaagaaacaa aacaaatcac atacatacat ttaaaaaaaa    8460
aacaacaacc cacgaggagt ctgaggctgt gaatagttta tggttttggg gaaaggctga    8520
```

```
tggtgaagcc tcctgaccct ccccgctgtg gttggcagcc acccacccca gaggctggca    8580
gagggaaagg ggtacactga gggagaaagg aaaaggaaac ttcaaacaat atagaattaa    8640
atgtaaaagg aagcactcct gtgtacagat gcgatcaagg ttcctgttta ttgccacttc    8700
acccccctgc ccagctcgta gccacccctc tctgccagca gaaaggccag tgtccccagg    8760
cagaggggca caaacacagg caggtgaccc ccacccaggc cccagcaggc aggcccagaa    8820
aaactaatct tttccttttt ttttttttt ttttttttg caagaaaata aaatgatact    8880
tttcctagga tttcaacaca aaataatagg tgcaggtaga aggaggaggg ctggctcccc    8940
aagggctcct ggatactctg gtagtctgag tcatgggccc atcctggcac tccacaggtg    9000
ggcaggccac cccacccacg cacccccact ccagacacct cccttctgca ccccaccctg    9060 gcccctggg ctggggaagg agccctgact gtccgtccct ggctcccaag cccctgaccg    9120
aggcctcact ctcctgttgc ctcctctgtt ctaaaaccac caaaccaccc acaaaggcag    9180
aagtggcagg gcccgagccc tagcggccgt tcctgagact gggttttggg ttttgtttca    9240
tcttggtccc tggggtacaa gggagcctgt tcccctcatg gctgggtttt tccagttctc    9300
cacagcagag gtttgcgggg aactgtttca ggaccacttt gccacaggac cgtttccccc    9360
cgtccctgcc cctgtctcca ctaccccaag gaaatacca caactgtggc tggtggatac    9420
ggcctggacc tgtttgctgt cttacacctc ttttttaaaa agagagagga tggtgtttga    9480
tacttcaccc agccaccaca gattcttttg acctagagga ttttgaatt gtcctaactc    9540 gttggaattc tccaaagcaa tcagtgtgag ccagtgcctc ttccttaccc acatctctac    9600
tttcaagaag ctgccctgca tttcctgggg caaaactcta ctttgtaaga aaataatag    9660 gaccagaaat ttaaatccca aattgaacta tggaacttga actctagcgt gttcgcccca    9720
actgggagag gtgagctttt tcccagtgtt tcagaactga ttttctttac tttctacaag    9780
ggagggcagc acagggacta cggttgaggc ccgtgaaggc tgggtttgat gccaccctat    9840
acagagcagg gacctctctg gctaatcccc agtcctcagc caggctgtgt gaatcaagtg    9900
cctgccccag ggctcttgag ctattgaagc tgcttgggta caggacacag taggtgggga    9960
gggttaagac ccttctgtga gttccctgtg cggggctgta cttgcctctt ccaattcgtg    10020
gcctttccct gcttggtccc tactagacag acaaaccagc cacagtccag cctgcagcca    10080
gaccaccttg ttcactcatt ctcctttgcc tcagagctaa gacaaaaatg agacagaagg    10140
cagggctccc tgggagtcca ctgtgctcca gggttctggg gaatcagggt tagccagcag    10200
ctcctggctg cttccctcag agactagggc tctcatcctc cccaagagaa gcagcaagcc    10260
cagcctggac cacactgtcc atattgctgg acagtggcct gacagaaagt gactcctcca    10320
agtcccagga ggccagggct tttctcatcc ttgcctttca gccctaaccc atgggactgc    10380
ccacggattg gagacttcaa gggctgaggt ctgggagctg cataaagggc attgcttcag    10440
cccaggttag aaatctgcct gggcaagctc ttcctgcccc agacctacaa agcagcagac    10500
cgggggctct ggtggactag cccctgacat tggtggggg ccccacacca ctccacccca    10560
ccctgccttc cagctctcct gggcattttt ctccctgtac tcaaacagcc tacccaccca    10620
aggtttcctc cctgggcagc ctagcaatga acagtgcagc cggcagggca gaggcccggc    10680
agtcaccggg cccgtcaggc tcaggcagag aagccacagg ggccaggagt cactggagac    10740
tatttctaaa tgatggggt aaatgcacaa atagaatctc accaaagggc tgcctccaca    10800
ttgatgccgt gcccagaggg acagaaccaa tgccaccagc ctgggtatat gtcactgggc    10860
```

```
acagctctaa ccccctcctc cggactctag tcccgctcct ctgcgcacag agcccccagc   10920
ccacaggtac accttcatga tttggagaaa gacgctcgcc ccatgcacgc cctcctctgg   10980
gccttctgcc ctgctcccag tcacttccaa gcttcctgtt tgcctgtgat gttattgtgc   11040
ctgttgaggg aagcagcaga ggaggcagtg gctgacttgg cacagatgcc tgctacgtgc   11100
tctgttgaaa tgcgcggggt ggccattcct cggtacagac tagtcctggt ccttgggtgt   11160
gggcagtggg ggaggaacca actggtcgag gtttcagagc caaaccttgc ctttggttgg   11220
tgagtccttg ccccccaggc ctgcgctcca cgatgccttt cacccttggc aatctcaggg   11280
ccatcctggg tagtaacccc actcctctct gctcccgccc gcacctgtgg ctctcactct   11340
gggctcaacc cctgcaaccc tccaggagcc cgacagcagc cagctgcctg cactgtcgcc   11400
tccgtaagct ccaacttcca gacccagaag tccctctgct tccctctgtt ggaaaaagcc   11460
taaaagaatt agcttccaga ttcctctagc ccctgctcca ttcccaccca gtccttctga   11520
agaggaatga gcaatacatc tgagctggat ttctctctag tcctttctcc agacaaatcc   11580
ttcttaaagc aaaagtcctg gctgagcacc tgtccttggg gaccgatctg ccgtgtgacc   11640
aggggaagaa agttcccgaa agcctgttcc accaattctg cttctgtgtt gtgaatccag   11700 tctgcttttcc attagaaaac cgcttcggca cttatggtca ctttaataaa tctagtatgt   11760
aaaaaaagaa agaaagaaaa gaaacagaaa aagaaacgt gcaggcaaat gtaaaataca   11820
atgctctctg taagataaat atttgccttt ttttctaaaa ggtgtacgta ttctgtatgt   11880
gaaattgtct gtagaaagtt tctatgttct aaatggcaa tacattccaa aaattgtact   11940
gtagatatgt acagcaaccg cactgggatg gggtagtttt gcctgtaatt ttatttaaac   12000
tccagtttcc acacttgctc ttgcaatgtt ggtatggtat atatcagtgc aaaagaaaaa   12060
acaaaacaga aacaaacaaa aaaaaaaaac aaaaatccac gcaggtctaa agcacagagt   12120
ctgacgtaca aaaggaaaaa tgctcagtat tgatgtgtgt gacctttgtt gtaaattaca   12180
tctgtactgt gaatgagaag ttttttacaag tataataatt gcctttatta cagctctggc   12240
tgagtgttca gcctgaggat atttttaaa aaaaaaagaa ttagcatgtt ggaataaatt   12300
tgaaaatccc aacataaaaa aa                                            12322
```

<210> SEQ ID NO 70
<211> LENGTH: 2405
<212> TYPE: PRT
<213> ORGANISM: Homo sapiens

<400> SEQUENCE: 70

Met Asp Pro Glu Gln Ser Val Lys Gly Thr Lys Lys Ala Glu Gly Ser
1               5                   10                  15

Pro Arg Lys Arg Leu Thr Lys Gly Glu Ala Ile Gln Thr Ser Val Ser
            20                  25                  30

Ser Ser Val Pro Tyr Pro Gly Ser Gly Thr Ala Ala Thr Gln Glu Ser
        35                  40                  45

Pro Ala Gln Glu Leu Leu Ala Pro Gln Pro Phe Pro Gly Pro Ser Ser
    50                  55                  60

Val Leu Arg Glu Gly Ser Gln Glu Lys Thr Gly Gln Gln Lys Pro
65                  70                  75                  80

Pro Lys Arg Pro Pro Ile Glu Ala Ser Val His Ile Ser Gln Leu Pro
                85                  90                  95

Gln His Pro Leu Thr Pro Ala Phe Met Ser Pro Gly Lys Pro Glu His
            100                 105                 110

```
Leu Leu Glu Gly Ser Thr Trp Gln Leu Val Asp Pro Met Arg Pro Gly
            115                 120                 125

Pro Ser Gly Ser Phe Val Ala Pro Gly Leu His Pro Gln Ser Gln Leu
        130                 135                 140

Leu Pro Ser His Ala Ser Ile Ile Pro Pro Glu Asp Leu Pro Gly Val
145                 150                 155                 160

Pro Lys Val Phe Val Pro Arg Pro Ser Gln Val Ser Leu Lys Pro Thr
                165                 170                 175

Glu Glu Ala His Lys Lys Glu Arg Lys Pro Gln Lys Pro Gly Lys Tyr
            180                 185                 190

Ile Cys Gln Tyr Cys Ser Arg Pro Cys Ala Lys Pro Ser Val Leu Gln
        195                 200                 205

Lys His Ile Arg Ser His Thr Gly Glu Arg Pro Tyr Pro Cys Gly Pro
    210                 215                 220

Cys Gly Phe Ser Phe Lys Thr Lys Ser Asn Leu Tyr Lys His Arg Lys
225                 230                 235                 240

Ser His Ala His Arg Ile Lys Ala Gly Leu Ala Ser Gly Met Gly Gly
                245                 250                 255

Glu Met Tyr Pro His Gly Leu Glu Met Glu Arg Ile Pro Gly Glu Glu
            260                 265                 270

Phe Glu Glu Pro Thr Glu Gly Glu Ser Thr Asp Ser Glu Glu Glu Thr
        275                 280                 285

Ser Ala Thr Ser Gly His Pro Ala Glu Leu Ser Pro Arg Pro Lys Gln
    290                 295                 300

Pro Leu Leu Ser Ser Gly Leu Tyr Ser Ser Gly Ser His Ser Ser Ser
305                 310                 315                 320

His Glu Arg Cys Ser Leu Ser Gln Ser Ser Thr Ala Gln Ser Leu Glu
                325                 330                 335

Asp Pro Pro Pro Phe Val Glu Pro Ser Ser Glu His Pro Leu Ser His
            340                 345                 350

Lys Pro Glu Asp Thr His Thr Ile Lys Gln Lys Leu Ala Leu Arg Leu
        355                 360                 365

Ser Glu Arg Lys Lys Val Ile Asp Glu Gln Ala Phe Leu Ser Pro Gly
    370                 375                 380

Ser Lys Gly Ser Thr Glu Ser Gly Tyr Phe Ser Arg Ser Glu Ser Ala
385                 390                 395                 400

Glu Gln Gln Val Ser Pro Pro Asn Thr Asn Ala Lys Ser Tyr Ala Glu
                405                 410                 415

Ile Ile Phe Gly Lys Cys Gly Arg Ile Gly Gln Arg Thr Ala Met Leu
            420                 425                 430

Thr Ala Thr Ser Thr Gln Pro Leu Leu Pro Leu Ser Thr Glu Asp Lys
        435                 440                 445

Pro Ser Leu Val Pro Leu Ser Val Pro Arg Thr Gln Val Ile Glu His
    450                 455                 460

Ile Thr Lys Leu Ile Thr Ile Asn Glu Ala Val Val Asp Thr Ser Glu
465                 470                 475                 480

Ile Asp Ser Val Lys Pro Arg Arg Ser Ser Leu Ser Arg Arg Ser Ser
                485                 490                 495

Met Glu Ser Pro Lys Ser Ser Leu Tyr Arg Glu Pro Leu Ser Ser His
            500                 505                 510

Ser Glu Lys Thr Lys Pro Glu Gln Ser Leu Leu Ser Leu Gln His Pro
        515                 520                 525

Pro Ser Thr Ala Pro Pro Val Pro Leu Leu Arg Ser His Ser Met Pro
```

```
                    530                 535                 540
Ser Ala Ala Cys Thr Ile Ser Thr Pro His His Pro Phe Arg Gly Ser
545                 550                 555                 560

Tyr Ser Phe Asp Asp His Ile Thr Asp Ser Glu Ala Leu Ser His Ser
                565                 570                 575

Ser His Val Phe Thr Ser His Pro Arg Met Leu Lys Arg Gln Pro Ala
                580                 585                 590

Ile Glu Leu Pro Leu Gly Gly Glu Tyr Ser Ser Glu Glu Pro Gly Pro
                595                 600                 605

Ser Ser Lys Asp Thr Ala Ser Lys Pro Ser Asp Glu Val Glu Pro Lys
                610                 615                 620

Glu Ser Glu Leu Thr Lys Lys Thr Lys Lys Gly Leu Lys Thr Lys Gly
625                 630                 635                 640

Val Ile Tyr Glu Cys Asn Ile Cys Gly Ala Arg Tyr Lys Lys Arg Asp
                645                 650                 655

Asn Tyr Glu Ala His Lys Lys Tyr Tyr Cys Ser Glu Leu Gln Ile Ala
                660                 665                 670

Lys Pro Ile Ser Ala Gly Thr His Thr Ser Pro Glu Ala Glu Lys Ser
                675                 680                 685

Gln Ile Glu His Glu Pro Trp Ser Gln Met Met His Tyr Lys Leu Gly
                690                 695                 700

Thr Thr Leu Glu Leu Thr Pro Leu Arg Lys Arg Arg Lys Glu Lys Ser
705                 710                 715                 720

Leu Gly Asp Glu Glu Pro Pro Ala Phe Glu Ser Thr Lys Ser Gln
                    725                 730                 735

Phe Gly Ser Pro Gly Pro Ser Asp Ala Ala Arg Asn Leu Pro Leu Glu
                740                 745                 750

Ser Thr Lys Ser Pro Ala Glu Pro Ser Lys Ser Val Pro Ser Leu Glu
                755                 760                 765

Gly Pro Thr Gly Phe Gln Pro Arg Thr Pro Lys Pro Gly Ser Gly Ser
                770                 775                 780

Glu Ser Gly Lys Glu Arg Arg Thr Thr Ser Lys Glu Ile Ser Val Ile
785                 790                 795                 800

Gln His Thr Ser Ser Phe Glu Lys Ser Asp Ser Leu Glu Gln Pro Ser
                805                 810                 815

Gly Leu Glu Gly Glu Asp Lys Pro Leu Ala Gln Phe Pro Ser Pro
                820                 825                 830

Pro Ala Pro His Gly Arg Ser Ala His Ser Leu Gln Pro Lys Leu Val
                835                 840                 845

Arg Gln Pro Asn Ile Gln Val Pro Glu Ile Leu Val Thr Glu Glu Pro
850                 855                 860

Asp Arg Pro Asp Thr Glu Pro Glu Pro Pro Lys Glu Pro Glu Lys
865                 870                 875                 880

Thr Glu Glu Phe Gln Trp Pro Gln Arg Ser Gln Thr Leu Ala Gln Leu
                885                 890                 895

Pro Ala Glu Lys Leu Pro Pro Lys Lys Lys Arg Leu Arg Leu Ala Glu
                900                 905                 910

Met Ala Gln Ser Ser Gly Glu Ser Ser Phe Glu Ser Ser Val Pro Leu
                915                 920                 925

Ser Arg Ser Pro Ser Gln Glu Ser Asn Val Ser Leu Ser Gly Ser Ser
                930                 935                 940

Arg Ser Ala Ser Phe Glu Arg Asp Asp His Gly Lys Ala Glu Ala Pro
945                 950                 955                 960
```

-continued

```
Ser Pro Ser Ser Asp Met Arg Pro Lys Pro Leu Gly Thr His Met Leu
            965                 970                 975

Thr Val Pro Ser His His Pro His Ala Arg Glu Met Arg Arg Ser Ala
            980                 985                 990

Ser Glu Gln Ser Pro Asn Val Ser His Ser Ala His Met Thr Glu Thr
            995                1000                1005

Arg Ser Lys Ser Phe Asp Tyr Gly Ser Leu Ser Leu Thr Gly Pro
           1010                1015                1020

Ser Ala Pro Ala Pro Val Ala Pro Pro Ala Arg Val Ala Pro Pro
           1025                1030                1035

Glu Arg Arg Lys Cys Phe Leu Val Arg Gln Ala Ser Leu Ser Arg
           1040                1045                1050

Pro Pro Glu Ser Glu Leu Glu Val Ala Pro Lys Gly Arg Gln Glu
           1055                1060                1065

Ser Glu Glu Pro Gln Pro Ser Ser Ser Lys Pro Ser Ala Lys Ser
           1070                1075                1080

Ser Leu Ser Gln Ile Ser Ser Ala Ala Thr Ser His Gly Gly Pro
           1085                1090                1095

Pro Gly Gly Lys Gly Pro Gly Gln Asp Arg Pro Pro Leu Gly Pro
           1100                1105                1110

Thr Val Pro Tyr Thr Glu Ala Leu Gln Val Phe His His Pro Val
           1115                1120                1125

Ala Gln Thr Pro Leu His Glu Lys Pro Tyr Leu Pro Pro Pro Val
           1130                1135                1140

Ser Leu Phe Ser Phe Gln His Leu Val Gln His Glu Pro Gly Gln
           1145                1150                1155

Ser Pro Glu Phe Phe Ser Thr Gln Ala Met Ser Ser Leu Leu Ser
           1160                1165                1170

Ser Pro Tyr Ser Met Pro Pro Leu Pro Pro Ser Leu Phe Gln Ala
           1175                1180                1185

Pro Pro Leu Pro Leu Gln Pro Thr Val Leu His Pro Gly Gln Leu
           1190                1195                1200

His Leu Pro Gln Leu Met Pro His Pro Ala Asn Ile Pro Phe Arg
           1205                1210                1215

Gln Pro Pro Ser Phe Leu Pro Met Pro Tyr Pro Thr Ser Ser Ala
           1220                1225                1230

Leu Ser Ser Gly Phe Phe Leu Pro Leu Gln Ser Gln Phe Ala Leu
           1235                1240                1245

Gln Leu Pro Gly Asp Val Glu Ser His Leu Pro Gln Ile Lys Thr
           1250                1255                1260

Ser Leu Ala Pro Leu Ala Thr Gly Ser Ala Gly Leu Ser Pro Ser
           1265                1270                1275

Thr Glu Tyr Ser Ser Asp Ile Arg Leu Pro Pro Val Ala Pro Pro
           1280                1285                1290

Ala Ser Ser Ser Ala Pro Thr Ser Ala Pro Pro Leu Ala Leu Pro
           1295                1300                1305

Ala Cys Pro Asp Thr Met Val Ser Leu Val Val Pro Val Arg Val
           1310                1315                1320

Gln Thr Asn Met Pro Ser Tyr Gly Ser Ala Met Tyr Thr Thr Leu
           1325                1330                1335

Ser Gln Ile Leu Val Thr Gln Ser Gln Gly Ser Ser Ala Thr Val
           1340                1345                1350
```

```
Ala Leu Pro Lys Phe Glu Glu Pro Pro Ser Lys Gly Thr Thr Val
    1355                1360                1365

Cys Gly Ala Asp Val His Glu Val Gly Pro Gly Pro Ser Gly Leu
    1370                1375                1380

Ser Glu Glu Gln Ser Arg Ala Phe Pro Thr Pro Tyr Leu Arg Val
    1385                1390                1395

Pro Val Thr Leu Pro Glu Arg Lys Gly Thr Ser Leu Ser Ser Glu
    1400                1405                1410

Ser Ile Leu Ser Leu Glu Gly Ser Ser Thr Ala Gly Gly Ser
    1415                1420                1425

Lys Arg Val Leu Ser Pro Ala Gly Ser Leu Glu Leu Thr Met Glu
    1430                1435                1440

Thr Gln Gln Gln Lys Arg Val Lys Glu Glu Ala Ser Lys Ala
    1445                1450                1455

Asp Glu Lys Leu Glu Leu Val Lys Pro Cys Ser Val Val Leu Thr
    1460                1465                1470

Ser Thr Glu Asp Gly Lys Arg Pro Glu Lys Ser His Leu Gly Asn
    1475                1480                1485

Gln Gly Gln Gly Arg Arg Glu Leu Glu Met Leu Ser Ser Leu Ser
    1490                1495                1500

Ser Asp Pro Ser Asp Thr Lys Glu Ile Pro Pro Leu Pro His Pro
    1505                1510                1515

Ala Leu Ser His Gly Thr Ala Pro Gly Ser Glu Ala Leu Lys Glu
    1520                1525                1530

Tyr Pro Gln Pro Ser Gly Lys Pro His Arg Arg Gly Leu Thr Pro
    1535                1540                1545

Leu Ser Val Lys Lys Glu Asp Ser Lys Glu Gln Pro Asp Leu Pro
    1550                1555                1560

Ser Leu Ala Pro Pro Ser Ser Leu Pro Leu Ser Glu Thr Ser Ser
    1565                1570                1575

Arg Pro Ala Lys Ser Gln Glu Gly Thr Asp Ser Lys Lys Val Leu
    1580                1585                1590

Gln Phe Pro Ser Leu His Thr Thr Thr Asn Val Ser Trp Cys Tyr
    1595                1600                1605

Leu Asn Tyr Ile Lys Pro Asn His Ile Gln His Ala Asp Arg Arg
    1610                1615                1620

Ser Ser Val Tyr Ala Gly Trp Cys Ile Ser Leu Tyr Asn Pro Asn
    1625                1630                1635

Leu Pro Gly Val Ser Thr Lys Ala Ala Leu Ser Leu Leu Arg Ser
    1640                1645                1650

Lys Gln Lys Val Ser Lys Glu Thr Tyr Thr Met Ala Thr Ala Pro
    1655                1660                1665

His Pro Glu Ala Gly Arg Leu Val Pro Ser Ser Arg Lys Pro
    1670                1675                1680

Arg Met Thr Glu Val His Leu Pro Ser Leu Val Ser Pro Glu Gly
    1685                1690                1695

Gln Lys Asp Leu Ala Arg Val Glu Lys Glu Glu Arg Arg Gly
    1700                1705                1710

Glu Pro Glu Glu Asp Ala Pro Ala Ser Gln Arg Gly Glu Pro Ala
    1715                1720                1725

Arg Ile Lys Ile Phe Glu Gly Gly Tyr Lys Ser Asn Glu Glu Tyr
    1730                1735                1740

Val Tyr Val Arg Gly Arg Gly Arg Gly Lys Tyr Val Cys Glu Glu
```

```
            1745                1750                1755
Cys Gly Ile Arg Cys Lys Lys Pro Ser Met Leu Lys Lys His Ile
    1760                1765                1770
Arg Thr His Thr Asp Val Arg Pro Tyr Val Cys Lys His Cys His
    1775                1780                1785
Phe Ala Phe Lys Thr Lys Gly Asn Leu Thr Lys His Met Lys Ser
    1790                1795                1800
Lys Ala His Ser Lys Lys Cys Gln Glu Thr Gly Val Leu Glu Glu
    1805                1810                1815
Leu Glu Ala Glu Glu Gly Thr Ser Asp Asp Leu Phe Gln Asp Ser
    1820                1825                1830
Glu Gly Arg Glu Gly Ser Glu Ala Val Glu Glu His Gln Phe Ser
    1835                1840                1845
Asp Leu Glu Asp Ser Asp Ser Asp Ser Asp Leu Asp Glu Asp Glu
    1850                1855                1860
Asp Glu Asp Glu Glu Ser Gln Asp Glu Leu Ser Arg Pro Ser
    1865                1870                1875
Ser Glu Ala Pro Pro Pro Gly Pro Pro His Ala Leu Arg Ala Asp
    1880                1885                1890
Ser Ser Pro Ile Leu Gly Pro Gln Pro Pro Asp Ala Pro Ala Ser
    1895                1900                1905
Gly Thr Glu Ala Thr Arg Gly Ser Ser Val Ser Glu Ala Glu Arg
    1910                1915                1920
Leu Thr Ala Ser Ser Cys Ser Met Ser Ser Gln Ser Met Pro Gly
    1925                1930                1935
Leu Pro Trp Leu Gly Pro Ala Pro Leu Gly Ser Val Glu Lys Asp
    1940                1945                1950
Thr Gly Ser Ala Leu Ser Tyr Lys Pro Val Ser Pro Arg Arg Pro
    1955                1960                1965
Trp Ser Pro Ser Lys Glu Ala Gly Ser Arg Pro Pro Leu Ala Arg
    1970                1975                1980
Lys His Ser Leu Thr Lys Asn Asp Ser Ser Pro Gln Arg Cys Ser
    1985                1990                1995
Pro Ala Arg Glu Pro Gln Ala Ser Ala Pro Ser Pro Pro Gly Leu
    2000                2005                2010
His Val Asp Pro Gly Arg Gly Met Gly Ala Leu Pro Cys Gly Ser
    2015                2020                2025
Pro Arg Leu Gln Leu Ser Pro Leu Thr Leu Cys Pro Leu Gly Arg
    2030                2035                2040
Glu Leu Ala Pro Arg Ala His Val Leu Ser Lys Leu Glu Gly Thr
    2045                2050                2055
Thr Asp Pro Gly Leu Pro Arg Tyr Ser Pro Thr Arg Arg Trp Ser
    2060                2065                2070
Pro Gly Gln Ala Glu Ser Pro Pro Arg Ser Ala Pro Pro Gly Lys
    2075                2080                2085
Trp Ala Leu Ala Gly Pro Gly Ser Pro Ser Ala Gly Glu His Gly
    2090                2095                2100
Pro Gly Leu Gly Leu Asp Pro Arg Val Leu Phe Pro Pro Ala Pro
    2105                2110                2115
Leu Pro His Lys Leu Leu Ser Arg Ser Pro Glu Thr Cys Ala Ser
    2120                2125                2130
Pro Trp Lys Ala Glu Ser Arg Ser Pro Ser Cys Ser Pro Gly Pro
    2135                2140                2145
```

```
Ala His Pro Leu Ser Ser Arg Pro Phe Ser Ala Leu His Asp Phe
    2150            2155            2160

His Gly His Ile Leu Ala Arg Thr Glu Glu Asn Ile Phe Ser His
    2165            2170            2175

Leu Pro Leu His Ser Gln His Leu Thr Arg Ala Pro Cys Pro Leu
    2180            2185            2190

Ile Pro Ile Gly Gly Ile Gln Met Val Gln Ala Arg Pro Gly Ala
    2195            2200            2205

His Pro Thr Leu Leu Pro Gly Pro Thr Ala Ala Trp Val Ser Gly
    2210            2215            2220

Phe Ser Gly Gly Gly Ser Asp Leu Thr Gly Ala Arg Glu Ala Gln
    2225            2230            2235

Glu Arg Gly Arg Trp Ser Pro Thr Glu Ser Ser Ser Ala Ser Val
    2240            2245            2250

Ser Pro Val Ala Lys Val Ser Lys Phe Thr Leu Ser Ser Glu Leu
    2255            2260            2265

Glu Gly Gly Asp Tyr Pro Lys Glu Arg Glu Arg Thr Gly Gly Gly
    2270            2275            2280

Pro Gly Arg Pro Pro Asp Trp Thr Pro His Gly Thr Gly Ala Pro
    2285            2290            2295

Ala Glu Pro Thr Pro Thr His Ser Pro Cys Thr Pro Pro Asp Thr
    2300            2305            2310

Leu Pro Arg Pro Pro Gln Gly Arg Arg Ala Ala Gln Ser Trp Ser
    2315            2320            2325

Pro Arg Leu Glu Ser Pro Arg Ala Pro Thr Asn Pro Glu Pro Ser
    2330            2335            2340

Ala Thr Pro Pro Leu Asp Arg Ser Ser Ser Val Gly Cys Leu Ala
    2345            2350            2355

Glu Ala Ser Ala Arg Phe Pro Ala Arg Thr Arg Asn Leu Ser Gly
    2360            2365            2370

Glu Pro Arg Thr Arg Gln Asp Ser Pro Lys Pro Ser Gly Ser Gly
    2375            2380            2385

Glu Pro Arg Ala His Pro His Gln Pro Glu Asp Arg Val Pro Pro
    2390            2395            2400

Asn Ala
    2405
```

GENE THERAPEUTICS FOR TREATING BONE DISORDERS

RELATED APPLICATIONS

This Application is a national stage filing under 35 U.S.C. § 371 of international PCT application, PCT/US2019/023759, filed Mar. 22, 2019, which claims priority under 35 U.S.C. § 119(e) to U.S. provisional patent application Ser. No. 62/799,843, filed Feb. 1, 2019, and 62/647,595, filed Mar. 23, 2018, the entire contents of each of which are incorporated herein by reference.

BACKGROUND

Defects in bone metabolism give rise to various different bone disorders, including disorders associated with a pathological depletion or bone mass and disorders associated with a pathological increase in bone mass. Effects on bone mass may be systemic or local. For example osteoporosis is a disease characterized by loss of bone mass, and is a major source of frailty and suffering associated with aging. An estimated 10 million Americans over age 50 have osteoporosis, and osteoporosis-related fractures occur in approximately 1.5 million individuals per year, with serious health consequences. Most existing therapeutic agents for osteoporosis inhibit resorption of bone by osteoclasts (OCs) and this inhibition is accompanied by numerous side effects, including atypical fractures and osteonecrosis of the jaw. Intermittent parathyroid hormone (PTH) is an anabolic agent that promotes osteoblast (OB) function and is available for the treatment of patients with osteoporosis. However, this agent is limited in its use because of the fear of PTH-induced bone tumors. Additionally, a newly developed anabolic agent, the anti-sclerostin antibody, promotes OB differentiation through enhanced Wnt signaling. However, in the context of inflammatory arthritis, anti-sclerostin antibody has been observed to increase bone destruction in the context of TNF-dependent inflammation and elevate the risk of stroke. Similarly, a small molecule inhibitor of Cathepsin K (e.g., odanacatib) was withdrawn from FDA consideration due to an elevated incidence in stroke.

SUMMARY

Aspects of the disclosure relate to compositions and methods for modulating (e.g., increasing or decreasing) bone formation and/or metabolism. The disclosure is based, in part, on recombinant adeno-associated viruses (rAAVs) that encode one or more transgenes that modulate bone metabolism. Thus, in some embodiments, rAAVs described by the disclosure are useful for treating a disease or disorder associated with dysregulated bone metabolism (e.g., decreased bone density, increased bone density, etc.).

Accordingly, in some aspects, the disclosure provides an isolated nucleic acid encoding: a first region comprising a first adeno-associated virus (AAV) inverted terminal repeat (ITR), or a variant thereof; and, a second region comprising a transgene encoding at least one bone metabolism modulating agent.

In some embodiments, a bone metabolism modulating agent is a bone formation promoting agent. In some embodiments, a bone formation promoting agent is selected from the group consisting of a protein that promotes OB and/or osteocyte (OCY) differentiation or activity, a protein that inhibits OC differentiation or activity, and an inhibitory nucleic acid that inhibits OC differentiation or activity.

In some embodiments, a bone metabolism-modulating agent is a bone formation inhibiting agent. In some embodiments, a bone formation-inhibiting agent is selected from the group consisting of a protein that inhibits OB and/or OCY differentiation or activity, a protein that promotes OC differentiation or activity, and an inhibitory nucleic acid that inhibits OB expression or activity.

In some embodiments, a transgene encodes a bone formation promoting agent selected from the group consisting of parathyroid hormone (PTH), PTH-related protein (PTHrP), deglycase DJ1, an inhibitory nucleic acid targeting sclerostin (SOST), an inhibitory nucleic acid targeting schnurri-3 (SHN3), and an inhibitory nucleic acid targeting cathepsin K (CTSK).

In some embodiments, a transgene encodes a bone formation inhibiting agent selected from the group consisting of sclerostin (SOST), schnurri-3 (SHN3), cathepsin K (CTSK), an inhibitory nucleic acid targeting parathyroid hormone (PTH), an inhibitory nucleic acid targeting PTH-related protein (PTHrP), and an inhibitory nucleic acid targeting deglycase DJ1.

In some embodiments, a transgene encodes at least one inhibitory nucleic acid selected from the group consisting of dsRNA, siRNA, shRNA, miRNA, and artificial miRNA (amiRNA).

In some embodiments, an inhibitory nucleic acid functions as a mutant terminal repeat (mTR).

In some embodiments, a transgene comprises a sequence set forth in any one of SEQ ID NOs: 1-15. In some embodiments, a transgene targets (e.g., hybridizes with or binds to) a sequence set forth in any one of SEQ ID NOs: 1-15, or a complement thereof.

In some embodiments, an isolated nucleic acid described by the disclosure further comprises at least one promoter that is operably linked to the transgene.

In some embodiments, an isolated nucleic acid described by the disclosure further comprises a third region comprising a second AAV ITR or a variant thereof.

In some aspects, the disclosure provides a vector comprising an isolated nucleic acid as described by the disclosure. In some embodiments, a vector is a plasmid.

In some aspects, the disclosure provides a host cell comprising an isolated nucleic acid or vector as described by the disclosure. In some embodiments, a host cell is a bacterial cell, yeast cell, insect (e.g., Sf9) cell, or a mammalian cell.

The disclosure is based, in part, on rAAVs that are characterized by an increased tropism for bone cells, such as OBs, OCYs, OCs, etc. In some embodiments, rAAVs described by the disclosure comprise a heterologous bone-targeting peptide or are conjugated to a bone-targeting moiety.

Accordingly, in some aspects, the disclosure provides an isolated nucleic acid encoding a recombinant adeno-associated virus (rAAV) capsid protein comprising a heterologous bone-targeting peptide. In some embodiments, a heterologous bone-targeting peptide targets OCs (e.g., specifically, or preferentially targets OCs relative to OBs). In some embodiments, a heterologous bone-targeting peptide targets OBs (e.g., specifically, or preferentially targets OBs relative to OCs). In some embodiments, a heterologous bone-targeting peptide comprises the amino acid sequence set forth in SEQ ID NOs: 16, 17, 57, 58, 59, 60, 61, 62, and 63.

In some aspects, the disclosure provides an rAAV capsid protein comprising one or more azide-bearing unnatural amino acids. In some embodiments, a capsid protein is conjugated to one or more alendronate (Ale) moiety via one or more azide-bearing unnatural amino acids.

In some aspects, the disclosure provides a recombinant adeno-associated virus (rAAV) comprising: a capsid protein; and, an isolated nucleic acid as described by the disclosure.

In some embodiments, a capsid protein is of a serotype selected from AAV1, AAV2, AAV3, AAV4, AAV5, AAV6, AAV6.2, AAV7, AAV8, AAV9, AAV.rh8, AAV.rh10, AAV.rh39, AAV.43, AAV2/2-66, AAV2/2-84, and AAV2/2-125, or a variant of any of the foregoing SEQ ID NOs: 18-34.

In some embodiments, a capsid protein transduces OBs and/or OCYs. In some embodiments, a capsid protein (e.g., a capsid protein that transduces OBs and/or OCYs) is of a serotype selected from AAV4, AAV1, AAV6, AAV6.2, and AAV9, or a variant of any of the foregoing.

In some embodiments, a capsid protein transduces OCs. In some embodiments, a capsid protein (e.g., a capsid protein that transduces OCs) is of a serotype selected from AAV1, AAV5, AAV6, AAV6.2, AAV7, AAV8, AAV9, AAV10, AAV.rh39, and AAV.rh43, or a variant of any of the foregoing.

In some embodiments, a capsid protein comprises a heterologous bone-targeting peptides, for example heterologous bone-targeting peptide comprising the amino acid sequence set forth in SEQ ID NO: 16, 17, 57, 58, 59, 60, 61, 62, and 63. In some embodiments, a heterologous bone-targeting peptide targets OCs (e.g., specifically, or preferentially targets OCs relative to OBs). In some embodiments, a heterologous bone-targeting peptide targets OBs (e.g., specifically, or preferentially targets OBs relative to OCs).

In some embodiments, a nucleic acid sequence encoding heterologous bone-targeting peptides is inserted into a VP2 open reading frame of a capsid protein. In some embodiments, the nucleic acid sequence is inserted between codons corresponding to N587 and R588 or N-terminus of a nucleic acid sequence encoding an AAV2 capsid protein. In some embodiments, the nucleic acid sequence is inserted between codons corresponding to Q588 and A589 or N-terminus of a nucleic acid sequence encoding an AAV9 capsid protein.

In some embodiments, a capsid protein is encoded by an amino acid sequence having one or more azide-bearing unnatural amino acids. In some embodiments, a capsid protein is conjugated to one or more alendronate (Ale) moiety via one or more azide-bearing unnatural amino acids.

In some embodiments, an rAAV is a self-complementary AAV (scAAV).

In some aspects, the disclosure provides a method for delivering a transgene to bone tissue, the method comprising administering to a subject an isolated nucleic acid, composition, or rAAV as described by the disclosure.

In some aspects, the disclosure provides a method for treating a disease or disorder associated with reduced bone density, the method comprising administering to a subject having or suspected of having a disease or disorder associated with reduced bone density as described herein, wherein the transgene of the rAAV encodes a bone formation promoting agent. In some embodiments, the bone formation promoting agent is selected from the group consisting of a protein that promotes OB and/or OCY differentiation or activity, a protein that inhibits OC differentiation or activity, and an inhibitory nucleic acid that inhibits OC differentiation or activity.

In some embodiments, the bone formation promoting agent selected from the group consisting of parathyroid hormone (PTH), PTH-related protein (PTHrP), deglycase DJ1, an inhibitory nucleic acid targeting sclerostin (SOST), an inhibitory nucleic acid targeting Schnurri-3 (SHN3), and an inhibitory nucleic acid targeting cathepsin K (CTSK).

In some embodiments, a disease or disorder associated with reduced bone density is selected from the group consisting of osteoporosis, a critical sized-bone defect, a mechanical disorder resulting from disuse or injury, and secondary disorders such as breast cancer or prostate cancer metastasis, type 1 diabetes, lupus, rheumatoid arthritis, inflammatory bowel disease, hyperthyroidism, celiac disease, asthma, periodontitis, and multiple sclerosis.

In some aspects, the disclosure provides a method for treating a disease or disorder associated with increased bone density, for example a disease selected from the group consisting of osteopetrosis, osteosarcoma, and heterotropic ossification, the method comprising administering to a subject having or suspected of having a disease or disorder associated with increased bone density an rAAV as described herein, wherein the transgene of the rAAV encodes a bone formation inhibiting agent. In some embodiments, the bone formation inhibiting agent is selected from the group consisting of a protein that inhibits OB and/or OCY differentiation or activity, a protein that promotes OC differentiation or activity, and an inhibitory nucleic acid that inhibits OC differentiation or activity.

In some embodiments, the bone formation inhibiting agent selected from the group consisting of sclerostin (SOST), schnurri-3 (SHN3), cathepsin K (CTSK), an inhibitory nucleic acid targeting parathyroid hormone (PTH), an inhibitory nucleic acid targeting PTH-related protein (PTHrP), and an inhibitory nucleic acid targeting deglycase DJ1.

In some embodiments, a disease or disorder associated with reduced bone density is selected from the group consisting of osteopetrosis, pycnodysostosis, sclerosteosis, acromegaly, fluorosis, myelofibrosis, hepatitis C-associated osteosclerosis, and cancers of bone such as osteosarcoma and metastatic cancer of the bone.

In some embodiments of methods described by the disclosure, administration occurs by injection. In some embodiments, injection is systemic injection (e.g., tail vein injection), local injection (e.g., intramuscular (IM) injection, knee injection, or femoral intramedullary injection).

In some embodiments, administration occurs by implantation of a tissue or graft comprising an rAAV as described by the disclosure into a subject.

In some embodiments, administration results in transduction of a cell type selected from the group consisting of OB, OCY, OC, and chondrocyte.

BRIEF DESCRIPTION OF DRAWINGS

(FIGS. 13C and 13D) Transduced OBs were cultured under OB differentiation conditions RT-PCR and alizarin red staining were performed at 6 and 15 days of the culture. *: P, 0.05, **: P, 0.005.

FIGS. 18C-18D show transduced OBs were cultured in the presence of Rank ligand and 3 days later, OC differentiation was assessed by TRAP activity (FIG. 18C, top) and staining (FIG. 18C, bottom) and OC gene expression by RT-PCR (normalized to Hprt, FIG. 18 D). *: P, 0.05, **: P, 0.005.

FIGS. 22A and 22B show calvarial osteoblasts (COB), bone marrow-derived osteoclast precursors (BM-OCP), or chondrogenic cells (ATDC5), were treated with PBS or 14 different AAV capsids packaged with the same CB-Egfp transgene. Two days later, EGFP expression was assessed by immunoblotting with an anti-GFP antibody. The anti-Hsp90 antibody was used as a loading control. Immunoblot quantification of EGFP protein was measured as a percentage of endogenous Hsp90 protein level by Image J software. FIG. 22C shows a single dose of $1\times10^{11}$ genome copies of scAAV was intraarticularly (i.a.) injected into the knee joints of two-month-old male mice, and EGFP expression in the hindlimb was monitored by IVIS-100 optical imaging. FIG. 22D shows femurs were cryo-sectioned and EGFP expression was assessed by fluorescence microscopy. FIGS. 22E and 22F show high-magnification images of EGFP-expression osteoblasts (OB) osteocytes (OCY), and mature osteoclasts (OC). FIG. 22G Cryo-sectioned femurs were also immunostained with an anti-Bglap antibody to identify mature osteoclast. TB, trabecular bone; BM, bone marrow; GP, growth plate; CB, cortical bone. Scale bars: 500 µm (FIG. 22D); 100 µm (FIG. 22E); 75 µm (left) and 25 µm (middle, right) (FIG. 22F); and 25 µm (FIG. 22G).

FIGS. 23A-23K shows inducible deletion of Shn3 in osteoblasts increases bone accrual in adult mice. In FIGS. 23A-23D, a single dose of $4\times10^{11}$ genome copies of scAAV9-Egfp was intravenously (i.v.) injected into two-month-old male mice. FIG. 23A shows EGFP expression in individual tissues monitored by IVIS-100 optical imaging two weeks post-injection. y-axis, radiant efficiency (p/sec/cm$^2$/sr/µW/cm$^2$). FIGS. 23B and 23C shows EGFP expression in cryo-sectioned heart and liver (23B) and femur (23C, high magnification on the right). FIG. 23D is an immunoblot of tissue lysates with an anti-EGFP antibody. In FIGS. 23E-23G, two-month-old female Ocn-Ert; Rosa$^{mT/mG}$ and Shn3$^{Ocn-Ert}$; Rosa$^{mT/mG}$ mice were treated with 100 mg/kg tamoxifen for 5 consecutive days. In FIG. 23E, femurs were cross-sectioned two months later to identify EGFP-expressing osteoblasts. FIGS. 23F and 23G shows a representative 3D construction of femoral trabecular bone mass assessed by microCT (FIG. 23F) and relative quantification (FIG. 23G). Trabecular bone volume/total volume (Tb.BV/TV), trabecular thickness (Tb.Th), trabecular number per cubic millimeter (Tb.N) and trabecular space (Tb.Sp) (n=6/group). In FIGS. 23H-23K, a single dose of $4\times10^{11}$ genome copies of scAAV9-Egfp or scAAV9-Cre was i.v. injected into three-month-old male Shn3$^{fl/fl}$; Rosa$^{mTmG}$ mice. FIG. 23H shows Cre and Shn3 mRNA levels in tibial bone RNA and normalized to Hprt expression two months after treatment. FIG. 23I shows fluorescence microscopy on cryo-sectioned femurs to identify EGFP-expressing cells (FIG. 23I), and femoral trabecular bone mass was assessed by microCT. FIG. 23J shows representative 3D-reconstruction and FIG. 23K shows relative quantification. Trabecular bone volume/total volume (Tb. BV/TV), trabecular thickness (Tb.Th), trabecular number per cubic millimeter (Tb.N), and consecutive density (Conn.Dn) (n=6/group). Scale bars: 50 µm (23B); 500 µm (left), 75 µm (right) (23C); 25 µm (23E); 1 mm (23F and 23J); 250 µm (23I). Values represent mean±standard deviation: *, P<0.05; , P<0.01; and *, P<0.001 by an unpaired two-tailed Student's t-test (23G, 23H, and 23K).

FIG. 24A shows a diagram of the scAAV9 construct containing a CMV enhancer/chicken β-actin promoter (CB), amiR-ctrl or amiR-shn3, an Egfp reporter gene (EGFP), β-globin polyA sequence (PA), and inverted terminal repeat (ITR). In FIGS. 24B-24D, two weeks after intraarticular (i.a.) injection of scAAV9 encoding amiR-ctrl or amiR-shn3 into knee joints of two month-old male mice, EGFP expression was assessed by IVIS 100 optical imaging (FIG. 24B) and fluorescence microscopy of cryo-sectioned femurs (FIG. 24C). In FIG. 24D, levels of EGFP protein (top) and shn3 mRNAs are normalized to hprt (bottom) were assessed in fluoresence activated cell sorted (FACS)-sorted EGFP-expressing cells from the femur. In FIGS. 24E-24F, two months after i.a. injection of scAAV9 carrying amiR-ctrl or amiR-shn3 into knee joints of two-month-old female mice, femoral trabecular bone mass was assessed by microCT. Representative 3D-reconstruction (FIG. 24E) and relative quantification (FIG. 24F) are displayed (n=6/group). In FIGS. 24G-24K, a single dose of $4 \times 10^{11}$ genome copies of AAV9 encoding amiR-ctrl or amiR-shn3 were i.v. injected into three-month-old female mice. Two months later, shn3 mRNA levels were measured in the tibial bone RNA and normalized to hprt (FIG. 24G, n=8/group). Femoral trabecular bone mass was measured by microCT. Representative 3D-reconstruction (FIG. 24H) and relative quantification (FIG. 24I) are displayed (n=8/group). Representative calcein/alizarin red labeling (FIG. 24J) and relative histomorphometric quantification of BFR/BS, MAR, and Ob.S/BS are displayed (FIG. 24K). Arrows indicate the distance between calcein and alizarin red labeling. BFR/BS, bone formation rate/bone surface; MAR, mineral apposition rate; Ob.S/BS, osteoblast surface/bone surface. GP, growth plate; BM, bone marrow; TB, trabecular bone. Scale bars: 250 µm, (FIG. 24C); 1 mm (FIGS. 24E and 24H); 50 µm (FIG. 24J). Values represent mean±SD: , $P<0.01$; *, $P<0.001$; and ****, $P<0.0001$ by an unpaired two-tailed Student's t-test (FIGS. 24F, 24G, 24I, and 24K).

FIGS. 25A-25J show silencing of Shn3 by systemically delivered AAV9 prevents bone loss in a mouse model of postmenopausal osteoporosis. FIGS. 25A-25B show sham or OVX surgery was performed on three-month-old female Shn3$^{+/+}$ and Shn3$^{-/-}$ mice and two months later, femoral trabecular bone mass was assessed by microCT. Representative images of the femur (FIG. 25A) and relative BV/TV (FIG. 25B) are displayed (n=6/group). FIG. 25C shows a diagram of the study and treatment methods. Sham or OVX surgery was performed on three-month-old female mice and six weeks later, a single dose of $4 \times 10^{11}$ genome copies of scAAV9 carrying amiR-ctrl or amiR-shn3 was i.v. injected. Seven weeks after injection, femurs were cryo-sectioned to identify EGFP-expressing cells (FIG. 25D). shn3 mRNA levels in tibial bone are displayed after normalization to hprt (n=8~12/group) (FIG. 25E). Femoral trabecular bone mass was assessed by microCT. Representative 3D-reconstruction (FIG. 25F) and relative quantification (FIG. 25G) are displayed (n=7~8/group). Representative images of calcein/alizarin red labeling (FIG. 25H) and relative histomorphometric quantification of BFR/BS and MAR (FIG. 25I). Arrows indicate the distance between calcein and alizarin red. Femoral biomechanical properties, including bending rigidity, bending moment, apparent bending modulus, and apparent bending stress were quantified (n=5~9/group) (FIG. 25J). Scale bars: 1 mm, (25A and 25F); 250 µm, (FIG. 25D); and 50 µm, (FIG. 25H). Values represent mean±SD: N.S., not significant; *, $P<0.05$; , $P<0.01$; *, $P<0.001$; and ****, $P<0.0001$ by an unpaired two-tailed Student's t-test (FIG. 25B) and one-way ANOVA test (FIGS. 25E, 25G, 25I, and 25J).

FIG. 26A is a diagram of constructs for rationally designed bone-specific AAV capsids. The bone-targeting peptide motif (DSS, red) was inserted into the AAV9 capsid between Q588 and A589 (DSS-588) or at the N-terminus of AAV9-VP2 (DSS-Nter). cap: capsid proteins. FIGS. 26B and 26C shows that two days after infection with different concentrations of scAAV9, scAAV9.DSS-587, or scAAV9.DSS-Nter, COBs were cultured under osteogenic conditions for six days. EGFP expression was assessed by immunoblotting with an anti-EGFP antibody (FIG. 26B) or fluorescence microscopy (FIG. 26C). ALP activity was assessed by fast blue staining (FIG. 26C). FIGS. 26D-26H show a single dose of $4 \times 10^{11}$ genome copies of scAAV9 or scAAV9.DSS-Nter was i.v. injected into two-month-old male mice. EGFP expression in individual tissues was monitored by IVIS-100 optical imaging two weeks post-injection (FIG. 26D). Immunoblotting shows EGFP expression in tissue lysates (FIG. 26E) and relative quantification by the Image J software (FIG. 26F, n=3/group). Fluorescence microscopy was performed on cryo-sectioned femurs to identify EGFP-expressing cells (FIG. 26G) and the number of EGFP-expressing cells per bone surface in femurs were quantified by the Image J software (FIG. 26H, n=5/group). (FIGS. 26I-26M) show sham or OVX surgery was performed on three-month-old female mice. Six weeks later, a single dose of $4 \times 10^{11}$ genome copies of scAAV9.DSS-Nter carrying amiR-ctrl or amiR-shn3 was i.v. injected. Seven weeks after injection, shn3 mRNA levels were assessed in the tibial bone (FIG. 26I, n=10/group). Trabecular bone mass in the femur and lumbar vertebrae was assessed by microCT. Quantification (FIGS. 26J and 26M) and representative 3D-reconstruction (FIGS. 26K and 26L) are displayed (n=6~8/group). GP, growth plate; BM, bone marrow; TB, trabecular bone. Scale bars: 100 µm, (FIGS. 26C and 26G); 1 mm, (FIGS. 26K and 26L). Values represent mean±SD: N.S., not significant; *, $P<0.05$; , $P<0.01$; *, $P<0.001$; and ****, $P<0.0001$ by an unpaired two-tailed Student's t-test (FIGS. 26F and 26H) and one-way ANOVA test (FIGS. 26I, 26J, and 26M).

FIGS. 29A and 29B show a single dose of PBS or $4 \times 10^{11}$ genome copies of scAAV9-EGFP was intravenously (i.v.) injected into two-month-old male mice and EGFP expression was monitored by IVIS-100 optical imaging two weeks post-injection.

EGFP expression in whole body (FIG. 29A) and the quantification of EGFP expression in the dissected tissues shown in FIG. 28A are displayed (FIG. 29B). PBS-injection was used as a negative control. FIGS. 29C and 29D show tissues dissected from PBS- or rAAV9-EGFP-injected mice were cryo-sectioned to locate EGFP-expressing cells. Scale bars: 100 μm, FIG. 29C; 500 μm, FIG. 29D.

FIG. 31A shows a diagram of rAAV9 constructs containing the CMV enhancer/chicken β-actin promoter (CB), an EGFP reporter gene (EGFP), or Cre recombinase (Cre), β-globin polyA sequence (PA), and inverted terminal repeat (ITR). FIG. 31B shows that COBs infected with scAAV9-EGFP or scAAV9-Cre for two days and cells were lysed and immunoblotted with the indicated antibodies. FIGS. 31C-31E show two days after treatment with scAAV9-EGFP or scAAV9-Cre, COBs were cultured under osteogenic conditions for six days and mRNA levels of Shn3 (FIG. 31C) and osteogenic genes (FIG. 31D) were measured by RT-PCR. After 21 days of the culture, mineralization was assessed by alizarin red staining (FIG. 31E). Values represent mean±SD: ***, $P<0.001$ by an unpaired two-tailed Student's t-test (FIGS. 31C and 31D).

FIGS. 35A-35C show the characterization of scAAV9.DSS vectors in vitro or in vivo. (FIG. 35A) A single dose of $1 \times 10^{11}$ genome copies of scAAV9-Egfp, scAAV9.DSS-588-Egfp or rAAV9.DSS-Nter-Egfp was i.a. injected into knee joints of two-month-old male mice and femurs were cryo-sectioned to identify EGFP-expressing cells two weeks post-injection. GP, growth plate; CB, cortical bone; BM, bone marrow. Scale bar: 500 μm, FIG. 35A. FIGS. 35B and 35C show two days after infection with scAAV9-Egfp, scAAV9.DSS-588-Egfp or scAAV9.DSS-Nter-Egfp, COBs were cultured under osteogenic conditions for six days. Osteoblast differentiation was assessed by ALP activity (FIG. 35B) and osteogenic gene expression (FIG. 35C). Values represent mean±SD: N.S, non-significant by one-way ANOVA test (FIGS. 35B and 35C).

FIGS. 36A-36E show the tissue distribution of systematically delivered scAAV9.DSS-Nter in mice. A single dose of PBS or $4 \times 10^{11}$ genome copies of scAAV9, scAAV9.DSS-588, or scAAV9.DSS-Nter was i.v. injected into two-month-old male mice and EGFP expression was monitored using IVIS-100 optical imaging two weeks post-injection. EGFP expression in the whole body (FIG. 36A) and quantification of EGFP expression in dissected tissues (FIG. 36B) are displayed. Heart (FIG. 36C), liver (FIG. 36D), and lumbar vertebrae (FIG. 36E) were cryo-sectioned to identify EGFP-expressing cells. GP, growth plate; BM, bone marrow. Scale bar: 100 μm, (FIGS. 36C, 36D, and 36E). Values represent mean±SD: *, $P<0.05$; , $P<0.01$ and *, $P<0.001$ by one-way ANOVA test (FIG. 36B).

DETAILED DESCRIPTION

Figure 1:
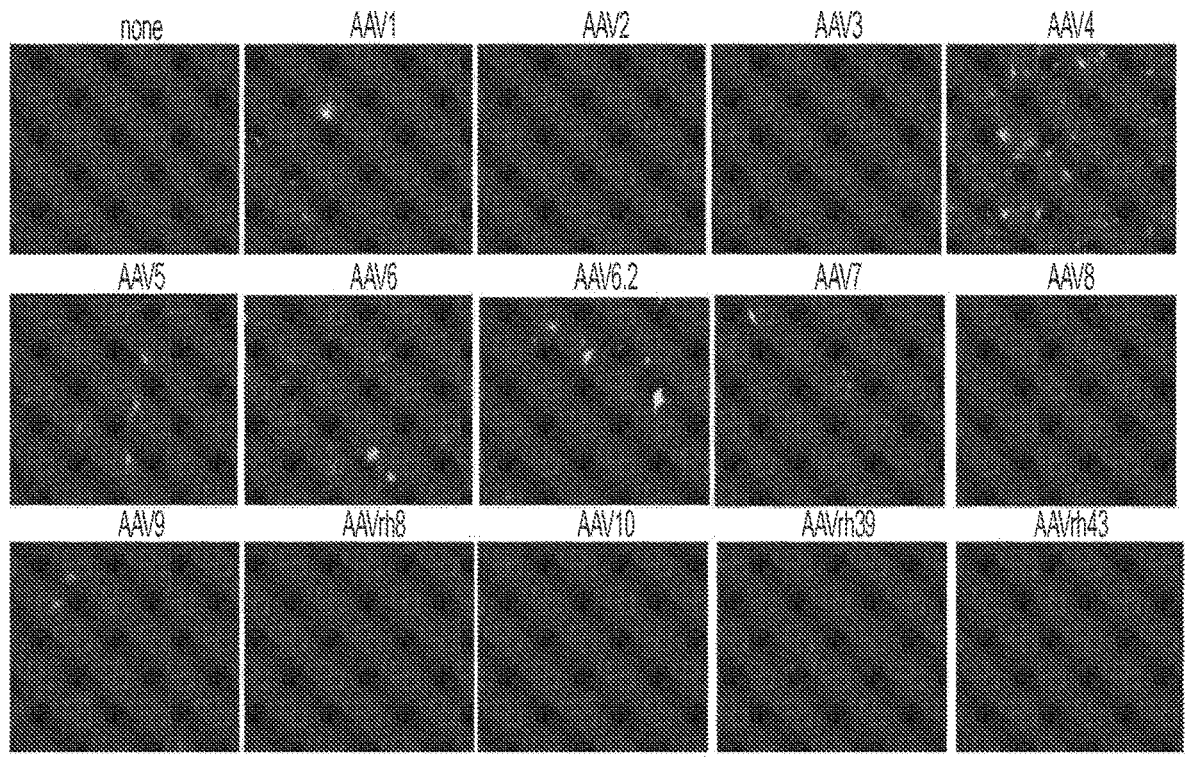
FIG. 1 shows identification of scAAV serotypes that transduce mouse primary OB precursors in vitro. Mouse OB precursors were isolated from the calvaria of neonates at postnatal day 3-5 and cultured in the growth media for amplification. Cells were incubated with 14 different scAAV serotypes encoding GFP proteins for 2 days and their transduction efficiency was analyzed by GFP expression using epifluorescence microscopy.

Aspects of the disclosure relate to compositions (e.g., isolated nucleic acids, rAAVs, etc.) that when delivered to a subject are effective for modulating bone metabolism, for example by promoting or inhibiting bone formation and/or promoting or inhibiting bone resorption. Accordingly, methods and compositions described by the disclosure are useful, in some embodiments, for the treatment of diseases and disorders associated with dysregulated bone metabolism, such as osteoporosis, inflammation-induced bone loss, bone loss induced by breast or prostate cancer metastasis, osteopetrosis, osteosarcoma, and heterotrophic ossification Isolated Nucleic Acids Compositions and methods for delivering a transgene (e.g. an inhibitory RNA, such as an shRNA, miRNA, etc.) to a subject are provided in the disclosure. The compositions typically comprise an isolated nucleic acid encoding a transgene (e.g., a protein, an inhibitory nucleic acid, etc.) capable of modulating bone metabolism. For example, in some embodiments, a transgene reduces expression of a target protein, such as a target protein associated with promoting or inhibiting bone formation.

"Bone metabolism" generally refers to a biological process involving bone formation and/or bone resorption. In some embodiments, bone metabolism involves the formation of new bone as produced by osteoblasts (OBs) and differentiated osteocytes, and/or mature bone tissue being resorbed by osteoclasts (OCs). OBs arise from the bone marrow derived mesenchymal cells that ultimately differentiate terminally into osteocytes. OB (and osteocyte) functions or activities include but are not limited to bone formation, bone mineralization, and regulation of OC activity. Decreased bone mass has been observed to result from inhibition of OB and/or osteocyte function or activity. Increased bone mass has been observed to result from increased OB and/or osteocyte function or activity. OCs arise from bone marrow-derived monocytes and in some embodiments have been observed to be controlled by signals from OBs. OC functions include bone resorption. In some embodiments, decreased bone mass has been observed to result from increased OC activity. In some embodiments, increased bone mass has been observed to result from inhibition of OC activity.

In some embodiments, an isolated nucleic acid or an rAAV as described by the disclosure comprises a transgene encoding at least one bone metabolism modulating agent (e.g., 1, 2, 3, 4, 5, 6, 7, 8, 9, 10, or more bone metabolism modulating agents). As used herein, a "bone metabolism modulating agent" refers to a molecule (a nucleic acid or protein encoded by a nucleic acid, e.g., a transgene) that either induces or inhibits bone formation or deposition, for example by increasing or decreasing expression, activity, and/or function of proteins, cells, etc., that are involved in bone formation or bone resorption. Generally, a bone metabolism modulating agent can be a peptide, protein, or an interfering nucleic acid (e.g., dsRNA, siRNA, shRNA, miRNA, artificial miRNA, etc.). In some embodiments, a bone metabolism modulating agent is a bone formation inducing agent. In some embodiments, a bone metabolism modulating agent is a bone formation inhibiting agent.

A "bone formation inducing agent" refers to a molecule that promotes bone synthesis either by promoting OB and/or osteocyte (OCY) differentiation or activity and/or by inhibiting OC activity. In some embodiments, a bone formation inducing agent is a nucleic acid (e.g., RNAi oligonucleotide or miRNA oligonucleotide or antisense oligonucleotide) or protein encoded by a nucleic acid (e.g., a transgene) that promotes OB and/or osteocyte function or activity (e.g., bone formation, mineralization, regulation of osteoclast activity or function, etc.).

In some embodiments, examples of bone formation inducing agents that promote OB and/or osteocyte activity or function include but are not limited to parathyroid hormone (PTH), PTH-related protein (PTHrP), deglycase DJ1. In some embodiments, a bone formation inducing agent is an inhibitory nucleic acid that inhibits OC differentiation or activity, such as an inhibitory nucleic acid that targets sclerostin (SOST), schnurri-3 (SHN3), cathepsin K (CTSK), etc.

A "bone formation inhibiting agent" refers to a molecule that inhibits OB and/or osteocyte differentiation or activity and/or increases OC differentiation, activity or function. In some embodiments, a bone formation inhibiting agent is a nucleic acid (e.g., RNAi oligonucleotide or miRNA oligonucleotide or antisense oligonucleotide) or protein encoded by a nucleic acid (e.g., a transgene) that inhibits OB and/or osteocyte differentiation or activity. In some embodiments, examples of bone formation inhibiting agents that inhibit OB and/or osteocyte activity or function include but are not limited to a MAPK inhibitor, and pro-inflammatory cytokines (e.g., tumor necrosis factor alpha (TNF-α), etc. In some embodiments, a bone formation inhibiting agent is an inhibitory nucleic acid that inhibits OB and/or osteocyte differentiation or activity.

In some embodiments, an isolated nucleic acid encodes one or more (e.g., 1, 2, 3, 4, 5, 6, 7, 8, 9, 10, or more) inhibitory nucleic acids, for example dsRNA, siRNA, shRNA, miRNA, artificial microRNA (ami-RNA), etc.). Generally, an inhibitory nucleic acid specifically binds to (e.g., hybridizes with) at least two (e.g., 2, 3, 4, 5, 6, 7, 8, 9, 10, 11, 12, 13, 14, 15, 16, 17, 18, 19, 20, 21, 22, 23, 24, 25, or more) continuous bases of a gene encoding a gene product (e.g., a protein) associated with bone metabolism (e.g., PTH, PTHrP, DJ1, SOST, SHN3, CTSK, etc.). As used herein "continuous bases" refers to two or more nucleotide bases that are covalently bound (e.g., by one or more phosphodiester bond, etc.) to each other (e.g. as part of a nucleic acid molecule). In some embodiments, the at least one inhibitory nucleic acid is about 50%, about 60% about 70% about 80% about 90%, about 95%, about 99% or about 100% identical to the two or more (e.g., 2, 3, 4, 5, 6, 7, 8, 9, 10, 11, 12, 13, 14, 15, 16, 17, 18, 19, 20, 21, 22, 23, 24, 25, or more) continuous nucleotide bases of a gene encoding a gene product (e.g., a protein) associated with bone metabolism (e.g., PTH, PTHrP, DJ1, SOST, SHN3, CTSK, RANK, etc.).

A "microRNA" or "miRNA" is a small non-coding RNA molecule capable of mediating transcriptional or post-translational gene silencing. Typically, miRNA is transcribed as a hairpin or stem-loop (e.g., having a self-complementarity, single-stranded backbone) duplex structure, referred to as a primary miRNA (pri-miRNA), which is enzymatically processed (e.g., by Drosha, DGCR8, Pasha, etc.) into a pre-miRNA. The length of a pri-miRNA can vary. In some embodiments, a pri-miRNA ranges from about 100 to about 5000 base pairs (e.g., about 100, about 200, about 500, about 1000, about 1200, about 1500, about 1800, or about 2000 base pairs) in length. In some embodiments, a pri-miRNA is greater than 200 base pairs in length (e.g., 2500, 5000, 7000, 9000, or more base pairs in length.

Pre-miRNA, which is also characterized by a hairpin or stem-loop duplex structure, can also vary in length. In some embodiments, pre-miRNA ranges in size from about 40 base pairs in length to about 500 base pairs in length. In some embodiments, pre-miRNA ranges in size from about 50 to 100 base pairs in length. In some embodiments, pre-miRNA ranges in size from about 50 to about 90 base pairs in length (e.g., about 50, about 52, about 54, about 56, about 58, about 60, about 62, about 64, about 66, about 68, about 70, about 72, about 74, about 76, about 78, about 80, about 82, about 84, about 86, about 88, or about 90 base pairs in length).

Generally, pre-miRNA is exported into the cytoplasm, and enzymatically processed by Dicer to first produce an imperfect miRNA/miRNA* duplex and then a single-stranded mature miRNA molecule, which is subsequently loaded into the RNA-induced silencing complex (RISC). Typically, a mature miRNA molecule ranges in size from about 19 to about 30 base pairs in length. In some embodiments, a mature miRNA molecule is about 19, about 20, about 21, about 22, about 23, about 24, about 25, about 26, about 27, about 28, about 29, or 30 base pairs in length.

In some aspects, the disclosure provides isolated nucleic acids and vectors (e.g., rAAV vectors) that encode one or more artificial miRNAs. As used herein "artificial miRNA" or "amiRNA" refers to an endogenous pri-miRNA or pre-miRNA (e.g., a miRNA backbone, which is a precursor miRNA capable of producing a functional mature miRNA), in which the miRNA and miRNA* (e.g., passenger strand of the miRNA duplex) sequences have been replaced with corresponding amiRNA/amiRNA* sequences that direct highly efficient RNA silencing of the targeted gene, for example as described by Eamens et al. (2014), *Methods Mol. Biol.* 1062:211-224. For example, in some embodiments an artificial miRNA comprises a miR-155 pri-miRNA backbone into which a sequence encoding a bone metabolism modulating (e.g., bone formation inhibiting agent) miRNA has been inserted in place of the endogenous miR-155 mature miRNA-encoding sequence. In some embodiments, miRNA (e.g., an artificial miRNA) as described by the disclosure comprises a miR-155 backbone sequence, a miR-30 backbone sequence, a mir-64 backbone sequence, or a miR-122 backbone sequence.

In some embodiments, the present disclosure provides an isolated nucleic acid comprising a transgene encoding an artificial microRNA targeting the SHN3 gene (GeneID: 59269), which encodes the Schnurri-3 protein. The Schnurri-3 (SHN3) protein is a transcription factor that regulates NK-κβ protein expression and immunoglobulin and T-cell receptor antibody recombination. In some embodiments, the SHN3 gene is represented by the NCBI Accession Number NM_001127714.2 or NM_024503.5. In some embodiments, the SHN3 protein is represented by the NCBI Accession Number NP_001121186.1 or NP_078779.2.

In some aspects, the disclosure relates to an isolated nucleic acid comprising a transgene encoding an artificial microRNA is used to reduce SHN3 expression (e.g., expression of one or more gene products from an SHN3 gene, for example an mRNA encoded by the nucleotide sequence in SEQ ID NO: 69 or the encodes a protein having the amino acid sequence set forth in SEQ ID NO: 70.

In some embodiments, an artificial microRNA targets (e.g., binds to, or comprises a region of complementarity with) at least 6 continuous nucleotides of a SHN3 gene. In some embodiments, an artificial microRNA targets (e.g., binds to, or comprises a region of complementarity with) between 6 and 30 continuous nucleotides of a SHN3 gene. In some embodiments, an artificial microRNA targets between 12-24 continuous nucleotides of a SHN3 gene. In some embodiments, an artificial microRNA targets between 9-27 continuous nucleotides of the SHN3 gene. In some embodiments, an artificial microRNA targets at least 6, 7, 8, 9, 10, 11, 12, 13, 14, 15, 16, 17, 18, 19, 20, 21, 22, 23, 24, 25, 26, 27, 28, 29, or 30 continuous nucleotides of a SHN3 gene.

In some embodiments, an artificial microRNA is between 6-50 nucleotides in length. In some embodiments, an artificial microRNA is between 8-24 nucleotides in length. In some embodiments, an artificial microRNA is between 12-36 nucleotides in length. In some embodiments, an artificial microRNA is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, an isolated inhibitory nucleic acid decreases expression of a target gene by between 50% and 99% (e.g., any integer between 50% and 99%, inclusive). In some aspects, an isolated inhibitory nucleic acid decreases expression of a target gene by between 75% and 90%. In some aspects, an isolated inhibitory nucleic acid decreases expression of a target gene by between 80% and 99%. In some embodiments, an isolated inhibitory nucleic acid decreases expression of a SHN3 gene by between 50% and 99% (e.g., any integer between 50% and 99%, inclusive). In some embodiments, an isolated inhibitory nucleic acid decreases expression of a SHN3 gene by between 75% and 90%. In some aspects, an isolated inhibitory nucleic acid decreases expression of a SHN3 gene by between 80% and 99%.

A region comprising a transgene (e.g., a second region, third region, fourth region, etc.) may be positioned at any suitable location of the isolated nucleic acid. The region may be positioned in any untranslated portion of the nucleic acid, including, for example, an intron, a 5' or 3' untranslated region, etc.

In some cases, it may be desirable to position the region (e.g., the second region, third region, fourth region, etc.) upstream of the first codon of a nucleic acid sequence encoding a protein (e.g., a protein coding sequence). For example, the region may be positioned between the first codon of a protein coding sequence) and 2000 nucleotides upstream of the first codon. The region may be positioned between the first codon of a protein coding sequence and 1000 nucleotides upstream of the first codon. The region may be positioned between the first codon of a protein coding sequence and 500 nucleotides upstream of the first codon. The region may be positioned between the first codon of a protein coding sequence and 250 nucleotides upstream of the first codon. The region may be positioned between the first codon of a protein coding sequence and 150 nucleotides upstream of the first codon.

In some cases (e.g., when a transgene lacks a protein coding sequence), it may be desirable to position the region (e.g., the second region, third region, fourth region, etc.) upstream of the poly-A tail of a transgene. For example, the region may be positioned between the first base of the poly-A tail and 2000 nucleotides upstream of the first base. The region may be positioned between the first base of the poly-A tail and 1000 nucleotides upstream of the first base. The region may be positioned between the first base of the poly-A tail and 500 nucleotides upstream of the first base. The region may be positioned between the first base of the poly-A tail and 250 nucleotides upstream of the first base. The region may be positioned between the first base of the poly-A tail and 150 nucleotides upstream of the first base. The region may be positioned between the first base of the poly-A tail and 100 nucleotides upstream of the first base. The region may be positioned between the first base of the poly-A tail and 50 nucleotides upstream of the first base. The region may be positioned between the first base of the poly-A tail and 20 nucleotides upstream of the first base. In some embodiments, the region is positioned between the last nucleotide base of a promoter sequence and the first nucleotide base of a poly-A tail sequence.

In some cases, the region may be positioned downstream of the last base of the poly-A tail of a transgene. The region may be between the last base of the poly-A tail and a position 2000 nucleotides downstream of the last base. The region may be between the last base of the poly-A tail and a position 1000 nucleotides downstream of the last base. The region may be between the last base of the poly-A tail and a position 500 nucleotides downstream of the last base. The region may be between the last base of the poly-A tail and a position 250 nucleotides downstream of the last base. The region may be between the last base of the poly-A tail and a position 150 nucleotides downstream of the last base.

It should be appreciated that in cases where a transgene encodes more than one miRNA, each miRNA may be positioned in any suitable location within the transgene. For example, a nucleic acid encoding a first miRNA may be positioned in an intron of the transgene and a nucleic acid sequence encoding a second miRNA may be positioned in another untranslated region (e.g., between the last codon of a protein coding sequence and the first base of the poly-A tail of the transgene).

In some embodiments, the transgene further comprises a nucleic acid sequence encoding one or more expression control sequences (e.g., a promoter, etc.). Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, a tissue-specific promoter is a bone tissue-specific promoter. Examples of bone tissue-specific promoters include but are not limited to promoters of osterix, osteocalcin, type 1 collagen α1, DMP1, cathepsin K, Rank, etc.

Aspects of the disclosure relate to an isolated nucleic acid comprising more than one promoter (e.g., 2, 3, 4, 5, or more promoters). For example, in the context of a construct having a transgene comprising a first region encoding a protein and an second region encoding an inhibitory RNA (e.g., miRNA), it may be desirable to drive expression of the protein coding region using a first promoter sequence (e.g., a first promoter sequence operably linked to the protein coding region), and to drive expression of the inhibitory RNA encoding region with a second promoter sequence (e.g., a second promoter sequence operably linked to the inhibitory RNA encoding region). Generally, the first promoter sequence and the second promoter sequence can be the same promoter sequence or different promoter sequences. In some embodiments, the first promoter sequence (e.g., the promoter driving expression of the protein coding region) is a RNA polymerase III (polIII) promoter sequence. Non-limiting examples of polIII promoter sequences include U6 and H1 promoter sequences. In some embodiments, the second promoter sequence (e.g., the promoter sequence driving expression of the inhibitory RNA) is a RNA polymerase II (polII) promoter sequence. Non-limiting examples of polII promoter sequences include T7, T3, SP6, RSV, and cytomegalovirus promoter sequences. In some embodiments, a polIII promoter sequence drives expression of an inhibitory RNA (e.g., miRNA) encoding region. In some embodiments, a polII promoter sequence drives expression of a protein coding region.

Recombinant AAVs (rAAVs)

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins and/or inhibitory nucleic acids (e.g., shRNA, miRNAs, etc.) comprising a nucleic acid that targets an endogenous mRNA of a subject. The transgene may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

As used herein, the term "self-complementary AAV vector" (scAAV) refers to a vector containing a double-stranded vector genome generated by the absence of a terminal resolution site (TR) from one of the ITRs of the AAV. The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle. The instant invention is based, in part, on the recognition that DNA fragments encoding RNA hairpin structures (e.g. shRNA, miRNA, and AmiRNA) can serve a function similar to a mutant inverted terminal repeat (mTR) during viral genome replication, generating self-complementary AAV vector genomes. For example, in some embodiments, the disclosure provides rAAV (e.g. self-complementary AAV; scAAV) vectors comprising a single-stranded self-complementary nucleic acid with inverted terminal repeats (ITRs) at each of two ends and a central portion comprising a promoter operably linked with a sequence encoding a hairpin-forming RNA (e.g., shRNA, miRNA, ami-RNA, etc.). In some embodiments, the sequence encoding a hairpin-forming RNA (e.g., shRNA, miRNA, ami-RNA, etc.) is substituted at a position of the self-complementary nucleic acid normally occupied by a mutant ITR.

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, and/or AAVrh10 ITR sequence.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g. AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV6.2, AAV7, AAV8, AAVrh8, AAV9, AAVrh10, AAVrh39, AAVrh43, AAV2/2-66, AAV2/2-84, AAV2/2-125. In some embodiments, an AAV capsid protein is of a serotype derived from a non-human primate, for example scAAV.rh8, AAV.rh39, or AAV.rh43 serotype. In some embodiments, an AAV capsid protein is of an AAV9 serotype.

The disclosure is based, in part, on rAAVs comprising capsid proteins that have increased tropism for bone tissue. In some embodiments, the capsid proteins are grafted to a bone-targeting peptide. A heterologous bone-targeting peptide may target OCs (e.g., specifically, or preferentially targets OCs relative to OBs) or OBs (e.g., specifically, or preferentially targets OBs relative to OCs). In some embodiments, a bone-targeting peptide is an (AspSerSer)$_6$ peptide, which may also be referred to as a DSS$_6$ peptide (e.g. SEQ ID NO: 16). Additional bone-targeting peptide is a HABP-19 peptide (CγEPRRγEVAγELγEPRRγEVAγEL; SEQ ID NO: 17), which may also be referred to as a HABP peptide. In some embodiments, a bone-targeting peptide is an (Asp)$_{8-14}$ peptide comprising 8-14 aspartic acid residues (e.g., as set forth in SEQ ID NOs: 57-63). Further examples of bone-targeting peptides include but are not limited to those described by Ouyang et al. (2009) *Lett. Organic Chem* 6(4):272-277. In some embodiments, bone-targeting peptides comprise the sequence set forth in SEQ ID NO: 16, 17, 57, 58, 59, 60, 61, 62, and 63.

As used herein, "grafting" refers to joining or uniting of one molecule with another molecule. In some embodiments, the term grafting refers to joining or uniting of at least two molecules such that one of the at least two molecules is inserted within another of at least two molecules. In some embodiments, the term grafting refers to joining or uniting of at least two polymeric molecules such that one of at least two molecules is appended to another of at least two molecules. In some embodiments, the term grafting refers to joining or uniting of one polymeric molecule (e.g., a nucleic acid, a polypeptide) with another polymeric molecule (e.g., a nucleic acid, a polypeptide). In some embodiments, the term grafting refers to joining or uniting of at least two nucleic acid molecules such that one of at least two molecules is appended to another of at least two nucleic acid molecules.

In some embodiments, the term grafting refers to joining or uniting of at least two nucleic acid molecules such that one of the at least two nucleic acid molecules is inserted within another of the at least two nucleic acid molecules. For example, it has been observed that targeting peptides may be grafted to certain loci of a nucleic acid encoding a VP2 AAV capsid protein. In some embodiments, a targeting peptide (e.g. a bone-targeting peptide) is inserted at a position corresponding to the position between the codons encoding Q588 and A589 and/or N587 and R588 of an AAV2 or AAV9 VP2 capsid protein. In some embodiments, a targeting peptide is inserted at a position between the codons encoding N587 and R588 of an VP3 capsid protein (or a position corresponding to such amino acid positions in AAV2 or AAV9). In some embodiments, a targeting peptide is inserted at a position between the codons encoding S452 and G453 of an VP1 capsid protein. Other potential positions may be N587 and R588.

In some embodiments, a nucleic acid formed through grafting (a grafted nucleic acid) encodes a chimeric protein. In some embodiments, a grafted nucleic acid encodes a chimeric protein, such that one polypeptide is effectively inserted into another polypeptide (e.g. not directly conjugated before the N-terminus or after the C-terminus), thereby creating a contiguous fusion of two polypeptides. In some embodiments, a grafted nucleic acid encodes a chimeric protein, such that one polypeptide is effectively appended to another polypeptide (e.g. directly conjugated before the N-terminus or after the C-terminus), thereby creating a contiguous fusion of two polypeptides. In some embodiments, the term grafting refers to joining or uniting of at least two polypeptides, or fragments thereof, such that one of the at least two polypeptides or fragments thereof is inserted within another of the at least two polypeptides or fragments thereof. In some embodiments, the term grafting refers to joining or uniting of at least two polypeptides or fragments thereof such that one of the at least two polypeptides or fragments thereof is appended to another of the at least two polypeptides or fragments thereof.

In some embodiments, the disclosure relates to an adeno-associated virus (AAV) capsid protein that is conjugated to one or more bone-targeting moieties. A "bone-targeting moiety" generally refers to a small molecule, peptide, nucleic acid, etc., that facilitates trafficking of an rAAV to bone or bone tissue. For example, in some embodiments, a bone-targeting moiety is a peptide or small molecule that binds to a receptor on a bone cell (e.g., OB, OC, osteocyte, etc.). Examples of bone-targeting moieties include but are not limited to alendronate (ALE), polypeptides such as cyclic arginine-glycine-aspartic acid-tyrosine-lysine (cRGCyk), Asp-Asp-Asp-Asp-Asp-Asp-Asp-Asp (D-Asp8), and aptamers such as CH6. A bone-targeting moiety may be conjugated directly to a capsid protein or conjugated to a capsid protein via a linker molecule (e.g., an amino acid linker, a PEG linker, etc.).

In some embodiments, a linker is a glycine-rich linker. In some embodiments, a linker comprises at least two glycine residues. In some embodiments, a linker comprises GGGGS (SEQ ID NO: 64). In some embodiments, the linker comprises a formula selected from the group consisting of: $[G]_n$ (SEQ ID NO: 65), $[G]_nS$ (SEQ ID NO: 66), $[GS]_n$ (SEQ ID NO: 67), and $[GGSG]_n$ (SEQ ID NO: 68), wherein G is glycine and wherein n is an integer greater than one (e.g., 2, 3, 4, 5, 6, 7, 8, 9, 10, 11, 12, 13, 14, 15, 16, 17, 18, 19, 20, 21, 22, 23, 24, 25 or more). In some embodiments, n is an integer in a range of 2 to 10, 2 to 20, 5 to 10, 5 to 15, or 5 to 25. Accordingly, in some embodiments, a heterologous targeting peptide is conjugated to a linker.

In some embodiments, a capsid protein comprises one or more azide-bearing unnatural amino acids which are capable of reacting with an ADIBO-tagged bone-targeting moiety (e.g., via "click chemistry" to form a capsid protein-bone-targeting moiety conjugate. Capsid proteins comprising unnatural azide-bearing amino acids are described, for example by Zhang et al. (2016) Biomaterials 80:134-145, and use of ADIBO-based click chemistry for peptide conjugation is described, for example by Prim et al. (2013) *Molecules* 18(8):9833-49.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. In some embodiments, a host cell is a bacterial cell, yeast cell, insect cell (Sf9), or a mammalian (e.g., human, rodent, non-human primate, etc.) cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

In some aspects, the present disclosure provides a recombinant AAV comprising a capsid protein and an isolated nucleic acid comprising a first region encoding an AAV ITR and a second region comprising a transgene, wherein the transgene encodes an artificial microRNA. The artificial microRNA may decrease the expression of a target gene in a cell (e.g. osteoblasts, osteoclasts, osteocytes, chondrocytes) or a subject. In some embodiments, the rAAV comprises an artificial microRNA that decreases the expression of SHN3 in a cell or a subject.

The rAAV may comprise at least one modification which increases targeting of the rAAV to bone cells (e.g., osteoblasts, osteoclasts, osteocytes, chondrocytes). Non-limiting examples of modifications which increase targeting of the rAAV to bone cells include heterologous bone-targeting peptides (e.g., as set forth in any one of SEQ ID NOs: 16, 17, 57, 58, 59, 60, 61, 62, or 63), AAV capsid serotypes (e.g., AAV1, AAV4, AAV5, AAV6, AAV6.2, AAV7, AAV8, AAV9, AAV10, AAVrh39, AAVrh43).

Expression of SHN3 in a cell or subject may be decreased by between 50% and 99% (e.g., any integer between 50% and 99%, inclusive) using rAAVs of the present disclosure. Expression of SHN3 in a cell or subject may be decreased by between 75% and 90% using rAAVs of the present disclosure. Expression of SHN3 in a cell or subject may be decreased by between 80% and 99% using rAAVs of the present disclosure.

The foregoing methods for packaging recombinant vectors in desired AAV capsids to produce the rAAVs of the disclosure are not meant to be limiting and other suitable methods will be apparent to the skilled artisan.

Modes of Administration and Compositions

The rAAVs of the disclosure may be delivered to a subject in compositions according to any appropriate methods known in the art. For example, an rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the bone (e.g., bone tissue) of a subject. By "bone tissue" is meant all cells and tissue of the bone and/or joint (e.g., cartilage, axial and appendicular bone, etc.) of a vertebrate. Thus, the term includes, but is not limited to, osteoblasts, osteocytes, osteoclasts, chondrocytes, and the like. Recombinant AAVs may be delivered directly to the bone by injection into, e.g., directly into the bone, via intrasynovial injection, knee injection, femoral intramedullary injection, etc., with a needle, catheter or related device, using surgical techniques known in the art. In some embodiments, rAAV as described in the disclosure are administered by intravenous injection. In some embodiments, the rAAV are administered by intramuscular injection.

Aspects of the instant disclosure relate to compositions comprising a recombinant AAV comprising a capsid protein and a nucleic acid encoding a transgene, wherein the transgene comprises a nucleic acid sequence encoding one or more bone metabolism modulating agents. In some embodiments, the nucleic acid further comprises one or more AAV ITRs. In some embodiments, the rAAV comprises an rAAV vector comprising the sequence set forth in any one of SEQ ID NO: 1-15 (or the complementary sequence thereof), or a portion thereof. In some embodiments, a composition further comprises a pharmaceutically acceptable carrier.

In some embodiments, compositions comprise a recombinant AAV comprising a capsid protein and a nucleic acid comprising a first region encoding an AAV ITR and a second region comprising a transgene, wherein the transgene encodes an artificial microRNA that targets SHN3. In some embodiments, the recombinant AAV comprises a sequence as set forth in SEQ ID NO: 3. In some embodiments, the capsid protein further comprises a heterologous bone-targeting peptide as set forth in SEQ ID NOs: 16-17 or 57-63.

Aspects of the disclosure provide a method of decreasing SHN3 expression in a cell. A cell may be a single cell or a population of cells (e.g., culture). A cell may be in vivo (e.g., in a subject) or in vitro (e.g., in culture). A subject may be a mammal, optionally a human, a mouse, a rat, a non-human primate, a pig, a dog, a cat, a chicken, or a cow.

Expression of SHN3 in a cell or subject may be decreased by between 50% and 99% (e.g., any integer between 50% and 99%, inclusive) using isolated nucleic acids, rAAVs, or compositions of the present disclosure. Expression of SHN3 in a cell or subject may be decreased by between 75% and 90% using isolated nucleic acids, rAAVs, or compositions of the present disclosure. Expression of SHN3 in a cell or subject may be decreased by between 80% and 99% using isolated nucleic acids, rAAVs, or compositions of the present disclosure.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An "effective amount" of an rAAV is an amount sufficient to target infect an animal, target a desired tissue (e.g., bone tissue). The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target bone tissue.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, femoral intramedullary, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Therapeutic Methods

Methods for delivering an effective amount of a transgene (e.g., an isolated nucleic acid or rAAV encoding one or more bone metabolism modulating agent) to a subject are provided by the disclosure. In some embodiments, the methods comprise the step of administering to a subject an effective amount of an isolated nucleic acid encoding an interfering RNA capable of promoting or inhibiting bone formation. In some embodiments, the methods comprise the step of administering to a subject an effective amount of an isolated nucleic acid encoding an interfering RNA capable of promoting or inhibiting bone resorption. Thus, in some embodiments, isolated nucleic acids, rAAVs, and compositions described herein are useful for treating a subject having or suspected of having a disease or disorder associated with dysregulated bone metabolism.

As used herein, a "disease or disorder associated with dysregulated bone metabolism" refers to a condition characterized by an imbalance between bone deposition and bone resorption resulting in either 1) abnormally increased bone deposition (e.g., formation) relative to a healthy individual (e.g., a subject not having a disease characterized by imbalance between bone deposition and bone resorption), or 2) abnormally decreased bone deposition (e.g., formation) relative to a healthy individual (e.g., a subject not having a disease characterized by an imbalance between bone deposition and bone resorption), or 3) abnormally increased bone resorption (e.g., breakdown) relative to a healthy individual (e.g., a subject not having a disease characterized by imbalance between bone deposition and bone resorption), or 4) abnormally decreased bone resorption (e.g., breakdown) relative to a healthy individual (e.g., a subject not having a disease characterized by imbalance between bone deposition and bone resorption).

A "disease associated with reduced bone density" refers to a condition characterized by increased bone porosity resulting from either 1) abnormally decreased bone deposition (e.g., formation) relative to a healthy individual (e.g., a subject not having a disease characterized by decreased bone density), or 2) abnormally increased bone resorption (e.g., breakdown) relative to a healthy individual (e.g., a subject not having a disease characterized by decreased bone density). A disease associated with increased bone porosity may arise from either 1) abnormally decreased OB and/or osteocyte differentiation, function, or activity relative to a healthy individual (e.g., a subject not having a disease characterized by decreased bone density) and/or 2) abnormally increased OC differentiation, function, or activity relative to a healthy individual (e.g., a subject not having a disease characterized by decreased bone density). "Porosity" generally refers to the volume of fraction of bone not occupied by bone tissue.

A "disease associated with increased bone density" refers to a condition characterized by decreased bone porosity resulting from either 1) abnormally increased bone deposition (e.g., formation) relative to a healthy individual (e.g., a subject not having a disease characterized by increased bone density), or 2) abnormally decreased bone resorption (e.g., breakdown) relative to a healthy individual (e.g., a subject not having a disease characterized by increased bone density). A disease associated with decreased bone porosity may arise from either 1) abnormally increased OB and/or osteocyte differentiation, function, or activity relative to a healthy individual (e.g., a subject not having a disease characterized by increased bone density) and/or 2) abnormally decreased OC differentiation, function, or activity relative to a healthy individual (e.g., a subject not having a disease characterized by increased bone density).

Aspects of the present disclosure provide methods of treating a disease or disorder associated with dysregulated bone metabolism. Dysregulated bone metabolism may be diseases associated with reduced bone density (e.g., osteoporosis, critical sized-bone defects, a mechanical disorder resulting from disuse or injury). Dysregulated bone metabolism may be diseases associated with increased bone density (e.g., osteopetrosis, pycnodysostosis, sclerosteosis, acromegaly, fluorosis, myelofibrosis, hepatitis C-associated osteosclerosis, heterotrophic ossification).

In some embodiments, methods of treating a disease or disorder associated with a dysregulated bone metabolism comprise administering to a subject in need thereof a recombinant AAV (rAAV) comprising a transgene. A rAAV may comprise a modification that promotes its targeting to bone cells (e.g., osteoclasts and osteoblasts). Non-limiting modifications of rAAVs that promote its targeting to bone cells include the heterologous bone-targeting peptide in SEQ ID NOs: 16-17 or 57-63, bone-specific promoters, and AAV serotypes with increased targeting to bone relative to other tissues. In some embodiments, methods of treating a dysregulated bone metabolism comprise administering to a subject in need thereof a rAAV comprising a heterologous bone-targeting peptide as in SEQ ID NOs: 16-17 or 57-63.

In some embodiments, the rAAV comprising the heterologous bone-targeting peptide comprises a transgene which upregulates or downregulates a target gene associated with dysregulation of bone metabolism. In some embodiments, the transgene upregulates the expression of a target gene that is decreased in a disorder associated with reduced bone density (e.g., osteoporosis, critical sized-bone defects, a mechanical disorder resulting from disuse or injury). In some embodiments, the transgene downregulates the expression of a target gene that is increased in a disorder associated with reduced bone density. In some embodiments, the transgene upregulates the expression of a target gene that is decreased in a disorder associated with reduced bone density (e.g., osteoporosis, critical sized-bone defects, a mechanical disorder resulting from disuse or injury). In some embodiments, the transgene downregulates the expression of a target gene that is increased in a disorder associated with reduced bone density.

Aspects of the disclosure provide methods for treating a disease or disorder associated with a disease of disorder characterized by dysregulation of bone metabolism comprising administering to a subject a rAAV comprising a capsid protein and an isolated nucleic acid encoding an inhibitory nucleic acid. The rAAV may comprise an inhibitory nucleic acid (e.g., siRNA, shRNA, miRNA, or amiRNA). The inhibitory nucleic acid may decrease or increase expression of a target gene associated with a disease or disorder characterized by dysregulation of bone metabolism.

In some embodiments, the present disclosure provides a method of treating disease or disorder associated with reduced bone density. The method comprises administering to a subject in need thereof a rAAV or an isolated nucleic acid comprising a transgene that targets a gene associated with reduced bone density. In some embodiments, the rAAV or isolated nucleic acid comprises a transgene encoding an artificial microRNA that targets a gene associated with reduced bone density. In some embodiments, the target gene is SHN3, PTH, PTHrP, DJ1, SOST, CTSK, or RANK.

Aspects of the present disclosure provide methods of treating a disease or disorder associated with reduced bone density comprising administering an rAAV or an isolated nucleic acid. In some embodiments, the rAAV or isolated nucleic acid comprise a sequence as set forth in SEQ ID NO: 3, or the complement thereof. In some embodiments, the rAAV comprises a capsid protein comprising a sequence as set forth in any one of SEQ ID NOs: 18-34. In some embodiments, the rAAV comprises a heterologous bone-targeting peptide comprising a sequence as set forth in any one of SEQ ID NOs: 16-17 and 57-63.

Expression of SHN3 in a cell or subject may be decreased by between 50% and 99% (e.g., any integer between 50% and 99%, inclusive) using methods of the present disclosure. Expression of SHN3 in a cell or subject may be decreased by between 75% and 90% using methods of the present disclosure. Expression of SHN3 in a cell or subject may be decreased by between 80% and 99% using methods of the present disclosure.

In some embodiments, an "effective amount" of a substance is an amount sufficient to produce a desired effect (e.g., to transduce bone cells or bone tissue). In some embodiments, an effective amount of an isolated nucleic acid is an amount sufficient to transfect (or infect in the context of rAAV-mediated delivery) a sufficient number of target cells of a target tissue of a subject. In some embodiments, a target tissue is bone tissue (e.g., bone and bone tissue cells, such as OBs, OCs, osteocytes, chondrocytes, etc.). In some embodiments, an effective amount of an isolated nucleic acid (e.g., which may be delivered via an rAAV) may be an amount sufficient to have a therapeutic benefit in a subject, e.g., to increase activity or function of OBs and/or osteocytes, to inhibit activity of OBs and/or osteocytes, to increase activity of function of OCs, to inhibit activity or function of OCs, etc. The effective amount will depend on a variety of factors such as, for example, the species, age, weight, health of the subject, and the tissue to be targeted, and may thus vary among subject and tissue as described elsewhere in the disclosure.

Exemplary embodiments of the invention will be described in more detail by the following examples. These embodiments are exemplary of the invention, which one skilled in the art will recognize is not limited to the exemplary embodiments.

EXAMPLES

Example 1

Several key regulators of bone formation have been identified as therapeutic targets to osteoporosis. For instance, suppression of naturally occurring inhibitors of bone formation, sclerostin (SOST) or the adaptor protein schnurri-3 (SHN3, also HIVEP3) results in a progressive increase in bone mass due to augmented OB activity. Unlike SHN3 and SOST that primarily function in OBs, cathepsin K (CTSK) is highly expressed in OCs and its inhibition increases bone mass by blocking OC activity. Lastly, treatment with bone anabolic factors, including PTH, PTH-related protein (PTHrP), or DJ-1 promotes bone formation. In this example, gene therapeutics that can manipulate expression of these candidate genes using bone-targeting adeno-associated virus (AAV)-mediated gene silencing or addition are described. In some embodiments, therapeutics (e.g., compositions described by the disclosure) prevent bone loss by promoting OB function and bone formation or by suppressing OC activity and bone destruction with limited adverse effects on bone remodeling and regeneration activity.

Development of Gene Therapeutics Using Bone-Targeting Adeno-Associated Viruses (BT-AAVs)

The high efficiency of transduction, persistent transgene expression, and lack of post-infection immunogenicity and pathogenicity make AAVs very attractive viral vectors for use in gene therapy. To date, AAV vectors have been evaluated in over 130 clinical trials and 2,000 patients worldwide. However, non-specific cell targeting, possible pre-existing immunity, and other rate-limiting events necessitate identification of more natural AAV serotypes and improvement of the properties and functions of AAV serotypes by vector engineering. Here, AAV serotypes that can transduce OBs and/or OCs in vitro and in vivo were identified.

Identification of AAV Serotypes that Transduce OBs, OCs, and Chondrocytes

To this end, enhanced green fluorescent protein (GFP) reporter gene was packaged into 17 AAV capsids (scAAV1, scAAV2, scAAV3, scAAV4, scAAV5, scAAV6, scAAV6.2, scAAV7, scAAV8, scAAV9, scAAVrh8, scAAVrh10, scAAVrh39, scAAVrh43, scAAV2/2-66, scAAV2/2-84, scAAV2/2-125). The ability of these purified AAV serotype vectors to transduce mouse OB- or chondrocyte-lineage cells originated from mesenchymal stem cells (MSCs) or mouse OCs originated from bone marrow monocytes (BM-MO) were assessed by monitoring GFP expression using epifluorescence microscopy. First, to test their transduction capability to OB- or chondrocyte-lineage cells, mouse MSCs and chondrocyte progenitor line (ATDC5) were purchased from Cyagen and ATCC, respectively. Additionally, mouse OB precursors (pre-OB) were isolated from the calvaria of mouse neonates at postnatal day 3-5 on three different congenic backgrounds (C57BL/6J, BALB/cJ, 129S1/SvlmJ), and cultured in osteogenic medium for 6 days to differentiate into mature OBs (mOB). A single dose of $10^{12}$~$10^{13}$/ml genome copies of 17 purified AAV serotypes were incubated with these cells for 2 days and GFP expression was analyzed by epifluorescence microscopy (Table 1) and immunoblotting against EGFP (FIG. 22).

TABLE 1

Identification of scAAV serotypes that can transduce mouse MSC-lineage cells in vitro.

| | AAV serotypes | Titer | Pre-OB (B6) | Pre-OB (129) | Pre-OB (Balbc) | mOB (129) | mOB (Balbc) | MSC | ATDC5 |
|---|---|---|---|---|---|---|---|---|---|
| 1 | scAAV1.CB6-eGFP | $1.8 \times 10^{13}$ GC/mL | + | + | ++ | + | ++ | + | + |
| 2 | scAAV2.CB6-eGFP | $1.5 \times 10^{12}$ GC/mL | − | − | − | − | − | − | − |
| 3 | scAAV3.CB6-eGFP | $6 \times 10^{13}$ GC/mL | − | − | − | − | − | − | − |
| 4 | scAAV4.CB6-eGFP | $6.5 \times 10^{12}$ GC/mL | +++ | ++ | ++ | ++ | ++ | + | − |

TABLE 1-continued

Identification of scAAV serotypes that can transduce mouse MSC-lineage cells in vitro.

| | AAV serotypes | Titer | Pre-OB (B6) | Pre-OB (129) | Pre-OB (Balbc) | mOB (129) | mOB (Balbc) | MSC | ATDC5 |
|---|---|---|---|---|---|---|---|---|---|
| 5 | scAAV5.CB6-eGFP | $1.4 \times 10^{13}$ GC/mL | + | + | ++ | + | ++ | ++ | ++ |
| 6 | scAAV6.CB6-eGFP | $8 \times 10^{12}$ GC/mL | ++ | + | ++ | + | ++ | + | ++ |
| 7 | scAAV6.2.CB6-eGFP | $8 \times 10^{12}$ GC/mL | ++ | + | + | ++ | ++ | + | ++ |
| 8 | scAAV7.CB6-eGFP | $1.5 \times 10^{13}$ GC/mL | + | − | + | − | +/− | + | − |
| 9 | scAAV8.CB6-eGFP | $7 \times 10^{12}$ GC/mL | − | + | − | − | +/− | − | + |
| 10 | scAAV9.CB6-eGFP | $1.5 \times 10^{13}$ GC/mL | ++ | − | − | +/− | +/− | − | − |
| 11 | scAAVrh8.CB6-eGFP | $8 \times 10^{12}$ GC/mL | − | − | − | − | − | − | − |
| 12 | scAAV10.CB6-eGFP | $8 \times 10^{12}$ GC/mL | − | − | − | − | +/− | − | − |
| 13 | scAAVrh39.CB6-eGFP | $1 \times 10^{13}$ GC/mL | + | − | − | +/− | +/− | − | − |
| 14 | scAAVrh43.CB6-eGFP | $6 \times 10^{12}$ GC/mL | − | − | − | − | − | − | +/− |
| 15 | scAAV2/2-66.CB6-eGFP | $1 \times 10^{13}$ GC/mL | ND | − | − | − | − | ND | +/− |
| 16 | scAAV2/2-84.CB6-eGFP | $4 \times 10^{12}$ GC/mL | ND | − | − | − | − | ND | +/− |
| 17 | scAAV2/2-125.CB6-eGFP | $5 \times 10^{12}$ GC/mL | ND | − | − | − | − | ND | +/− |

Figure 2:
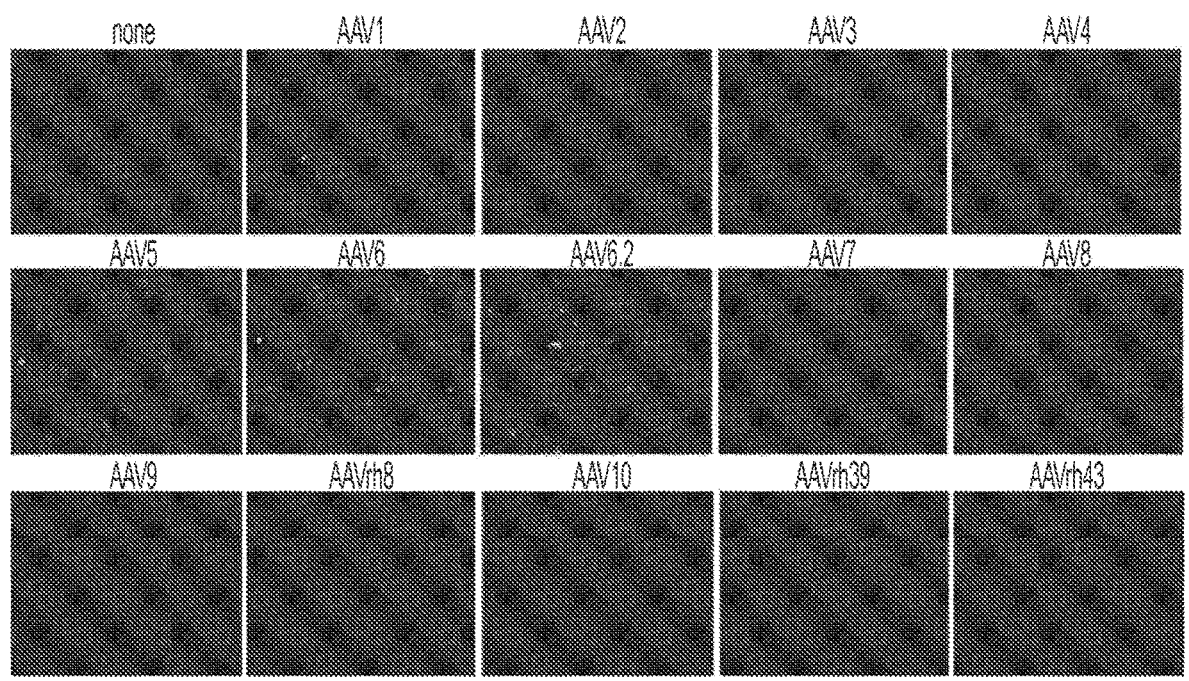
FIG. 2 shows identification of scAAV serotypes that transduce mouse ATDC5 chondrocyte line in vitro. Mouse chondrocyte progenitor cell line ATDC5 was incubated with 14 different scAAV serotypes encoding GFP proteins for 2 days and their transduction efficiency was analyzed by GFP expression using epifluorescence microscopy.

Among 17 AAV serotypes, scAAV4 was most effective to transduce mouse OB-lineage cells on three different mouse backgrounds, scAAV1, scAAV5, scAAV6, and scAAV6.2 (engineered version of scAAV6) transduced both mouse OB and chondrocyte-lineage cells on three different mouse backgrounds, and scAAV9 transduced only pre-OBs on the C57B6/J background (representative images in FIG. 1 and FIG. 2).

Figure 3:
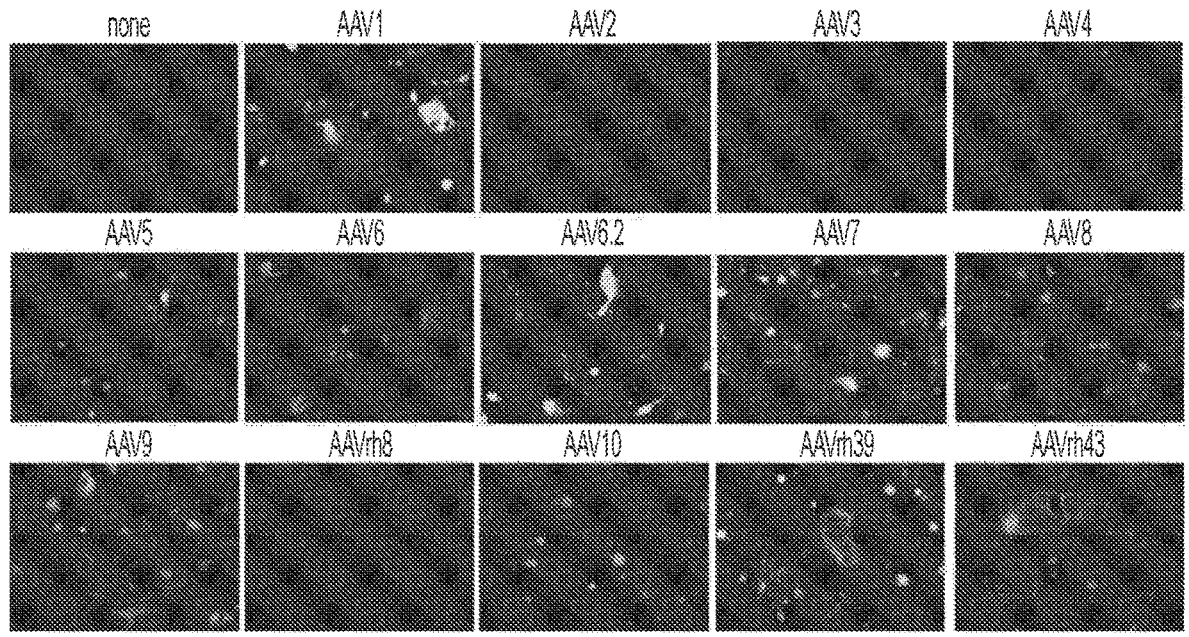
FIG. 3 shows identification of scAAV serotypes that can transduce mouse primary OCs in vitro. Bone marrow-derived monocytes (BM-MOs) were isolated from the long bones of 2-month old mice (C57BL/6J) and amplified by the addition of mouse m M-CSF (40 ng/ml). BM-MOs were incubated with 15 different scAAV serotypes encoding GFP proteins in the presence of mouse M-CSF (40 ng/ml) and mouse Rank ligand (10 ng/ml) for 6 days their transduction efficiency was analyzed by GFP expression using epifluourescence microscopy.
Figure 4:
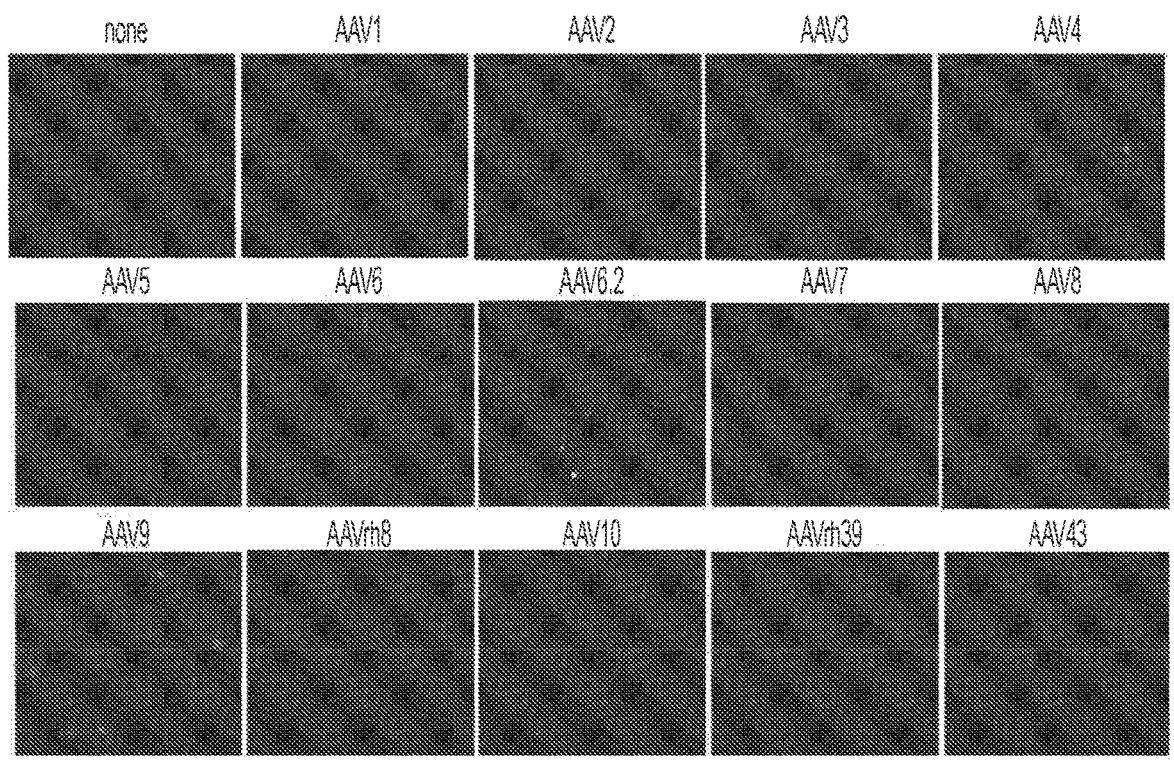
FIG. 4 shows identification of scAAV serotypes that can transduce mouse Raw264.7 OC line in vitro. 2 days after the treatment with mouse Rank ligand (5 ng/ml), Raw264.7 cells were incubated with 17 different scAAV serotypes encoding GFP proteins in the presence of mouse Rank ligand (5 ng/ml) for 6 days. Their transduction efficiency was analyzed by GFP expression using epifluorescence microscopy.

Next, the ability of purified AAV serotypes to transduce mouse OC precursors was investigated. Mouse primary OC precursors (BM-MO, bone-marrow derived monocyte) were isolated from the long bones of 2-month old mice (C57BL/6J) and amplified by the addition of mouse M-CSF (40 ng/ml, R&D systems). BM-MOs were cultured in the presence of mouse M-CSF (40 ng/ml) and mouse Rank ligand (10 ng/ml, R&D systems) for 6 days to differentiate into mature OCs (FIG. 3). Additionally, mouse OC precursor line (Raw264.7) was differentiated into mature OCs 4 days after culture with mouse Rank ligand (10 ng/ml) (FIG. 4). A single dose of $10^{12}$~$10^{13}$/ml genome copies of 17 purified AAV serotypes were incubated with these cells for 2 days and GFP expression was analyzed by epifluorescence microscopy (Table 2).

TABLE 2

Identification of scAAV serotypes that transduce mouse OCs in vitro.

| | AAV serotypes | Titer | BM-MO (B6) | BM-OC (B6) | Raw-OC |
|---|---|---|---|---|---|
| 1 | scAAV1.CB6-eGFP | $1.8 \times 10^{13}$ GC/mL | − | + | ++ |
| 2 | scAAV2.CB6-eGFP | $1.5 \times 10^{12}$ GC/mL | − | + | − |
| 3 | scAAV3.CB6-eGFP | $6 \times 10^{13}$ GC/mL | − | − | − |
| 4 | scAAV4.CB6-eGFP | $6.5 \times 10^{12}$ GC/mL | − | + | − |
| 5 | scAAV5.CB6-eGFP | $1.4 \times 10^{13}$ GC/mL | − | + | ++ |
| 6 | scAAV6.CB6-eGFP | $8 \times 10^{12}$ GC/mL | − | + | ++ |
| 7 | scAAV6.2.CB6-eGFP | $8 \times 10^{12}$ GC/mL | − | + | ++ |
| 8 | scAAV7.CB6-eGFP | $1.5 \times 10^{13}$ GC/mL | − | + | ++ |
| 9 | scAAV8.CB6-eGFP | $7 \times 10^{12}$ GC/mL | − | − | ++ |
| 10 | scAAV9.CB6-eGFP | $1.5 \times 10^{13}$ GC/mL | − | ++ | ++ |
| 11 | scAAVrh8.CB6-eGFP | $8 \times 10^{12}$ GC/mL | − | − | − |
| 12 | scAAV10.CB6-eGFP | $8 \times 10^{12}$ GC/mL | − | − | ++ |
| 13 | scAAVrh39.CB6-eGFP | $1 \times 10^{13}$ GC/mL | − | − | ++ |
| 14 | scAAVrh43.CB6-eGFP | $6 \times 10^{12}$ GC/mL | − | − | ++ |
| 15 | scAAV2/2-66.CB6-eGFP | $1 \times 10^{13}$ GC/mL | − | − | − |
| 16 | scAAV2/2-84.CB6-eGFP | $4 \times 10^{12}$ GC/mL | − | − | − |
| 17 | scAAV2/2-125.CB6-eGFP | $5 \times 10^{12}$ GC/mL | − | − | − |

Among 17 AAV serotypes, scAAV1, 5, 6, 6.2, 7, and 9 were effective to transduce both mouse primary OCs and Raw264.7 OC line while scAAV8 and 10, scAAVrh39 and 43 transduced only Raw264.7 OC line. (representative images in FIGS. 3 and 4).

Figure 5:
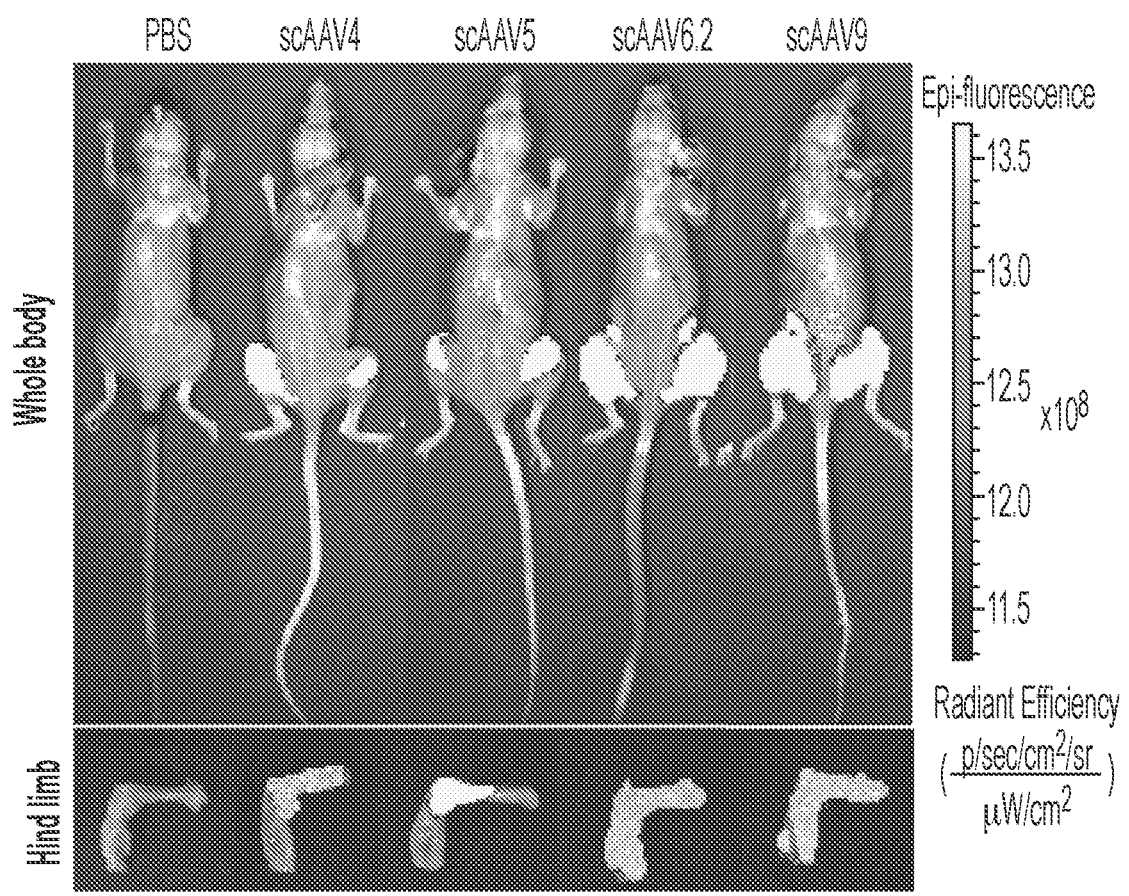
FIG. 5 shows optical images of GFP-expressing AAV-transduced tissues in mice. A single dose of PBS or $10^{12}$~$10^{13}$/ml genome copies of GFP-encoding scAAV serotypes (scAAV4, 5, 6.2, and 9) was injected into both knee joints of 2 month old mice (C57BL/6J) and 4 weeks later, mice were euthanized, and GFP expression in the knee joints was monitored by the IVIS-100 optical imaging system (whole body, top). The right hindlimbs were dissected and after removal of muscle GFP expression was monitored by the IVIS-100 optical imaging system (hindlimb, bottom).
Figure 6A:
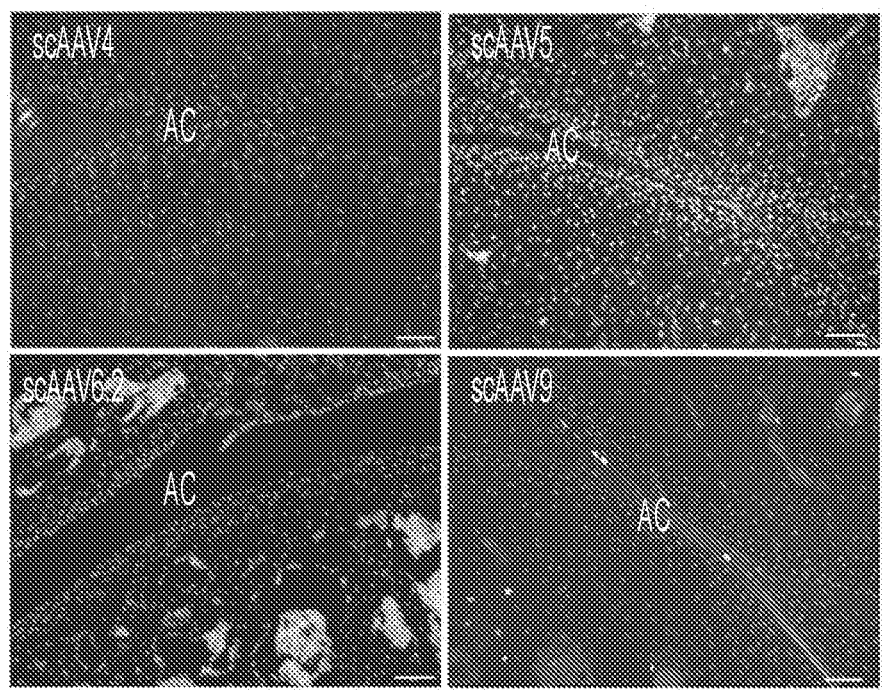
FIGS. 6A-6B show identification of scAAV serotypes that can transduce chondrocytes in articular cartilage and/or OBs and/or OCs on the bone surface. A single dose of $10^{12}$~$10^{13}$/ml genome copies of GFP-encoding scAAV serotypes (scAAV4, 5, 6.2, and 9) was injected into both knee joints of 2 month old mice (C57BL/6J) and 4 weeks later, knee joints (FIG. 6A) and femurs (FIG. 6B) were frozen-sectioned for histology. AC: articular cartilage, CB: cortical bone, BM: bone marrow, Bar: 50 μm.
Figure 28A:
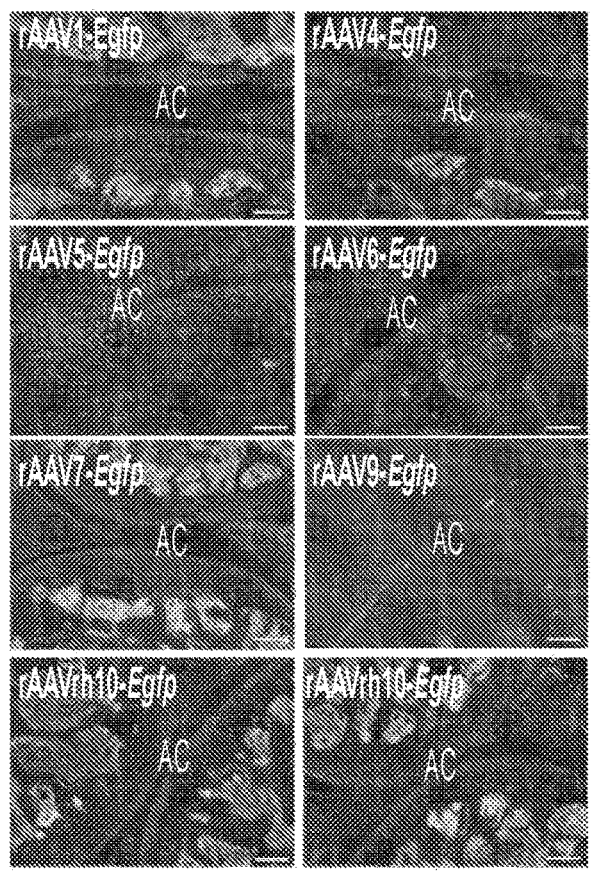
FIGS. 28A-28B show the identification of scAAV serotypes that transduce bone and cartilage. A single dose of PBS or $1 \times 10^{11}$ genome copies of scAAV9-EGFP was intraarticularly (i.a.) injected into knee joints of two-month-old male mice. Knee joints (FIG. 28A) and femurs (FIG. 28B) were cryo-sectioned to identify EGFP-expressing cells. DAPI was used to stain nuclei. AC, articular cartilage; M, muscle; CB, cortical bone; BM, bone marrow. Scale bars: 100 µm, panel (FIG. 28A; 250 µm, FIG. 28B).
Figure 28B:
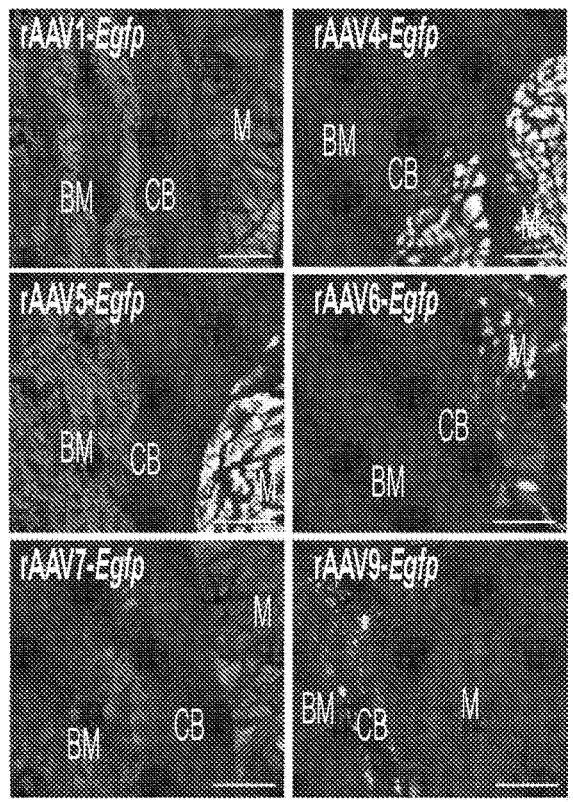
Figure 29A:
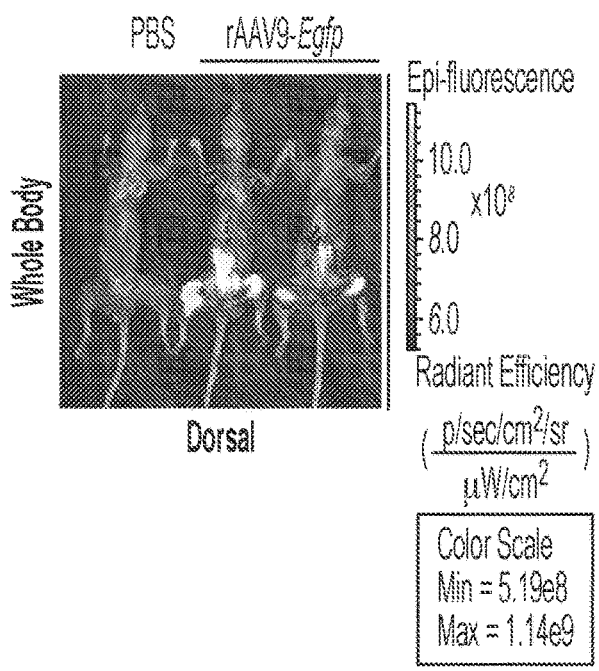
FIGS. 29A-29D show the tissue distribution of systematically-delivered scAAV9 in mice.
Figure 29A:
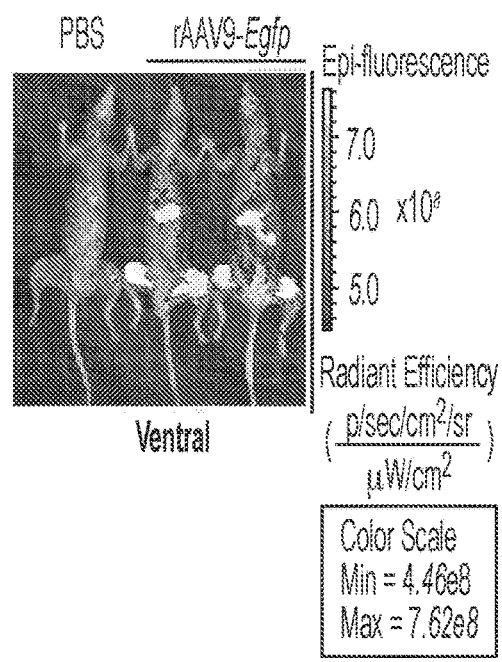
Figure 29B:
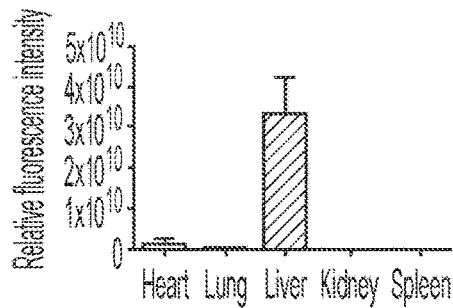
Figure 29C:
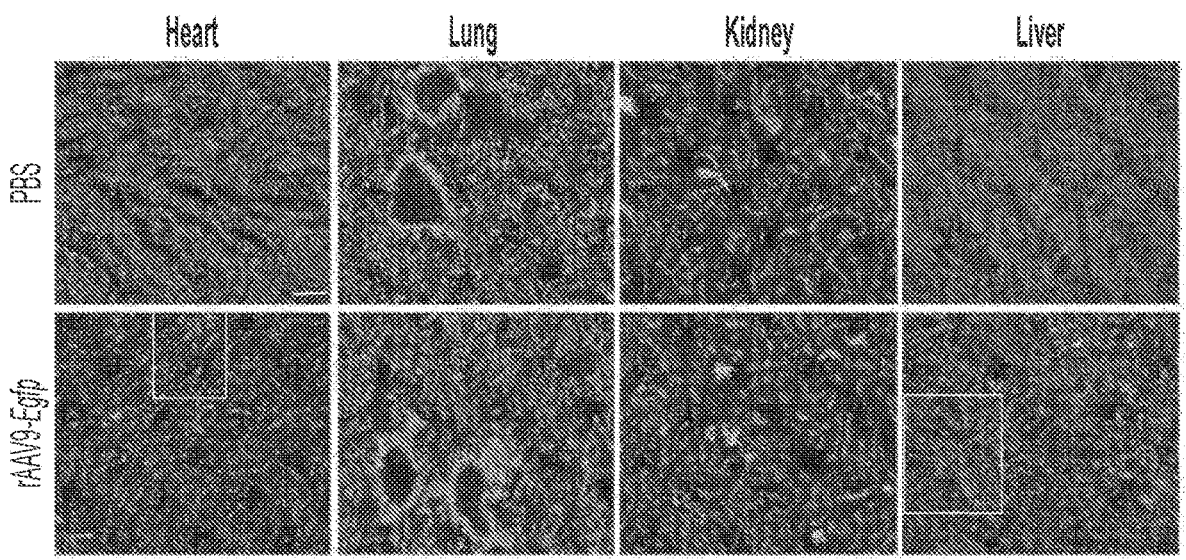
Figure 29D:
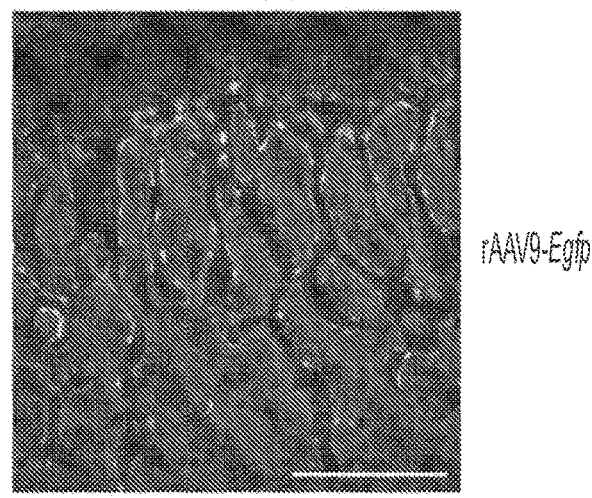

To examine the tropism of AAV capsids to articular cartilage and bone, eight scAAV-Egfp vectors selected from the in vitro screen (scAAV1, scAAV4, scAAV5, scAAV6, scAAV7, scAAV9, scAAVrh.10, and scAAVrh.39). To test their ability to transduce chondrocytes on articular cartilage and/or OBs and/or OCs on bone surface, a single dose of $10^{12}$~$10^{13}$/ml genome copies of the eight selected GFP-encoding AAV serotypes was injected into both knee joints of 2 month old mice (C57BL/6J) and 4 weeks later, mice were euthanized, and AAV transduction to articular cartilage and/or bone was monitored by the IVIS-100 optical imaging system at the UMMS optical imaging facility (FIG. 5). As a negative control, mice were injected with PBS. Little to no expression of EGFP in the articular cartilage (FIG. 28) or the growth plate (FIG. 22) for the majority of capsids. This discrepancy may be due to the poor accessibility of scAAV vectors to chrondrocytes, where are embedded in the avascular microenvironment of these structures. Alternatively, vectors may simply exhibit a lower infectivity of primary chondrocytes in adult mice. GFP proteins were highly expressed in the knee joints and hindlimbs and their expression was restricted to the local injection area (FIG. 5, top, FIG. 28). In particular, GFP expression was detected in the bone and the knee joints even after removal of the muscles (FIG. 5, bottom). To confirm GFP expression in chondrocytes in the articular cartilage and/or in OBs and/or OCs on the bone surface, histology on frozen sections of the knee joints and femurs was performed. As seen in FIG. 6A, no or little expression of GFP proteins in articular cartilage was detected in the knee joints injected with scAAV1, scAAV4, scAAV5, scAAV6, scAAV7, scAAV9, scAAVrh.10, and scAAVrh.39. In the knee joints injected with scAAV9, GFP expression was detected in a small population of chondrocytes. In contrast to in vitro data using the chondrocyte precursor line ATDC5, these results indicate that certain scAAV serotypes are not effective to transduce chondrocytes in articular cartilage in vivo.

Figure 30:
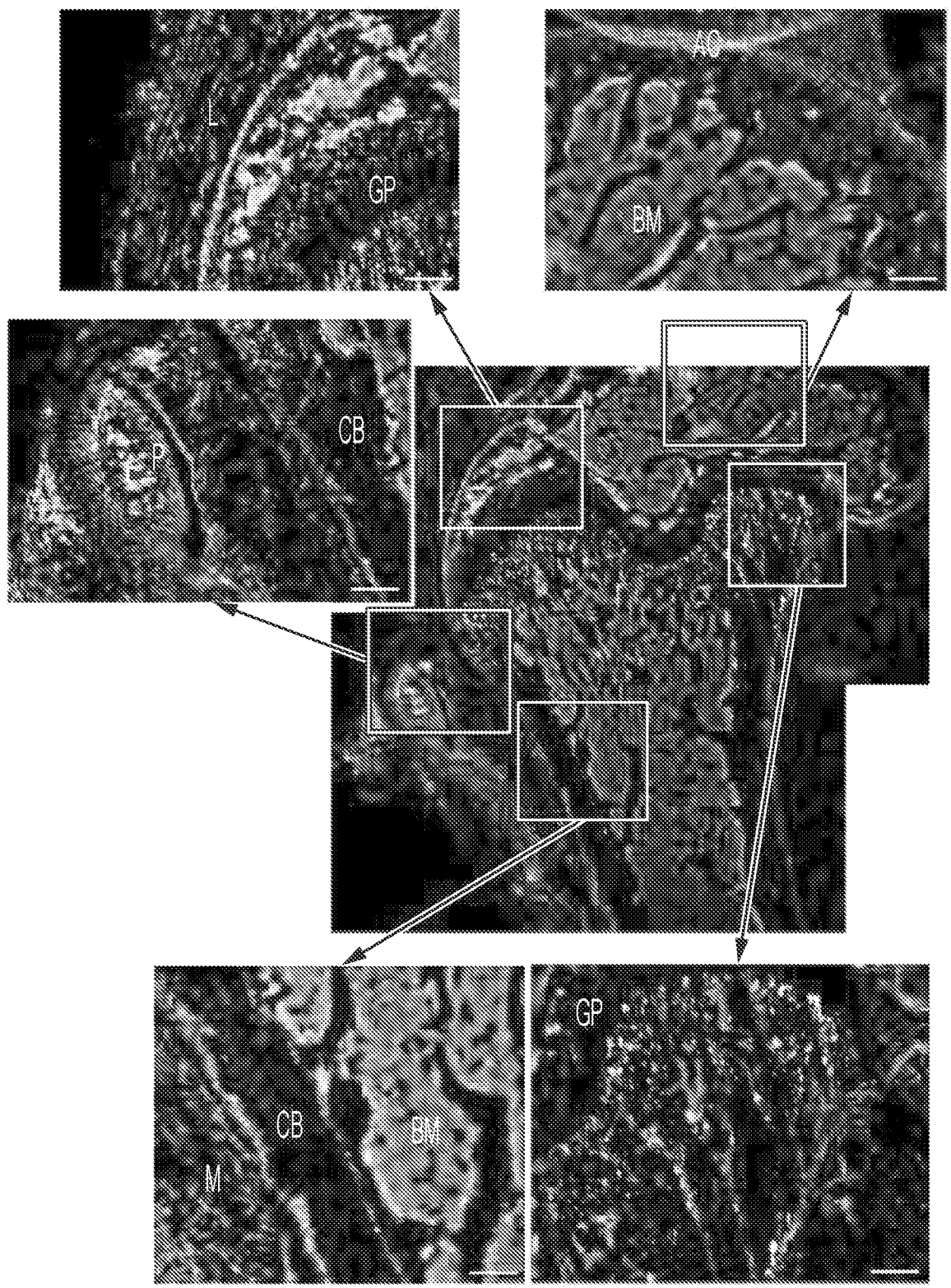
FIG. 30 shows the distribution of systematically-delivered scAAV9 in the femur. A single dose of $4 \times 10^{11}$ genome copies of scAAV-EGFP was i.v. injected into two-month-old male mice and EGFP expression was assessed in the cryo-sectioned femurs two weeks post-injection. L, ligament; GP, growth plate; AC, articular cartilage; BM, bone marrow; CB, cortical bone; P, patella; M, muscle. Scale bars: 100 μm.
Figure 31A:
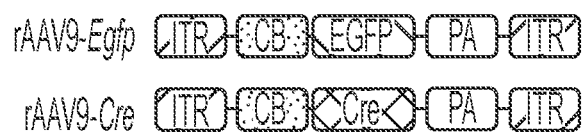
FIGS. 31A-31E show the in vitro characterization of scAAV9-Cre in Shn3$^{fl/fl}$ osteoblasts.
Figure 31B:
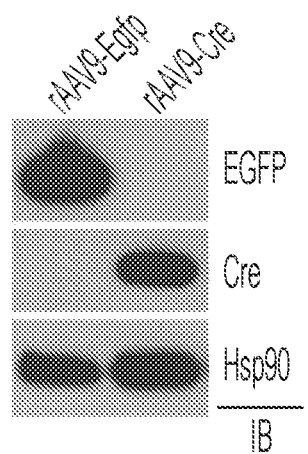
Figure 31C:
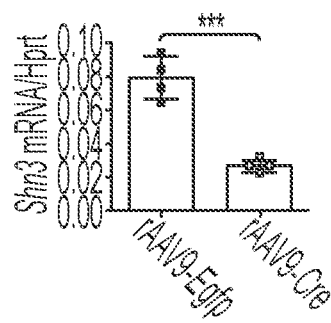
Figure 31D:
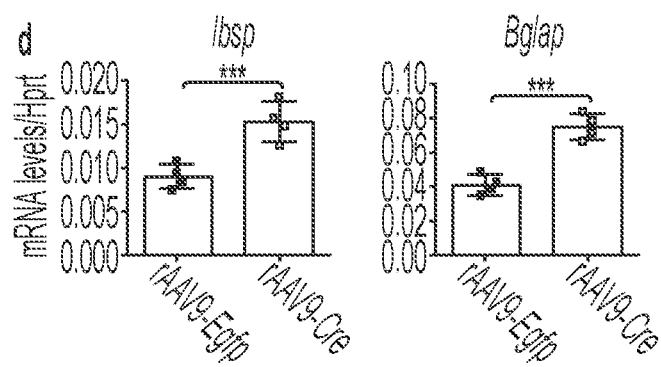
Figure 31E:
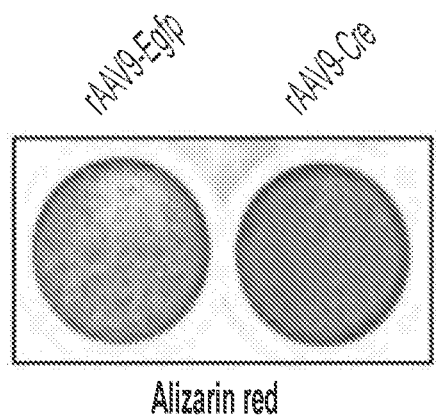

By contrast, GFP proteins were highly expressed in OBs and osteocytes that reside in cortical bones when scAAV9 was injected into the knee joints. Whole body and individual organ imaging of treated mice showed that EGFP expression was highest in the liver and hindlimbs (FIGS. 23 and 29). Expression in the heart and femur was modest, while expression in the lung, kidney, and spleen was not detected. Expression of EGFP in the heart, liver, and femur was further confirmed by fluorescence microscopy and by immunoblot analysis (FIG. 23). As observed, EGFP protein was primarily expressed in endosteal osteoblasts and osteocytes in cortical and trabecular bones, but not in the ligament, articular cartilage, growth plate, periosteal osteoblasts, bone marrow, and patellta (FIGS. 23 and 30). These results demonstrate that systemically delivered scAAV9 vector targets osteoblast lineage cells residing in the endosteal bone.

Figure 6B:
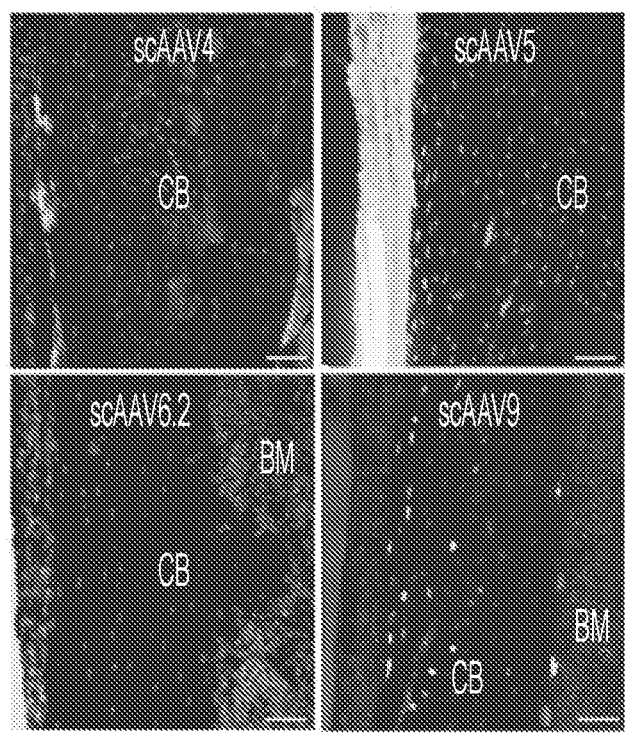
Figure 7:
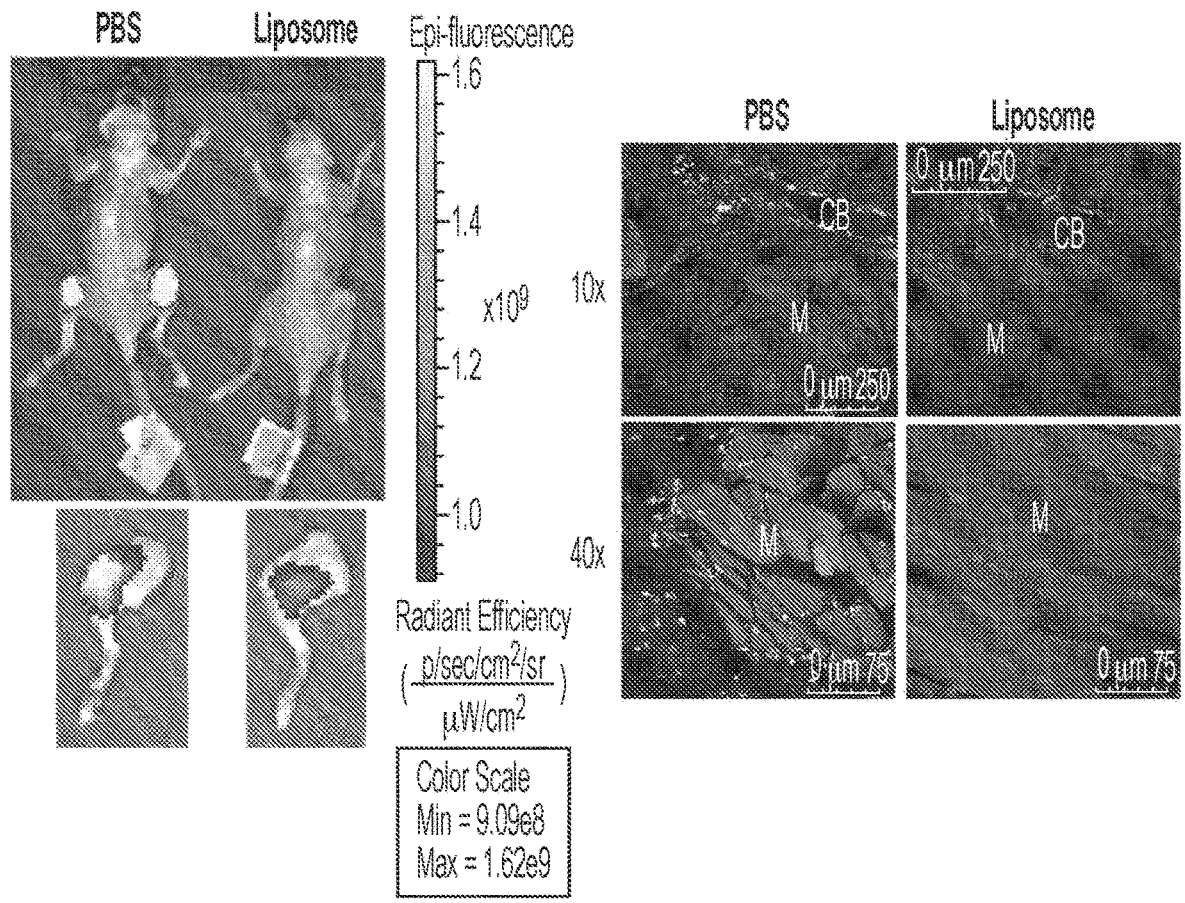
FIG. 7 shows that liposomes can enhance the selectivity of scAAV9-transduction to bone cells by reducing its infectivity to muscle in mice. $10^{12}$~$10^{13}$/ml genome copies of GFP-encoding scAAV9 serotype were mixed with PBS or X-tremeGENE (liposome, Roche) at 1:1 ratio. 1 hour after incubation, a single dose of the mixture was injected into knee joints of 2 month old mice (C57BL/6J). 1 week later, mice were euthanized, and GFP expression in the knee joints was monitored by the IVIS-100 optical imaging system (left). Femurs were frozen-sectioned for histology (right). CB: cortical bone, M: muscle.
Figure 8:
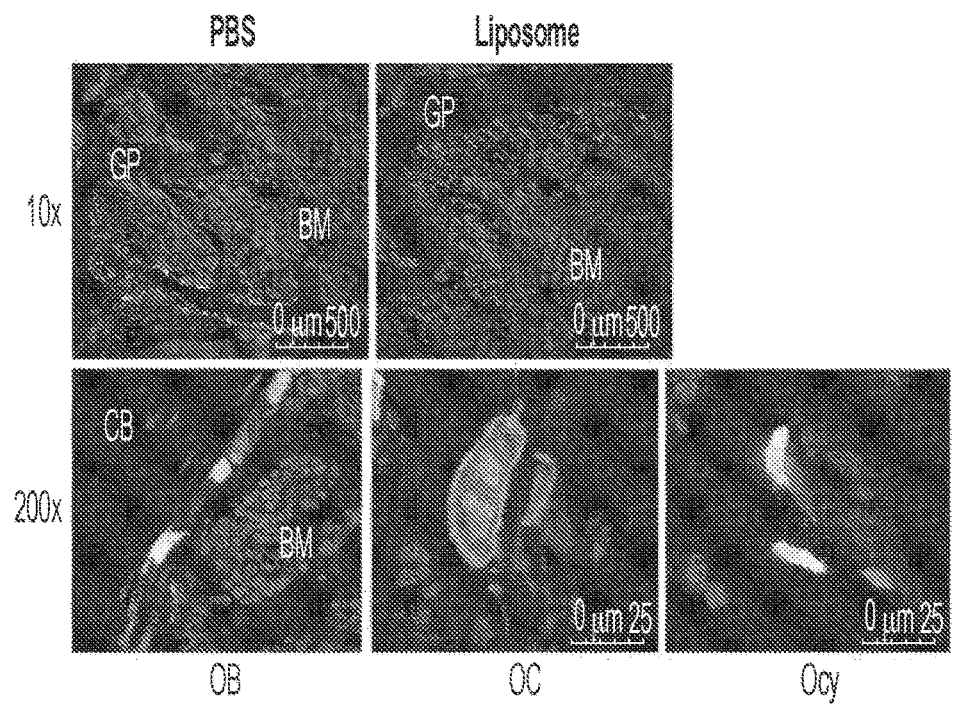
FIG. 8 shows GFP-encoding scAAV9 serotype can transduce OBs, and OCs, and OCYs on the bone surface in mice. $10^{12}$~$10^{13}$/ml genome copies of GFP-encoding scAAV9 serotype were mixed with PBS or X-tremeGENE (liposome) at 1:1 ratio. 1 hour after incubation, a single dose of the mixture was injected into knee joints of 2 month old mice (C57BL/6J). 1 A single dose of $10^{12}$~$10^{13}$/ml genome copies of GFP-encoding scAAV9 serotype was injected into knee joints of 2 month old mice (C57BL/6J) and 4 weeks later, femurs were frozen-sectioned for histology and GFP expression was viewed by a confocal microscope. High-powered pictures show scAAV9-transduced OBs, OCs, and OCYs in the femur treated with a mixture of GFP-encoding scAAV9 serotype with X-tremeGENE (bottom). GFP expression was observed in the cortical bone viewed by a phase-contrast microscope (left). GP: growth plate, TB: trabecular bone, CB: cortical bone, BM: bone marrow; Bar: 50 μm.

In addition to scAAV9, a high GFP expression in periosteal cells and a low GFP expression in osteocytes in cortical bones was observed in the treatment of scAAV5. A small population of periosteal cells expressed GFP proteins when injected with scAAV4 whereas no GFP expression was detected in the treatment of scAAV6.2 (FIG. 6B). Thus, these results indicate that scAAV9 serotype is most effective to transduce OBs and OCs on the bone surface in mice. To increase transduction efficacy of scAAV9 to bone tissue, scAAV9 was formulated with PBS or X-tremeGene 9 DNA transfection reagent (Roche), a blend of lipids with extremely low cytotoxicity, and injected into knee joints of mice (FIGS. 7 and 8). When formulated with X-tremeGene 9 (liposome), GFP proteins were highly expressed in active OBs and OCs under growth plate and on trabecular bone surface (epiphysis) as well as terminally differentiated OBs, osteocytes in cortical bones (diaphysis). However, GFP expression was markedly reduced in the muscle, indicating that X-tremeGene 9 formulation alters the in vivo tropism of scAAV9.

Development of Bone Targeting-scAAV9 (BT-scAA9) Serotype Via Genetic or Chemical Modifications of Capsid Proteins To maximize AAV-mediated gene therapy in osteoporosis, it is desirable for scAAV9 serotype to home to and accumulate on the bone surface where OBs and OCs reside. It has been observed that bone-targeting peptides, ((AspSerSer)$_6$, DSS) are effective in directing osteogenic siRNA-encapsulated liposomes to the bone-formation surface. Additional bone-targeting peptide, HABP-19 (CγEPRRγEVAγ-ELγEPRRγEVAγEL; SEQ ID NO: 17) has been reported to selectively bind to the bone hydroxyapatite in the culture as well as in mice. HABP-19 is a biomimic of osteocalcin, the most abundant non-collagenous protein secreted from OBs. γ (Gla residue)-carboxylated glutamic acid (Glu) is derived from Glu by vitamin K-dependent γ-carboxylation.

Figure 9:
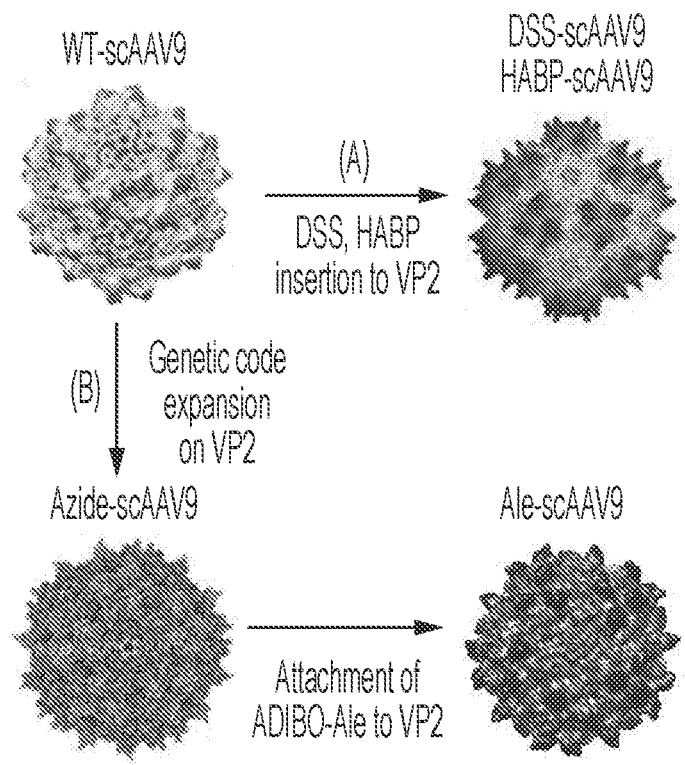
FIG. 9 shows development of bone-seeking AAV vectors. (A) Bone-targeting peptides, DSS ((AspSerSer)$_6$ or HABP) or (CγEPRRγEVAγELγEPRRγEVAγEL) are inserted into the VP2 capsid protein via a genetic manipulation. (B) WT AAV vector are site-specifically labeled with azide-bearing amino acids and then attached with a bone-seeking molecule (ADIBO-Ale).
Figure 10:
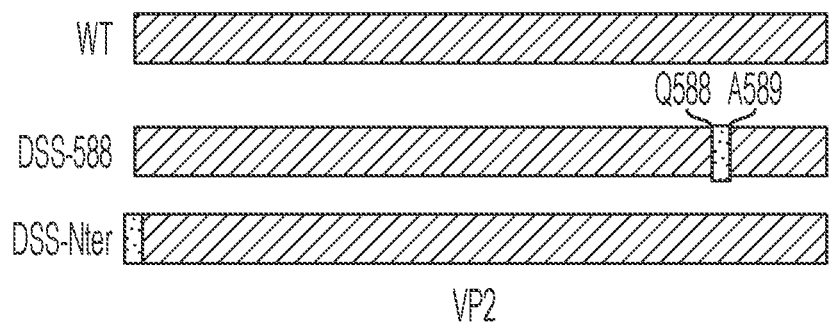
FIG. 10 shows a diagram depicting the VP2 capsid protein with bone-targeting peptides, (box; (AspSerSer)$_6$, DSS). DSS are inserted into between Q588 and A589 or the N-terminus of the VP2 capsid protein via a genetic manipulation.

This example describes inserting bone-targeting peptides into AAV capsids in order to direct engineered scAAV9 serotype to the bone (FIG. 9A, DSS-scAAV9, HABP-scAAV9). The DNA sequences encoding (AspSerSer)$_6$ (SEQ ID NO: 16) are inserted into the capsid protein VP2 open reading frame (ORF) between glutamine 587 and alanine 588 (DSS-587), between glutamine 588 and arginine 589 (DSS-588) or N-terminus of VP2-ORF (DSS-Nter) using a standard cloning method (FIGS. 10 and 26). Additionally, AAV capsids conjugated to a validated bone-seeking molecule via a chemical reaction (FIG. 9B) are produced. It has been observed that attachment of a bone-seeking molecule (ADIBO-Ale) to azide moieties on the cell surface significantly enhanced the ability of non-bone cells (e.g., Jurkat T leukemia line) to bind to bone fragments.

Figure 35A:
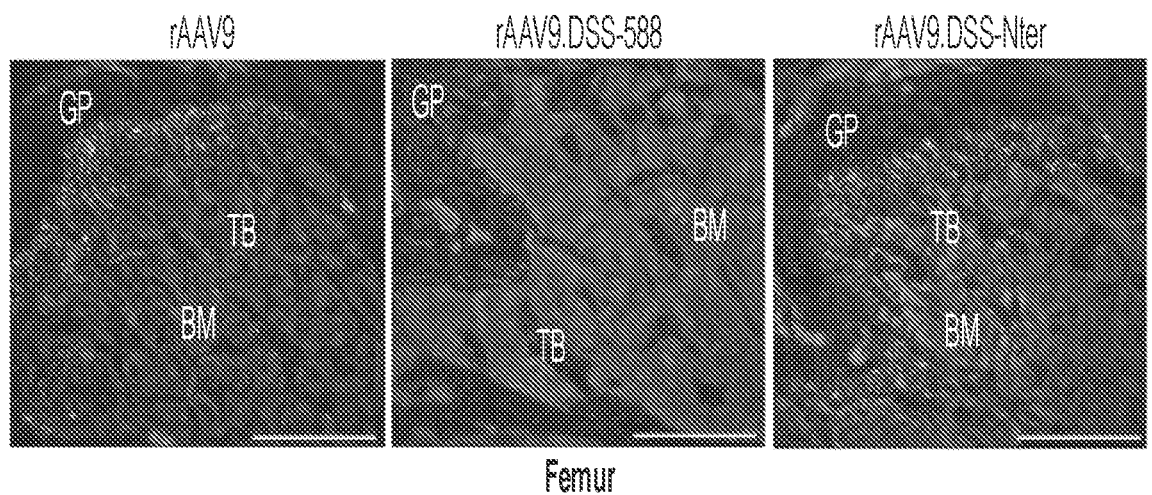
Figure 35B:
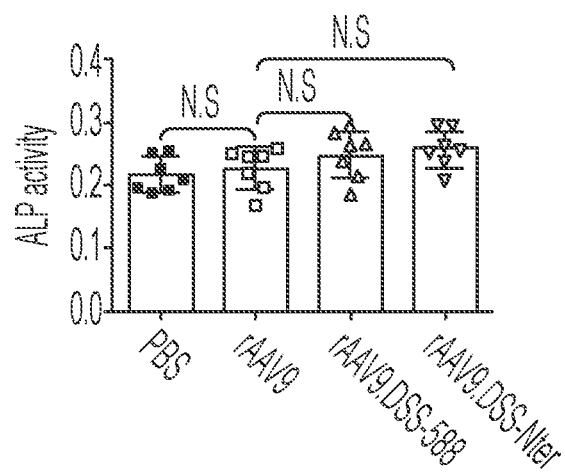

To examine whether the DSS insertion affects infectivity of scAAV9, vectors packaged into prototypical AAV9, AAV9.DSS-587, or AAV9.DSS-Nter capsids were infected into COBs, and EGFP expression was assessed by immunoblotting or by fluorescence microscopy (FIG. 29). Compared to scAAV9, the scAAV9.-DSS-Nter showed a modest reduction in infectivity at lower MOI ($10^9$ GC/mL), whereas little EGFP expression was detected in COBs treated with scAAV9.DSS-587 (FIG. 29). Similarly, when treating mice via i.a. injections, scAAV9, and scAAV9.DSS-Nter strongly transduced femurs as before (FIG. 35). In contrast, the scAAV9.DSS-587 yielded little to no transgene expression. Additionally, alkaline phosphatase (ALP) activity and expression of osteogenic genes were comparable in COBs treated with scAAV9 and scAAV9.DSS vectors, indicating no adverse effects by scAAVs on osteoblast differentiation (FIGS. 29 and 35).

Engineered scAAV9 serotype (Ale-scAAV9), which is decorated with the bone-targeting molecule on the capsid proteins, is tested. In order to create azide-bearing amino acids on AAV capsid proteins, asparagine 587 in the VP3 capsid protein is changed to the amber codon (TAG) or this amber codon is inserted between asparagine 587 and arginine 588. Together with these mutant VP3 plasmids, pHelper, pAAV-GFP, and pPyIRS/tRNACUA are transiently transfected into AAV-293 packaging cells at a molar ratio of 1:1:1:2 using a DNA transfection reagent. Six hours later, the medium is replaced with fresh medium containing 1 mM N-2-azideoethyloxycarbonyl-L-lysine (NAEK) and 72 hours later, scAAV9 serotype with azide-bearing amino acids (Azide-scAAV9) is harvested from the transfected cells. The orthogonal amber suppressor aminoacyl-tRNA synthetase/tRNA-CUA pairs expressed from the pPyIRS/tRNACUA plasmid synthesize an azide-bearing unnatural amino acid at the site of amber codon in the presence of NAEK.

Expression of the azide moiety-containing VP3 mutants is confirmed by immunoblotting with anti-VP3 antibody. Once confirmed, the ability of Azide-scAAV9 serotype to transduce OBs or OCs is assessed by monitoring GFP expression. Primary mouse OBs are treated with GFP-encoding Azide-scAAV9 serotype and GFP expression is assessed by epifluorescence microscopy. Additionally, these scAAV9 serotypes are used for infection of mouse BM-MO (OC precursors) in the presence of M-CSF and Rank ligand. Their transduction efficiency is compared with GFP-encoding WT-scAAV9 serotype.

Next, bone-targeting scAAV9 serotype (Ale-scAAV9) is produced by cross-linking the bone-seeking molecule (ADIBO-Ale) to azide-bearing amino acids in the VP3 capsid proteins of the Azide-scAAV9 serotype via a click chemistry. Azide-scAAV9 serotype is incubated with different concentrations of ADIBO-Ale (FutureChem) at room temperature and 2 hours later, unbound ADIBO-Ale is removed using dialysis. The ability of Ale-scAAV9 serotype to transduce primary OBs or OCs is examined by monitoring GFP expression.

Validation of DSS-scAAV9 Transduction to Bone Cells and Tissue

Figure 11A:
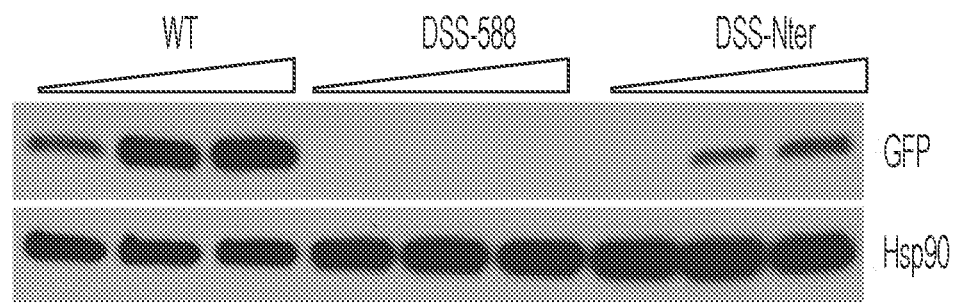
FIGS. 11A-11C show in vitro characterization of DSS-scAAV9s in OBs. Mouse OB precursors were incubated with scAAV9-WT (WT) or two DSS-scAAV9s (DSS-588, DSS-Nter) for 2 days. Their transduction efficiency was analyzed by GFP expression using western blotting with anti-GFP (FIG. 11A) and epifluorescence (FIG. 11B, left). Hsp90 was used as a loading control. Alternatively, transduced OBs were cultured under OB differentiation conditions for 6 days and OB differentiation was assessed by alkaline phosphatase (ALK) staining (FIG. 11B, right) and OB gene expression by RT-PCR (normalized to Hprt, FIG. 11C). N.S.: not significant.
Figure 11B:
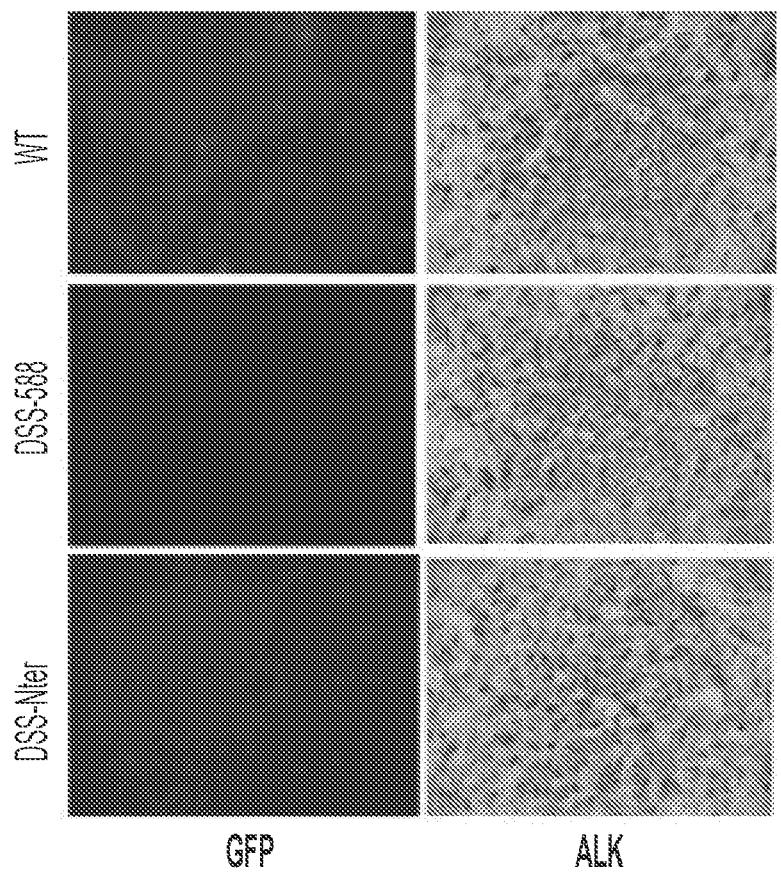
Figure 11C:
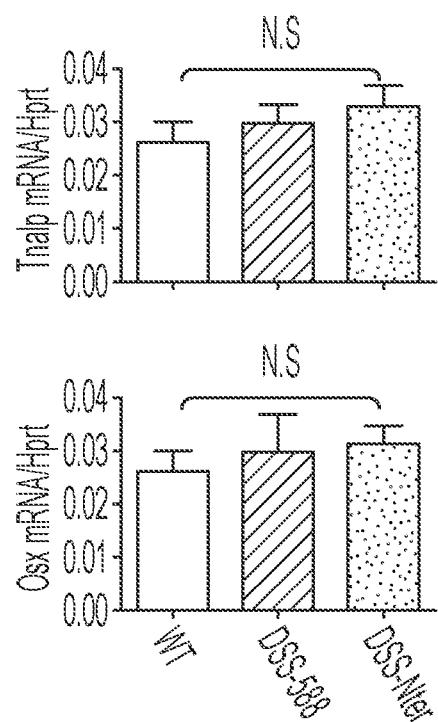
Figure 12A:
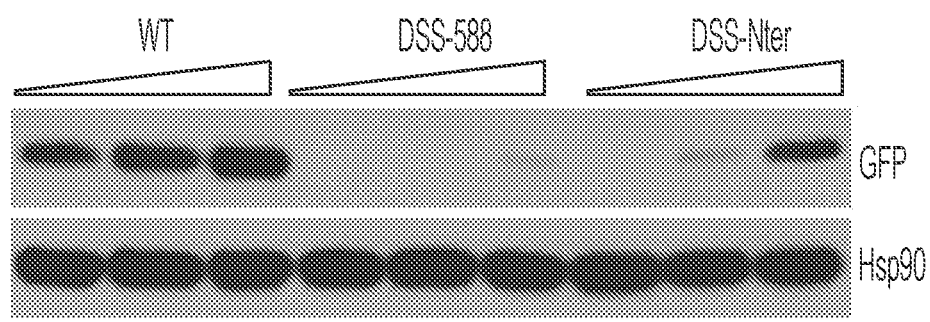
FIGS. 12A-12C show in vitro characterization of DSS-scAAV9s in OCs. 2 days after the treatment with mouse Rank ligand (5 ng/ml), Raw264.7 were treated with scAAV9-WT (WT) or two DSS-scAAV9s (DSS-588, DSS-Nter). 2 days after transduction, their transduction efficiency was analyzed by GFP expression using western blotting with anti-GFP antibody (FIG. 12A) using epifluorescence (FIG. 12B, left). Transduced OCs were cultured in the presence of Rank ligand and 3 days later, OC differentiation was assessed by TRAP staining (FIG. 12B, right) and OC gene expression by RT-PCR (normalized to Hprt, FIG. 12C). N.S: not significant.
Figure 12B:
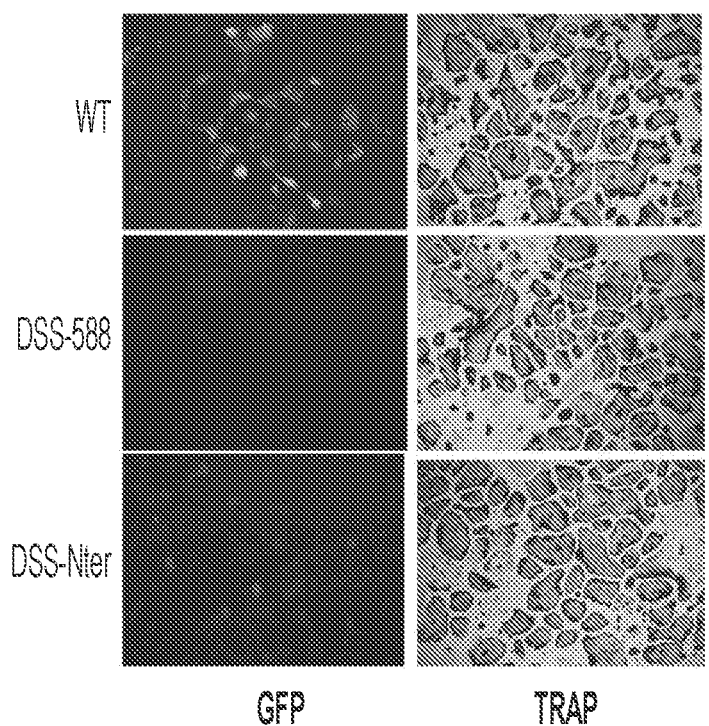
Figure 12C:
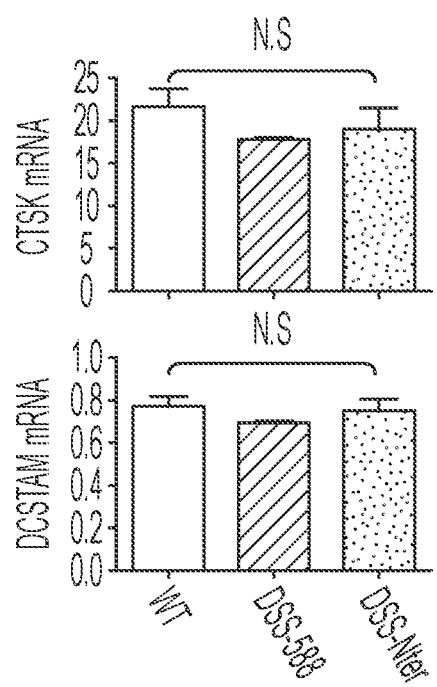

It has been previously reported that when peptides are inefficiently or inappropriately fused into AAV capsids, the transduction efficiency of AAV can be markedly reduced. To test effects of the DSS peptide insertion on the ability of scAAV9 to transduce to OBs and OCs, mouse OB and OC precursors were treated with different doses of GFP-encoding scAAV9s (WT-, DSS-588, DSS-Nter). 2 days later, GFP expression was analyzed by western blotting using anti-GFP antibody and by epifluorescence microscopy. As seen in FIGS. 11 and 12 (A and B-left), little or no expression of GFP proteins was detected in both OBs and OCs when treated with the DSS-588. By contrast, compared with WT-scAAV9, treatment of DSS-Nter scAAV9 showed a decrease in GFP expression in OBs and OCs and, its expression was increased in a dose-dependent manner. Differentiation of OBs (FIGS. 11B-right and 11C) and OCs (FIGS. 12B-right and 12C) is normal in the treatment of these scAAV9, demonstrating that scAAV9 transduction does not affect OB and OC function.

Figure 13:
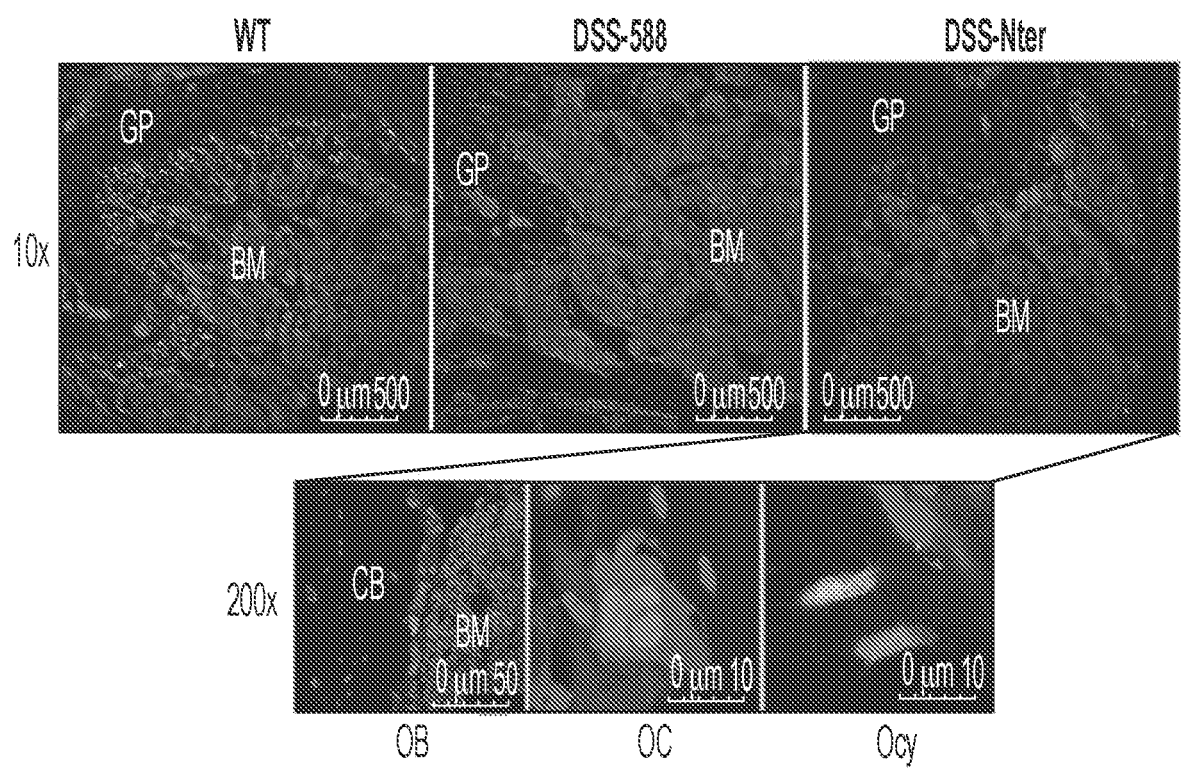
FIG. 13 shows that DSS-scAAV9 (Nter) can transduce OBs, OCs, and OCYs on the bone surface in mice. 1011~1012/ml genome copies of GFP-encoding scAAV9-WT (WT) or two DSS-scAAV9s (DSS-588, DSS-Nter) were mixed with X-tremeGENE (liposome) at 1:1 ratio. 1 hour after incubation, a single dose of the mixture was injected into knee joints of 2 month old mice (C57BL/6J). 1 week later, femurs were frozen-sectioned for histology and GFP expression was viewed by a confocal microscope. High-powered pictures show scAAV9-transduced OBs, OCs, and OCYs in the femur treated with a mixture of GFP-encoding scAAV9 serotype with X-tremeGENE (bottom). GP: growth plate, CB: cortical bone, BM: bone marrow; GFP: green, DAPI: blue.

Next, the ability of DSS-scAAV9 vectors to transduce to bone cells in vivo was investigated. GFP-encoding scAAV9 vectors (WT-, DSS-588, DSS-Nter) were formulated with X-tremeGene 9 and a single dose of $10^{12}$~$10^{13}$/ml genome copies these scAAV9 vectors was injected into knee joints of 2 months old mice (C57BL/6J) 1 week later, histology was performed on frozen sections of the femur and GFP expression in OBs, OCs, and/or osteocytes was assessed using a confocal microscopy (FIG. 13). PBS injection serves as a non-GFP expressing control. Similar to in vitro experiments (FIGS. 11 and 12), little or no GFP expression was observed in the femur treated with DSS-588 scAAV9. Although a population of GFP-expressing cells were reduced compared to WT-scAAV9, DSS-Nter scAAV successfully transduced all of the bone cells, including OBs, OCs, and osteocytes.

Figure 36C:
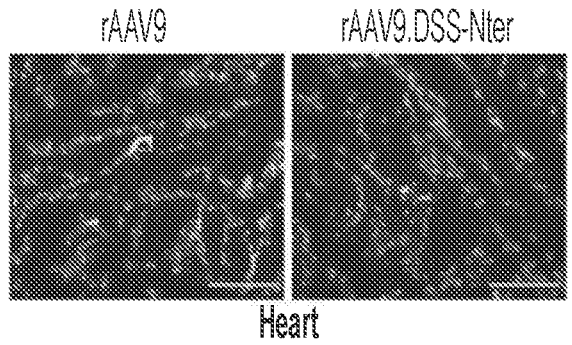
Figure 36D:
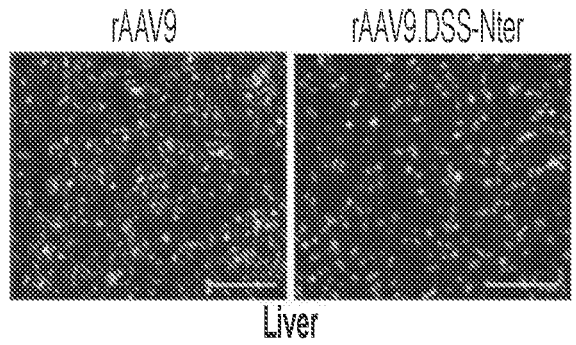
Figure 36E:
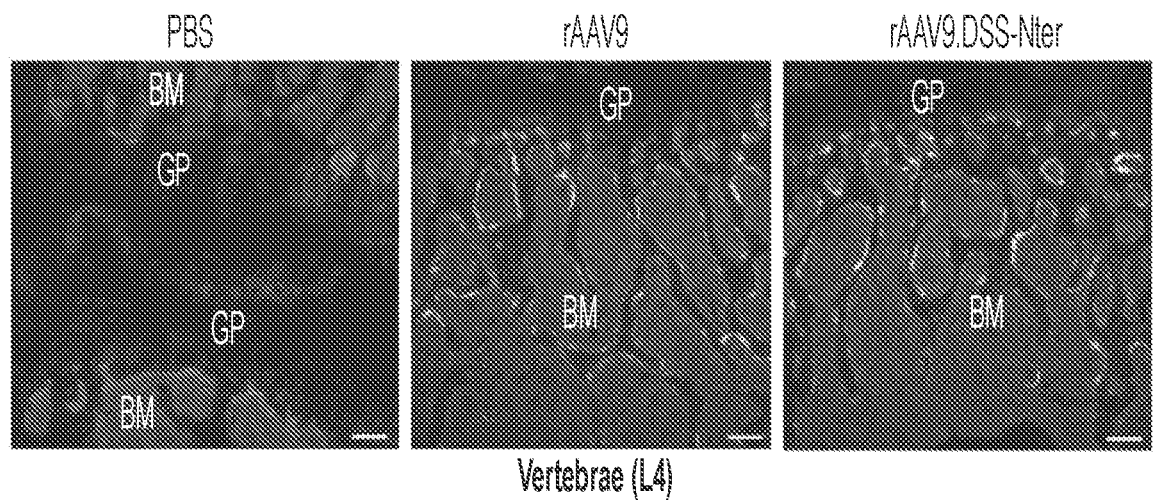

The AAV capsid was tested for bone-targeting activity in vivo. As before, scAAV9 or scAAV9-DSS-Nter was i.v. injected into two-month-old mice and tissue distributions were assessed by EGFP expression two weeks post-injection. While equivalent levels of EGFP protein were observed in the whole bodies of mice systemically treated with either scAAV9 or scAAV9-DSS-Nter (FIG. 36), mice injected with the scAAV9.DSS-Nter yielded EGFP expression levels of ~55% and ~75% of those achieved by scAAV9 in the heart and liver, respectively (FIG. 26 and FIG. 36). Importantly, expression in femurs and lumbar vertebrae were relatively comparable between treatment groups (FIGS. 26 and 36). Notably, scAAV9.DSS-Nter-treated femurs showed increased numbers of EGFP-expressing cells in comparison to scAAV9-treated femurs (FIG. 26). These results demonstrated that the engineered VP2 capsid protein fused with the bone-targeting peptide motif (DSS) improves bone-homing specificity of scAAV9 by detargeting delivery to non-skeletal tissues, and in turn, increase its tropism to the bone.

Validation of Systemic Delivery of BT-scAAV9 Serotypes for Specific Bone Transduction In Vivo To examine the ability of BT-scAAV9 serotypes to home to the bone in vivo, a single dose of $1\times10^{10}$ genome copies of GFP-encoding scAAV9 vectors (WT-, DSS- or HABP, Ale) is administered locally or systemically into mice. For local administration, these scAAV9 serotypes are injected into the knee joints of 2 months old mice (C57BL/6J) and 1 week or 4 weeks later, AAV delivery to OBs, OCs, and/or osteocytes on the bone is monitored by an IVIS-100 optical imaging system. Additionally, histology is performed on frozen sections of the femur to detect GFP-expressing OBs, OCs, and/or osteocytes transduced by these scAAV9 serotypes. PBS injection serves as a non-GFP expressing control. For systemic administration, GFP-encoding WT-, DSS-, HABP- or Ale-scAAV9 serotype are administered to mice via intravenous (IV) or intraperitoneal (IP) injection. 1 week or 4 weeks later, AAV delivery to the bone is monitored by the IVIS-100 optical imaging system and GFP-positive bones will be further frozen-sectioned for histology.

Generation of scAAV9 Vectors Encoding shRNAs Specific to Mouse Schnurri-3 (SHN3), Sclerostin (SOST), or Cathepsin K (CTSK)

Sclerosteosis is a rare genetic disorder with high bone mass, and has been observed to be associated with a loss-of-function mutation in SOST gene, the gene that encodes sclerostin. Sclerostin is secreted from osteocytes, terminally-differentiated osteoblasts, and inhibits bone formation and enhances bone resorption. Treatment with a monoclonal human anti-sclerostin antibody restores bone loss in human patients and animal models with osteoporosis by promoting bone formation and inhibiting bone resorption. However, FDA approval is currently unlikely due to an increased risk of stroke. Unlike sclerostin that inhibit osteoblast differentiation, Cathepsin K (CTSK), a lysosomal cysteine proteinase, is highly expressed in mature osteoclasts important for bone resorption. Pycnodysostosis, a rare genetic disorder with high bone mass, results from inactivating mutations in CTSK gene in humans. Treatment with a small molecule inhibitor of CTSK prevents bone loss in human patients and animal models with osteoporosis by suppressing bone resorption while limiting adverse effects on bone regeneration activity. However, it was recently withdrawn from FDA consideration due to an elevated incidence of stroke.

Figure 14:
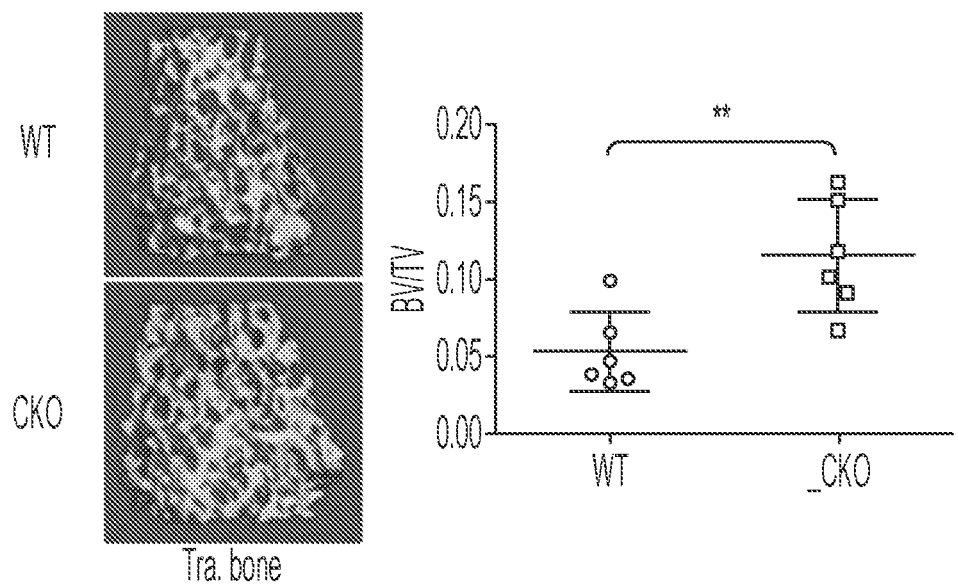
FIG. 14 shows that transient deletion of SHN3 in mature OBs increases bone mass in adult mice. 1 month-old female Shn3-fl/fl (WT) or Shn3-fl/fl; OCN/ERT-cre (CKO) mice were treated with tamoxifen (50 mg/kg) for 5 days and 6 weeks later bone mass was measured by microCT analysis. Displayed are 3D reconstructions of trabecular bones (left) and quantitative parameters are displayed in the right panel: bone volume/total volume (BV/TV). **: P, 0.005.
Figure 15:
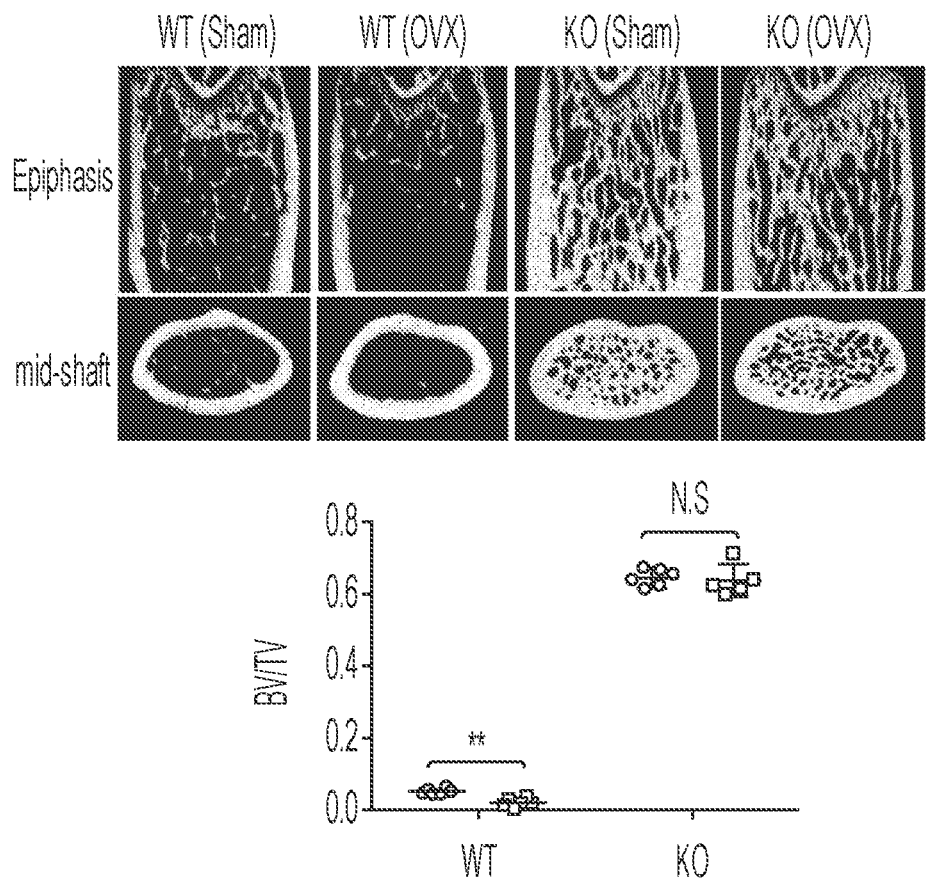
FIG. 15 shows that SHN3 deletion prevents estrogen deficiency-induced bone loss in mice. 3 month-old female mice have undergone ovariectomy (OVX) surgery or have undergone Sham surgery (Sham) and 2 month after the surgery bone mass was measured by microCT analysis. Displayed are 3D reconstructions of trabecular bones (left top) and midshaft cortical bones (left bottom). Quantitative parameters are displayed in the right panel: bone volume/total volume (BV/TV). **: P, 0.005, N.S: non-significant.

Schnurri-3 (SHN3) as a novel suppressor of osteoblast differentiation. Transient deletion of SHN3 in OBs using an inducible loxP:Cre system resulted in a significant increase in bone mass in mice, indicating that down-regulation of SHN3 expression provides an attractive therapeutic approach to restore low bone mass in osteoporosis (FIG. 14). Likewise, inhibition of SHN3 prevents bone loss in a mouse model of osteoporosis by promoting bone formation (FIG. 15). However, unlike sclerostin and CTSK, SHN3 deficiency is specific to bone and is not associated with phenotypes in non-skeletal tissues. Thus, the bone-targeting scAAV9 vectors described in Example 1 were used subsequently for vectors to silence mouse SHN3, SOST, or CTSK in OBs and/or OCs in vitro and in vivo.

Two shRNA hairpins targeting the above-noted genes (e.g., SHN3, CTSK) were adapted to surrogate mutant inverted terminal repeats (mTRs) that is required for functional self-complementary AAV vectors (e.g., mTRs) and the modified shRNA-mTR sequences are described in the Sequences section. These modified shRNA-mTRs were cloned into the pAAVscCB6-EGFP vector at the restriction enzyme sites, PstI and Bgl2, and packaged to scAAV9 capsids.

Figure 16A:
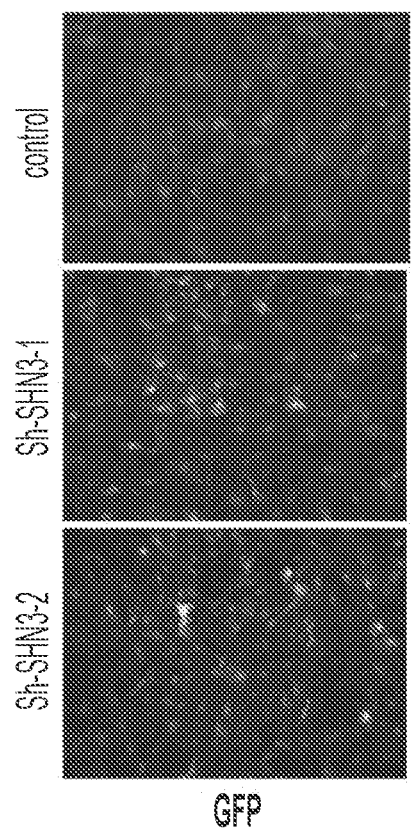
FIGS. 16A-16D show in vitro characterization of scAAV9-mSHN3i in OBs. Mouse primary calvarial OBs were treated with scAAV9 encoding-control vector (control) or two mouse -SHN3 shRNAsi (Sh-SHN3-1, -2). 3 days after transduction, their transduction efficiency (FIG. 13A) and knockdown efficiency (FIG. 13B) were analyzed by GFP expression using epifluorescence and by SHN3 mRNA levels using RT-PCR, respectively.
Figure 16B:
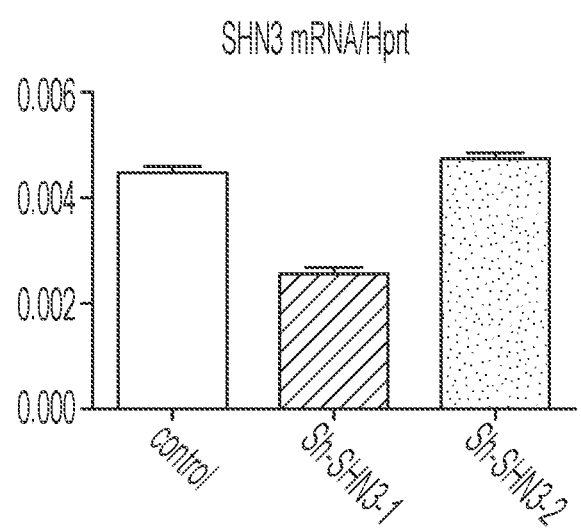
Figure 16C:
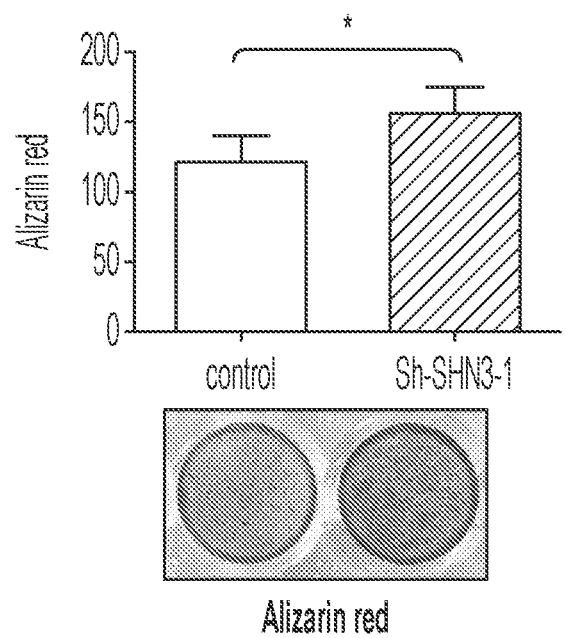
Figure 16D:
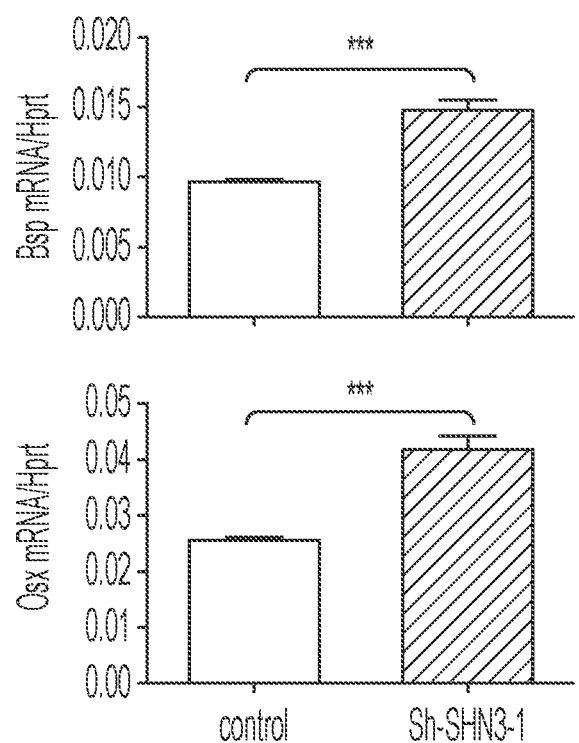

The purified scAAV9 vectors expressing two shRNA hairpins specific to mouse schnurri-3 (SHN3) and mouse cathepsin K (CTSK) (scAAV9-mSHN3i and scAAV9-mCTSKi) were produced. For in vitro characterization, infectivity, knockdown efficiency, and functional activity of scAAV9-mSHN3i and scAAV9-mCTSKi were tested in OBs and OCs, respectively. First, a single dose of $10^{12}$~$10^{13}$/ml genome copies of two scAAV9-mSHN3 is (Sh-SHN3-1, -2) or scAAV-vector control (control) were treated with mouse primary OB precursors. 2 days after transduction, GFP expression was monitored by epifluorescence microscopy and knockdown efficiency were assessed by measuring SHN3 mRNA levels using RT-PCR. OB differentiation was assessed by measuring expression of OB differentiation genes (e.g., bone sialoprotein (BSP) and osterix (OSX)) and mineralization activity by alizarin red staining at day 6 and 15 of the OB culture, respectively (FIGS. 16A-16D). Transduction of scAAV9-mSHN3 is to OBs was as effective as that of scAAV9-control. The scAAV9-mSHN3i (Sh-SHN3-1) was able to decrease SHN3 mRNA levels by 50% (FIGS. 16A-16B). SHN3 knockdown increased mineralization activity and expression of OB differentiation genes (FIGS. 16C-16D).

Figure 17A:
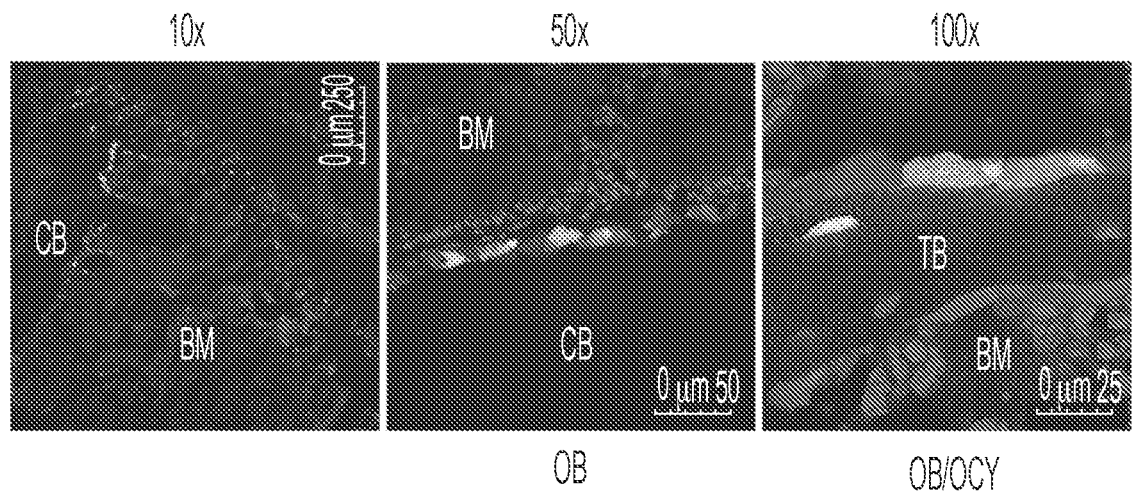
FIGS. 17A-17B show in vivo characterization of scAAV9-mSHN3i. $10^{12}$~$10^{13}$/ml genome copies of GFP-encoding scAAV9 (control, Sh-SHN3-1) were mixed with X-tremeGENE (liposome) at 1:1 ratio. 1 hour after incubation, a single dose of the mixture was injected into knee joints of 2 month old mice (C57BL/6J). 1 week later, femurs were frozen-sectioned for histology and GFP expression was viewed by a confocal microscope. High-powered pictures show GFP-expressing OBs and OCYs in the femur, demonstrating that similar to control-scAAV9 vector, Sh-SHN3-1 scAAV9 vector can transduce OBs and OCYs in the bone (FIG. 17A). Femurs were processed with mechanical and enzymatic digestion (type 2 collagenase and dispase) to dissociate BMSCs. GFP-expressing cells were further isolated from BMSCs using FACS sorting and used for RT-PCR analysis to measure SHN3 mRNA levels (FIG. 17B). CB: cortical bone, BM: bone marrow, TB: trabecular bone.
Figure 17B:
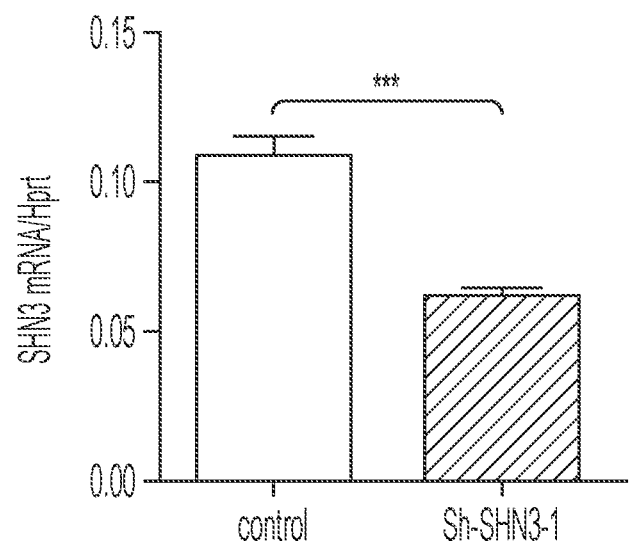

Next, transduction and knockdown efficacy of scAAV9-mSHN3i vector in vivo was examined (FIG. 17). GFP-encoding scAAV9 vector (Sh-SHN3-1) was formulated with X-tremeGene 9 and a single dose of $10^{12}$~$10^{13}$/ml genome copies of this scAAV9 vector was injected into knee joints of 2 months old mice (C57BL/6J). 1 week later, histology was performed on frozen sections of the femur and GFP expression in OBs and osteocytes was assessed using a confocal microscopy. PBS injection serves as a non-GFP expressing control. Similar to control scAAV9, GFP expression in OBs and osteocytes was observed in the femur treated with scAAV9-mSHN3i vector (FIG. 17A). Alternatively, GFP-expressing cells were isolated from the femur using FACS sorting and SHN3 mRNA levels were assessed by RT-PCR, demonstrating 50% reduction in SHN3 mRNA levels by transduction of scAAV9-Sh-SHN3-1 vector (FIG. 17B).

Figure 18A:
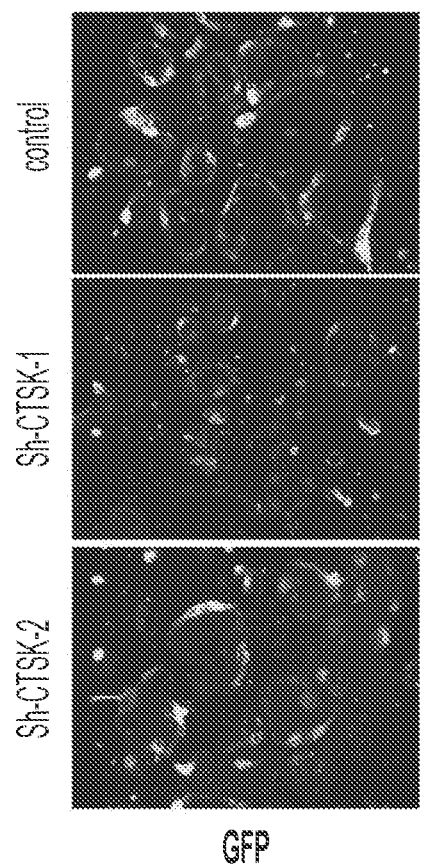
FIGS. 18A-18D show in vitro characterization of scAAV9-mCTSKi in OCs. 2 days after the treatment with mouse Rank ligand (5 ng/ml), Raw264.7 were treated with scAAV9-control (control) or two scAAV9-mCTSKi (Sh-CTSK-1, -2). 2 days after transduction, their transduction efficiency (FIG. 18A) and knockdown efficiency (FIG. 18B) were analyzed by GFP expression using epifluorescence and by CTSK mRNA levels using RT-PCR, respectively.
Figure 18B:
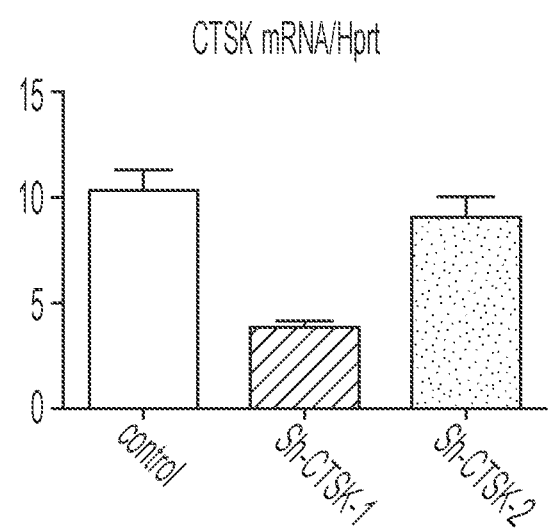
Figure 18C:
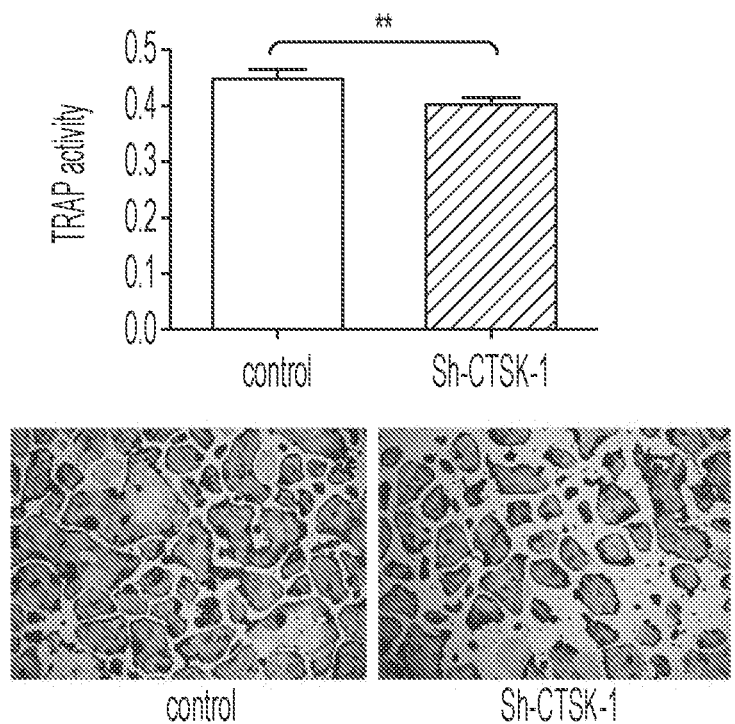
Figure 18D:
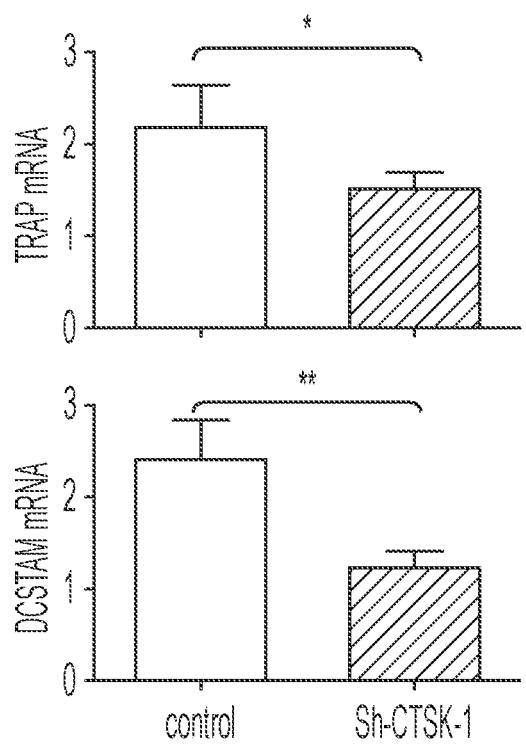
Figure 19A:
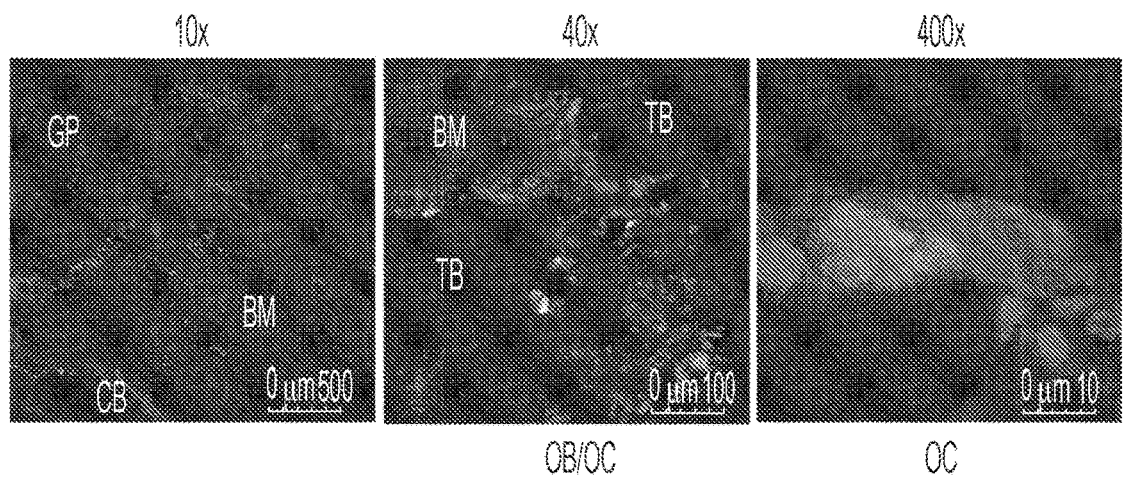
FIGS. 19A-19B show in vivo characterization of scAAV9-mCTSKi. $10^{12}$~$10^{13}$/ml genome copies of GFP-encoding scAAV9 (control, Sh-CTSK-1) were mixed with X-tremeGENE (liposome) at 1:1 ratio. 1 hour after incubation, a single dose of the mixture was injected into knee joints of 2 month old mice (C57BL/6J). 1 week later, femurs were frozen-sectioned for histology and GFP expression was viewed by a confocal microscope. High-powered pictures show scAAV9-transduced OBs and OCs in the femur (FIG. 19A). Frozen-sectioned femurs were stained with anti-CTSK antibody to assess CTSK expression in GFP-expressing OCs. IgG antibody was used as a negative control. High-powered pictures show a reduced expression of CTSK in GFP-expressing OCs transduced with scAAV9-mCTSKi (FIG. 19B). GP: growth plate, CB: cortical bone, BM: bone marrow, TB: trabecular bone; GFP: green, DAPI: blue, CTSK: red.
Figure 19B:
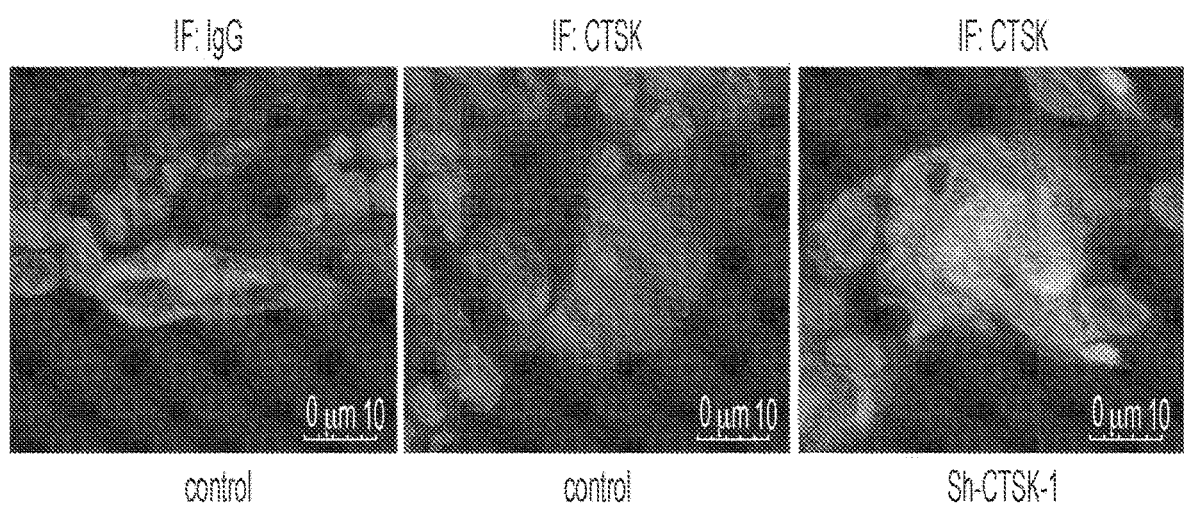

Additionally, infectivity, knockdown efficiency, and functional activity of scAAV9-mCTSKi was also investigated in mouse OCs. To obtain OC precursors, mouse monocyte line, Raw264.7 were treated with Rank ligand (5 ng/ml) for 2 days. Subsequently, these OC precursors were treated with a single dose of $10^{12}$~$10^{13}$/ml genome copies of two scAAV9-mCTSKis (Sh-CTSK-1, -2) or scAAV-vector control (control) for 2 days. Transduction efficiency was assessed by GFP expression using epifluorescence microscopy (FIGS. 18A-18D) and knockdown efficiency were assessed by measuring CTSK mRNA levels using RT-PCR (FIG. 18B). Additionally, OC differentiation was assessed by measuring TRAP enzymatic activity, multi-nucleation of TRAP-stained OCs, and expression of OC differentiation genes (e.g., dendritic cell-specific transmembrane protein (DC-STAMP) and TRAP) (FIGS. 18C and 18D). Transduction of scAAV9-mCTSKis to OC precursors was as effective as that of scAAV9-control. The scAAV9-mCTSKi (Sh-CTSK-1) was able to decrease CTSK mRNA levels by 70% (FIGS. 18A-18B). CTSK knockdown resulted in a mild decrease in OC differentiation (FIGS. 18C-18D). To examine the ability of scAAV9-mCTSKi vector to transduce to OCs in vivo, a single dose of $10^{12}$~$10^{13}$/ml genome copies of formulation of GFP-encoding scAAV9 vector (Sh-CTSK-1) with X-tremeGene 9 was injected into knee joints of 2 months old mice (C57BL/6J). Immunofluorescence analysis to GFP and CTSK expression confirmed that both of control-scAAV9 and, scAAV9-mCTSKi vectors can transduce OCs on the bone surface in vivo (FIG. 19A). CTSK expression was markedly reduced in GFP-expressing OCs only when transduced with scAAV9-mCTSKi vector (FIG. 19B).

Knockdown efficiency of the pAAVscCB6 vector encoding two shRNA hairpins specific to mouse sclerostin (SOST) shRNAs (scAAV9-mSOSTi) was validated in GFP-DMP1-expressing osteocyte line with high expression of sclerostin. Once generated, a single dose of $10^{12}$~$10^{13}$/ml genome copies of two scAAV9-mCTSKi or scAAV9-vector control (control) is injected into a mouse osteocyte line with high expression of sclerostin. 2 days after transduction, GFP expression is assessed by Western blotting, and the knockdown efficiency is assessed by measuring SOST mRNA levels using RT-PCR.

Figure 20:
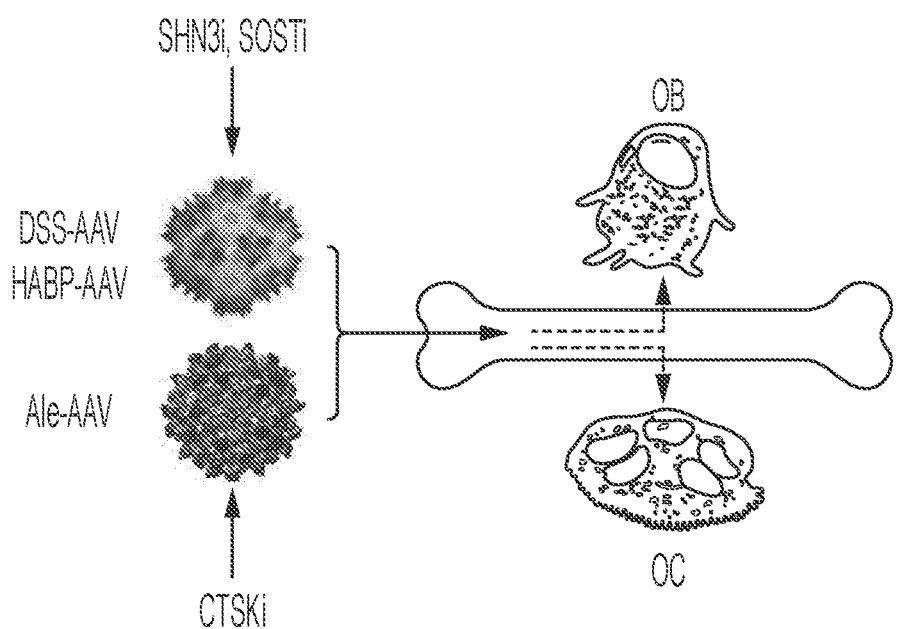
FIG. 20 shows a strategy of bone-targeting scAAV9-mediated gene silencing. ShRNAs specific to OB genes (SHN3i, SOSTi) or to OC gene (CTSKi) are cloned into BT-scAAV9 serotypes (DSS or HABP-scAAV9, Ale-scAAV9). These scAAV9 serotypes are injected into the intramedullary femur of mice for local delivery. For systemic delivery, they are IP or IV injected into mice in order to silence expression of SHN3 or SOST in OBs or osteocytes or to silence CTSK expression in OCs on the bone surface.

Development of Gene Therapeutics for Osteoporosis Using BT-AAV-Mediated Gene Silencing This example describes testing of functional efficacy of the scAAV9 serotypes encoding shRNA hairpins specific to mouse SHN3, SOST, CTSK (SHN3i, SOSTi, CTSKi). shRNA hairpins are cloned into GFP-encoding AAV vectors and packaged into the BT-AAV capsids (DSS-scAAV9, Ale-scAAV9) (FIG. 20). As a negative control, control ShRNA (cont-i) is cloned into the AAV vector. BT-AAV serotypes encoding cont-i, SHN3i, or SOSTi are transduced into primary mouse OBs and 3 days later, knockdown efficiency of SOST or SHN3 is assessed by quantitative PCR. Mouse primary OC precursors are transduced by BT-AAV serotypes encoding cont-i or CTSKi and cultured in the presence of M-CSF and RANK ligand. Three days after the transduction, knockdown efficiency of CTSK is analyzed by quantitative PCR, and 6 days later the ability of CSTK silencing to inhibit OC differentiation is assessed.

To examine the ability of these gene therapeutics to prevent bone loss in mouse models of osteoporosis, 4 weeks after sham or OVX surgery, 4-months-old female mice (C57BL/6J, n=12 mice/group) are IV or IP injected with a single dose of $1 \times 10^{12}$ genome copies of these BT-scAAV9 serotypes. Alternatively, 22-months-old female mice (C57BL/6J, n=12 mice/group) are IV or IP injected. As a negative control, GFP-encoding scAAV9 vector with control shRNA (cont-i) is administered into these mice. Two months after treatment, mice are labeled with calcein and alizarin red and subjected to dynamic histomorphometry in order to assess the number of OBs and OCs, bone formation rate, and OC resorption activity in vivo. In order to locate GFP-expressing scAAV9-transduced cells, IVIS-100 optical imaging is performed in a whole body. GFP-expressing tissues are further processed for histology on frozen sections. Furthermore, scAAV9-transduced OBs and/or OCs that express GFP proteins are isolated from long bones using FACS sorting, and SOST, SHN3, or CTSK mRNA levels are assessed by quantitative PCR. For skeletal analysis, microCT of long bones and vertebrae is performed to analyze bone mass and structure.

Additionally, histologic sections are stained with tartrate-resistant acid phosphatase (TRAP) as a marker of OC differentiation and immunohistochemistry (IHC) for type I Collagen α1 (Col1) and Runx2 as markers of OB differentiation. This analysis is accompanied by quantitative PCR analysis of bone RNA measuring expression of OB differentiation genes. Lastly, as in human patients with osteoporosis, systemic OB and OC activity is analyzed by measuring the levels of serum bone turnover markers, including type I collagen C-terminal telopeptide (CTX), N-terminal propeptide of type 1 procollagen (P1NP), and bone-specific alkaline phosphatase (BSAP) using ELISAs.

Example 2: Development of Novel Gene Therapeutics for Osteoporosis Using AAV-Mediated Gene Addition Intermittent treatment of recombinant PTH peptides (1-34 aa) or recombinant PTHrP peptides (1-36 aa) via subcutaneous injection, in some embodiments, increases OB activity and promotes bone formation in human patients and animal models with osteoporosis. These peptides (teriparatide, abaloparatide) are FDA-approved and currently used for human patients with osteoporosis. In some embodiments, secretary factor DJ-1 functions as a mediator of the cross-talk between OBs and endothelial cells. Treatment with DJ-1, in some embodiments, promotes OB differentiation in human MSCs and angiogenesis in human endothelial cells while it suppresses OC differentiation.

Figure 21:
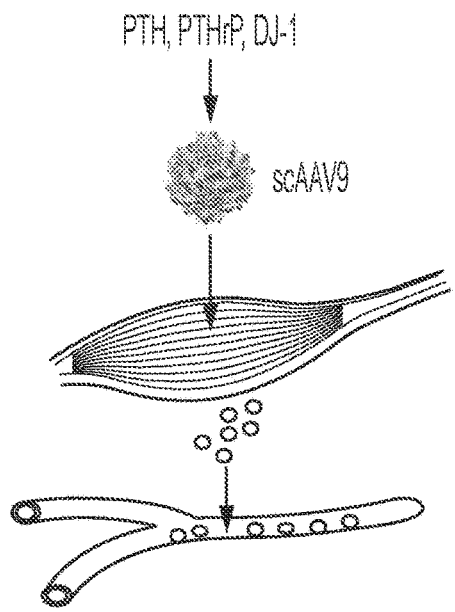
FIG. 21 shows AAV-mediated gene addition for systemic production. Human PTH (1-84 aa), human PTHrP (1-140 aa), or mouse DJ-1 cDNA was cloned into scAAV9 vectors and they are intramuscularly injected to mice for systemic expression.
Figure 22A:
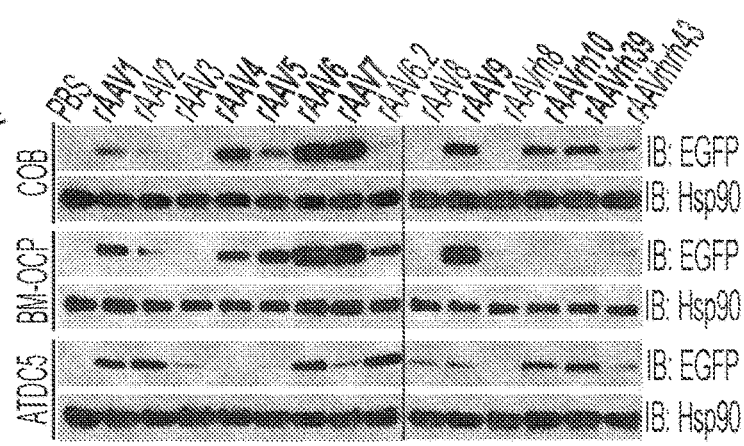
FIGS. 22A-22G shows scAAV vectors that transduce bone cells in vitro and in vivo.
Figure 22B:
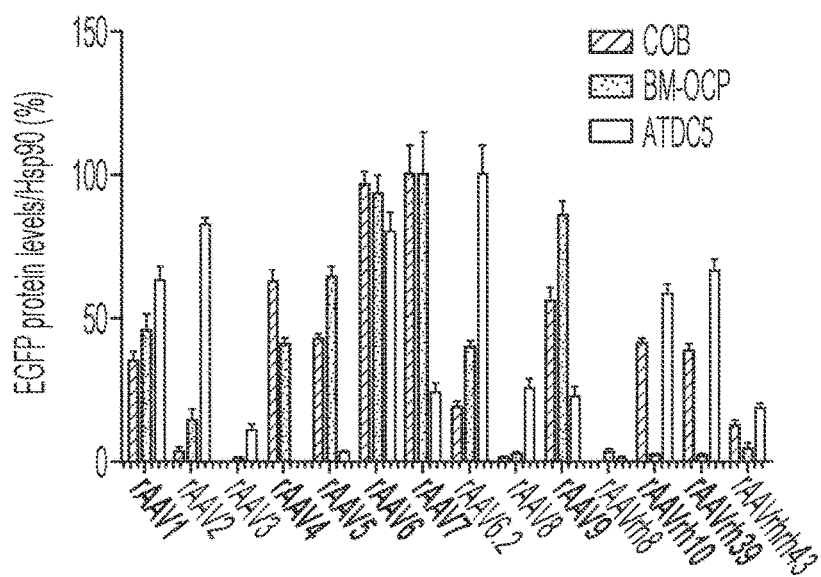
Figures 22C, 22D, 22E:
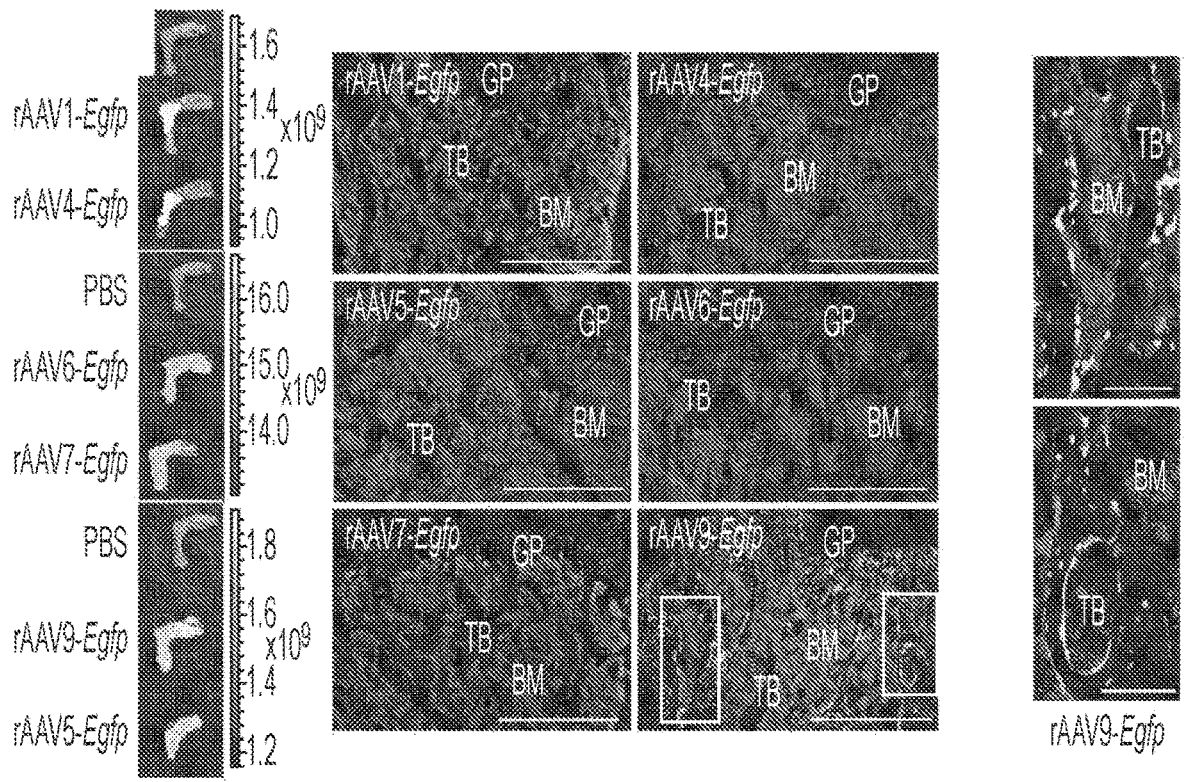
Figures 22F, 22G:
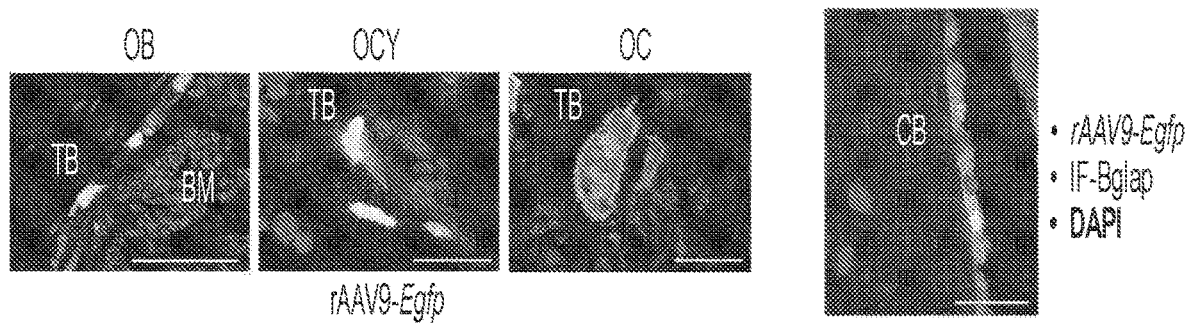
Figures 23A, 23B:
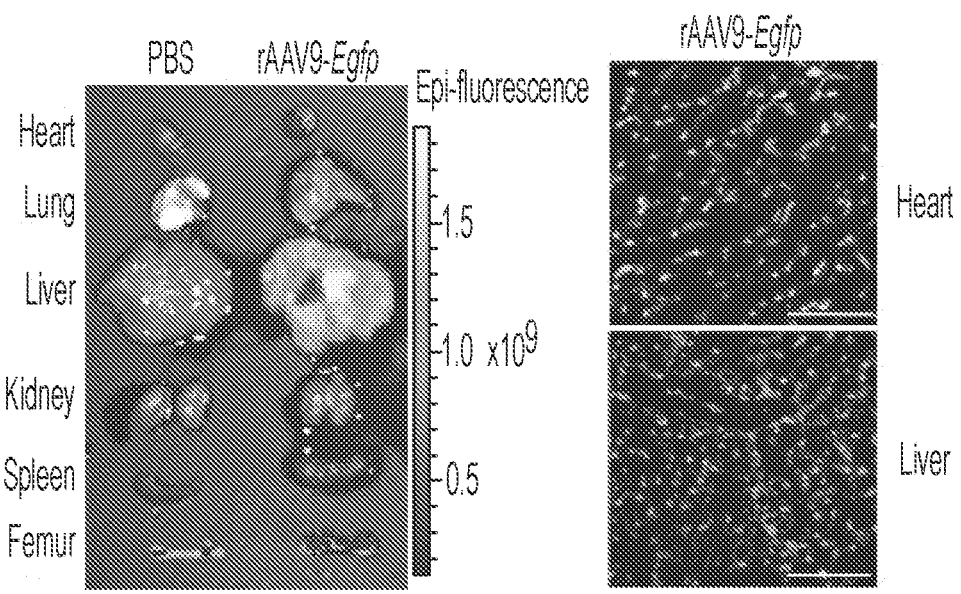
Figure 23C:
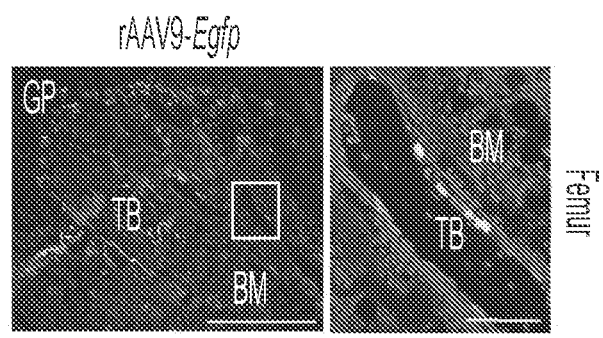
Figure 23D:
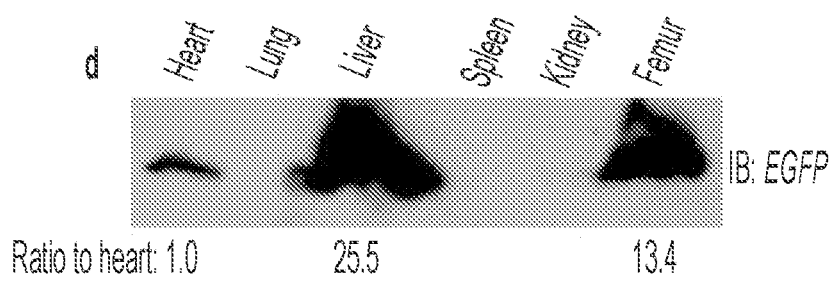
Figure 23I:
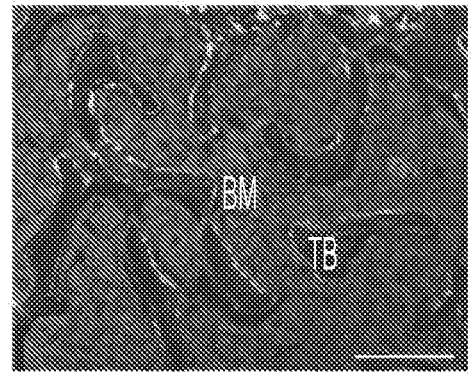
Figure 23J:
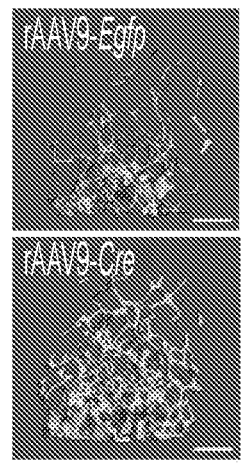
Figure 23K:
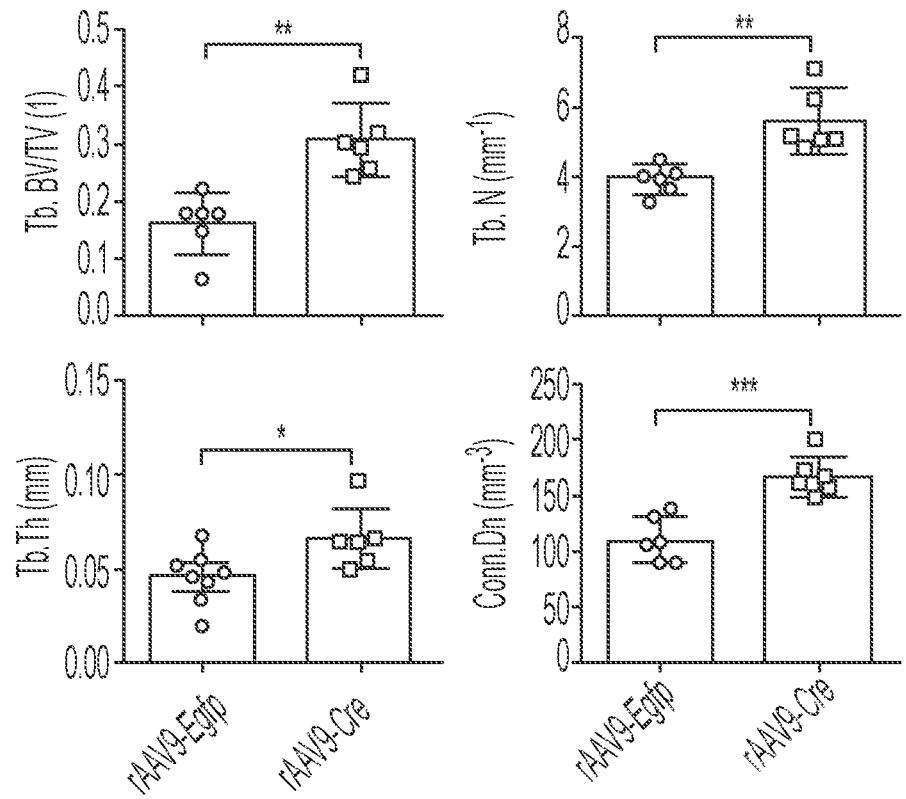
Figure 24A:
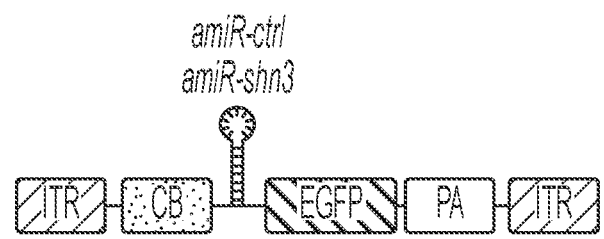
FIGS. 24A-24K show the silencing of SHN3 by systematically delivered AAV9 promotes bone formation.
Figure 24B:
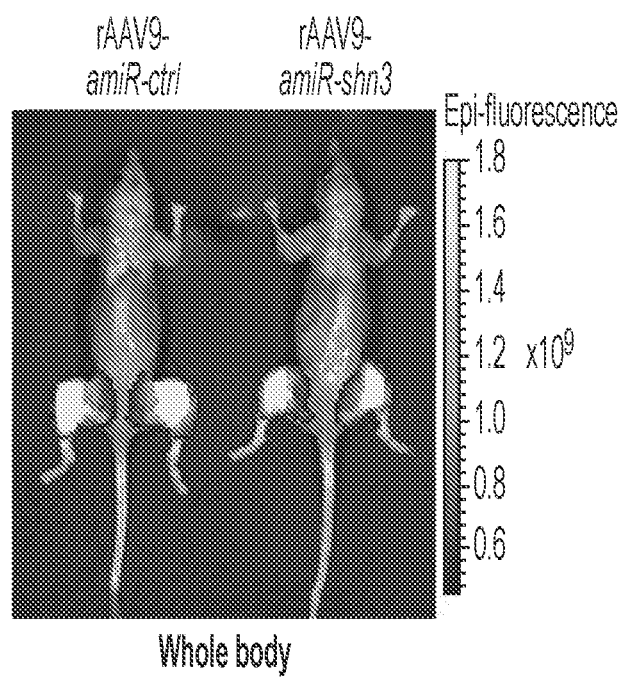
Figure 24C:
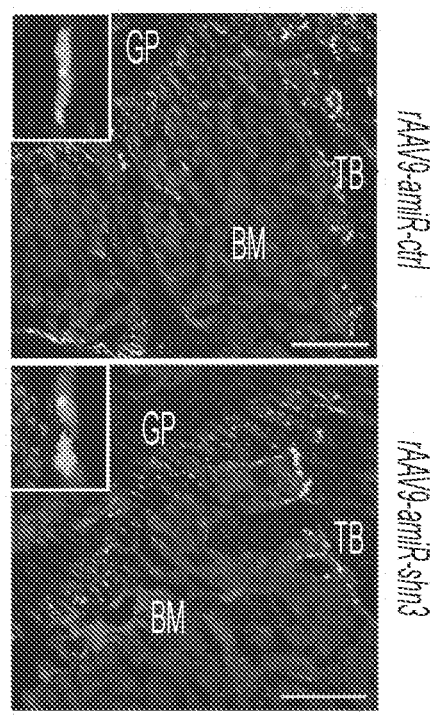
Figure 24D:
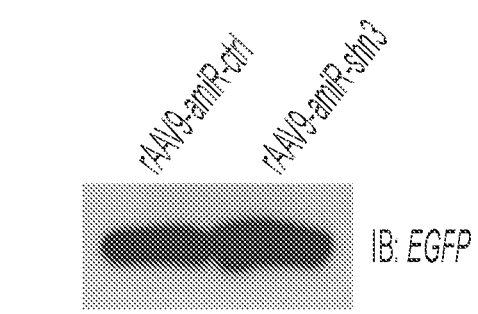
Figure 24D:
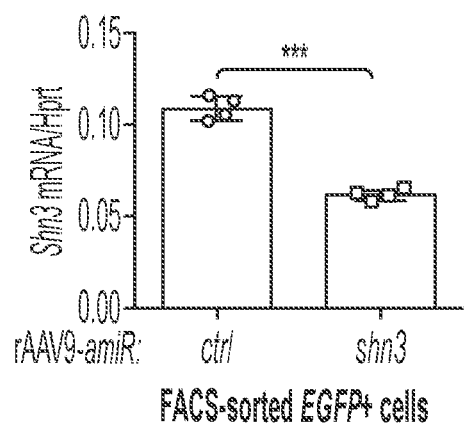
Figure 24E:
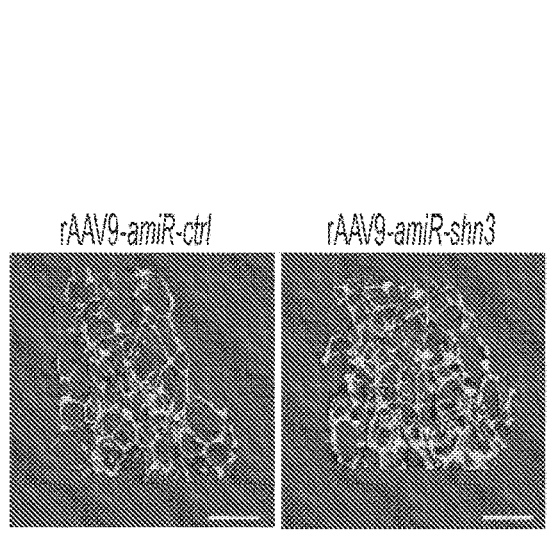
Figure 24F:
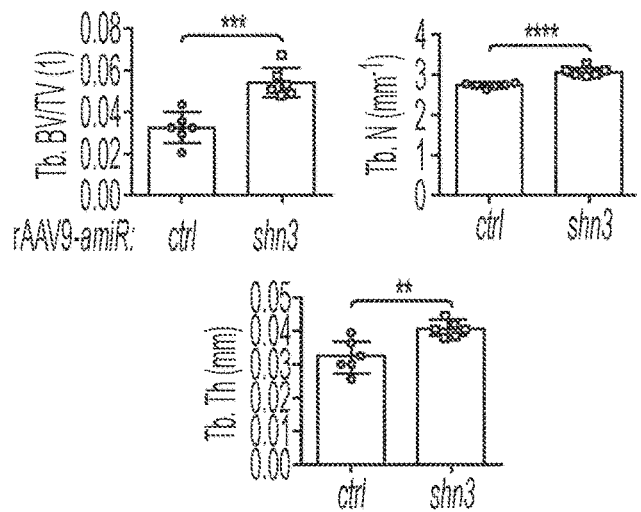
Figure 24G:
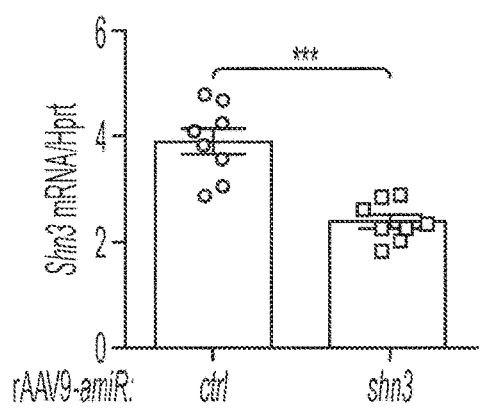
Figure 24H:
Figure 24I:
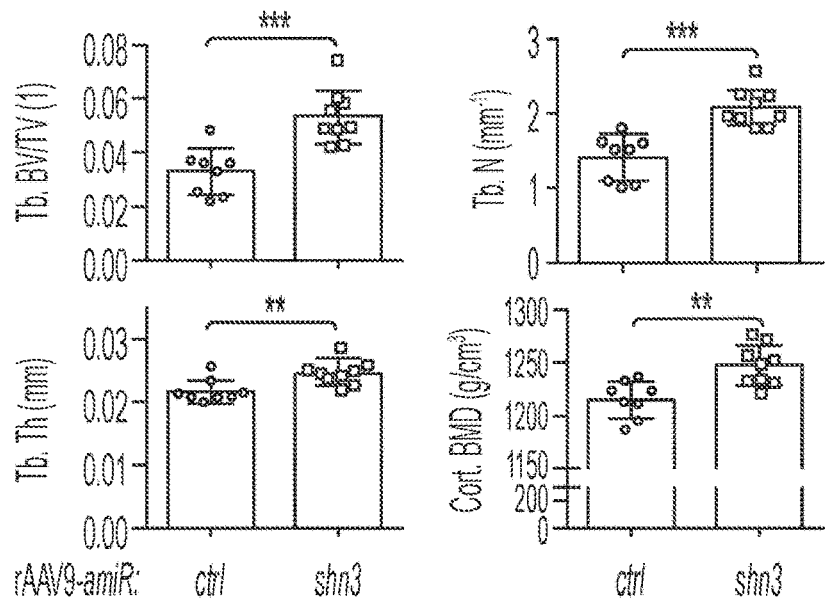
Figure 24J:
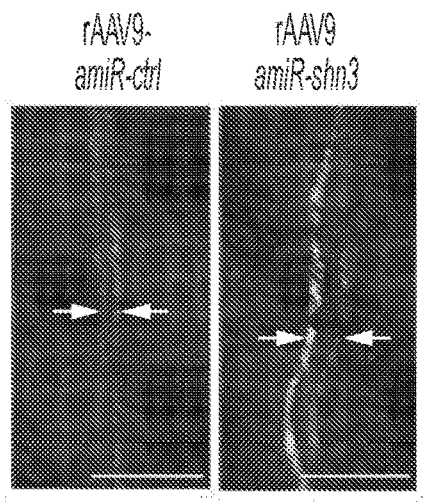
Figure 24K:
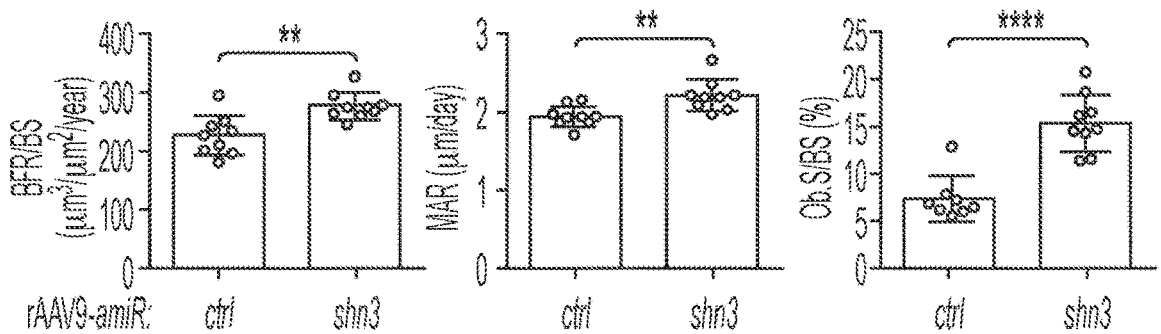
Figure 25A:
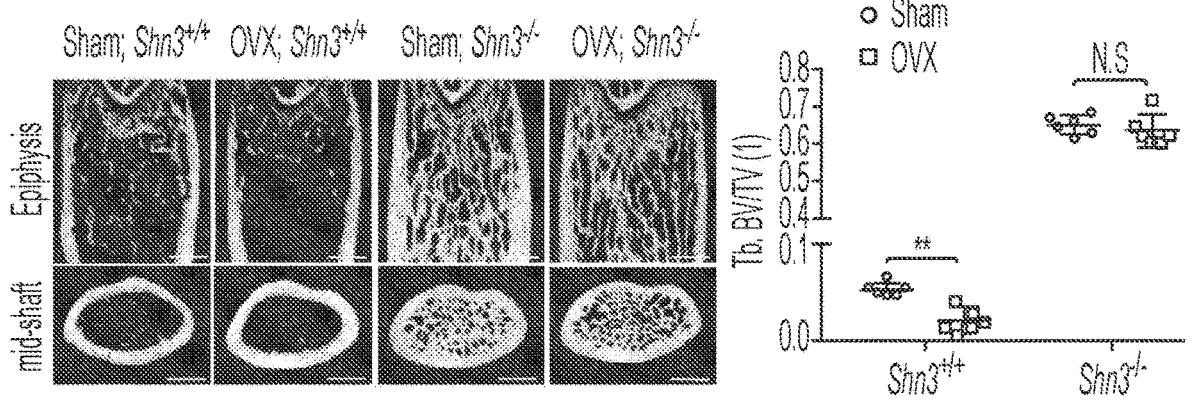
Figure 25B:
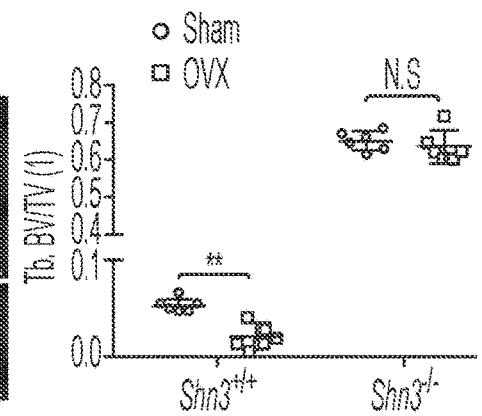
Figure 25C:
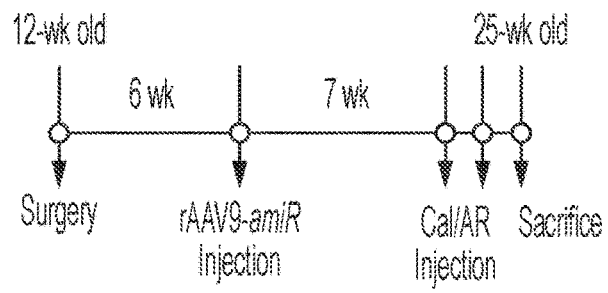
Figure 25D:
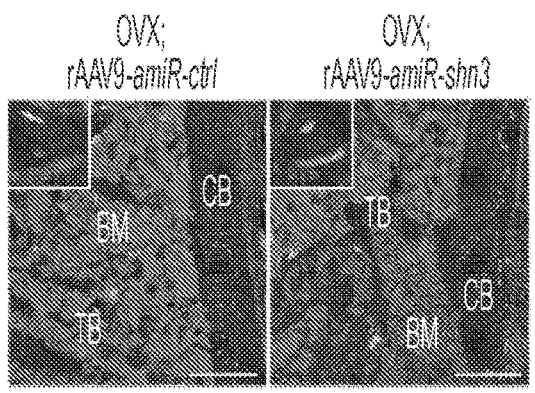
Figure 25E:
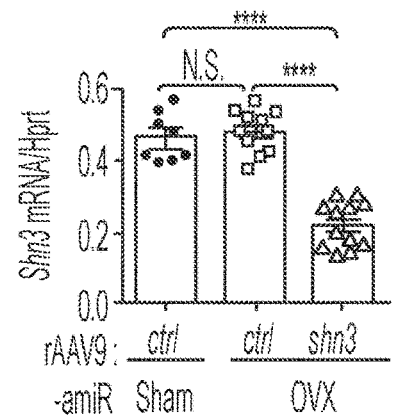
Figure 25J:
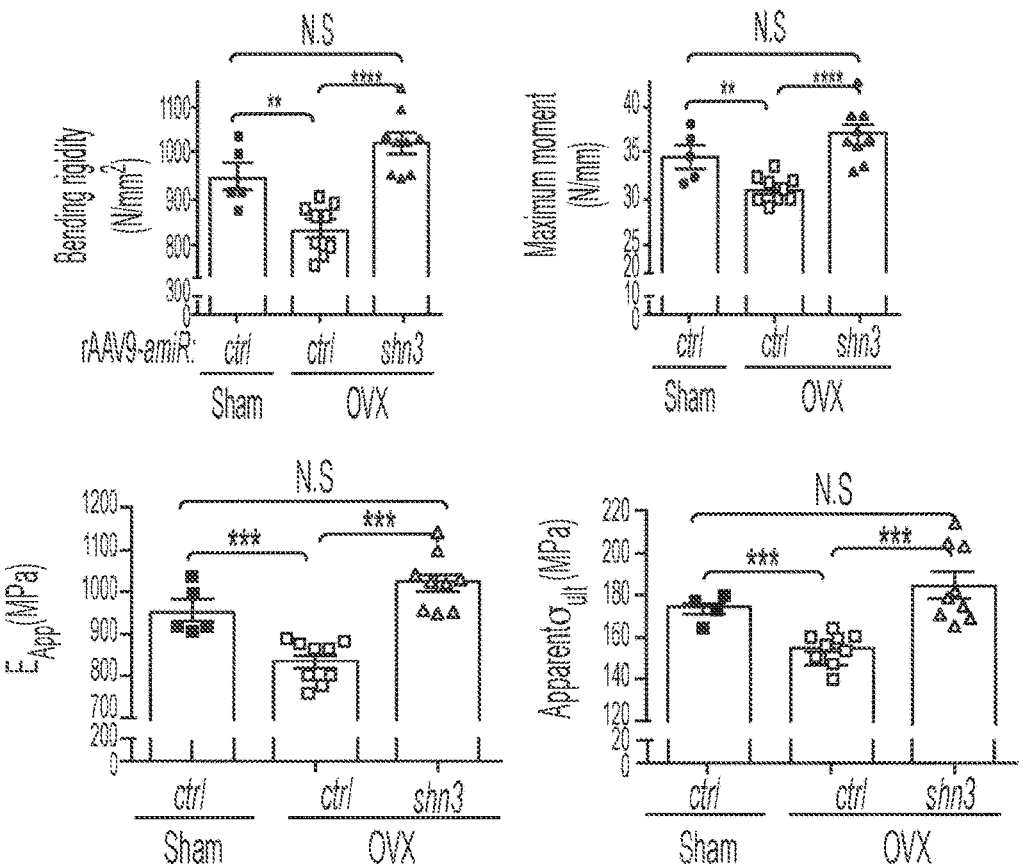
Figure 26A:
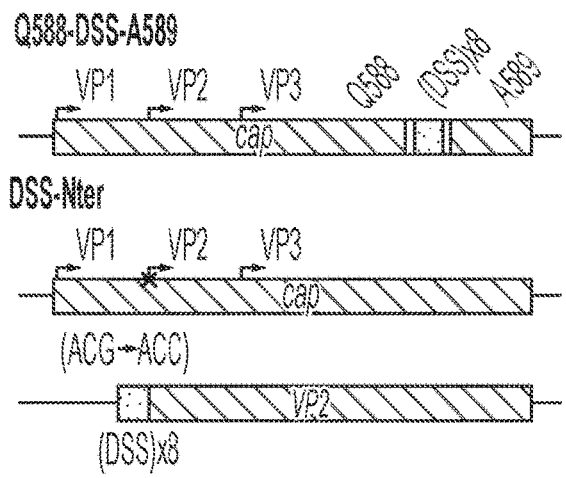
FIGS. 26A-26M: The bone-homing AAV9.DSS-Nter capsid mediates silencing of Shn3 to prevent bone loss in a mouse model of postmenopausal osteoporosis.
Figure 26B:
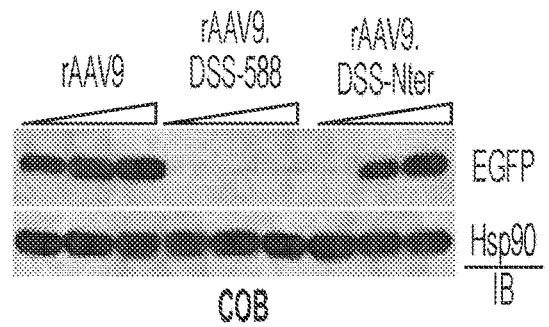
Figure 26C:
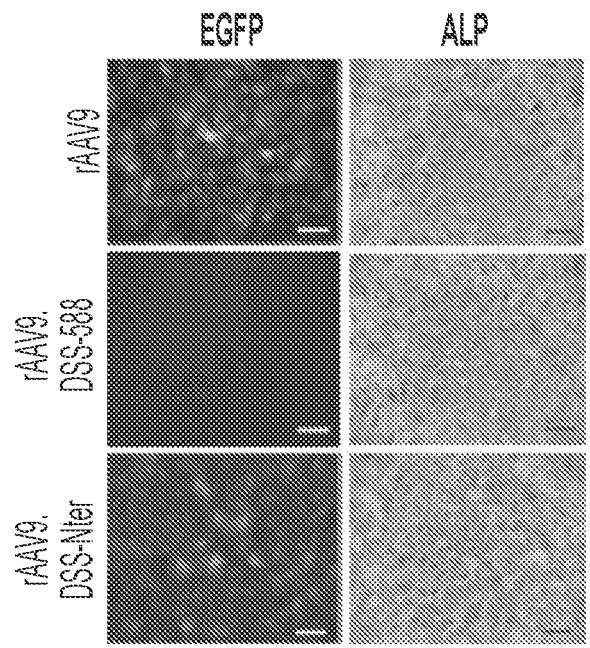
Figure 26D:
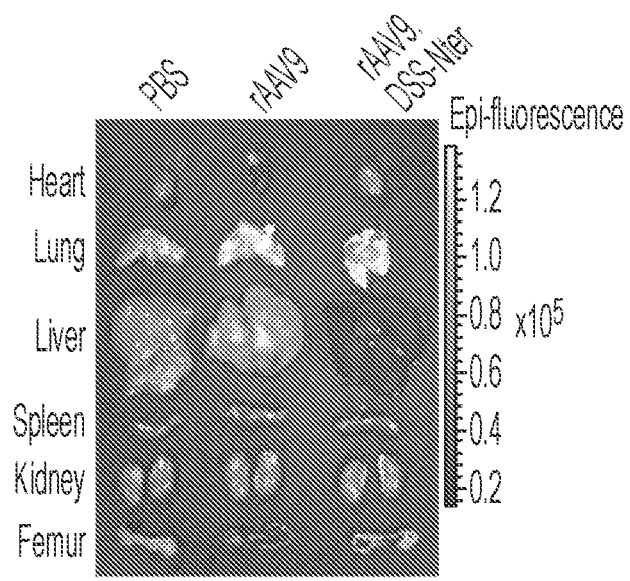
Figure 26E:
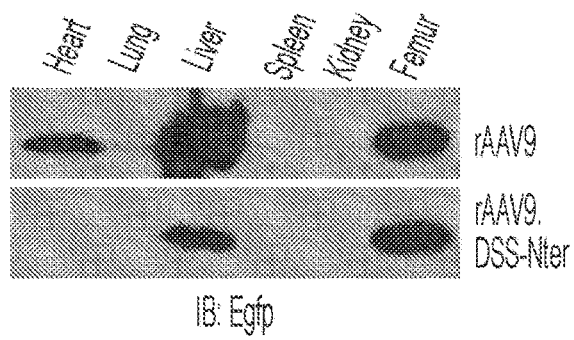
Figure 26F:
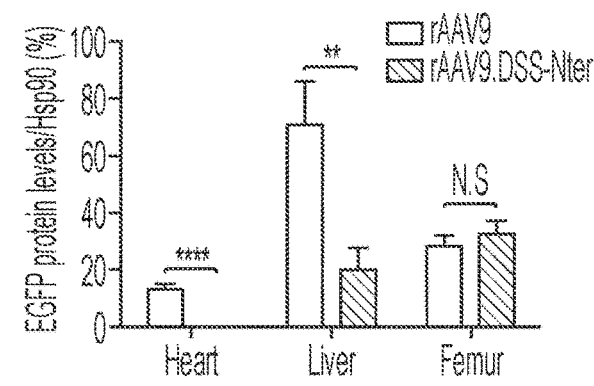
Figure 26G:
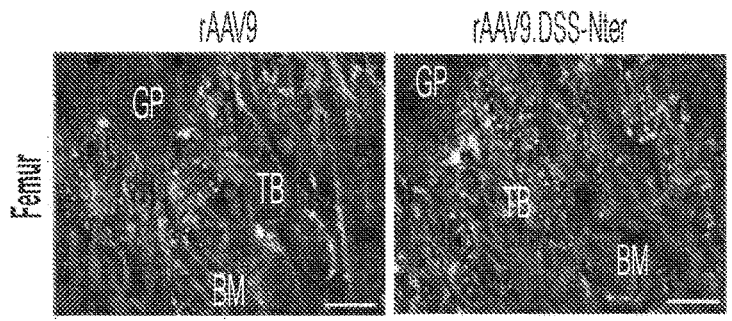
Figure 26H:
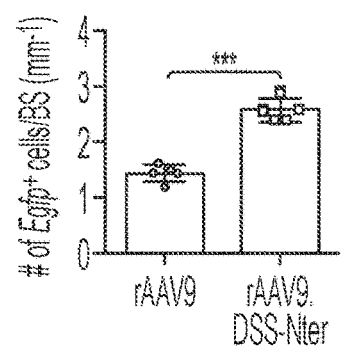
Figure 26I:
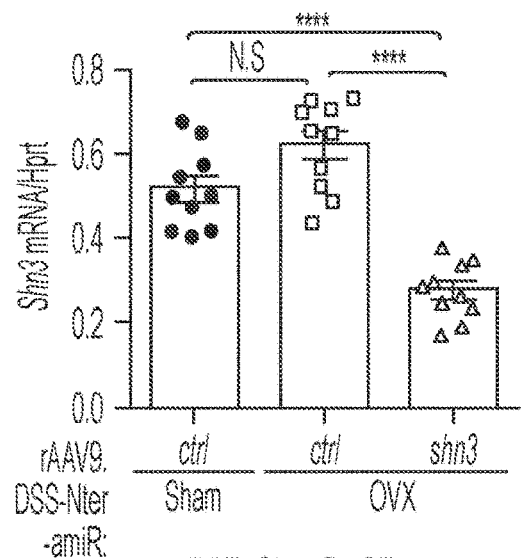
Figure 26J:
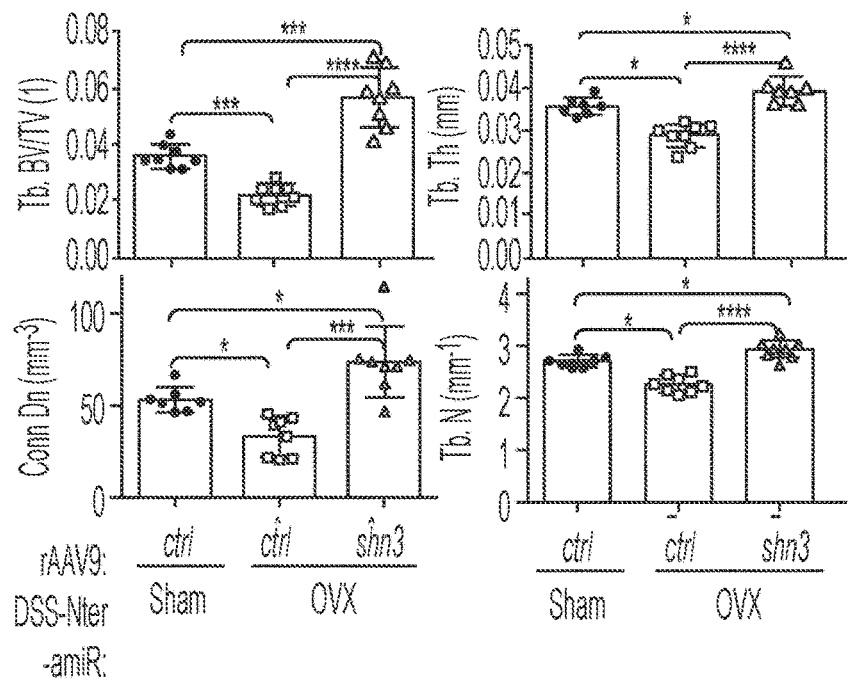
Figures 26K, 26L:
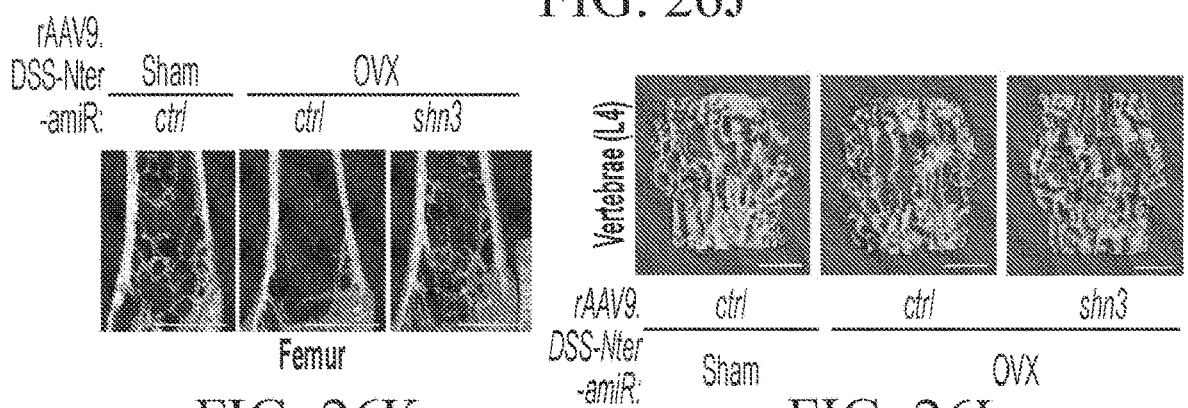
Figure 26M:
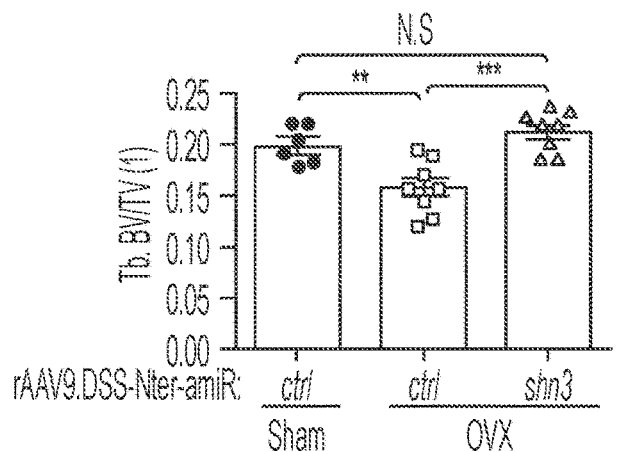

This example describes delivery of scAAV9 serotypes encoding secretory osteogenic factors to animals via intramuscular (IM) injection through which the injected muscle serves as a bio-pump, providing stable, high expression of these factors in blood circulation to promote bone formation in the setting of osteoporosis (FIG. 21). To this end, cDNAs encoding human PTH (1-84 aa), human PTHrP (1-140 aa), or mouse DJ-1 (1-190 aa) is cloned into the pAAVscCB6-EGFP vector that contains a conventional signal peptide for protein secretion at the restriction enzyme sites, Age1 and Hind3 vector, and packaged into muscle tropic AAV capsids (PTH-scAAV9, PTHrP-scAAV9, DJ-1-scAAV9). These cDNA sequences are described in the Sequences.

To validate the production of these secretory osteogenic factors in the AAV-transduced cells in vitro, scAAV9 serotypes are used to transduce mouse myoblast cell line (C2C12) and three days after culture, the supernatant is harvested and levels of secretory factors are measured by ELISAs. Alternatively, cells are lysed and intracellular proteins are assessed by immunoblotting. Once their secretion is confirmed, these osteogenic factors are incubated with mouse primary OBs under osteogenic culture conditions and their osteogenic potential will be assessed. As a negative control, GFP-encoding scAAV9 serotype is used.

Next, whether AAV-mediated gene addition of secretory osteogenic factors prevent bone loss in the setting of osteoporosis is investigated. Sham or OVX surgery is conducted in 4-months-old female mice (C57BL/6J, n=12 mice/group) and 4 weeks after surgery, a single dose of 1×10$^{10}$ genome copies of GFP-encoding scAAV9 serotypes that express PTH, PTHrP, or DJ-1 (PTH-scAAV9, PTHrP-scAAV9, DJ-1-scAAV9) are administered into the quadriceps muscle of hindlimbs via IM injection. As a negative control, GFP-encoding scAAV9 vector control (cont-scAAV9) is administered into these mice. Alternatively, these AAV serotypes are IM injected into 22-months-old female mice (C57BL/6J, n=12 mice/group). Two months after treatment, mice are labeled with calcein and alizarin red and subjected to dynamic histomorphometry in order to assess in vivo OB and OC activities. For skeletal analysis, microCT, TRAP staining (OC differentiation), and IHC for Col1 and Runx2 (OB differentiation) are performed in long bones and vertebrae. Lastly, serum levels of CTX (bone resorption), P1NP and BSAP (bone formation), and calcium and phosphorus (mineral homeostasis) are measured by ELISAs or colorimetric analysis. This analysis is accompanied by qPCR analysis of bone RNA measuring expression of OB differentiation genes. Lastly, serum levels of transgenes (PTH, PTHrP, or DJ-1) are measured by ELISAs.

Example 3 Inducible Deletion of Shn3 in Osteoblasts Promotes Bone Formation in Adult Mice To examine the effects of short-term inhibition of SHN3 on bone formation, an inducible, osteoblast-specific Shn3-knockout mice were generated by crossing Shn3$^{fl/fl}$ mice with osteocalcin-CreERT mice expressing a tamoxifen-induced Cre recombinase in mature osteoblasts (Shn3$^{Ocn-Ert}$) These mice were further crossed with the Cre reporter Rosa$^{mT/mG}$ mice to visualize Cre-expressing cells (Shn3$^{Ocn-Ert}$; Rosa$^{mT/mG}$). Treatment of Shn3$^{Ocn-Ert}$ Rosa$^{mT/mG}$ mice with tamoxifen resulted in the expression of GFP in mature osteoblasts at the surface of trabecular and cortical bones, indicating osteoblast-specific deletion of Shn3 (FIG. 23). Accordingly, these mice showed a significant increase in trabecular bone mass compared to tamoxifen-treated control mice (FIG. 23). These results indicate that inducible deletion of Shn3 in mature osteoblasts is sufficient to increase bone mass in adult mice.

Cre-encoding scAAV9 vector (scAAV9-Cre, FIG. 30) were generated to serve as a facilitator for Cre-recombination in Shn3$^{fl/fl}$ mice. The Shn3$^{fl/fl}$ mice were first treated scAAV9-Cre in cultured COBs isolated from Shn3 mice (FIG. 30), and as expected, scAAV9-mediated Cre expression in Shn3$^{fl/fl}$ COBs resulted in the deletion of Shn3 and enhanced osteoblast differentiation (FIG. 31). Next, scAAV9-Cre was injected into two-month-old Shn3$^{fl/fl}$; Rosa$^{mT/mG}$ mice via i.v. administration. Two months after injection, expression of Cre mRNA in the femur (FIG. 31) and Cre-mediated expression of EGFP protein in osteoblast lineage cells residing on the bone surface (FIG. 30) were validated by RT-PCR and fluorescence microscopy, respectively. Compared to scAAV9-EGFP treated femurs, scAAV9-Cre-treated femurs showed a significant decrease in shn3 mRNA levels (FIG. 31) and an increase in relative trabecular bone mass (FIG. 31). These results demonstrate that systemically delivered scAAV9-Cre in Shn3$^{fl/fl}$ mice targets osteoblast lineage cells and mediates Shn3 deletion to increase bone mass. Importantly, these results demonstrate the potency of scAAV9-mediated transgene delivery to osteoblast lineage cells to dramatically alter bone physiology.

Figure 32A:
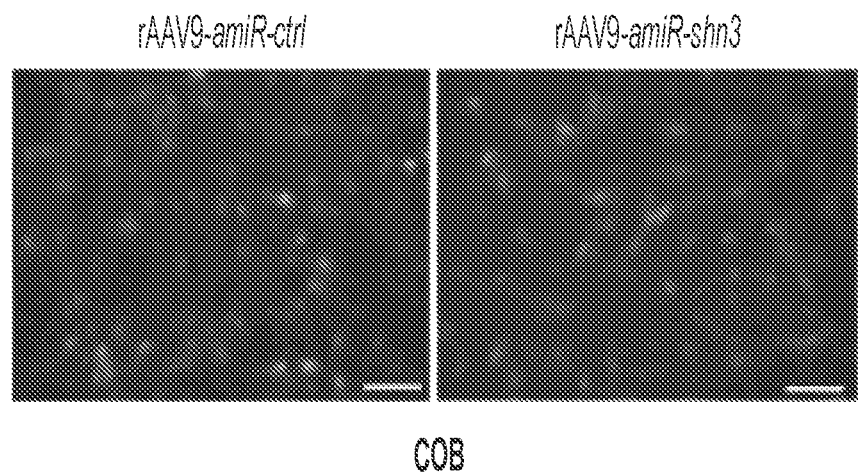
FIGS. 32A-32C show the in vitro characterization of scAAV9 carrying amiR-shn3 in osteoblasts. Two days after treatment with scAAV9 carrying amiR-ctrl or amiR-shn3, COBs were cultured under osteogenic conditions. EGFP expression (FIG. 32A), mRNA levels of Shn3 and osteogenic gene (FIG. 32B), and mineralization (FIG. 32C), were assessed by fluorescence microscopy, RT-PCR, and alizarin red staining, respectively. Scale bar: 100 mm, (FIG. 32A). Values represent mean±SD: *, $P<0.05$; *, $P<0.001$; and **, $P<0.0001$ by an unpaired two-tailed Student's t-test (FIGS. 32B and 32C).
Figure 32B:
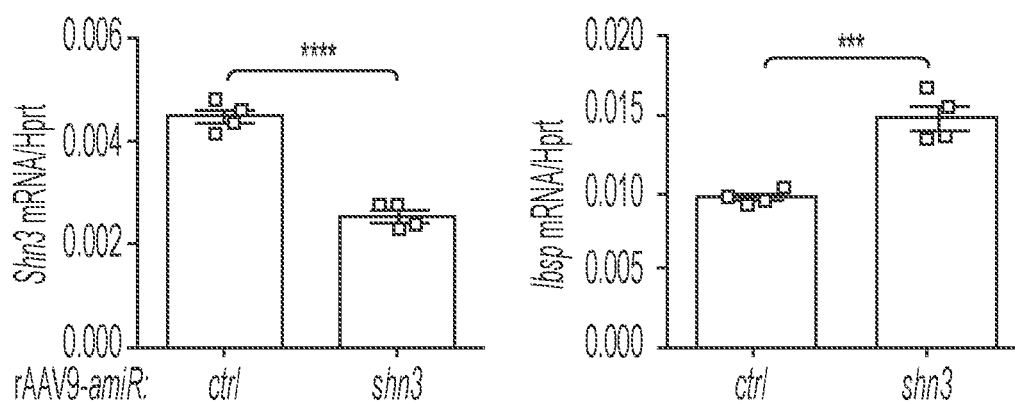
Figure 32C:
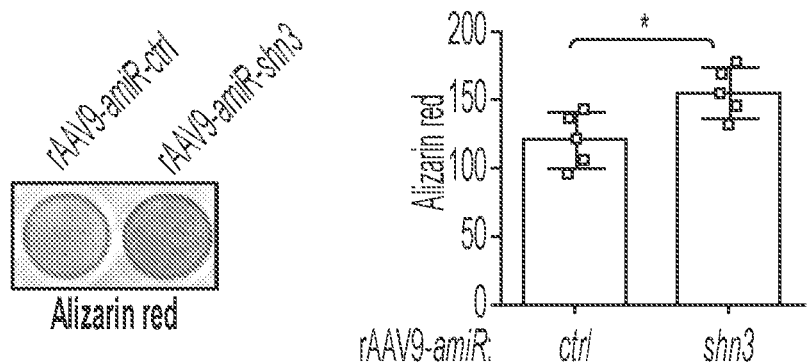
Figure 33A:
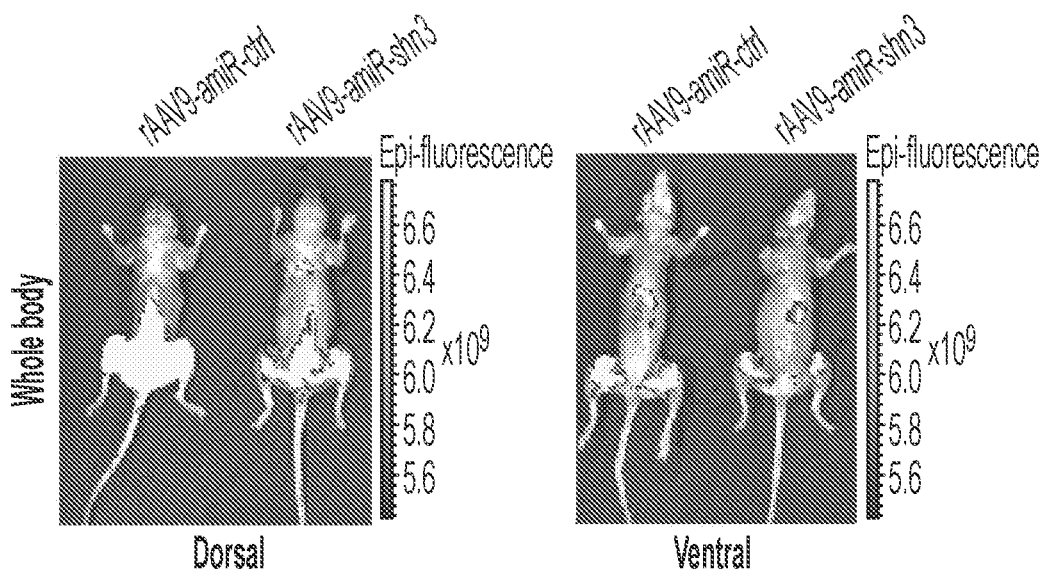
FIGS. 33A-33F show the characterization of mice treated with systematically delivered scAAV9 carrying amiR-shn3. A single dose of $4 \times 10^{11}$ genome copies of scAAV9 carrying amiR-ctrl or amiR-shn3 was i.v. injected into three-month-old female mice. Two months following treatment, mice were labeled with calcein and alizarin red for dynamic histomorphometry. Non-labeled mice were used to monitor EGFP expression using IVIS-100 optical imaging. EGFP expression in the whole body (FIG. 33A) and the dissected tissues (FIG. 33B) are displayed. Femurs were cryo-sectioned to identify EGFP-expressing osteoblast lineage cells (FIG. 33C). TRAP-stained longitudinal sections (FIG. 33D) and histomorphometric analysis (FIG. 33E) of femurs from five-month-old female mice treated with scAAV9 carrying amiR-ctrl or amiR-shn3 (n=6~7). The number of osteoclasts per bone perimeter (N.Oc/B.Pm). Serum CTX levels were assessed by ELISA (n=6) (FIG. 33F). Scale bars: 100 μm, FIG. 33C; 50 mm, FIG. 33D. Values represent mean±SD; N.S., not significant by an unpaired two-tailed Student's t-test (FIGS. 33E and 33F).
Figure 33B:
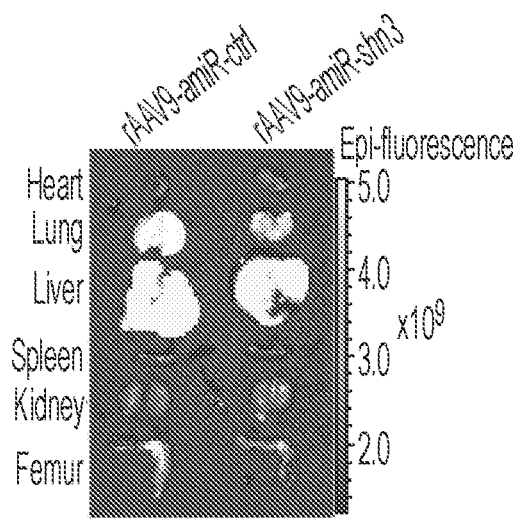
Figure 33C:
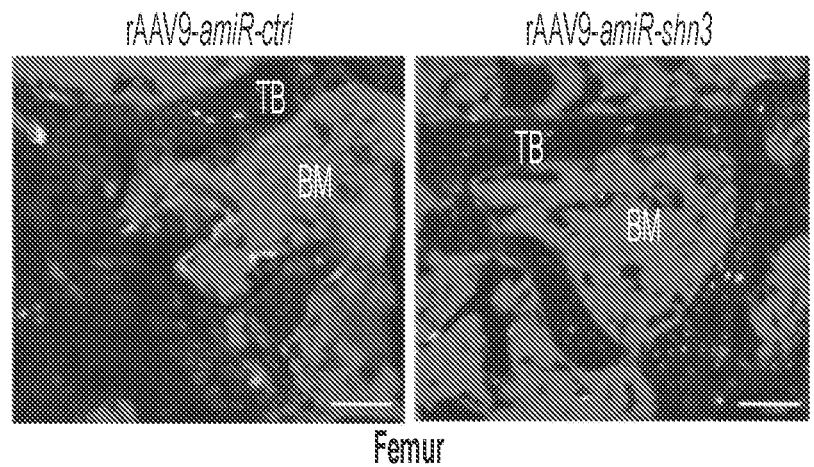
Figure 33D:
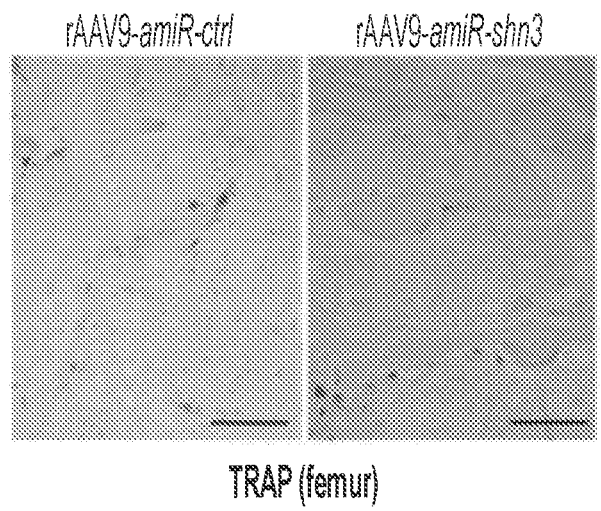
Figures 33E, 33F:
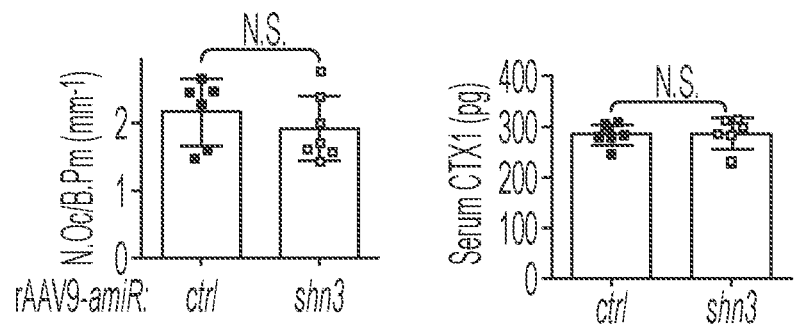

Example 4: Silencing of Shn3 by scAAV9 Carrying the amiR-Shn3 Transgene Promotes Bone Formation In Vivo Artificial microRNAs (amiRs), siRNA cassettes designed into miRNA scaffolds have been shown to efficiently promote target message degradation in vivo. In addition, such designs allow expression cassettes to be driven by pol II promoters, expanding the ability to control gene knockdown with scAAV vectors. Artificial microRNA cassettes were engineered to target shn3 (amiR-shn3) or a control (amiR-ctrl). In this design, the amiR is inserted intronically between the CB promoter and the Egfp reporter gene (FIG. 24), which allows for visual tracking of positively transduced cells or tissues. The test cassettes were then packaged into AAV9 capsids. Treatment with scAAV9-amiR-shn3 or scAAV9-amiR-ctrl resulted in positively transduce COBs in vitro (FIG. 32). Compared to amiR-ctrl-treated COBs, treatment with scAAV9-amiR-shn3 resulted in ~50% reduction of shn3 mRNA levels, and relative increases in ibsp expression and mineralization (FIG. 32).

To examine the ability of amiRs to enhance bone anabolic activity in vivo, the scAAV9-amiR-shn3 vector was injected via i.a. administration into the knee joints of two-month-old mice. Two months following treatment, EGFP expression in hindlimbs and femurs was examined by IVIS optical imaging (FIG. 24) and fluorescence microscopy (FIG. 24), respectively. Importantly, FACS-sorted EGFP-expressing cells isolated from the femur showed ~50% reduction of shn3 mRNA levels (FIG. 24). Compared to amiR-ctrl-treated femurs, amiR-shn3-treated femurs showed a significant increase in relative trabecular bone mass (FIG. 24). These results demonstrate that local delivery of scAAV9-amiR-shn3 is effective in knocking down SHN3 expression in osteoblast lineage cells and in turn increases bone mass in vivo.

The ability of scAAV9-amiR-shn3 could promote in vivo bone anabolic activity following systemic delivery was then examined. Two months after i.v. administration into three-month-old mice, EGFP expression was predominantly detected in the hindlimbs, liver, and femurs as expected (FIG. 33). Femurs transduced by scAAV9-amiR-shn3 displayed ~50% reduction of shn3 mRNA levels (FIG. 24) and a significant increase in trabecular bone mass and cortical bone mineral density (FIG. 24). Likewise, in vivo osteoblast activity was increased in these mice, as shown by greater bone formation rate (BFR), mineral apposition rate (MAR), and osteoblast surface per bone surface (Ob.S/BS) (FIG. 24). However, the number of tartrate-resistant acid phosphatase (TRAP)-positive osteoclasts and serum levels of the bone resorption marker C-terminal telopeptide type I collagen (CTX) were unchanged in these mice (FIG. 33). These results demonstrate that systemically delivered AAV9-amiR-shn3 reduced shn3 expression in osteoblast lineage cells, augmented osteoblast activity, and increased bone mass without any alteration in osteoclast number and function in vivo. Thus, the scAAV9-amiR-shn3 vector may be useful for the treatment of osteoporosis as a potent bone anabolic agent.

Example 4: scAAV9-Mediated Silencing of Shn3 Counteracts Bone Loss in Postmenopausal Osteoporosis Inhibition of Wnt antagonists has been recognized as a new approach for therapeutic intervention in patients with osteoporosis. Previous studies identified SHN3 as an inhibitor of osteoblast differentiation via perturbation of Wnt signaling. Ovariectomized (OVX) mice are an established models for postmenopausal osteoporosis. To further establish that inhibition of Shn3 may be an attractive target to promote bone formation as a therapy for osteoporosis, three-month-old female mice lacking SHN3 (Shn3$^{-/-}$) were subjected to ovariectomies, and bone mass was assessed by microCT two months post-surgery. While OVX surgery induced a significant reduction in trabecular bone mass in WT mice, OVX-induced bone loss was completely prevented by Shn3 deletion, as trabecular bone mass was comparable between sham-Shn3$^{-/-}$ mice and OVX-Shn3$^{-/-}$ mice (FIG. 25). Thus, targeting Shn3 has therapeutic potential to prevent bone loss in postmenopausal osteoporosis.

Figure 34A:
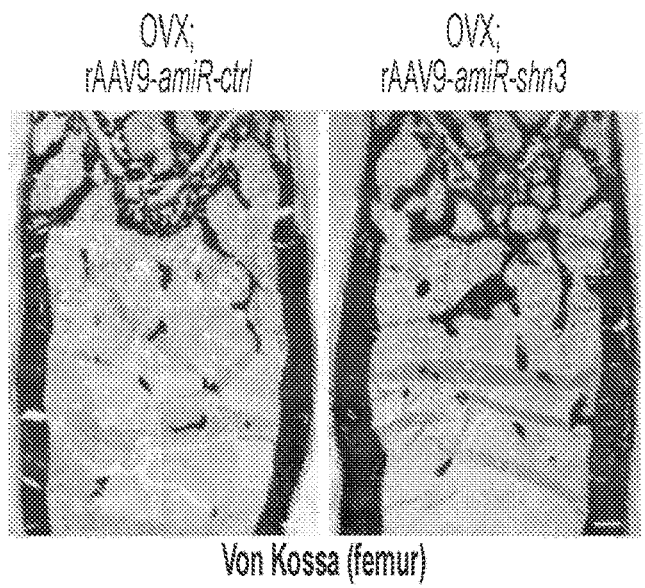
FIGS. 34A-34C show the therapeutic effects of systematically delivered scAAV9-amiR-shn3 in a mouse model of postmenopausal osteoporosis. Sham or OVX surgery was performed on three-month-old female mice and six weeks later, a single dose of $4 \times 10^{11}$ genome copies of scAAV9 carrying amiR-ctrl or amiR-shn3 was i.v. injected. Seven weeks after injection, mice were labeled with calcein and alizarin red for dynamic histomorphometry. Staining by Von Kossa (FIG. 34A) or TRAP (FIG. 34B) was performed in longitudinal sections of femurs from five-month-old female OVX mice treated with scAAV9 carrying amiR-ctrl or amiR-shn3. Serum CTX levels were assessed by ELISA (n=7) (FIG. 34C). Scale bar: 1 mm, (FIG. 34A); 50 mm, (FIG. 34B). Values represent mean±SD; NS, not significant, *, $P<0.001$ and **, $P<0.0001$ by an unpaired two-tailed Student's t-test (FIG. 34C).
Figure 34B:
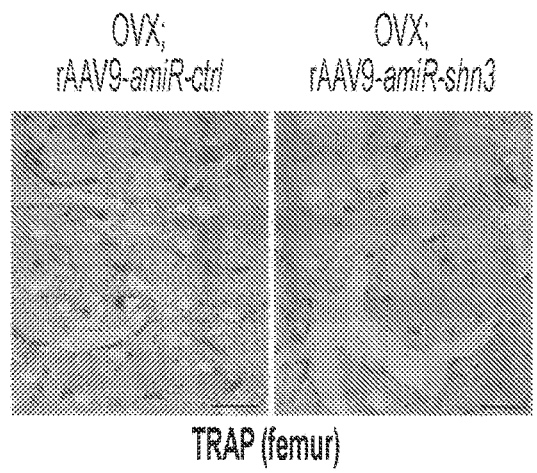
Figure 34C:
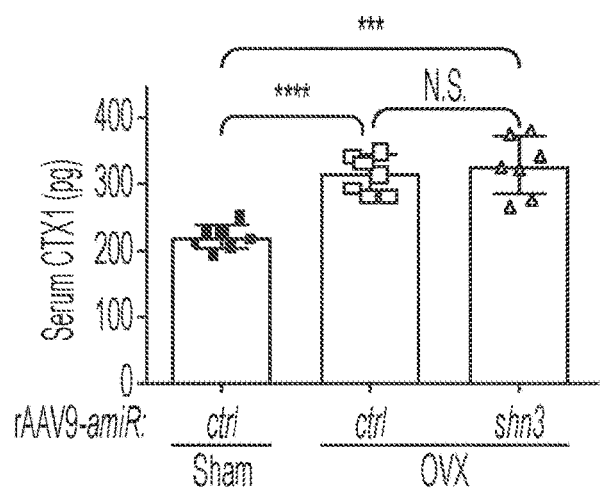

To test the therapeutic effects of scAAV9-amiR-shn3 in postmenopausal osteoporosis, sham or OVX surgery was conducted on three-month-old wild-type female mice, and vector was i.v. injected six weeks post-surgery (FIG. 25). Seven weeks later, treated femurs showed efficient transduction, leading to ~50% knockdown of shn3 (FIG. 25). As expected, amiR-ctrl-expressing OVX mice showed a significant decrease in trabecular bone mass relative to sham mice. However, when treated with scAAV9-amiR-shn3, bone loss was completely reversed in the femur of OVX mice, as shown by greater trabecular BV/TV, thickness, and connectivity density (FIG. 25 and FIG. 34) Likewise, femoral BFR and MAR were increased in these mice relative to amiR-ctrl-expressing OVX mice, demonstrating enhanced osteoblast activity in vivo (FIG. 25). Notably, shn3 silencing by scAAV9-amiR-shn3 does not alter osteoclast function in vivo as the number of TRAP-positive osteoclasts and bone resorption activity are comparable between OVX mice expressing amiR-ctrl and amiR-shn3 (FIG. 34). Finally, biomechanical testing showed that the strength and stiffness of femurs were considerably protected from OVX-induced bone loss of mice treated with scAAV9-amiR-shn3 (FIG. 25), indicating that scAAV9-mediated silencing of shn3 improves clinically meaningful endpoints in osteoporotic mice. Taken together, these results demonstrate that systemically delivered scAAV9-amiR-shn3 promotes bone formation and enhances clinically relevant mechanical properties of bone after the onset of OVX-induced osteoporosis.

Figure 27A:
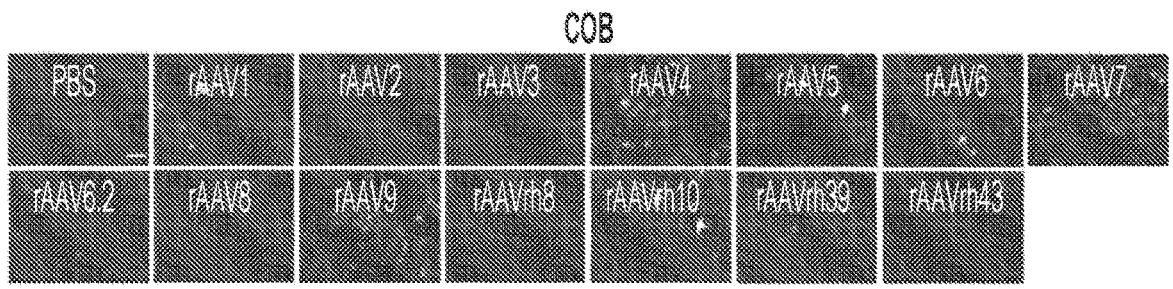
FIGS. 27A-27C show the identification of scAAV serotypes that transduce osteoblasts, osteoclasts, and chondrocytes in vitro. Calvarial osteoblasts (COBs, FIG. 27A), bone marrow-derived osteoclast precursors (BM-OCP, FIG. 27B), or a chondrogenic cell line (ATDC5, FIG. 27C) were treated with PBS or 14 different AAV serotypes. Two days later, EGFP expression was monitored by fluorescence microscopy. Scale bar: 100 µm.
Figure 27B:
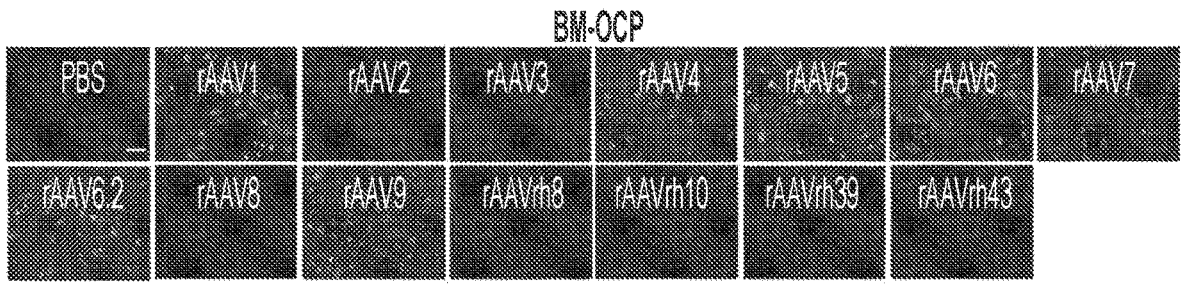
Figure 27C:
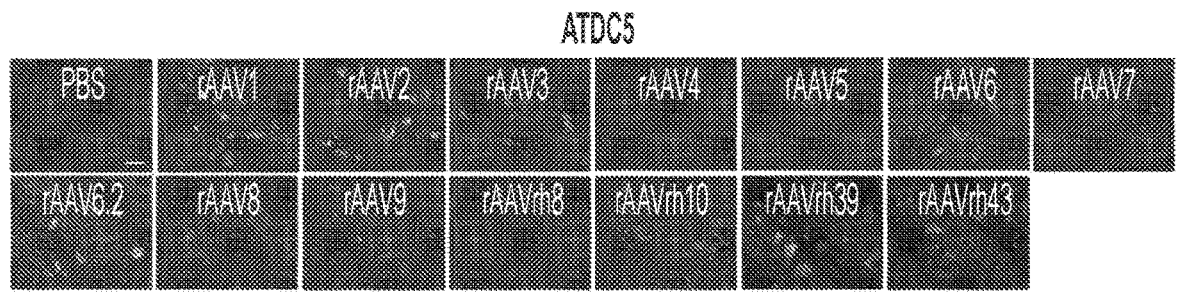
Figure 37A:
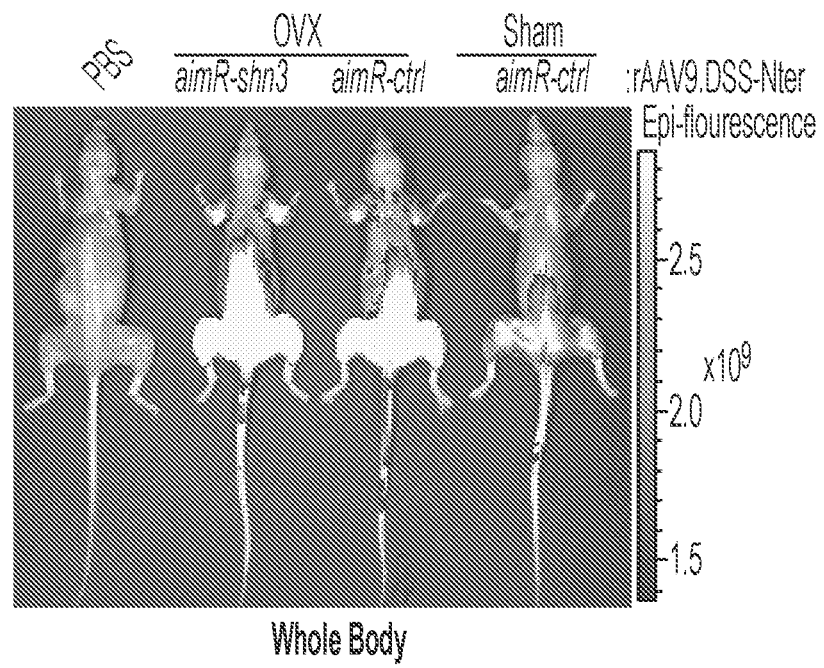
FIGS. 37A-37C show the therapeutic effects of systematically delivered scAAV9.DSS-Nter carrying amiR-shn3 in a mouse model of postmenopausal osteoporosis. Sham or OVX surgery was performed on three-month-old female mice and six weeks later, a single dose of PBS or $4 \times 10^{11}$ genome copies of scAAV9.DSS-Nter carrying amiR-ctrl or amiR-shn3 were i.v. injected. Seven weeks after injection, EGFP expression was monitored by IVIS-100 optical imaging (FIG. 37A). EGFP-expressing cells in the cryo-sectioned femurs were identified by fluorescence microscopy (FIG. 37B). Trabecular bone mass in lumbar vertebrae was assessed by microCT and quantification is displayed (n=7~8/group) (FIG. 37C). Trabecular number per cubic millimeter (Tb.N), trabecular thickness (Tb.Th), and trabecular space (Tb. Sp). TB, trabecular bone; BM, bone marrow. Scale bar: 100 mm, panel b. Values represent mean±SD: N.S, non-significant; *, $P<0.05$; , $P<0.01$; *, $P<0.001$ by one-way ANOVA test (FIG. 37C).
Figure 37B:
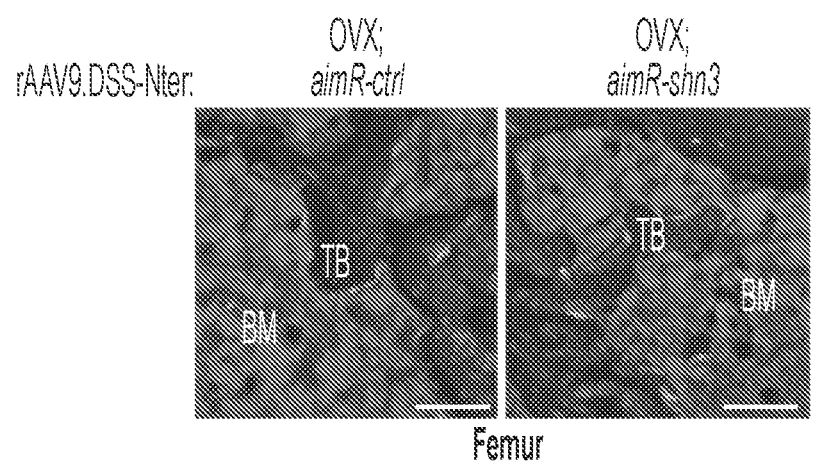
Figure 37C:
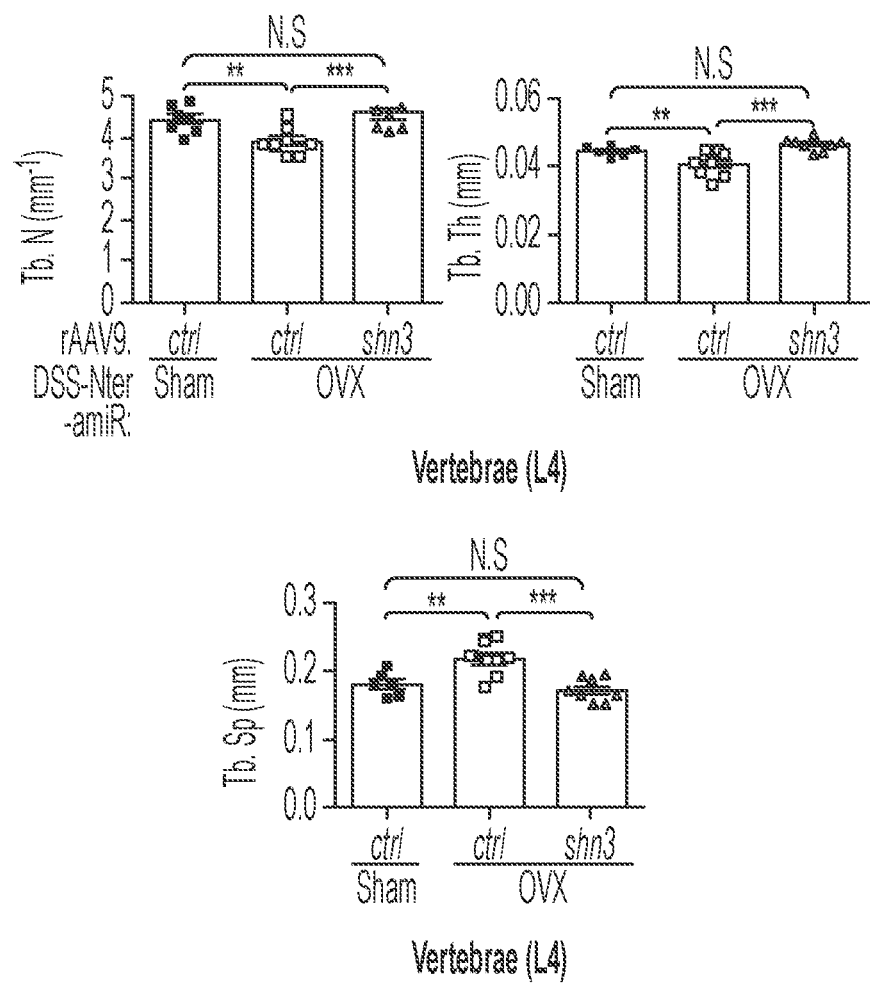

Example 5: Grafting of a Bone-Targeting Peptide Motif onto the AAV9 Capsid Improves Bone-Specific Transduction The capacity for the new AAV9.DSS-Nter bone-tropic capsid to deliver the therapeutic amiR-shn3 transgene (scAAV9.DSS-Nter-amiR-shn3) to OVX mice was examined. Sham or OVX surgery was conducted on three-month-old female mice and scAAV9.DSS-Nter-amiR-shn3 was i.v. injected six weeks post-surgery. Seven weeks after injection, animals exhibit strong EGFP expression throughout the hind section of the animals (FIG. 37) and in osteoblast lineage cells of the femurs (FIG. 37), indicating robust transduction. Levels of shn3 mRNAs were markedly reduced in amiR-shn3-expressing OVX femurs relative to amiR-ctrl-expressing sham or OVX femurs (FIG. 27). While amiR-ctrl-expressing OVX mice showed a significant reduction in trabecular bone mass relative to sham mice, bone loss was completely reversed in the femurs (FIG. 27) and lumbar vertebrae (FIG. 27, FIG. 37) of OVX mice treated with scAAV9.DSS-Nter-amiR-shn3, as shown by the greater trabecular BV/TV, thickness, number, and connectivity density. Taken together, these results demonstrate that delivery of amiR-shn3 by the bone-tropic AAV9.DSS-Nter capsid can counteract bone loss in postmenopausal osteoporosis.

Example 6: Inhibition of Bone Loss in Human Patients and Animal Models of Osteoporosis A humanized biologic antibody against the receptor activation of NF-κβ (RANK, TNFRSF11A) ligand interferes with the interaction between RANK ligand (RANKL) and RANK, which inhibits the RANK signaling required for osteoclast differentiation. Thus, its treatment prevents bone loss in human patients and animal models with osteoporosis by suppressing osteoclast-mediated bone resorption.

The capacity for the new AAV9.DSS-Nter bone-tropic capsid to deliver a therapeutic amiR-33-mRANKi transgenes (scAAV9.DSS-Nter-amiR-mRANKi 1/2) is being examined for suppression of osteoclast differentiation by silencing RANK in osteoclast precursors, thereby inhibiting bone loss in human patients and animals models of osteoporosis.

Methods scAAV Vector Design and Production

DNA sequences for amiR-33-ctrl and amiR-33-shn3 were synthesized as gBlocks and cloned into the intronic region of the pAAVsc-CB6-Egfp plasmid at the restriction enzyme sites (PstI and BglII). The pAAVsc-CB6-Cre vector was generated by replacing the Egfp reporter with Cre recombinase. Constructs were verified by sequencing. Previous studies indicated that doxycycline-inducible expression of shRNA targeting mouse Shn3 in transgenic mice resulted in a decrease in shn3 mRNA levels and a relative increase in bone mass. The same targeting sequence was used to generate the amiR-33-shn3 cassette. The pAAV-amiR-ctrl and pAAV-amiR-shn3 constructs were packaged into AAV9 capsids. Additionally, the pAAVsc-CB6-Egfp construct was packaged into AAV1, AAV2, AAV3, AAV4, AAV5, AAV6, AAV6.2, AAV7, AAV8, AAV9, AAV9-HR, AAVrh8, AAVrh10, AAVrh39, and AAVrh43 capsids. scAAV production was performed by transient transfection of HEK293 cells, purified by CsCl sedimentation, titered by droplet digital PCR (ddPCR) on a QX200 ddPCR system (Bio-Rad) using the Egfp prime/probe set as previously described. The sequences of gBlocks and oligonucleotides for ddPCR and are listed in Table 3.

TABLE 3

Sequences of primers, probes, and qblocks

| Gene | Forward | SEQ ID NO: | Reverse | SEQ ID NO: |
|---|---|---|---|---|
| Mouse Shn3 | AGAGGCCATTCAGAC GAGTGT | 35 | CTGCGGAAGCTGAG AGATGT | 36 |
| Mouse Alp | CACAATATCAAGGAT ATCGACGTGA | 37 | ACATCAGTTCTGTTC TTCGGGTACA | 38 |
| Mouse Runx2 | TACAAACCATACCCA GTCCCTGTTT | 39 | AGTGCTCTAACCACA GTCCATGCA | 40 |
| Mouse Bsp | CAGGGAGGCAGTGAC TCTTC | 41 | AGTGTGGAAAGTGT GGCGTT | 42 |
| Mouse Osx | ATGGCGTCCTCTCTGC TTGA | 43 | GAAGGGTGGGTAGT CATTTG | 44 |
| Mouse Ocn | GCAGCACAGGTCCTA AATAG | 45 | GGGCAATAAGGTAG TGAACAG | 46 |
| Mouse Col1a1 | CTGTCCCAACCCCCA AAG | 47 | ACGTATTCTTCCGGG CAGAA | 48 |
| Mouse Hprt | CTGGTGAAAAGGACC TCTCGAAG | 49 | CCAGTTTCACTAATG ACACAAACG | 50 |
| EGFP | AGCAAAGACCCCAAC GAGAA | 51 | GGCGGCGGTCACGA A | 52 |
| EGFP-probe | 6FAM-CGCGATCACATGGTCCTGCTGG-TAMRA | | | 53 |
| amiR-33-ctrl (amiR-ctrl) | TTTGTCTTTTATTTCAGGTCCCAGATCTAGGGCTCTGCGTTT GCTCCAGGTAGTCCGCTGCTCCCTTGGGCCTGGGCCCACTG ACAGCCCTGGTGCCTCTGGCCGGCTGCACACCTCCTGGCGG GCAGCTGTGTACAAACTACTTGAGAGCAGGTGTTCTGGCAA TACCTGCCTGCTCTGTAATAGTTTGTACACGGAGGCCTGCCC TGACTGCCCACGGTGCCGTGGCCAAAGAGGATCTAAGGGCA CCGCTGAGGGCCTACCTAACCATCGTGGGGAATAAGGACAG TGTCACCCCTGCAGGGGATCCGGTGGTGGTGCAAATCA | | | 54 |

Generation of Bone-Targeting scAAV9 Vector

The DNA sequence encoding the bone-targeting peptide motif DSS (AspSerSer)₆ (SEQ ID NO: 16) was codon-optimized. To generate the Q588-DSS-A589 capsid (DSS-588), a plasmid expressing AAV2 rep gene and AAV9 cap gene (pAAV2/9) was modified to insert the DSS sequence into the AAV9 cap gene between the Q588 and A589 codons (pAAV2/9.Q588-DSS-A589). This plasmid was used in scAAV production. To generate the DSS-Nter capsid, a pair of plasmids were used. First, the start codon of VP2 in pAAV2/9 was mutated (ACG→ACC), so that only VP1 and VP3 are expressed (pAAV2/9.noVP2). In another plasmid, the DSS sequence was fused to the N-terminus of the AAV9 VP2 ORF. A Kozak sequence and ATG start codon were placed immediately upstream of the DSS sequence allowing for optimal expression driven by the CMV promoter [pcDNA.DSS-VP2(AAV9)]. The plasmids pAAV2/9.noVP2 and pcDNA.DSS-VP2(AAV9) were used in scAAV production.

Cells

The chondrogenic ATDC5 cells were purchased from Sigma and cultured in DMEM/Ham's F12 medium supplemented with 2% FBS, 2 mM L-glutamine and 1% penicillin/ streptomycin. Additionally, primary osteoprogenitors (COB) were isolated from calvaria of five-day-old wild type neonates (C57BL/6J) using Collagenase type II (50 mg/ml, Worthington, LS004176) and Dispase II (100 mg/ml, Roche, 10165859001) and were maintained in α-MEM medium (Gibco) containing 10% FBS (Gibco), 2 mM L-glutamine (Corning), 1% penicillin/streptomycin (Corning), and 1% nonessential amino acids (Corning). COBs were differentiated with ascorbic acid (200 uM, Sigma, A8960) and β-glycerophosphate (10 mM, Sigma, G9422). Finally, bone marrow cells were flushed from the femurs and tibias of two-month-old mice (C57BL/6J), and cultured in petri dishes in α-MEM medium with 10% FBS and 20 ng/ml of M-CSF (R&D systems) to obtain bone marrow-derived osteoclast precursors (BM-OCP). 12 hours later, nonadherent cells were re-plated into tissue culture dishes and cultured in the same medium for three days. BM-OCPs then differentiated into osteoclasts in the presence of RAMKL (20 ng/ml; R&D systems) and M-CSF (20 ng/ml; R&D systems) for six days.

Mice

Shn3$^{-/-}$ mice and Shn3$^{fl/fl}$ mice were generated as previously described and maintained on BALB/cJ and C57BL/6J background, respectively. Osteocalcin-ERT/Cre mice with tamoxifen-induced Cre recombinase expression in mature osteoblasts were crossed with Shn3$^{fl/fl}$ mice to obtain Shn3$^{fl/fl}$; Ocn-ERT/Cre mice. To label Cre-expressing cells, Shn3$^{fl/fl}$; Ocn-ERT/Cre mice were further crossed with Rosa$^{mT/mG}$ cre reporter mice. For postnatal activation of ERT/Cre, 100 mg/kg tamoxifen (Sigma) in corn oil (Sigma) was intraperitoneally injected to 2-month-old female mice once a day for 5 consecutive days.

Mouse genotypes were determined by PCR on tail genomic DNA. Primer sequences are available upon request. Control littermates were used and analyzed in all experiments.

MicroCT Analysis

MicroCT was used for qualitative and quantitative assessment of trabecular and cortical bone microarchitecture and performed by an investigator blinded to the genotypes of the animals under analysis. Femurs excised from the indicated mice were fixed with 10% neutral buffered formalin and scanned using a microCT 35 (Scanco Medical) with a spatial resolution of 7 μm. For trabecular bone analysis of the distal femur, an upper 2.1 mm region beginning 280 μm proximal to the growth plate was contoured. For cortical bone analysis of femur, a midshaft region of 0.6 mm in length was used. MicroCT scans of L4 spinal segments were performed using isotropic voxel sizes of 12 μm. 3D reconstruction images were obtained from contoured 2D images by methods based on distance transformation of the binarized images. Alternatively, the Inveon multimodality 3D visualization program was used to generate fused 3D viewing of multiple static or dynamic volumes of microCT modalities (Siemens Medical Solutions USA, Inc). All images presented are representative of the respective genotypes (n>5).

Histology, Histomorphometry, and Immunofluorescence

For histological analysis, femurs and vertebrae were dissected from the mice treated with rAAVs vectors, fixed in 10% neutral buffered formalin for two days, and decalcified by 5% tetrasodium EDTA for 2-4 weeks. Tissues were dehydrated by passage through an ethanol series, cleared twice in xylene, embedded in paraffin, and sectioned at a thickness of 6 μm along the coronal plate from anterior to posterior. Decalcified femoral sections were stained with hematoxylin and eosin (H&E) or tartrate-resistant acid phosphatase (TRAP).

For dynamic histomorphometric analysis, 25 mg/kg calcein (Sigma, C0875) and 50 mg/kg alizarin-3-methylimino-diacetic acid (Sigma, A3882) dissolved in 2% sodium bicarbonate solution were subcutaneously injected into mice at six day-interval. After fixed in 10% neutral buffered formalin for two days, undecalcified femur samples were embedded in methylmethacrylate and proximal metaphysis is sectioned longitudinally (5 μm) and stained with McNeal's trichrome for osteoid assessment, toluidine blue for osteoblasts, and TRAP for osteoclasts. A region of interest is defined and bone formation rate/bone surface (BFR/BS), mineral apposition rate (MAR), bone surface (BS), osteoblast surface (Ob.S/BS), and osteoclast surface (Oc.S/BS) are measured using a Nikon Optiphot 2 microscope interfaced to a semiautomatic analysis system (Osteometrics). Measurements were taken on two sections/sample (separated by ~25 μm) and summed prior to normalization to obtain a single measure/sample in accordance with ASBMR standards. This methodology has undergone extensive quality control and validation and the results were assessed by two different researchers in a blinded fashion.

For immunofluorescence, fresh femurs and vertebrae dissected from rAAV-treated mice were collected and immediately fixed in ice-cold 4% paraformaldehyde solution for two days. Semi-decalcification was carried out for five days in 0.5 M EDTA pH 7.4 at 4° C. with constant shaking (age ≥1 week), and infiltration was followed with a mixture of 20% sucrose phosphate buffer for one day and with 25% sucrose phosphate buffer next day. All samples were embedded in 50/50 mixture of 25% sucrose solution and OCT compound (Sakura) and cut into 12-um-thick sagittal sections using a cryostat (Leica). Immunofluorescence staining and analysis was performed as described previously. Briefly, after treatment with 0.2% Triton X-100 for 10 min, sections were blocked with 5% donkey serum at room temperature for 30 min and incubated overnight at 4° C. with anti-BGLAP antibody (sc-365797, Santa Cruz, 1:150). Primary antibodies were visualized with donkey anti-rat IgG Alexa-594 (1:500, Molecular Probes). Nuclei were counterstained with DAPI. An Olympus IX81 confocal microscope or Leica TCS SP5 II Zeiss LSM-880 confocal microscope was used to image samples.

Biomechanical Analysis

Femora were mechanically tested in three-point bending using an electrical force mechanical testing machine (Electroforce 3230, Bose Corporation, Eden Prairie, MN) at the Center for Skeletal Research Imaging and Biomechanical Testing Core. The bending fixture had a bottom span length of 8 mm. The test was performed with the load point in displacement control moving at a rate of 0.05 mm/sec with force and displacement data collected at 60 Hz. All of the bones were positioned in the same orientation during testing with the cranial surface resting on the supports and being loaded in tension. Bending rigidity (EI, N-mm2), apparent modulus of elasticity (Eapp, MPa), ultimate moment (Mult, N-mm), apparent ultimate stress (aapp, MPa), work to fracture (Wfrac, mJ), and apparent toughness (Uapp, mJ/mm3) were calculated based on the force and displacement data from the tests and the mid-shaft geometry measured with microCT. Work to fracture is the energy that that was required to cause the femur to fracture, and it was calculated by finding the area under the force-displacement curve using the Riemann Sum method. Bending rigidity was calculated using the linear portion of the force-displacement curve. The minimum moment of inertia (Imin) was used when calculating the apparent modulus of elasticity.

ELISA Analysis

CTX1 ELISA (Abclonal MC0850) analysis was performed by using a kit according to the manufacturer's instructions.

Osteoblast Differentiation Analysis

For alkaline phosphatase (ALP) staining, osteoblasts were fixed with 10% neutral formalin buffer and stained with the solution containing Fast Blue (Sigma, FBS25) and Naphthol AS-MX (Sigma, 855). Alternatively, osteoblasts were incubated with 10-fold diluted Alamar Blue solution (Invitrogen, DAL1100) for cell proliferation. Subsequently, cells were washed and incubated with a solution containing 6.5 mM $Na_2CO_3$, 18.5 mM $NaHCO_3$, 2 mM $MgCl_2$, and phosphatase substrate (Sigma, S0942), and ALP activity was measured by luminometer (Biorad).

To assess extracellular matrix mineralization in mature osteoblasts, cells were washed twice with phosphate-buffered saline (PBS) and fixed in 70% EtOH for 15 min at room temperature. Fixed cells were washed twice with distilled water and then stained with a 2% alizarin red solution (Sigma, A5533) for 5 min. Cells were then washed three times with distilled water and examined for the presence of calcium deposits. Mineralization was quantified by the acetic acid extraction method.

Quantitative RT-PCR Analysis

Total RNA was purified from cells using QIAzol (QIAGEN) and cDNA was synthesized using the High-Capacity cDNA Reverse Transcription Kit from Applied Biosystems. Quantitative RT-PCR was performed using SYBR® Green PCR Master Mix (Bio-Rad) with CFX connect RT-PCR detection system (Bio-Rad). To measure Shn3 mRNA levels in bone tissues, after removal of bone marrow, tibias were snap-frozen in liquid nitrogen for 30 sec and in turn homogenized in 1 ml of QIAzol for 1 min.

Alternatively, femurs and tibias dissected from rAAV9-treated mice were crushed in Hanks Balanced Salt Solution (Life Technologies) containing 10 mM HEPES (pH 7.2) (CellGro) and enzymatically digested with 2.5 mg/mL Collagenase A (Roche) and 1 unit/mL Dispase II (Roche) for 15 min at 37° C. under gentle agitation. The resulting cell suspensions were filtered (40 μm), washed using PBS (pH 7.2) containing 0.5% BSA (Fraction V) and 2 mM EDTA. After washing, cells were resuspended in PBS (pH 7.2) with 2 mM EDTA and 1 μg/mL 4-6,Diamidino-2-Phenylindole (DAPI) (live/dead exclusion) and EGFP-expressing cells were sorted using a FACS Aria II SORP cell sorter (Becton Dickinson) with exclusion of DAPI+ cells and doublets. Total RNA was purified from cells using QIAzol. Primers used for PCR are described in Table 3.

Immunoblotting Analysis

Cells were lysed in TNT lysis buffer (50 mM Tris-HCl (pH 7.4), 150 mM NaCl, 1% Triton X-100, 1 mM EDTA, 1 mM EGTA, 50 mM NaF, 1 mM $Na_3VO_4$, 1 mM PMSF and protease inhibitor cocktail (Sigma)) and protein amounts from cell lysates were measured using DC protein assay (Bio-Rad). Equivalent amounts of proteins were subjected to SDS-PAGE, transferred to Immunobilon-P membranes (Millipore), immunoblotted with anti-GFP antibody (JL-8, 632381, Takara, 1:1000), anti-Cre recombinase antibody (ab24607, Abcam, 1:1000), anti-Hsp90 antibody (675402, Biolegend, 1:1000), and developed with ECL (Thermo fisher scientific). Immunoblotting with anti-HSP90 antibody was used as a loading control. Alternatively, dissected femurs and soft tissues were homogenized in RIPA lysis buffer (89900, Thermo fisher scientific) and tissue lysates were subjected to immunoblotting analysis.

Screening of rAAV Serotypes that Transduce Osteoblasts, Osteoclasts, or Chondrocytes In Vitro ATDC5 cells or primary COBs were plated at a density of $1\times10^4$ cells/well in 24-well plate and 24 hrs later, they were incubated with rAAV1, rAAV2, rAAV3, rAAV4, rAAV5, rAAV6, rAAV6.2, rAAV7, rAAV8, rAAV9, rAAVrh8, rAAVrh10, rAAVrh39, or rAAVrh43 vectors packaging the CB-Egfp reporter transgene at three different titers ($10^9$-$10^{10}$ genome copies). 48 hrs later. cells were washed with PBS and EGFP expression was monitored by the EVOS FL imaging system (Thermo fisher scientific). Alternatively, cells were lysed in TNT lysis buffer and EGFP expression was assessed by immunoblotting with anti-EGFP antibody and quantified using Image J software. Lastly, primary bone marrow monocytes were plated at a density of $5\times10^5$ cells/well in 24-well plates and cultured in the presence of 10 ng/ml of RAMKL and 20 ng/ml of M-CSF for two days to differentiate to osteoclast precursors. Three days after treatment with rAAV-Egfp vectors, EGFP expression was assessed by ENOS FL imaging system and by immunoblotting with anti-EGFP antibody.

For screening rAAV vectors in vivo, 10 μl of rAAV-Egfp vectors ($1\times10^{11}$ GC; $5\times10^{12}$ GC/kg) was intraarticularly (i.a.) injected into knee joints of two-month-old male mice (Jackson Laboratory). Two weeks after injection, femurs and knee joints were dissected for IVIS-100 optical imaging or cryo-sectioning.

Effects of rAAV9-Mediated Delivery of Cre-Recombinase or amiR-Shn3 on Bone Formation For a local delivery, 10 μl of rAAV9 carrying amiR-ctrl or amiR-shn3 ($1\times10^{11}$ GC; $5\times10^{12}$ GC/kg) was i.a. injected into knee joints of two-month-old male mice. Two months after injection, femurs were dissected for microCT analysis.

For a systemic delivery, 200 μl of rAAV9 carrying Egfp, Cre, amiR-ctrl or amiR-shn3 ($4\times10^{11}$ GC; $2\times10^{13}$ GC/kg) was intravenously (i.v.) injected into mice and two months later, mice were subcutaneously injected with calcein and alizarin-3-methyliminodiacetic acid at six day-interval for dynamic histomorphometric analysis. Non-labeled mice were used to monitor EGFP expression using the IVIS-100 optical imaging or cryo-sections.

Therapeutic Effects of Systematically Delivered rAAV9-amiR-Shn3 in a Mouse Model of Postmenopausal Osteoporosis Mouse models of postmenopausal osteoporosis were generated by anesthetizing and bilaterally ovariectomizing (OVX) three-month-old female mice (Jackson Laboratory). Six weeks after the surgery, sham or OVX mice were i.v. injected with 200 μl of rAAV9 or rAAV9.DSS-Nter carrying amiR-ctrl or amiR-shn3 ($4\times10^{11}$ GC; $2\times10^{13}$ GC/kg). Mice were randomly divided into six groups with rAAV9 or rAAV9.DSS-Nter: sham+rAAV9-amiR-ctrl, OVX+rAAV9-amiR-ctrl, OVX+rAAV9-amiR-shn3, sham+rAAV9.DSS-Nter-amiR-ctrl, OVX+rAAV9.DSS-Nter-amiR-ctrl, OVX+rAAV9.DSS-Nter-amiR-shn3. Seven weeks after the injection, mice were subcutaneously injected with calcein and alizarin-3-methyliminodiacetic acid at six day-intervals for dynamic histomorphometric analysis. Non-labeled mice were used to monitor EGFP expression using the IVIS-100 optical imaging or frozen-sections.

Statistical Methods

All data were presented as the mean±s.e.m. Sample sizes were calculated on the assumption that a 30% difference in the parameters measured would be considered biologically significant with an estimate of sigma of 10-20% of the expected mean. Alpha and Beta were set to the standard values of 0.05 and 0.8, respectively. No animals or samples were excluded from analysis, and animals were randomized to treatment versus control groups, where applicable. For relevant data analysis, where relevant, the Shapiro-Wilk normality test was first performed for checking normal distributions of the groups. If normality tests passed, two-tailed, unpaired Student's t-test and if normality tests failed, and Mann-Whitney tests were used for the comparisons between two groups. For the comparisons of three or four groups, one-way ANOVA was used if normality tests passed, followed by Tukey's multiple comparison test for all pairs of groups. If normality tests failed, Kruskal-Wallis test was performed and was followed by Dunn's multiple comparison test. The GraphPad PRISM software (v6.0a, La Jolla, CA) was used for statistical analysis. P<0.05 was considered statistically significant. *, P<0.05; , P<0.01; *, P<0.001; and ****, P<0.0001.

```
SEQUENCES
>SEQ ID NO: 1; amiR-33-mSHN3i-1:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGTACAAACTACTTGAGAGCAGGTGTTCTGGCAATACCTGCCTG

CTCTGTAATAGTTTGTACACGGAGGCCTGCCCTGACTGCCCACGGTGCCGTGGCC

AAAGAGGATCTAAGGGCACCGCTGAGGGCCTACCTAACCATCGTGGGGAATAAGG

ACAGTGTCACCCCTGCAGgggatccggtggtggtgcaaatca

>SEQ ID NO: 2; amiR-33-mSHN3i-2:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGACTACAGGTACTCACAAGCTCTGTTCTGGCAATACCTGGAGCT

TGTCTGCACCTGTAGTCACGGAGGCCTGCCCTGACTGCCCACGGTGCCGTGGCCA

AAGAGGATCTAAGGGCACCGCTGAGGGCCTACCTAACCATCGTGGGGAATAAGGA

CAGTGTCACCCCTGCAGgggatccggtggtggtgcaaatca

>SEQ ID NO: 3; amiR-33-hSHN3i-1:
GtcttttatttcaggtcccagatcttAGGGCTCTGCGTTTGCTCCAGGTAGTCCGCTGCTCCCTTGGG

CCTGGGCCCACTGACAGCCCTGGTGCCTCTGGCCGGCTGCACACCTCCTGGCGGGC

AGCTGTGtttccatggtaagttcaaggcTGTTCTGGCAATACCTGGCCTTGAAGATGCCATGGAA

ACACGGAGGCCTGCCCTGACTGCCCACGGTGCCGTGGCCAAAGAGGATCTAAGGGC

ACCGCTGAGGGCCTACCTAACCATCGTGGGGAATAAGGACAGTGTCACCCcctgcagg ggatccggtggtggtgcaaat >SEQ ID NO: 4; amiR-33-mCTSKi-1:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGTTTCATCATAGTACACACCTCTGTTCTGGCAATACCTGGAGGT

GTGATCCATGATGAAACACGGAGGCCTGCCCTGACTGCCCACGGTGCCGTGGCCA

AAGAGGATCTAAGGGCACCGCTGAGGGCCTACCTAACCATCGTGGGGAATAAGGA

CAGTGTCACCCCTGCAGgggatccggtggtggtgcaaatca

>SEQ ID NO: 5; amiR-33-mCTSKi-2:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGTTACTGTAGGATCGAGAGGGATGTTCTGGCAATACCTGTCCC

TCTCCTTACTACAGTAACACGGAGGCCTGCCCTGACTGCCCACGGTGCCGTGGCC

AAAGAGGATCTAAGGGCACCGCTGAGGGCCTACCTAACCATCGTGGGGAATAAGG

>SEQ ID NO: 6; amiR-33-hCTSK-1:
GtcttttatttcaggtcccagatcttAGGGCTCTGCGTTTGCTCCAGGTAGTCCGCTGCTCCCTTGGG

CCTGGGCCCACTGACAGCCCTGGTGCCTCTGGCCGGCTGCACACCTCCTGGCGGGC

AGCTGTGattatcgctattgcagctttcTGTTCTGGCAATACCTGGAAAGCTGGTACAGCGATAAT
```

CACGGAGGCCTGCCCTGACTGCCCACGGTGCCGTGGCCAAAGAGGATCTAAGGGCA

CCGCTGAGGGCCTACCTAACCATCGTGGGGAATAAGGACAGTGTCACCC ccctgcaggggatccggtggtggtgcaaat >SEQ ID NO: 7; amiR-33-hCTSK-2:
GtcttttatttcaggtcccagatcttAGGGCTCTGCGTTTGCTCCAGGTAGTCCGCTGCTCCCTTGGG

CCTGGGCCCACTGACAGCCCTGGTGCCTCTGGCCGGCTGCACACCTCCTGGCGGGC

AGCTGTGtcagattatcgctattgcagcTGTTCTGGCAATACCTGGCTGCAATTCCAATAATCTGA

CACGGAGGCCTGCCCTGACTGCCCACGGTGCCGTGGCCAAAGAGGATCTAAGGGCA

CCGCTGAGGGCCTACCTAACCATCGTGGGGAATAAGGACAGTGTCACCC ccctgcaggggatccggtggtggtgcaaat >SEQ ID NO: 8; amiR-33-mSOSTi-1:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGAcaagtaggcagatgaggcacTGTTCTGGCAATACCTGGTGCCTCAAG

TACCTACTTGTCACGGAGGCCTGCCCTGACTGCCCACGGTGCCGTGGCCAAAGAG

GATCTAAGGGCACCGCTGAGGGCCTACCTAACCATCGTGGGGAATAAGGACAGTG

TCACCCCTGCAGgggatccggtggtggtgcaaatca

>SEQ ID NO: 9; amiR-33-mSOSTi-2:
tttgtcttttatttcaggtcccAGATCTAGGGCTCTGCGTTTGCTCCAGGTAGTCCGCTGCTCCC

TTGGGCCTGGGCCCACTGACAGCCCTGGTGCCTCTGGCCGGCTGCACACCTCCTG

GCGGGCAGCTGTGtgacctctgtggcatcattccTGTTCTGGCAATACCTGGGAATGATCGCG

CAGAGGTCACACGGAGGCCTGCCCTGACTGCCCACGGTGCCGTGGCCAAAGAGG

ATCTAAGGGCACCGCTGAGGGCCTACCTAACCATCGTGGGGAATAAGGACAGTGT

CACCCCTGCAGgggatccggtggtggtgcaaatca

>SEQ ID NO: 10; amiR-33-hSosT-1:
GtcttttatttcaggtcccagatcttAGGGCTCTGCGTTTGCTCCAGGTAGTCCGCTGCTCCCTTGGG

CCTGGGCCCACTGACAGCCCTGGTGCCTCTGGCCGGCTGCACACCTCCTGGCGGGC

AGCTGTGatggtcttgttgttctccagcTGTTCTGGCAATACCTGGCTGGAGATGAGCAAGACCA

TCACGGAGGCCTGCCCTGACTGCCCACGGTGCCGTGGCCAAAGAGGATCTAAGGGC

ACCGCTGAGGGCCTACCTAACCATCGTGGGGAATAAGGACAGTGTCACCC ccctgcaggggatccggtggtggtgcaaat >SEQ ID NO: 11; amiR-33-hSosT-2:
GtcttttatttcaggtcccagatcttAGGGCTCTGCGTTTGCTCCAGGTAGTCCGCTGCTCCCTTGGG

CCTGGGCCCACTGACAGCCCTGGTGCCTCTGGCCGGCTGCACACCTCCTGGCGGGC

AGCTGTGACGtCtttGGtCtCAAAGGGGTGTTCTGGCAATACCTGCCCCTTTGTCATCAA

AGACGTCACGGAGGCCTGCCCTGACTGCCCACGGTGCCGTGGCCAAAGAGGATCTA

AGGGCACCGCTGAGGGCCTACCTAACCATCGTGGGGAATAAGGACAGTGTCACCC ccctgcaggggatccggtggtggtgcaaat >SEQ ID NO: 12; Human PTH (1-84 aa):
ggaattgtacccgcggccgatccAccggtGCCACCATGATACCTGCAAAAGACATGGCTAAAGTTA

TGATTGTCATGTTGGCAATTTGTTTTCTTACAAAATCGGATGGGAAATCTGTTAAGA

AGAGATCTGTGAGTGAAATACAGCTTATGCATAACCTGGGAAAACATCTGAACTCG

ATGGAGAGAGTAGAATGGCTGCGTAAGAAGCTGCAGGATGTGCACAATTTTGTTGC

-continued

CCTTGGAGCTCCTCTAGCTCCCAGAGATGCTGGTTCCCAGAGGCCCCGAAAAAAGG

AAGACAATGTCTTGGTTGAGAGCCATGAAAAAAGTCTTGGAGAGGCAGACAAAGCT

GATGTGAATGTATTAACTAAAGCTAAATCCCAGTGAagcttatcgataccgtcgactagagctc

>SEQ ID NO: 13; Human PTHrP (1-140 aa):
ggaattgtacccgcggccgatccAccggtGCCACCATGCAGCGGAGACTGGTTCAGCAGTGGAGCG

TCGCGGTGTTCCTGCTGAGCTACGCGGTGCCCTCCTGCGGGCGCTCGGTGGAGGGTC

TCAGCCGCCGCCTCAAAAGAGCTGTGTCTGAACATCAGCTCCTCCATGACAAGGGG

AAGTCCATCCAAGATTTACGGCGACGATTCTTCCTTCACCATCTGATCGCAGAAATC

CACACAGCTGAAATCAGAGCTACCTCGGAGGTGTCCCCTAACTCCAAGCCCTCTCCC

AACACAAAGAACCACCCCGTCCGATTTGGGTCTGATGATGAGGGCAGATACCTAAC

TCAGGAAACTAACAAGGTGGAGACGTACAAAGAGCAGCCGCTCAAGACACCTGGG

AAGAAAAAGAAAGGCAAGCCCGGGAAACGCAAGGAGCAGGAAAAGAAAAAACGG

CGAACTCGCTCTGCCTGGTTAGACTCTGGAGTGACTGGGAGTGGGCTAGAAGGGGA

CCACCTGTCTGACACCTCCACAACGTCGCTGGAGCTCGATTCACGGTAAagcttatcgatac cgtcgactagagctc

>SEQ ID NO: 14; Mouse DJ-1 (1-190 aa):
ggaattgtacccgcggccgatccaccggtcGCCACCATGGGATGGAGCTGTATTATCCTGTTTCT

CGTCGCTACTGCCACCGGAGCTCATTCCGCTTCCAAAAGAGCTCTGGTCATCCTGG

CCAAAGGAGCAGAGGAGATGGAGACAGTGATTCCTGTGGATGTCATGCGGCGAGC

CGGGATCAAAGTCACTGTTGCAGGCTTGGCTGGGAAGGACCCCGTGCAGTGTAGC

CGTGATGTAATGATTTGTCCAGATACCAGTCTGGAAGATGCAAAAACGCAGGGACC

ATACGATGTGGTGGTTCTTCCAGGAGGAAATCTGGGTGCACAGAATTTATCTGAGT

CGCCTATGGTGAAGGAGATCCTCAAGGAGCAGGAGAGCAGGAAGGGCCTCATAGC

TGCCATCTGTGCAGGTCCTACGGCTCTGTTGGCTCACGAAGTAGGTTTTGGATGCA

AGGTCACAACACACCCACTGGCTAAGGACAAAATGATGAATGGCAGTCACTACAGC

TACTCAGAGAGCCGCGTGGAGAAGGACGGCCTGATCCTCACCAGCCGCGGGCCG

GGGACCAGCTTTGAGTTTGCACTAGCCATTGTGGAGGCACTCGTGGGGAAAGACA

TGGCCAACCAAGTGAAGGCACCGCTTGTTCTCAAAGACTAGTAAagcttatcgataccgtc gactagagctcgctg

>SEQ ID NO: 15; Human DJ-1 (1-190 aa):
ggaattgtacccgcggccgatccaccggtc GCCACC ATG GGA TGG AGC TGT ATT

ATC CTG TTT CTC GTC GCT ACT GCC ACC GGA GCT CAT

TCCGCTTCCAAAAGAGCTCTGGTCATCCTGGCTAAAGGAGCAGAGGAAATGGAGAC

GGTCATCCCTGTAGATGTCATGAGGCGAGCTGGGATTAAGGTCACCGTTGCAGGCC

TGGCTGGAAAAGACCCAGTACAGTGTAGCCGTGATGTGGTCATTTGTCCTGATGCC

AGCCTTGAAGATGCAAAAAAGAGGGACCATATGATGTGGTGGTTCTACCAGGAGG

TAATCTGGGCGCACAGAATTTATCTGAGTCTGCTGCTGTGAAGGAGATACTGAAGG

AGCAGGAAAACCGGAAGGGCCTGATAGCCGCCATCTGTGCAGGTCCTACTGCTCTG

TTGGCTCATGAAATAGGTTTTGGAAGTAAAGTTACAACACACCCTCTTGCTAAAGAC

AAAATGATGAATGGAGGTCATTACACCTACTCTGAGAATCGTGTGGAAAAAGACGG

CCTGATTCTTACAAGCCGGGGCCTGGGACCAGCTTCGAGTTTGCGCTTGCAATTGT

TGAAGCCCTGAATGGCAAGGAGGTGGCGGCTCAAGTGAAGGCTCCACTTGTTCTTA

```
AAGACTAGTAAaagcttatcgataccgtcgactagagctcgctg
```

>SEQ ID NO: 16; (AspSerSer)₆ Bone-targeting Peptide
DSSDSSDSSDSSDSSDSS

>SEQ ID NO: 17; HABP-19, Bone-targeting Peptide
CγEPRRγEVAγELγEPRRγEVAγEL,
γ(Gla residue): γ-carboxylated glutamic acid (Glu) is derived
from Glu by vitamin K-dependent γ-carboxylation.

>SEQ ID NO 18: AAV-CAPSID 1;
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPATPAAVGPTTMASGGGAPMADNNEGADGVGNASGN

WHCDSTWLGDRVITTSTRTWALPTYNNHLYKQISSASTGASNDNHYFGYSTPWGYFDF

NRFHCHFSPRDWQRLINNNWGFRPKRLNFKLFNIQVKEVTTNDGVTTIANNLTSTVQVF

SDSEYQLPYVLGSAHQGCLPPFPADVFMIPQYGYLTLNNGSQAVGRSSFYCLEYFPSQM

LRTGNNFTFSYTFEEVPFHSSYAHSQSLDRLMNPLIDQYLYYLNRTQNQSGSAQNKDLL

FSRGSPAGMSVQPKNWLPGPCYRQQRVSKTKTDNNNSNFTWTGASKYNLNGRESIINP

GTAMASHKDDEDKFFPMSGVMIFGKESAGASNTALDNVMITDEEEIKATNPVATERFG

TVAVNFQSSSTDPATGDVHAMGALPGMVWQDRDVYLQGPIWAKIPHTDGHFHPSPLM

GGFGLKNPPPQILIKNTPVPANPPAEFSATKFASFITQYSTGQVSVEIEWELQKENSKRW

NPEVQYTSNYAKSANVDFTVDNNGLYTEPRPIGTRYLTRPL

>SEQ ID NO 19: AAV-CAPSID 2;
MAADGYLPDWLEDTLSEGIRQWWKLKPGPPPPKPAERHKDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPVEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLR

TGNNFTFSYTFEDVPFHSSYAHSQSLDRLMNPLIDQYLYYLSRTNTPSGTTTQSRLQFSQ

AGASDIRDQSRNWLPGPCYRQQRVSKTSADNNNSEYSWTGATKYHLNGRDSLVNPGP

AMASHKDDEEKFFPQSGVLIFGKQGSEKTNVDIEKVMITDEEEIRTTNPVATEQYGSVST

NLQRGNRQAATADVNTQGVLPGMVWQDRDVYLQGPIWAKIPHTDGHFHPSPLMGGF

GLKHPPPQILIKNTPVPANPSTTFSAAKFASFITQYSTGQVSVEIEWELQKENSKRWNPEI

QYTSNYNKSVNVDFTVDTNGVYSEPRPIGTRYLTRNL

>SEQ ID NO 20: AAV-CAPSID 3B;
MAADGYLPDWLEDNLSEGIREWWALKPGVPQPKANQQHQDNRRGLVLPGYKYLGPG

NGLDKGEPVNEADAAALEHDKAYDQQLKAGDNPYLKYNHADAEFQERLQEDTSFGG

NLGRAVFQAKKRILEPLGLVEEAAKTAPGKKRPVDQSPQEPDSSSGVGKSGKQPARKR

LNFGQTGDSESVPDPQPLGEPPAAPTSLGSNTMASGGGAPMADNNEGADGVGNSSGN

WHCDSQWLGDRVITTSTRTWALPTYNNHLYKQISSQSGASNDNHYFGYSTPWGYFDF

NRFHCHFSPRDWQRLINNNWGFRPKKLSFKLFNIQVKEVTQNDGTTTIANNLTSTVQVF

TDSEYQLPYVLGSAHQGCLPPFPADVFMVPQYGYLTLNNGSQAVGRSSFYCLEYFPSQ

MLRTGNNFQFSYTFEDVPFHSSYAHSQSLDRLMNPLIDQYLYYLNRTQGTTSGTTNQSR

-continued

LLFSQAGPQSMSLQARNWLPGPCYRQQRLSKTANDNNNSNFPWTAASKYHLNGRDSL

VNPGPAMASHKDDEEKFFPMHGNLIFGKEGTTASNAELDNVMITDEEEIRTTNPVATEQ

YGTVANNLQSSNTAPTTRTVNDQGALPGMVWQDRDVYLQGPIWAKIPHTDGHFHPSP

LMGGFGLKHPPPQIMIKNTPVPANPPTTFSPAKFASFITQYSTGQVSVEIEWELQKENSK

RWNPEIQYTSNYNKSVNVDFTVDTNGVYSEPRPIGTRYLTRNL

>SEQ ID NO 21: AAV-CAPSID 4:
MTDGYLPDWLEDNLSEGVREWWALQPGAPKPKANQQHQDNARGLVLPGYKYLGPGN

GLDKGEPVNAADAAALEHDKAYDQQLKAGDNPYLKYNHADAEFQQRLQGDTSFGGN

LGRAVFQAKKRVLEPLGLVEQAGETAPGKKRPLIESPQQPDSSTGIGKKGKQPAKKKLV

FEDETGAGDGPPEGSTSGAMSDDSEMRAAAGGAAVEGGQGADGVGNASGDWHCDST

WSEGHVTTTSTRTWVLPTYNNHLYKRLGESLQSNTYNGFSTPWGYFDFNRFHCHFSPR

DWQRLINNNWGMRPKAMRVKIFNIQVKEVTTSNGETTVANNLTSTVQIFADSSYELPY

VMDAGQEGSLPPFPNDVFMVPQYGYCGLVTGNTSQQQTDRNAFYCLEYFPSQMLRTG

NNFEITYSFEKVPFHSMYAHSQSLDRLMNPLIDQYLWGLQSTTTGTTLNAGTATTNFTK

LRPTNFSNFKKNWLPGPSIKQQGFSKTANQNYKIPATGSDSLIKYETHSTLDGRWSALTP

GPPMATAGPADSKFSNSQLIFAGPKQNGNTATVPGTLIFTSEEELAATNATDTDMWGNL

PGGDQSNSNLPTVDRLTALGAVPGMVWQNRDIYYQGPIWAKIPHTDGHFHPSPLIGGFG

LKHPPPQIFIKNTPVPANPATTFSSTPVNSFITQYSTGQVSVQIDWEIQKERSKRWNPEVQ

FTSNYGQQNSLLWAPDAAGKYTEPRAIGTRYLTHHL

>SEQ ID NO 22: AAV-CAPSID 5:
MSFVDHPPDWLEEVGEGLREFLGLEAGPPKPKPNQQHQDQARGLVLPGYNYLGPGNG

LDRGEPVNRADEVAREHDISYNEQLEAGDNPYLKYNHADAEFQEKLADDTSFGGNLG

KAVFQAKKRVLEPFGLVEEGAKTAPTGKRIDDHFPKRKKARTEEDSKPSTSSDAEAGPS

GSQQLQIPAQPASSLGADTMSAGGGGPLGDNNQGADGVGNASGDWHCDSTWMGDRV

VTKSTRTWVLPSYNNHQYREIKSGSVDGSNANAYFGYSTPWGYFDFNRFHSHWSPRD

WQRLINNYWGFRPRSLRVKIFNIQVKEVTVQDSTTTIANNLTSTVQVFTDDDYQLPYVV

GNGTEGCLPAFPPQVFTLPQYGYATLNRDNTENPTERSSFFCLEYFPSKMLRTGNNFEFT

YNFEEVPFHSSFAPSQNLFKLANPLVDQYLYRFVSTNNTGGVQFNKNLAGRYANTYKN

WFPGPMGRTQGWNLGSGVNRASVSAFATTNRMELEGASYQVPPQPNGMTNNLQGSN

TYALENTMIFNSQPANPGTTATYLEGNMLITSESETQPVNRVAYNVGGQMATNNQSST

TAPATGTYNLQEIVPGSVWMERDVYLQGPIWAKIPETGAHFHPSPAMGGFGLKHPPPM

MLIKNTPVPGNITSFSDVPVSSFITQYSTGQVTVEMEWELKKENSKRWNPEIQYTNNYN

DPQFVDFAPDSTGEYRTTRPIGTRYLTRPL

>SEQ ID NO 23: AAV-CAPSID 6:
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPFGLVEEGAKTAPGKKRPVEQSPQEPDSSSGIGKTGQQPAKKRL

NFGQTGDSESVPDPQPLGEPPATPAAVGPTTMASGGGAPMADNNEGADGVGNASGNW

HCDSTWLGDRVITTSTRTWALPTYNNHLYKQISSASTGASNDNHYFGYSTPWGYFDFN

RFHCHFSPRDWQRLINNNWGFRPKRLNFKLFNIQVKEVTTNDGVTTIANNLTSTVQVFS

DSEYQLPYVLGSAHQGCLPPFPADVFMIPQYGYLTLNNGSQAVGRSSFYCLEYFPSQML

RTGNNFTFSYTFEDVPFHSSYAHSQSLDRLMNPLIDQYLYYLNRTQNQSGSAQNKDLLF

-continued

SRGSPAGMSVQPKNWLPGPCYRQQRVSKTKTDNNNSNFTWTGASKYNLNGRESIINPG

TAMASHKDDKDKFFPMSGVMIFGKESAGASNTALDNVMITDEEEIKATNPVATERFGT

VAVNLQSSSTDPATGDVHVMGALPGMVWQDRDVYLQGPIWAKIPHTDGHFHPSPLMG

GFGLKHPPPQILIKNTPVPANPPAEFSATKFASFITQYSTGQVSVEIEWELQKENSKRWNP

EVQYTSNYAKSANVDFTVDNNGLYTEPRPIGTRYLTRPL

>SEQ ID NO 24: AAV-CAPSID 6.2;
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPATPAAVGPTTMASGGGAPMADNNEGADGVGNASGN

WHCDSTWLGDRVITTSTRTWALPTYNNHLYKQISSASTGASNDNHYFGYSTPWGYFDF

NRFHCHFSPRDWQRLINNNWGFRPKRLNFKLFNIQVKEVTTNDGVTTIANNLTSTVQVF

SDSEYQLPYVLGSAHQGCLPPFPADVFMIPQYGYLTLNNGSQAVGRSSFYCLEYFPSQM

LRTGNNFTFSYTFEDVPFHSSYAHSQSLDRLMNPLIDQYLYYLNRTQNQSGSAQNKDLL

FSRGSPAGMSVQPKNWLPGPCYRQQRVSKTKTDNNNSNFTWTGASKYNLNGRESIINP

GTAMASHKDDKDKFFPMSGVMIFGKESAGASNTALDNVMITDEEEIKATNPVATERFG

TVAVNLQSSSTDPATGDVHVMGALPGMVWQDRDVYLQGPIWAKIPHTDGHFHPSPLM

GGFGLKHPPPQILIKNTPVPANPPAEFSATKFASFITQYSTGQVSVEIEWELQKENSKRW

NPEVQYTSNYAKSANVDFTVDNNGLYTEPRPIGTRYLTRPL

>SEQ ID NO 25: AAV-CAPSID 7:
MAADGYLPDWLEDNLSEGIREWWDLKPGAPKPKANQQKQDNGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPAKKRPVEPSPQRSPDSSTGIGKKGQQPARKR

LNFGQTGDSESVPDPQPLGEPPAAPSSVGSGTVAAGGGAPMADNNEGADGVGNASGN

WHCDSTWLGDRVITTSTRTWALPTYNNHLYKQISSETAGSTNDNTYFGYSTPWGYFDF

NRFHCHFSPRDWQRLINNNWGFRPKKLRFKLFNIQVKEVTTNDGVTTIANNLTSTIQVF

SDSEYQLPYVLGSAHQGCLPPFPADVFMIPQYGYLTLNNGSQSVGRSSFYCLEYFPSQM

LRTGNNFEFSYSFEDVPFHSSYAHSQSLDRLMNPLIDQYLYYLARTQSNPGGTAGNREL

QFYQGGPSTMAEQAKNWLPGPCFRQQRVSKTLDQNNNSNFAWTGATKYHLNGRNSL

VNPGVAMATHKDDEDRFFPSSGVLIFGKTGATNKTTLENVLMTNEEEIRPTNPVATEEY

GIVSSNLQAANTAAQTQVVNNQGALPGMVWQNRDVYLQGPIWAKIPHTDGNFHPSPL

MGGFGLKHPPPQILIKNTPVPANPPEVFTPAKFASFITQYSTGQVSVEIEWELQKENSKR

WNPEIQYTSNFEKQTGVDFAVDSQGVYSEPRPIGTRYLTRNL

>SEQ ID NO 26: AAV-CAPSID 8:
MAADGYLPDWLEDNLSEGIREWWALKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEPSPQRSPDSSTGIGKKGQQPARKR

LNFGQTGDSESVPDPQPLGEPPAAPSGVGPNTMAAGGGAPMADNNEGADGVGSSSGN

WHCDSTWLGDRVITTSTRTWALPTYNNHLYKQISNGTSGGATNDNTYFGYSTPWGYF

DFNRFHCHFSPRDWQRLINNNWGFRPKRLSFKLFNIQVKEVTQNEGTKTIANNLTSTIQ

VFTDSEYQLPYVLGSAHQGCLPPFPADVFMIPQYGYLTLNNGSQAVGRSSFYCLEYFPS

QMLRTGNNFQFTYTFEDVPFHSSYAHSQSLDRLMNPLIDQYLYYLSRTQTTGGTANTQT

-continued

LGFSQGGPNTMANQAKNWLPGPCYRQQRVSTTTGQNNNSNFAWTAGTKYHLNGRNS

LANPGIAMATHKDDEERFFPSNGILIFGKQNAARDNADYSDVMLTSEEEIKTTNPVATE

EYGIVADNLQQQNTAPQIGTVNSQGALPGMVWQNRDVYLQGPIWAKIPHTDGNFHPSP

LMGGFGLKHPPPQILIKNTPVPADPPTTFNQSKLNSFITQYSTGQVSVEIEWELQKENSKR

WNPEIQYTSNYYKSTSVDFAVNTEGVYSEPRPIGTRYLTRNL

>SEQ ID NO 27: AAV-CAPSID 9:
MAADGYLPDWLEDNLSEGIREWWALKPGAPQPKANQQHQDNARGLVLPGYKYLGPG

NGLDKGEPVNAADAAALEHDKAYDQQLKAGDNPYLKYNHADAEFQERLKEDTSFGG

NLGRAVFQAKKRLLEPLGLVEEAAKTAPGKKRPVEQSPQEPDSSAGIGKSGAQPAKKR

LNFGQTGDTESVPDPQPIGEPPAAPSGVGSLTMASGGGAPVADNNEGADGVGSSSGNW

HCDSQWLGDRVITTSTRTWALPTYNNHLYKQISNSTSGGSSNDNAYFGYSTPWGYFDF

NRFHCHFSPRDWQRLINNNWGFRPKRLNFKLFNIQVKEVTDNNGVKTIANNLTSTVQV

FTDSDYQLPYVLGSAHEGCLPPFPADVFMIPQYGYLTLNDGSQAVGRSSFYCLEYFPSQ

MLRTGNNFQFSYEFENVPFHSSYAHSQSLDRLMNPLIDQYLYYLSKTINGSGQNQQTLK

FSVAGPSNMAVQGRNYIPGPSYRQQRVSTTVTQNNNSEFAWPGASSWALNGRNSLMN

PGPAMASHKEGEDRFFPLSGSLIFGKQGTGRDNVDADKVMITNEEEIKTTNPVATESYG

QVATNHQSAQAQAQTGWVQNQGILPGMVWQDRDVYLQGPIWAKIPHTDGNFHPSPL

MGGFGMKHPPPQILIKNTPVPADPPTAFNKDKLNSFITQYSTGQVSVEIEWELQKENSKR

WNPEIQYTSNYYKSNNVEFAVNTEGVYSEPRPIGTRYLTRNL

>SEQ ID NO 28: AAV-CAPSID rh8:
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPAAPSGLGPNTMASGGGAPMADNNEGADGVGNSSGN

WHCDSTWLGDRVITTSTRTWALPTYNNHLYKQISNGTSGGSTNDNTYFGYSTPWGYFD

FNRFHCHFSPRDWQRLINNNWGFRPKRLNFKLFNIQVKEVTTNEGTKTIANNLTSTVQV

FTDSEYQLPYVLGSAHQGCLPPFPADVFMVPQYGYLTLNNGSQALGRSSFYCLEYFPSQ

MLRTGNNFQFSYTFEDVPFHSSYAHSQSLDRLMNPLIDQYLYYLVRTQTTGTGGTQTLA

FSQAGPSSMANQARNWVPGPCYRQQRVSTTTNQNNNSNFAWTGAAKFKLNGRDSLM

NPGVAMASHKDDDDRFFPSSGVLIFGKQGAGNDGVDYSQVLITDEEEIKATNPVATEEY

GAVAINNQAANTQAQTGLVHNQGVIPGMVWQNRDVYLQGPIWAKIPHTDGNFHPSPL

MGGFGLKHPPPQILIKNTPVPADPPLTFNQAKLNSFITQYSTGQVSVEIEWELQKENSKR

WNPEIQYTSNYYKSTNVDFAVNTEGVYSEPRPIGTRYLTRNL

>SEQ ID NO 29: AAV-CAPSID rh10:
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEPSPQRSPDSSTGIGKKGQQPAKK

RLNFGQTGDSESVPDPQPIGEPPAGPSGLGSGTMAAGGGAPMADNNEGADGVGSSSGN

WHCDSTWLGDRVITTSTRTWALPTYNNHLYKQISNGTSGGSTNDNTYFGYSTPWGYFD

FNRFHCHFSPRDWQRLINNNWGFRPKRLNFKLFNIQVKEVTQNEGTKTIANNLTSTIQV

FTDSEYQLPYVLGSAHQGCLPPFPADVFMIPQYGYLTLNNGSQAVGRSSFYCLEYFPSQ

MLRTGNNFEFSYQFEDVPFHSSYAHSQSLDRLMNPLIDQYLYYLSRTQSTGGTAGTQQL

LFSQAGPNNMSAQAKNWLPGPCYRQQRVSTTLSQNNNSNFAWTGATKYHLNGRDSLV

NPGVAMATHKDDEERFFPSSGVLMFGKQGAGKDNVDYSSVMLTSEEEIKTTNPVATEQ

YGVVADNLQQQNAAPIVGAVNSQGALPGMVWQNRDVYLQGPIWAKIPHTDGNFHPSP

LMGGFGLKHPPPQILIKNTPVPADPPTTFSQAKLASFITQYSTGQVSVEIEWELQKENSKR

WNPEIQYTSNYYKSTNVDFAVNTDGTYSEPRPIGTRYLTRNL

>SEQ ID NO 30: AAV-CAPSID rh39:
MAADGYLPDWLEDNLSEGIREWWALKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEAAKTAPGKKRPVEPSPQRSPDSSTGIGKKGQQPAKK

RLNFGQTGDSESVPDPQPIGEPPAGPSGLGSGTMAAGGGAPMADNNEGADGVGSSSGN

WHCDSTWLGDRVITTSTRTWALPTYNNHLYKQISNGTSGGSTNDNTYFGYSTPWGYFD

FNRFHCHFSPRDWQRLINNNWGFRPKRLSFKLFNIQVKEVTQNEGTKTIANNLTSTIQVF

TDSEYQLPYVLGSAHQGCLPPFPADVFMIPQYGYLTLNNGSQAVGRSSFYCLEYFPSQM

LRTGNNFEFSYTFEDVPFHSSYAHSQSLDRLMNPLIDQYLYYLSRTQSTGGTQGTQQLL

FSQAGPANMSAQAKNWLPGPCYRQQRVSTTLSQNNNSNFAWTGATKYHLNGRDSLV

NPGVAMATHKDDEERFFPSSGVLMFGKQGAGRDNVDYSSVMLTSEEEIKTTNPVATEQ

YGVVADNLQQTNTGPIVGNVNSQGALPGMVWQNRDVYLQGPIWAKIPHTDGNFHPSP

LMGGFGLKHPPPQILIKNTPVPADPPTTFSQAKLASFITQYSTGQVSVEIEWELQKENSKR

WNPEIQYTSNYYKSTNVDFAVNTEGTYSEPRPIGTRYLTRNL

>SEQ ID NO 31: AAV-CAPSID rh43:
MAADGYLPDWLEDNLSEGIREWWDLKPGAPKPKANQQKQDDGRGLVLPGYKYLGPF

NGLDKGEPVNAADAAALEHDKAYDQQLEAGDNPYLRYNHADAEFQERLQEDTSFGG

NLGRAVFQAKKRVLEPLGLVEEGAKTAPGKKRPVEQSPQEPDSSSGIGKKGQQPARKR

LNFGQTGDSESVPDPQPLGEPPAAPSGVGPNTMAAGGGAPMADNNEGADGVGSSSGN

WHCDSTWLGDRVITTSTRTWALPTYNNHLYKQISNGTSGGATNDNTYFGYSTPWGYF

DFNRFHCHFSPRDWQRLINNNWGFRPKRLSFKLFNIQVKEVTQNEGTKTIANNLTSTIQ

VFTDSEYQLPYVLGSAHQGCLPPFPADVFMIPQYGYLTLNNGSQAVGRSSFYCLEYFPS

QMLRTGNNFQFTYTFEDVPFHSSYAHSQSLDRLMNPLIDQYLYYLSRTQTTGGTANTQT

LGFSQGGPNTMANQAKNWLPGPCYRQQRVSTTTGQNNNSNFAWTAGTKYHLNGRNS

LANPGIAMATHKDDEERFFPSNGILIFGKQNAARDNADYSDVMLTSEEEIKTTNPVATE

EYGIVADNLQQQNTAPQIGTVNSQGALPGMVWQNRDVYLQGPIWAKIPHTDGNFHPSP

LMGGFGLKHPPPQILIKNTPVPADPPTTFNQSKLNSFITQYSTGQVSVEIEWELQKENSKR

WNPEIQYTSNYYKSTVDFAVNTEGVYSEPRPIGTRYLTRNL

>SEQ ID NO 32: AAV-CAPSID 2/2-66:
MAADGYLPDWLEDTLSEGIRQWWKLKPGPPPPKPAERHQDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPAEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLR

TGNNFTFSYTFEDVPFHSSYAHSQSLDRLMNPLIDQYLYYLSKTNAPSGTTTMSRLQFSQ

AGASDIRDQSRNWLPGPCYRQQRVSKTAADNNNSDYSWTGATKYHLNGRDSLVNPGP

AMASHKDDEEKYFPQSGVLIFGKQDSGKTNVDIEKVMITDEEEIRTTNPVATEQYGSVS

TNLQSGNTQAATTDVNTQGVLPGMVWQDRDVYLQGPIWAKIPHTDGHFHPSPLMGGF

GLKHPPPQILIKNTPVPANPSTTFSAAKFASFITQYSTGQVSVEIEWELQKENSKRWNPEI

QYTSNYNKSVNVDFTVDTNGVYSEPRPIGTRYLTRNL

>SEQ ID NO 33: AAV-CAPSID 2/2-84:
MAADGYLPDWLEDTLSEGIRQWWKLKPGPPPPKPAERHQDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPAEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLR

TGNNFTFSYTFEDVPFHSSYAHSQSLDRLMNPLIDQYLYYLSKTNAPSGTTTMSRLQFSQ

AGASDIRDQSRNWLPGPCYRQQRVSKTAADNNNSDYSWTGATKYHLNGRDSLVNPGP

AMASHKDDEEKYFPQSGVLIFGKQDSGKTNVDIEKVMITDEEEIRTTNPVATEQYGSVS

TNLQSGNTQAATTDVNTQGVLPGMVWQDRDVYLQGPIWAKIPHTDGHFHPSPLMGGF

GLKHPPPQILIKNTPVPANPSTTFSAAKLASFITQYSTGQVSVEIEWELQKENSKRWNPEI

QYTSNYNKSVNVDFTVDTNGVYSEPRPIGTRYLTRNL

>SEQ ID NO 34: AAV-CAPSID 2/2-125:
MAADGYLPDWLEDTLSEGIRQWWKLKPGPPPPKPAERHKDDSRGLVLPGYKYLGPFN

GLDKGEPVNEADAAALEHDKAYDRQLDSGDNPYLKYNHADAEFQERLKEDTSFGGNL

ARAVFQAKKRVLEPLGLVEEPVKTAPGKKRPVEHSPAEPDSSSGTGKSGQQPARKRLNF

GQTGDADSVPDPQPLGQPPAAPSGLGTNTMASGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQTVGRSSFYCLEYFPSQMLR

TGNNFTFSYTFEDVPFHSSYAHSQSLDRLMNPLIDQYLYYLSRTNTPSGTTTQSRLRFSQ

AGASDIRDQSRNWLPGPCYRQQRVSKTAADNNNSDYSWTGATKYHLNGRDSLVNPGT

AMASHKDDEEKYFPQSGVLIFGKQDSGKTNVDIERVMITDEEEIRTTNPVATEQYGSVS

TNLQSGNTQAATSDVNTQGVLPGMVWQDRDVYLQGPIWAKIPHTDGHFHPSPLMGGF

GLKHPPPQILIKNTPVPANPSTTFSAAKFASFITQYSTGQVSVEIEWELQKENSKRWNPEI

QYTSNYNKSVNVDFTVDTNGVYSEPRPIGTRYLTRNL

>SEQ ID NO: 69 Human Schnurri-3 nucleotide sequence
CTCACAACCAGCCGACTCTCCCATTATCCAGCTGCCTAGTTTGGTGCTTCAATGTACA

TGGCTATTCCGTGTGCATATGTGTGTATACAAACACGCATGCATGCCTGGATGGACATA

CGTATGCACAGGTTATTTTTTAAGGACAATTCTTTCAATAAGGTCTTTACCCCTTACTT

GAAACAGGTGTTCATGAAAAAAATGCACAAAATCCTGCCTGGCCGGAATAATTCATG

AAGAAGGGGCTGGATCCGTGGGTCAGAGAACACAGGACCAGTTTGCCATCCCAAGG

CCGAAGGATTCGAGGCACAAACCCAGCAGCCTCAACCTAGTTCATGGAGGAGCCTC

GCGGGGTCCTGGCCAAGCAAGCCCGCCCCTCTGGTGGGAAGAGCGGCGCCTAGGTG

GAGGGTGGCTGCCGTAGGAGTGGACATGAATGCTGGCTTTCAGAGAGAACAGCGTT

-continued

```
TCAGTTTTGGTCATCGGAAGTGGTGCCTTCAGCACAGAAGAAGAGCGTGATTTCTCC

TCCAAGGCCGTTGATCTCCAACCCAGAACTAAAGGGGAGAAGAGCCACCCCCAGCA

TCCAGCGTGGCATCTCTTGTGCCAGGACCAGGGATGACTGGGCCATGGACACAGATG

TCTCCAACCTTCAACCGTTTGCATAGCACACGGGGGACTCGTGGGGGCCACCTGCCA

CTGCCAGCTGAAACAATACAATGGCAATACTGACATCCTTCATGACGTTTTCCCGACA

GACATTCAGGCAGAAAGTGCTGGTGCGTTTTCTGTCTGCAAAGTAGAGGGCCATGCC

TCACCAATAGAATAGCGTGGGCCCTGATGACCTGCTCCGAGTCCACTCACAGCCAGT

GACACTTGCAAAAAACTCCCAAAGCCGTCTTGGGTTTGGCTCCCACAGCTCTTGACC

AATGTGGCCAAAGCTGGACACCTCCTTGGGACACTGGGATTATTCATAAATGCAGCC

CGCCCTGACTCTCCCTGAATAGCATCTGAAGTCTTTGTGAAGGTCATGGATCCTGAAC

AAAGTGTCAAGGGCACCAAGAAGGCTGAGGGAAGTCCCCGGAAGCGGCTGACCAA

AGGAGAGGCCATTCAGACCAGTGTTTCTTCCAGCGTCCCATACCCAGGCAGCGGCAC

AGCTGCCACCCAAGAGAGCCCCGCCCAAGAGCTCTTAGCCCCGCAGCCCTTCCCGG

GCCCCTCATCAGTTCTTAGGGAAGGCTCTCAGGAGAAAACGGGCCAGCAGCAGAAG

CCCCCCAAAAGGCCCCCCATCGAAGCATCCGTCCACATCTCACAGCTTCCGCAGCAC

CCTCTGACACCAGCATTCATGTCGCCTGGCAAACCTGAGCATCTCCTGGAGGGGTCC

ACATGGCAACTGGTTGACCCCATGAGACCTGGACCCTCTGGCTCCTTCGTGGCCCCT

GGGCTCCATCCTCAGAGCCAGCTCCTTCCTTCCCACGCTTCCATCATTCCCCCCGAGG

ACCTTCCTGGAGTCCCCAAAGTCTTCGTGCCTCGTCCTTCCCAGGTCTCCTTGAAGC

CCACAGAAGAGGCACACAAGAAGGAGAGGAAGCCCCAGAAGCCAGGCAAGTACAT

CTGCCAGTACTGCAGCCGGCCCTGTGCCAAGCCCAGCGTGCTCCAGAAGCACATTCG

CTCACACACAGGTGAGAGGCCCTACCCCTGCGGCCCCTGTGGCTTCTCCTTCAAGAC

CAAGAGTAATCTCTACAAGCACAGGAAGTCCCATGCCCACCGCATCAAAGCAGGCCT

GGCCTCAGGCATGGGTGGCGAGATGTACCCACATGGGCTGGAGATGGAGCGGATCCC

TGGGGAAGAGTTTGAGGAGCCCACTGAGGGAGAAAGCACAGATTCTGAAGAGGAG

ACTAGTGCCACCTCTGGTCACCCTGCAGAGCTCTCCCCAAGACCCAAGCAGCCCCTT

CTCTCCAGCGGGCTATACAGCTCTGGGAGCCACAGTTCCAGCCACGAACGCTGTTCC

CTGTCCCAGTCCAGCACAGCCCAGTCACTCGAAGACCCCCCTCCATTTGTGGAACCC

TCATCTGAGCACCCCCTGAGCCATAAACCTGAAGACACCCACACGATTAAGCAGAAG

CTGGCCCTCCGCTTAAGCGAGAGGAAGAAGGTGATCGATGAGCAGGCGTTTCTGAG

CCCAGGCAGCAAAGGGAGTACTGAGTCTGGGTATTTCTCTCGCTCCGAGAGTGCAGA

GCAGCAGGTCAGCCCCCCAAACACCAACGCCAAGTCCTACGCTGAGATCATCTTTGG

CAAGTGTGGCGAATAGGACAGCGGACCGCCATGCTGACAGCCACCTCCACCCAGC

CCCTCCTGCCCCTGTCCACCGAAGACAAGCCCAGCCTGGTGCCTTTGTCTGTACCCC

GGACGCAGGTGATCGAGCACATCACGAAGCTCATCACCATCAACGAGGCCGTGGTG

GACACCAGCGAGATCGACAGCGTGAAGCCAAGGCGGAGCTCACTGTCCAGGCGCA

GCAGCATGGAGTCCCCAAAATCCAGCCTCTACCGGGAGCCCCTGTCATCCCACAGTG

AGAAAACCAAGCCTGAACAATCACTGCTGAGCCTCCAGCACCCGCCCAGTACCGCC

CCCCCTGTGCCTCTCCTGAGAAGCCACTCAATGCCTTCTGCCGCCTGCACTATCAGCA

CCCCCCACCACCCCTTCCGAGGTAGCTACTCCTTCGATGACCATATCACCGACTCCGA

AGCCCTGAGCCACAGCAGTCACGTGTTTACCTCCCACCCCCGGATGCTGAAGCGCCA
```

```
-continued

GCCGGCAATCGAATTACCTTTGGGAGGGGAATACAGTTCTGAGGAGCCTGGCCCAAG

CAGCAAAGACACAGCCTCCAAGCCCTCGGACGAAGTGGAACCCAAGGAAAGCGAG

CTTACCAAAAAGACCAAGAAGGGTTTGAAAACAAAAGGGGTGATCTACGAATGTAA

CATATGTGGTGCTCGGTACAAGAAAAGGGATAACTACGAAGCCCACAAAAAATACTA

CTGCTCAGAGCTTCAGATCGCAAAGCCCATCTCTGCAGGCACCCACACATCTCCAGA

AGCTGAAAAGAGTCAGATTGAGCATGAGCCGTGGTCCCAAATGATGCATTACAAACT

GGGAACCACCCTGGAACTCACTCCACTGAGGAAGAGGAGGAAAGAGAAGAGCCTT

GGGGACGAGGAAGAGCCACCTGCCTTTGAGTCCACAAAAAGTCAGTTTGGCAGCCC

CGGGCCATCTGATGCTGCTCGGAACCTTCCCCTGGAGTCCACCAAGTCACCAGCAGA

ACCAAGTAAATCAGTGCCCTCCTTGGAGGGACCCACGGGCTTCCAGCCAAGGACTC

CCAAGCCAGGGTCCGGTTCAGAATCAGGGAAGGAGAGGAGAACAACGTCCAAAGA

AATTTCTGTCATCCAGCACACCAGCTCCTTTGAGAAATCTGATTCTCTCGAGCAGCCG

AGTGGCTTGGAAGGGGAAGACAAACCTCTGGCCCAGTTCCCATCACCCCCACCTGC

CCCACACGGACGCTCTGCTCACTCCCTGCAGCCTAAGTTGGTCCGCCAGCCCAACAT

TCAGGTTCCTGAGATCCTAGTAACTGAGGAGCCTGACCGGCCGGACACAGAGCCAG

AGCCGCCCCTAAGGAACCTGAGAAGACTGAGGAGTTCCAATGGCCCCAGCGCAGC

CAGACACTTGCCCAGCTCCCAGCTGAGAAGCTGCCACCCAAAAAGAAGAGGTTGCG

CCTGGCAGAGATGGCCCAATCATCAGGGGAGTCCAGCTTCGAGTCCTCTGTGCCTCT

GTCTCGCAGCCCGAGCCAGGAAAGCAATGTCTCTTTGAGTGGGTCCAGCCGCTCAG

CCTCGTTTGAGAGGGATGACCATGGGAAAGCCGAGGCCCCCAGTCCCTCATCTGACA

TGCGCCCCAAACCCCTGGGCACCCACATGTTGACTGTCCCCAGCCACCACCCACATG

CCCGAGAGATGCGGAGGTCAGCCTCAGAGCAGAGCCCCAACGTTTCCCATTCTGCCC

ACATGACCGAGACACGCAGCAAATCCTTTGACTATGGCAGCTTGTCCTTGACAGGCC

CTTCTGCTCCAGCCCCAGTGGCTCCACCAGCGCGGGTGGCCCCGCCAGAGAGAAGA

AAATGCTTCTTGGTGAGACAGGCCTCTCTGAGCAGGCCTCCAGAATCTGAGTTGGAG

GTTGCCCCCAAGGGAAGACAGGAGAGCGAAGAACCACAGCCCTCATCCAGTAAACC

CTCTGCCAAAAGCTCATTGTCCCAGATTTCCTCTGCGGCCACCTCACATGGTGGACCC

CCGGGAGGCAAGGGCCCAGGGCAGGACAGGCCCCCATTGGGCCCACTGTGCCCTA

CACAGAAGCACTGCAAGTGTTCCACCACCCCGTTGCCCAGACACCCCTGCATGAGA

AGCCATACCTGCCCCCACCAGTCTCCCTTTTCTCCTTCCAGCATCTCGTGCAGCATGA

GCCAGGACAGTCTCCAGAATTCTTCTCCACCCAGGCCATGTCCAGCCTCCTGTCCTC

ACCATACTCCATGCCCCCACTTCCTCCCTCCTTATTTCAAGCCCCACCGCTTCCTCTCC

AGCCTACTGTTCTGCACCCAGGCCAACTCCATCTCCCCCAGCTCATGCCTCACCCAGC

CAACATCCCCTTCAGGCAGCCCCCTTCCTTCCTCCCCATGCCATACCCGACCTCCTCA

GCACTGTCTTCTGGGTTTTTCCTGCCTCTGCAATCCCAGTTTGCACTTCAGCTCCCTG

GTGATGTGGAAAGCCATCTGCCCCAGATCAAAACCAGCCTGGCCCCACTGGCAACA

GGAAGTGCTGGCCTCTCCCCCAGCACAGAGTACAGCAGTGACATCCGGCTACCCCCT

GTGGCTCCCCAGCCAGCTCCTCAGCACCTACATCAGCTCCTCCACTGGCCCTGCCT

GCCTGTCCAGACACCATGGTGTCCCTGGTTGTGCCTGTCCGTGTTCAGACCAATATGC

CGTCCTATGGGAGCGCAATGTACACCACCCTTTCCCAGATCTTGGTCACCCAGTCCCA
```

-continued

```
AGGCAGCTCAGCAACTGTGGCACTTCCCAAGTTTGAGGAACCCCCATCAAAGGGGA

CGACTGTATGTGGTGCAGATGTGCATGAGGTTGGGCCCGGCCCTTCTGGGTTAAGTG

AAGAGCAAAGCAGAGCTTTCCCAACTCCATACCTGAGAGTGCCTGTGACATTACCTG

AAAGAAAAGGCACTTCCCTGTCATCAGAGAGTATCTTGAGCCTGGAGGGGAGTTCAT

CAACAGCAGGGGAAGCAAACGTGTCCTTTCACCAGCTGGCAGCCTTGAACTTACC

ATGGAAACCCAGCAGCAAAAAAGAGTGAAGGAGGAGGAGGCTTCCAAGGCAGATG

AAAAACTTGAGCTGGTAAAACCATGCAGTGTGGTCCTACCAGCACCGAGGATGGGA

AGAGGCCAGAGAAATCCCACTTAGGCAACCAGGGCCAAGGCAGGAGGGAGCTAGA

AATGCTGTCCAGCCTGTCCTCAGATCCATCTGACACAAAGGAAATTCCTCCCCTCCCT

CACCCTGCATTGTCCCATGGGACAGCCCCAGGCTCAGAAGCTTTGAAGGAATATCCC

CAGCCATCTGGCAAACCTCACCGAAGAGGGTTGACCCCACTGAGCGTGAAGAAAGA

AGATTCCAAGGAACAACCTGATCTCCCCTCCTTGGCACCTCCGAGCTCTCTGCCTCT

GTCAGAAACGTCCTCCAGACCAGCCAAGTCACAAGAAGGTACGGACTCAAAGAAG

GTACTGCAGTTCCCCAGCCTCCACACAACCACTAATGTCAGTTGGTGCTATTTAAACT

ACATTAAGCCAAATCACATCCAGCATGCAGATAGGAGGTCCTCTGTTTACGCTGGTTG

GTGCATAAGTTTGTACAACCCCAACCTTCCGGGGGTTTCCACTAAAGCTGCTTTGTCC

CTCCTGAGGTCTAAGCAGAAAGTGAGCAAAGAGACATACACCATGGCCACAGCTCC

GCATCCTGAGGCAGGAAGGCTTGTGCCATCCAGCTCCCGCAAGCCCCGCATGACAG

AGGTTCACCTCCCTTCACTGGTTTCCCCGGAAGGCCAGAAAGATCTAGCTAGAGTGG

AGAAGGAAGAAGAGAGGAGAGGGGAGCCGGAGGAGGATGCTCCTGCCTCCCAGAG

AGGGGAGCCGGCGAGGATCAAAATCTTCGAAGGAGGGTACAAATCAAACGAAGAGT

ATGTATATGTGCGAGGCCGCGGCCGAGGGAAATATGTTTGTGAGGAGTGTGGAATTC

GCTGCAAGAAGCCCAGCATGCTGAAGAAACACATCCGCACCCACACTGACGTCCGG

CCCTATGTGTGCAAGCACTGTCACTTTGCTTTTAAAACCAAAGGGAATCTGACTAAG

CACATGAAGTCGAAGGCCCACAGCAAAAAGTGCCAAGAGACAGGGGTGCTGGAGG

AGCTGGAAGCCGAAGAAGGAACCAGTGACGACCTGTTCCAGGACTCGGAAGGACG

AGAGGGTTCAGAGGCTGTGGAGGAGCACCAGTTTTCGGACCTGGAGGACTCGGACT

CAGACTCAGACCTGGACGAAGACGAGGATGAGGATGAGGAGGAGAGCCAGGATGA

GCTGTCCAGACCATCCTCAGAGGCGCCCCCGCCTGGCCCACCACATGCACTGCGGGC

AGACTCCTCACCCATCCTGGGCCCTCAGCCCCAGATGCCCCCGCCTCTGGCACGGA

GGCTACACGAGGCAGCTCGGTCTCGGAAGCTGAGCGCCTGACAGCCAGCAGCTGCT

CCATGTCCAGCCAGAGCATGCCGGGCCTCCCCTGGCTGGGACCGGCCCCTCTGGGCT

CTGTGGAGAAAGACACAGGCTCAGCCTTGAGCTACAAGCCTGTGTCCCAAGAAGA

CCGTGGTCCCCAAGCAAAGAAGCAGGCAGCCGTCCACCACTAGCCCGCAAACACTC

GCTAACCAAAAACGACTCATCTCCCCAGCGATGCTCCCCGGCCCGAGAACCACAGG

CCTCAGCCCCAAGCCCACCTGGCCTGCACGTGGACCCAGGAAGGGGCATGGGCGCT

CTCCCTTGTGGGTCTCCAAGACTTCAGCTGTCTCCTCTCACCCTCTGCCCCCTGGGAA

GAGAACTGGCCCCTCGAGCACATGTGCTCTCCAAACTCGAGGGTACCACCGACCCA

GGCCTCCCCAGATACTCGCCCACCAGGAGATGGTCTCCAGGTCAGGCCGAGTCACCA

CCACGGTCAGCGCCGCCAGGGAAGTGGGCCTTGGCTGGGCCGGGCAGCCCCTCAGC

GGGGGAGCATGGCCCAGGCTTGGGGCTGGACCCACGGGTTCTCTTCCCGCCCGCGC
```

-continued

```
CTCTACCTCACAAGCTCCTCAGCAGAAGCCCAGAGACCTGCGCCTCCCCGTGGAAG

GCCGAGTCCCGAAGTCCCTCCTGCTCACCCGGCCCTGCTCATCCTCTCTCCTCCCGAC

CCTTCTCCGCCCTCCATGACTTCCACGGCCACATCCTGGCCCGGACAGAGGAGAACA

TCTTCAGCCACCTGCCTCTGCACTCCCAGCACTTGACCCGTGCCCCATGTCCCTTGAT

TCCCATCGGTGGGATCCAGATGGTGCAGGCCCGGCCAGGAGCCCACCCCACCCTGCT

GCCAGGGCCCACCGCAGCCTGGGTCAGTGGCTTCTCCGGGGTGGCAGCGACCTGA

CAGGGGCCCGGGAGGCCCAGGAGCGAGGCCGCTGGAGTCCCACTGAGAGCTCGTC

AGCCTCCGTGTCGCCTGTGGCTAAGGTCTCCAAATTCACACTCTCCTCAGAGCTGGA

GGGCGGGGACTACCCCAAGGAGAGGGAGAGGACCGGCGGAGGCCCGGGCAGGCCT

CCTGACTGGACACCCCATGGGACCGGGGCACCTGCAGAGCCCACACCCACGCACAG

CCCCTGCACCCCACCCGACACCTTGCCCCGGCCGCCCCAGGGACGCCGGGCAGCGC

AGTCCTGGAGCCCCGCTTGGGTCCCGCGTGCACCGACCAACCCCGAGCCTTCTGC

CACCCCGCCGCTGGACCGCAGCAGCTCTGTGGGCTGCCTGGCAGAGGCCTCTGCCC

GCTTCCCAGCCCGGACGAGGAACCTCTCCGGGGAACCCAGGACCAGGCAGGACTCC

CCCAAGCCCTCAGGAAGTGGGGAGCCCAGGGCACATCCACATCAGCCTGAGGACAG

GGTTCCCCCCAACGCTTAGCCTCTCTCCAACTGCTTCAGCATCTGGCTTCCAGTGTCC

AGCAACAGACGTTTCCAGCCACTTTCCTCGAATCATCCCACTTCCTCAGCCCCATCTG

TCCCTCCGTCCAGGAGCTCTCACGGCCCCATCTGTTGTACCTTCCCATGTATGCAGTT

ACCTGTGCCTTTTTCTACACCTTTTGTTGCTTAAAAAGAAACAAAACAAATCACATAC

ATACATTTAAAAAAAAAACAACAACCCACGAGGAGTCTGAGGCTGTGAATAGTTTAT

GGTTTTGGGAAAGGCTGATGGTGAAGCCTCCTGACCCTCCCCGCTGTGGTTGGCAG

CCACCCACCCCAGAGGCTGGCAGAGGGAAAGGGGTACACTGAGGGAGAAAGGAAA

AGGAAACTTCAAACAATATAGAATTAAATGTAAAAGGAAGCACTCCTGTGTACAGAT

GCGATCAAGGTTCCTGTTTATTGCCACTTCACCCCCCTGCCCAGCTCGTAGCCACCCC

TCTCTGCCAGCAGAAAGGCCAGTGTCCCCAGGCAGAGGGGCACAAACACAGGCAG

GTGACCCCCACCCAGGCCCAGCAGGCAGGCCCAGAAAAACTAATCTTTTCCTTTTT

TTTTTTTTTTTTTTTTTGCAAGAAAATAAAATGATACTTTTCCTAGGATTTCAACAC

AAAATAATAGGTGCAGGTAGAAGGAGGAGGGCTGGCTCCCCAAGGGCTCCTGGATA

CTCTGGTAGTCTGAGTCATGGGCCCATCCTGGCACTCCACAGGTGGGCAGGCCACCC

CACCCACGCACCCCCACTCCAGACACCTCCCTTCTGCACCCCACCCTGGCCCCTGG

GCTGGGGAAGGAGCCCTGACTGTCCGTCCCTGGCTCCCAAGCCCCTGACCGAGGCC

TCACTCTCCTGTTGCCTCCTCTGTTCTAAAACCACCAAACCACCCACAAAGGCAGAA

GTGGCAGGGCCCGAGCCCTAGCGGCCGTTCCTGAGACTGGGTTTTGGGTTTTGTTTC

ATCTTGGTCCCTGGGGTACAAGGGAGCCTGTTCCCCTCATGGCTGGGTTTTTCCAGTT

CTCCACAGCAGAGGTTTGCGGGGAACTGTTTCAGGACCACTTTGCCACAGGACCGT

TTCCCCCCGTCCCTGCCCCTGTCTCCACTACCCCAAGGAAATACCCACAACTGTGGCT

GGTGGATACGGCCTGGACCTGTTTGCTGTCTTACACCTCTTTTTTAAAAAGAGAGAG

GATGGTGTTTGATACTTCACCCAGCCACCACAGATTCTTTTGACCTAGAGGATTTTTG

AATTGTCCTAACTCGTTGGAATTCTCCAAAGCAATCAGTGTGAGCCAGTGCCTCTTCC

TTACCCACATCTCTACTTTCAAGAAGCTGCCCTGCATTTCCTGGGGCAAAACTCTACT
```

-continued

```
TTGTAAGAAAAATAATAGGACCAGAAATTTAAATCCCAAATTGAACTATGGAACTTGA
ACTCTAGCGTGTTCGCCCCAACTGGGAGAGGTGAGCTTTTTCCCAGTGTTTCAGAAC
TGATTTTCTTTACTTTCTACAAGGGAGGGCAGCACAGGGACTACGGTTGAGGCCCGT
GAAGGCTGGGTTTGATGCCACCCTATACAGAGCAGGGACCTCTCTGGCTAATCCCCA
GTCCTCAGCCAGGCTGTGTGAATCAAGTGCCTGCCCCAGGGCTCTTGAGCTATTGAA
GCTGCTTGGGTACAGGACACAGTAGGTGGGGAGGGTTAAGACCCTTCTGTGAGTTCC
CTGTGCGGGCTGTACTTGCCTCTTCCAATTCGTGGCCTTTCCCTGCTTGGTCCCTACT
AGACAGACAAACCAGCCACAGTCCAGCCTGCAGCCAGACCACCTTGTTCACTCATT
CTCCTTTGCCTCAGAGCTAAGACAAAAATGAGACAGAAGGCAGGGCTCCCTGGGAG
TCCACTGTGCTCCAGGGTTCTGGGGAATCAGGGTTAGCCAGCAGCTCCTGGCTGCTT
CCCTCAGAGACTAGGGCTCTCATCCTCCCCAAGAGAAGCAGCAAGCCCAGCCTGGA
CCACACTGTCCATATTGCTGGACAGTGGCCTGACAGAAAGTGACTCCTCCAAGTCCC
AGGAGGCCAGGGCTTTTCTCATCCTTGCCTTTCAGCCCTAACCCATGGGACTGCCCA
CGGATTGGAGACTTCAAGGGCTGAGGTCTGGGAGCTGCATAAAGGGCATTGCTTCAG
CCCAGGTTAGAAATCTGCCTGGGCAAGCTCTTCCTGCCCCAGACCTACAAAGCAGCA
GACCGGGGGCTCTGGTGGACTAGCCCCTGACATTGGTGGGGGCCCCACACCACTC
CACCCCACCCTGCCTTCCAGCTCTCCTGGGCATTTTTCTCCCTGTACTCAAACAGCCT
ACCCACCCAAGGTTTCCTCCCTGGGCAGCCTAGCAATGAACAGTGCAGCCGGCAGG
GCAGAGGCCCGGCAGTCACCGGGCCCGTCAGGCTCAGGCAGAGAAGCCACAGGGG
CCAGGAGTCACTGGAGACTATTTCTAAATGATGGGGGTAAATGCACAAATAGAATCTC
ACCAAAGGGCTGCCTCCACATTGATGCCGTGCCCAGAGGGACAGAACCAATGCCAC
CAGCCTGGGTATATGTCACTGGGCACAGCTCTAACCCCCTCCTCCGGACTCTAGTCCC
GCTCCTCTGCGCACAGAGCCCCCAGCCCACAGGTACACCTTCATGATTTGGAGAAAG
ACGCTCGCCCCATGCACGCCCTCCTCTGGGCCTTCTGCCCTGCTCCCAGTCACTTCCA
AGCTTCCTGTTTGCCTGTGATGTTATTGTGCCTGTTGAGGGAAGCAGCAGAGGAGGC
AGTGGCTGACTTGGCACAGATGCCTGCTACGTGCTCTGTTGAAATGCGCGGGGTGGC
CATTCCTCGGTACAGACTAGTCCTGGTCCTTGGGTGTGGGCAGTGGGGGAGGAACCA
ACTGGTCGAGGTTTCAGAGCCAAACCTTGCCTTTGGTTGGTGAGTCCTTGCCCCCCA
GGCCTGCGCTCCACGATGCCTTTCACCCTTGGCAATCTCAGGGCCATCCTGGGTAGTA
ACCCCACTCCTCTCTGCTCCCGCCCGCACCTGTGGCTCTCACTCTGGGCTCAACCCCT
GCAACCCTCCAGGAGCCCGACAGCAGCCAGCTGCCTGCACTGTCGCCTCCGTAAGC
TCCAACTTCCAGACCCAGAAGTCCCTCTGCTTCCCTCTGTTGGAAAAAGCCTAAAAG
AATTAGCTTCCAGATTCCTCTAGCCCCTGCTCCATTCCCACCCAGTCCTTCTGAAGAG
GAATGAGCAATACATCTGAGCTGGATTTCTCTCTAGTCCTTTCTCCAGACAAATCCTT
CTTAAAGCAAAAGTCCTGGCTGAGCACCTGTCCTTGGGGACCGATCTGCCGTGTGAC
CAGGGGAAGAAAGTTCCCGAAAGCCTGTTCCACCAATTCTGCTTCTGTGTTGTGAAT
CCAGTCTGCTTTCCATTAGAAAACCGCTTCGGCACTTATGGTCACTTTAATAAATCTA
GTATGTAAAAAAGAAAGAAAAGAAAGAAACAGAAAAAAGAAACGTGCAGGCAAA
TGTAAAATACAATGCTCTCTGTAAGATAAATATTTGCCTTTTTTTCTAAAAGGTGTACG
TATTCTGTATGTGAAATTGTCTGTAGAAAGTTTCTATGTTCTTAAATGGCAATACATTC
CAAAAATTGTACTGTAGATATGTACAGCAACCGCACTGGGATGGGGTAGTTTTGCCTG
```

-continued

TAATTTTATTTAAACTCCAGTTTCCACACTTGCTCTTGCAATGTTGGTATGGTATATATC

AGTGCAAAAGAAAAAACAAAACAGAAACAAACAAAAAAAAAAAACAAAAATCCA

CGCAGGTCTAAAGCACAGAGTCTGACGTACAAAAGGAAAAATGCTCAGTATTGATGT

GTGTGACCTTTGTTGTAAATTACATCTGTACTGTGAATGAGAAGTTTTTACAAGTATAA

TAATTGCCTTTATTACAGCTCTGGCTGAGTGTTCAGCCTGAGGATATTTTTAAAAAAA

AAAGAATTAGCATGTTGGAATAAATTTGAAAATCCCAACATAAAAAAA

>SEQ ID NO: 70 Human Schnurri-3 amino acid sequence
MDPEQSVKGTKKAEGSPRKRLTKGEAIQTSVSSSVPYPGSGTAA

TQESPAQELLAPQPFPGPSSVLREGSQEKTGQQQKPPKRPPIEASVHISQLPQHPLTP

AFMSPGKPEHLLEGSTWQLVDPMRPGPSGSFVAPGLHPQSQLLPSHASIIPPEDLPGV

PKVFVPRPSQVSLKPTEEAHKKERKPQKPGKYICQYCSRPCAKPSVLQKHIRSHTGER

PYPCGPCGFSFKTKSNLYKHRKSHAHRIKAGLASGMGGEMYPHGLEMERIPGEEFEEP

TEGESTDSEEETSATSGHPAELSPRPKQPLLSSGLYSSGSHSSSHERCSLSQSSTAQS

LEDPPPFVEPSSEHPLSHKPEDTHTIKQKLALRLSERKKVIDEQAFLSPGSKGSTESG

YFSRSESAEQQVSPPNTNAKSYAEIIFGKCGRIGQRTAMLTATSTQPLLPLSTEDKPS

LVPLSVPRTQVIEHITKLITINEAVVDTSEIDSVKPRRSSLSRRSSMESPKSSLYREP

LSSHSEKTKPEQSLLSLQHPPSTAPPVPLLRSHSMPSAACTISTPHHPFRGSYSFDDH

ITDSEALSHSSHVFTSHPRMLKRQPAIELPLGGEYSSEEPGPSSKDTASKPSDEVEPK

ESELTKKTKKGLKTKGVIYECNICGARYKKRDNYEAHKKYYCSELQIAKPISAGTHTS

PEAEKSQIEHEPWSQMMHYKLGTTLELTPLRKRRKEKSLGDEEEPPAFESTKSQFGSP

GPSDAARNLPLESTKSPAEPSKSVPSLEGPTGFQPRTPKPGSGSESGKERRTTSKEIS

VIQHTSSFEKSDSLEQPSGLEGEDKPLAQFPSPPPAPHGRSAHSLQPKLVRQPNIQVP

EILVTEEPDRPDTEPEPPPKEPEKTEEFQWPQRSQTLAQLPAEKLPPKKKRLRLAEMA

QSSGESSFESSVPLSRSPSQESNVSLSGSSRSASFERDDHGKAEAPSPSSDMRPKPLG

THMLTVPSHHPAREMRRSASEQSPNVSHSAHMTETRSKSFDYGSLSLTGPSAPAPVA

PPARVAPPERRKCFLVRQASLSRPPESELEVAPKGRQESEEPQPSSSKPSAKSSLSQI

SSAATSHGGPPGGKGPGQDRPPLGPTVPYTEALQVFHHPVAQTPLHEKPYLPPPVSLF

SFQHLVQHEPGQSPEFFSTQAMSSLLSSPYSMPPLPPSLFQAPPLPLQPTVLHPGQLH

LPQLMPHPANIPFRQPPSFLPMPYPTSSALSSGFFLPLQSQFALQLPGDVESHLPQIK

TSLAPLATGSAGLSPSTEYSSDIRLPPVAPPASSSAPTSAPPLALPACPDTMVSLVVP

VRVQTNMPSYGSAMYTTLSQILVTQSQGSSATVALPKFEEPPSKGTTVCGADVHEVGP

GPSGLSEEQSRAFPTPYLRVPVTLPERKGTSLSSESILSLEGSSSTAGGSKRVLSPAG

SLELTMETQQQKRVKEEEASKADEKLELVKPCSVVLTSTEDGKRPEKSHLGNQGQGRR

ELEMLSSLSSDPSDTKEIPPLPHPALSHGTAPGSEALKEYPQPSGKPHRRGLTPLSVK

KEDSKEQPDLPSLAPPSSLPLSETSSRPAKSQEGTDSKKVLQFPSLHTTTNVSWCYLN

YIKPNHIQHADRRSSVYAGWCISLYNPNLPGVSTKAALSLLRSKQKVSKETYTMATAP

HPEAGRLVPSSSRKPRMTEVHLPSLVSPEGQKDLARVEKEEERRGEPEEDAPASQRGE

PARIKIFEGGYKSNEEYVYVRGRGRGKYVCEECGIRCKKPSMLKKHIRTHTDVRPYVC

KHCHFAFKTKGNLTKHMKSKAHSKKCQETGVLEELEAEEGTSDDLFQDSEGREGSEAV

EEHQFSDLEDSDSDSDLDEDEDEDEEESQDELSRPSSEAPPPGPPHALRADSSPILGP

QPPDAPASGTEATRGSSVSEAERLTASSCSMSSQSMPGLPWLGPAPLGSVEKDTGSAL

-continued

SYKPVSPRRPWSPSKEAGSRPPLARKHSLTKNDSSPQRCSPAREPQASAPSPPGLHVD

PGRGMGALPCGSPRLQLSPLTLCPLGRELAPRAHVLSKLEGTTDPGLPRYSPTRRWSP

GQAESPPRSAPPGKWALAGPGSPSAGEHGPGLGLDPRVLFPPAPLPHKLLSRSPETCA

SPWKAESRSPSCSPGPAHPLSSRPFSALHDFHGHILARTEENIFSHLPLHSQHLTRAP

CPLIPIGGIQMVQARPGAHPTLLPGPTAAWVSGFSGGGSDLTGAREAQERGRWSPTES

SSASVSPVAKVSKFTLSSELEGGDYPKERERTGGGPGRPPDWTPHGTGAPAEPTPTHS

PCTPPDTLPRPPQGRRAAQSWSPRLESPRAPTNPEPSATPPLDRSSSVGCLAEASARFPAR

TRNLSGEPRTRQDSPKPSGSGEPRAHPHQPEDRVPPNA

>SEQ ID NO: 55; amiR-33-mRANKi-1:
AGGGCTCTGCGTTTGCTCCAGGTAGTCCGCTGCTCCCTTGGGCCTGGGCCCACTGAC

AGCCCTGGTGCCTCTGGCCGGCTGCACACCTCCTGGCGGGCAGCTGTGAATGGTCCA

CATTTCAGGGACTGTTCTGGCAATACCTGGTCCCTGATTTATGGACCATTCACGGAGG

CCTGCCCTGACTGCCCACGGTGCCGTGGCCAAAGAGGATCTAAGGGCACCGCTGAG

GGCCTACCTAACCATCGTGGGAATAAGGACAGTGTCACCC

>SEQ ID NO: 56; amiR-33-mRANKi-2:
AGGGCTCTGCGTTTGCTCCAGGTAGTCCGCTGCTCCCTTGGGCCTGGGCCCACTGAC

AGCCCTGGTGCCTCTGGCCGGCTGCACACCTCCTGGCGGGCAGCTGTGACAAATTAG

CTGTCAGCGCTGTTCTGGCAATACCTGGCGCTGACTGCAAATTTGTCACGGAGGCCT

GCCCTGACTGCCCACGGTGCCGTGGCCAAAGAGGATCTAAGGGCACCGCTGAGGGC

CTACCTAACCATCGTGGGAATAAGGACAGTGTCACCC

>SEQ ID NO: 57; Bone-resorbing peptide (8-mer)
DDDDDDDD

>SEQ ID NO: 58; Bone-resorbing peptide (9-mer)
DDDDDDDDD

>SEQ ID NO: 59; Bone-resorbing peptide (10-mer)
DDDDDDDDDD

>SEQ ID NO: 60; Bone-resorbing peptide (11-mer)
DDDDDDDDDDD

>SEQ ID NO: 61; Bone-resorbing peptide (12-mer)
DDDDDDDDDDDD

>SEQ ID NO: 62; Bone-resorbing peptide (13-mer)
DDDDDDDDDDDDD

>SEQ ID NO: 63; Bone-resorbing peptide (14-mer)
DDDDDDDDDDDDDD

---

What is claimed is:

1. An isolated nucleic acid encoding:
   (i) a first region comprising a first adeno-associated virus (AAV) inverted terminal repeat (ITR), or a variant thereof; and,
   (ii) a second region comprising a transgene encoding at least one bone metabolism modulating agent;
   wherein the transgene comprises the sequence set forth in any one of SEQ ID NOs: 1-15 and 55-56.

2. The isolated nucleic acid of claim 1, further comprising at least one promoter that is operably linked to the transgene.

3. The isolated nucleic acid of claim 1, further comprising a third region comprising a second AAV ITR or a variant thereof.

4. A vector comprising the isolated nucleic acid of claim 1.

5. A host cell comprising the isolated nucleic acid of claim 1.

6. A recombinant adeno-associated virus (rAAV) comprising:
   (i) a capsid protein; and,
   (ii) the isolated nucleic acid of claim 1.

7. A recombinant adeno-associated virus (rAAV) comprising:
   (i) a capsid protein; and,
   (ii) an isolated nucleic acid encoding:
      (i) a first region comprising a first adeno-associated virus (AAV) inverted terminal repeat (ITR), or a variant thereof; and,
      (ii) a second region comprising a transgene encoding at least one bone formation promoting agent;
   wherein the bone formation promoting agent encoded by the transgene comprises an inhibitory nucleic acid targeting sclerostin (SOST) or an inhibitory nucleic acid targeting schnurri-3 (SHN3);
   wherein the capsid protein is of a serotype selected from AAV1, AAV2, AAV3, AAV4, AAV5, AAV6, AAV6.2, AAV7, AAV8, AAV9, AAV.rh8, AAV.rh10, AAV.rh39, AAV.43, AAV2/2-66, AAV2/2-84, and AAV2/2-125, or a variant of any of the foregoing; and wherein the capsid protein comprises the sequence set forth in any one of SEQ ID NO: 18-34.

8. A recombinant adeno-associated virus (rAAV) comprising:
(i) a capsid protein; and,
(ii) an isolated nucleic acid encoding:
   (i) a first region comprising a first adeno-associated virus (AAV) inverted terminal repeat (ITR), or a variant thereof; and,
   (ii) a second region comprising a transgene encoding at least one bone formation promoting agent;
wherein the bone formation promoting agent encoded by the transgene comprises an inhibitory nucleic acid targeting sclerostin (SOST) or an inhibitory nucleic acid targeting schnurri-3 (SHN3);
wherein the capsid protein transduces osteoblast cells (OBs); and
wherein the capsid protein is of a serotype selected from AAV4, AAV1, AAV6, AAV6.2, and AAV9, or a variant of any of the foregoing.

9. A recombinant adeno-associated virus (rAAV) comprising:
(i) a capsid protein; and,
(ii) an isolated nucleic acid encoding:
   (i) a first region comprising a first adeno-associated virus (AAV) inverted terminal repeat (ITR), or a variant thereof; and,
   (ii) a second region comprising a transgene encoding at least one bone formation promoting agent;
wherein the bone formation promoting agent encoded by the transgene comprises an inhibitory nucleic acid targeting sclerostin (SOST) or an inhibitory nucleic acid targeting schnurri-3 (SHN3);
wherein the capsid protein transduces osteoclast cells (OCs); and
wherein the capsid protein is of a serotype selected from AAV1, AAV5, AAV6, AAV6.2, AAV7, AAV8, AAV9, AAV10, AAV.rh39, and AAV.rh43, or a variant of any of the foregoing.

10. The vector of claim 4, wherein the vector is a plasmid.

* * * * *